US012692262B2

(12) United States Patent
Armacost et al.

(10) Patent No.: US 12,692,262 B2
(45) Date of Patent: Jul. 28, 2026

(54) SUBSTITUTED UREAS AS OREXIN RECEPTOR AGONISTS

(71) Applicant: Merck Sharp & Dohme LLC, Rahway, NJ (US)

(72) Inventors: Kira A. Armacost, Doylestown, PA (US); Maria Irina Chiriac, Hatfield, PA (US); Danielle M. Hurzy, Garnet Valley, PA (US); Jeffrey C. Kern, Gilbertsville, PA (US); Jian Liu, Edison, NJ (US); Peter J. Manley, Harleysville, PA (US); Philippe Nantermet, Lansdale, PA (US); Vanessa L. Rada, Glenside, PA (US); Michael T. Rudd, Collegeville, PA (US); Craig A. Stump, Pottstown, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 455 days.

(21) Appl. No.: 18/256,463

(22) PCT Filed: Dec. 14, 2021

(86) PCT No.: PCT/US2021/063205
§ 371 (c)(1),
(2) Date: Jun. 8, 2023

(87) PCT Pub. No.: WO2022/132696
PCT Pub. Date: Jun. 23, 2022

(65) Prior Publication Data
US 2024/0101555 A1 Mar. 28, 2024

Related U.S. Application Data

(60) Provisional application No. 63/126,262, filed on Dec. 16, 2020.

(51) Int. Cl.
*A61K 31/17* (2006.01)
*C07C 275/04* (2006.01)
*C07D 471/04* (2006.01)
*C07D 487/04* (2006.01)
*C07D 519/00* (2006.01)

(52) U.S. Cl.
CPC ......... *C07D 471/04* (2013.01); *C07D 487/04* (2013.01); *C07D 519/00* (2013.01)

(58) Field of Classification Search
CPC .............................. A61K 31/17; C07C 275/04
USPC ............................................ 514/588; 564/32
See application file for complete search history.

(56) References Cited

U.S. PATENT DOCUMENTS

2004/0067951 A1 4/2004 Desimone et al.

FOREIGN PATENT DOCUMENTS

| | | |
|---|---|---|
| WO | 2004052876 A1 | 6/2004 |
| WO | 2010052448 A2 | 5/2010 |
| WO | 2010072722 A1 | 7/2010 |
| WO | 2014004863 A2 | 1/2014 |
| WO | 2016101119 A1 | 6/2016 |

OTHER PUBLICATIONS

Chemelli, Richard M. et al., Narcolepsy in orexin Knockout Mice: Molecular Genetics of Sleep Regulation, Cell, 1999, 437-451, 98.
Harris, Glenda C. et al., Arousal and reward: a dichotomy in orexin function, Trends in Neurosciences, 2006, 571-577, 29(10).
Mitchell, Scott A. et al., Imidazo[1,2-alpha]pyrazine diaryl ureas: Inhibitors of the receptor tyrosine kinase EphB4, Bioorganic & Medicinal Chemistry Letters, 2009, 6991-6995, 19.
Peyron, Christelle et al., Neurons Containing Hypocretin (Orexin) Project to Multiple Neuronal Systems, The Journal of Neuroscience, 1998, 9996-100150, 18(23).
Sakurai, Takeshi et al., Orexins and Orexin Receptors: A Family of Hypothalamic Neuropeptides and G Protein-Coupled Receptors that Regulate Feeding Behavior, Cell, 1998, 573-585, 92.
European Search Report, Application No. 21907595.9 dated Sep. 30, 2024, 7 pages.

*Primary Examiner* — Douglas M Willis
(74) *Attorney, Agent, or Firm* — Patricia A. Shatynski; John C. Todaro

(57) ABSTRACT

The present invention is directed to urea compounds of formula(s)

Ia

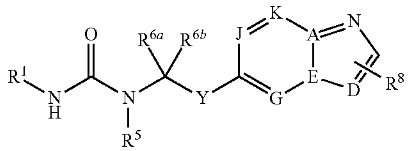

which are agonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

14 Claims, No Drawings

SUBSTITUTED UREAS AS OREXIN RECEPTOR AGONISTS

CROSS-REFERENCE TO RELATED APPLICATIONS

This application is a National Stage application of International Patent Application No. PCT/US2021/063205, filed Dec. 14, 2021, which claims priority to U.S. Provisional Patent Application No. 63/126,262, filed Dec. 16, 2020.

BACKGROUND OF THE INVENTION

The orexins (hypocretins) comprise two neuropeptides produced in the hypothalamus: orexin A (OX-A) (a 33 amino acid peptide) and the orexin B (OX-B) (a 28 amino acid peptide) (Sakurai T. et al., Cell, 1998, 92, 573-585). Orexins regulate states of sleep and wakefulness opening potentially novel therapeutic approaches for narcolepsy, idiopathic hypersomnia, excessive daytime sleepiness, shift work disorder, obstructive sleep apnea and insomnia (Chemelli R. M. et al., Cell, 1999, 98, 437-451). Orexins are found to stimulate food consumption in rats suggesting a physiological role for these peptides as mediators in the central feedback mechanism that regulates feeding behavior (Sakurai T. et al., Cell, 1998, 92, 573-585). Orexins have also been indicated as playing a role in arousal, emotion, energy homeostasis, reward, learning and memory (Peyron, et al., Journal Neurosci., 1998, 18(23):9996-100150, Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is partially selective for OX-A and the orexin-2 receptor (OX2 or OX2R) is capable of binding OX-A as well as OX-B with similar affinity. The physiological actions in which orexins are presumed to participate are thought to be expressed via one or both of OX1 receptor and OX2 receptor as the two subtypes of orexin receptors.

SUMMARY OF THE INVENTION

The present invention is directed to urea compounds which are agonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

DETAILED DESCRIPTION OF THE INVENTION

The present invention is directed to compounds of the formula I:

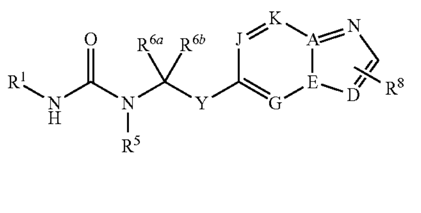

I wherein:

A is N or —C═;

D is N, —CH—, —CH═CH—, —N═CH—, —O— or —S—, or D and the adjacent non-bridgehead carbon form $—CH_2CH_2—$;

E is N or —C═;

G is N or —CH— —C(Cl)—, $—C(CH_3)—$,

J is N, —CH—, —C(Cl)—, $—C(CH_3)—$, $—C(O—CH_3)-$ or $—C(CH_2OCH_3)—$,

K is N or $—C(R^7)—$;

Y is phenyl, pyridyl, pyrazinyl, pyridazinyl, pyrimidinyl, pyridofuranyl, or imidazopyridyl, which is unsubstituted or substituted with one or more $R^4$;

$R^1$ is $C_{1-6}$alkyl, $C_{2-4}$alkenyl or $C_{3-6}$cycloalkyl, wherein the $C_{1-6}$alkyl, $C_{2-4}$alkenyl or $C_{3-6}$cycloalkyl is unsubstituted or substituted with substituent(s) selected from:

(1) hydroxyl,
(2) halogen,
(3) $C_{1-6}$alkyl, which is unsubstituted or substituted with one to six fluoro,
(4) $C_{2-4}$alkenyl,
(5) $C_{2-4}$alkynyl,
(6) —$C_{3-6}$cycloalkyl, which is unsubstituted or substituted with $C_{1-6}$alkyl, one to six fluoro, or trifluoromethyl,
(7) —O—$C_{1-6}$alkyl,
(8) —O—$C_{3-6}$cycloalkyl,
(9) —O(C═O)—$C_{1-6}$alkyl,
(10) —O—$C_{1-6}$alkyl,
(11) (C═O)—O—$C_{1-6}$alkyl,
(12) (C═O)—N($C_{1-6}$alkyl)($C_{1-6}$alkyl)
(13) —O(C═O)—N($C_{1-6}$alkyl)($C_{1-6}$alkyl)
(14) $—NH_2$,
(15) —NH—$C_{1-6}$alkyl,
(16) —N($C_{1-6}$alkyl)($C_{1-6}$alkyl),
(17) $—SO_2—$($C_{1-6}$alkyl)($C_{1-6}$alkyl),
(18) phenyl, which is unsubstituted or substituted with $C_{1-6}$alkyl, fluoro or trifluormethyl,
(19) keto,
(20) $—CO_2H$,
(21) $—SO_2—$$C_{1-6}$alkyl,
(22) $—SO_2—$$C_{3-5}$cycloalkyl,
(23) azetidinyl, which is unsubstituted or substituted with $C_{1-6}$alkyl,
(24) imidazolyl,
(25) triazolyl,
(26) oxadiazolyl,
(27) morpholinyl,
(28) oxomorpholinyl,
(29) piperidinyl, which is unsubstituted or substituted with $C_{1-6}$alkyl, fluoro or trifluormethyl,
(30) oxetanyl,
(31) oxo-oxazolidinyl,
(32) tetrahydrofuranyl, which is unsubstituted or substituted with $C_{1-6}$alkyl, fluoro or trifluormethyl,
(33) tetrahydropyranyl, which is unsubstituted or substituted with $C_{1-6}$alkyl, fluoro or trifluormethyl, and
(34) —CN;

$R^4$ is selected from:

(1) hydrogen,
(2) hydroxyl,
(3) halo,
(4) oxo,
(5) $C_{1-6}$alkyl, which is unsubstituted or substituted with one to six fluoro,
(6) —O—$C_{1-6}$alkyl, which is unsubstituted or substituted with one to six fluoro, (7) $C_{2-6}$alkenyl, which is unsubstituted or substituted with one to six fluoro, and (8) —S—$C_{1-4}$alkyl;

$R^5$ is selected from:

(1) —$C_{1-6}$alkyl, where the alkyl is unsubstituted or substituted with one to six substituents independently selected from halogen, and (2) —$C_{3-6}$cycloalkyl, where the —$C_{3-6}$cycloalkyl is unsubstituted or substituted with —$C_{1-6}$alkyl or halogen;

$R^{6a}$ and $R^{6b}$ are independently selected from:

(1) hydrogen, (2) —$C_{1-6}$alkyl, where the alkyl is unsubstituted or substituted with one to six substituents selected from halogen, (3) =$C_1$alkenyl, with the carbon to which it is attached, where the $C_1$alkenyl is unsubstituted or substituted with —$C_{1-6}$alkyl or fluoro, and (4) —$C_{3-6}$cycloalkyl, where the —$C_{3-6}$cycloalkyl is unsubstituted or substituted with —$C_{1-6}$alkyl or halogen, or $R^{6a}$ and $R^{6b}$ and the carbon to which they are attached are joined together to form a $C_{3-6}$cycloalkyl;

$R^7$ is selected from:

(1) hydrogen, (2) halogen, (3) —$C_{1-6}$alkyl, where the alkyl is unsubstituted or substituted with —O—$C_{1-6}$alkyl or one to six halogen, (4) —O—$C_{1-6}$alkyl, where the alkyl is unsubstituted or substituted with one to six substituents independently selected from halogen, (5) —S—$C_{1-6}$alkyl, (6) —$NH_2$, (7) —NH—$C_{1-6}$alkyl, and (8) —N($C_{1-6}$alkyl)($C_{1-6}$alkyl);

$R^8$ is selected from:

(1) hydrogen, (2) hydroxyl, (3) halogen, (4) cyano, (5) —$NH_2$, and (6) —$C_{1-6}$alkyl, where the alkyl is unsubstituted or substituted with one to six substituents independently selected from halogen;

or a pharmaceutically acceptable salt thereof.

An embodiment of the present invention includes compounds of the formula Ia:

Ia

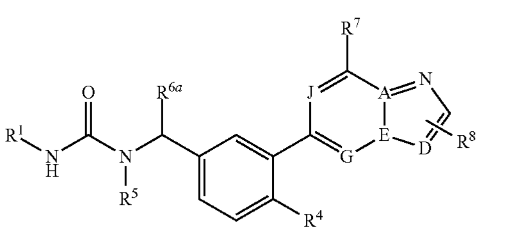

wherein A, D, E, G, J, $R^1$, $R^4$, $R^5$, $R^{6a}$, $R^7$ and $R^8$ are defined herein; or a pharmaceutically acceptable salt thereof.

An embodiment of the present invention includes compounds of the formula Ia':

Ia'

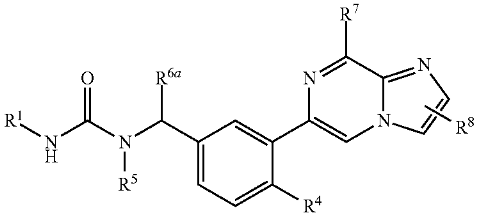

wherein $R^1$, $R^4$, $R^5$, $R^{6a}$, $R^7$ and $R^8$ are defined herein; or a pharmaceutically acceptable salt thereof.

An embodiment of the present invention includes compounds of the formula Ia":

Ia"

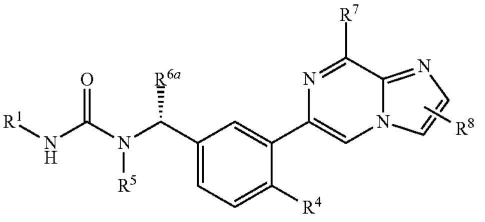

wherein $R^1$, $R^4$, $R^5$, $R^{6a}$, $R^7$ and $R^8$ are defined herein; or a pharmaceutically acceptable salt thereof.

An embodiment of the present invention includes compounds of the formula Ib:

Ib

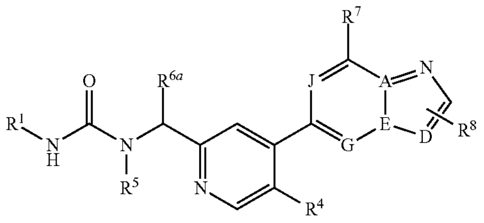

wherein A, D, E, G, J, $R^1$, $R^4$, $R^5$, $R^{6a}$, $R^7$ and $R^8$ are defined herein; or a pharmaceutically acceptable salt thereof.

An embodiment of the resent invention includes compounds of the formula Ib':

Ib'

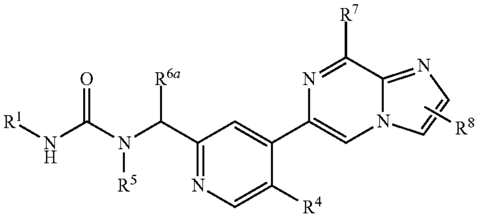

wherein $R^1$, $R^4$, $R^5$, $R^{6a}$, $R^7$ and $R^8$ are defined herein; or a pharmaceutically acceptable salt thereof.

An embodiment of the present invention includes compounds of the formula Ib":

Ib″

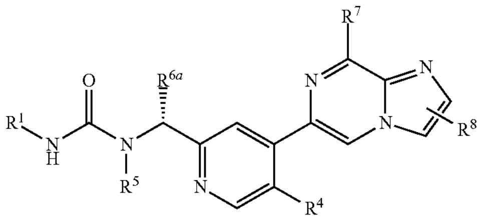

wherein $R^1$, $R^4$, $R^5$, $R^{6a}$, $R^7$ and $R^8$ are defined herein; or a pharmaceutically acceptable salt thereof.

An embodiment of the present invention includes compounds wherein the group:

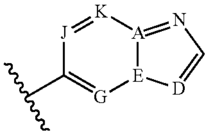

is selected from:

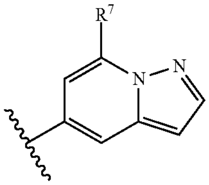,
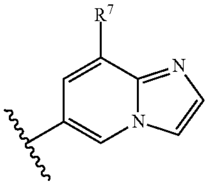,
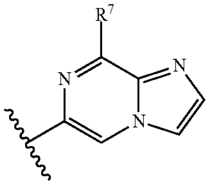,
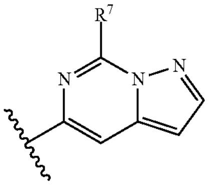,
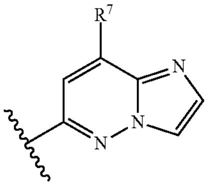,
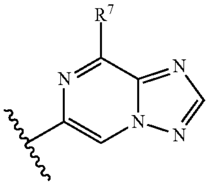,
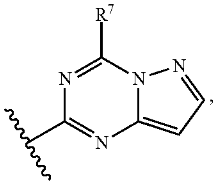,
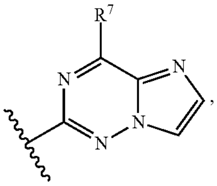, and
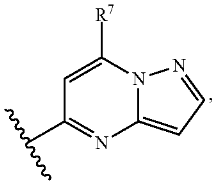, wherein $R^7$ is defined herein.

An embodiment of the present invention includes compounds wherein the group:

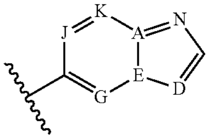

is:

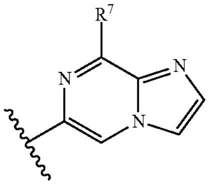

wherein $R^7$ is defined herein.

An embodiment of the present invention includes compounds wherein Y is selected from:

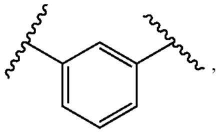,
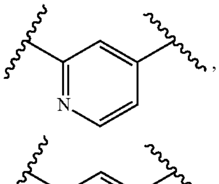,
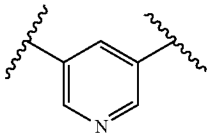,
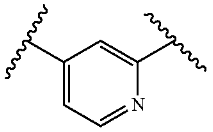,
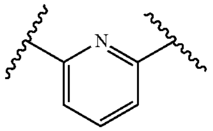,
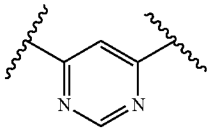,
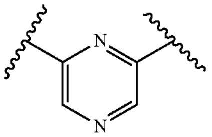, and
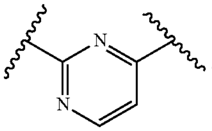.

which is unsubstituted or substituted with $R^4$.

An embodiment of the present invention includes compounds wherein Y is phenyl, pyridyl, pyrazinyl, or pyrimidinyl. An embodiment of the present invention includes compounds wherein Y is phenyl or pyridyl. An embodiment of the present invention includes compounds wherein Y is phenyl. An embodiment of the present invention includes compounds wherein Y is pyridyl.

An embodiment of the present invention includes compounds wherein K is —C($R^7$)—.

An embodiment of the present invention includes compounds wherein $R^1$ is —$C_{1-6}$alkyl which is unsubstituted or substituted with substituent(s) selected from:

(1) fluoro, (2) cyclopropyl, and (3) —$C_{1-6}$alkyl.

An embodiment of the present invention includes compounds wherein $R^1$ is 6,6,6-trifluorohexan-3-yl or 1,1,1,5,5,5-hexafluoropentan-2-yl. An embodiment of the present invention includes compounds wherein $R^1$ is 6,6,6-trifluorohexan-3-yl. An embodiment of the present invention includes compounds wherein $R^1$ is 1,1,1,5,5,5-hexafluoropentan-2-yl.

An embodiment of the present invention includes compounds wherein $R^4$ is selected from:

(1) hydrogen, (2) hydroxyl, (3) $C_{1-6}$alkyl, and (4) —O—$C_{1-6}$alkyl.

An embodiment of the present invention includes compounds wherein $R^4$ is hydrogen. An embodiment of the present invention includes compounds wherein $R^4$ is methyl. An embodiment of the present invention includes compounds wherein $R^4$ is —$OCH_3$.

An embodiment of the present invention includes compounds wherein $R^5$ is methyl or ethyl. An embodiment of the present invention includes compounds wherein $R^5$ is methyl. An embodiment of the present invention includes compounds wherein $R^5$ is ethyl.

An embodiment of the present invention includes compounds wherein $R^{6a}$ is methyl or trifluoromethyl, and $R^{6b}$ is hydrogen. An embodiment of the present invention includes compounds wherein $R^{6a}$ is methyl, and $R^{6b}$ is hydrogen. An embodiment of the present invention includes compounds wherein $R^{6a}$ is trifluoromethyl, and $R^{6b}$ is hydrogen. An embodiment of the present invention includes compounds wherein $R^{6b}$ is hydrogen.

An embodiment of the present invention includes compounds wherein $R^7$ is selected from:

(1) hydrogen, (2) —$C_{1-6}$alkyl, and (3) —O—$C_{1-6}$alkyl,

An embodiment of the present invention includes compounds wherein $R^7$ is selected from hydrogen, methyl and methoxy. An embodiment of the present invention includes compounds wherein $R^7$ is methoxy.

An embodiment of the present invention includes compounds wherein $R^8$ is hydrogen or methyl. An embodiment of the present invention includes compounds wherein $R^8$ is hydrogen. An embodiment of the present invention includes compounds wherein $R^8$ is methyl.

Certain embodiments of the present invention include a compound which is selected from the group consisting of the subject compounds of the Examples herein or a pharmaceutically acceptable salt thereof.

Certain embodiments of the present invention include a compound which is selected from:

1-ethyl-3-((S)-1,1,1,5,5,5-hexafluoropentan-2-yl)-1-((R)-1-(3-(imidazo[1,2-a]pyridin-6-yl)phenyl)ethyl)urea;

1-ethyl-3-((R)-1-(3-fluorophenyl)ethyl)-1-((R)-1-(3-(8-methoxyimidazo[1,2-a]pyrazin-6-yl)phenyl)ethyl)urea;

1-ethyl-1-((R)-1-(3-(8-methoxyimidazo[1,2-a]pyrazin-6-yl)phenyl)ethyl)-3-((1R,3S)-3-(trifluoromethyl)cyclopentyl)urea;

3-((R)-1-(4,4-difluorocyclohexyl)ethyl)-1-ethyl-1-((R)-1-(3-(8-methoxyimidazo[1,2-a]pyrazin-6-yl)phenyl)ethyl)urea;

(R)-1-ethyl-1-(1-(3-(8-methoxyimidazo[1,2-a]pyrazin-6-yl)phenyl)ethyl)-3-(2,2,2-trifluoroethyl)urea;

1-ethyl-1-((R)-1-(3-(8-methoxyimidazo[1,2-a]pyrazin-6-yl)phenyl)ethyl)-3-(((S)-5-oxomorpholin-3-yl)methyl)urea;

3-(2-(dimethylamino)-3,3,3-trifluoropropyl)-1-ethyl-1-((R)-1-(3-(8-methoxyimidazo[1,2-a]pyridin-6-yl)phenyl)ethyl)urea;

(R)-1-ethyl-1-(4-methoxy-3-(8-methoxyimidazo[1,2-a]pyridin-6-yl)benzyl)-3-(6,6,6-trifluorohexan-3-yl)urea;

3-(1-(3,3-difluorocyclohexyl)ethyl)-1-ethyl-1-((R)-1-(3-(8-methoxyimidazo[1,2-a]pyrazin-6-yl)phenyl)ethyl)urea;

3-(cyano(cyclopentyl)methyl)-1-ethyl-1-((R)-1-(3-(8-methoxyimidazo[1,2-a]pyrazin-6-yl)phenyl)ethyl)urea;

ethyl 3-(3-ethyl-3-((R)-1-(3-(8-methoxyimidazo[1,2-a]pyrazin-6-yl)phenyl)ethyl)ureido)-4,4,4-trifluorobutanoate 3-(cyano(3-(trifluoromethyl)phenyl)methyl)-1-ethyl-1-((R)-1-(3-(8-methoxyimidazo[1,2-a]pyrazin-6-yl)phenyl)ethyl)urea;

3-(3-(dimethylamino)-1,1,1-trifluoropropan-2-yl)-1-ethyl-1-((R)-1-(3-(7-methoxypyrazolo[1,5-a]pyridin-5-yl)phenyl)ethyl)urea;

3-(3-cyano-1,1,1-trifluoropropan-2-yl)-1-ethyl-1-((R)-1-(3-(8-methoxyimidazo[1,2-a]pyrazin-6-yl)phenyl)ethyl)urea;

1-ethyl-1-((R)-1-(3-(8-methoxyimidazo[1,2-a]pyrazin-6-yl)phenyl)ethyl)-3-(2,2,2-trifluoro-1-(1-methylazetidin-3-yl)ethyl)urea;

1-ethyl-1-((R)-1-(3-(8-methoxyimidazo[1,2-a]pyrazin-6-yl)phenyl)ethyl)-3-(1,1,1-trifluoro-3-(2H-1,2,3-triazol-2-yl)propan-2-yl)urea;

1-ethyl-1-((R)-1-(3-(8-methoxyimidazo[1,2-a]pyrazin-6-yl)phenyl)ethyl)-3-(1,1,1-trifluoro-3-(1H-1,2,3-triazol-1-yl)propan-2-yl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-((S)-1,1,1-trifluoropropan-2-yl)urea;

1-ethyl-3-(1,1,1,5,5,5-hexafluoro-4-methylpentan-2-yl)-1-((R)-1-(3-(8-methoxyimidazo[1,2-a]pyrazin-6-yl)phenyl)ethyl)urea;

1-ethyl-1-((R)-1-(3-(8-methoxyimidazo[1,2-a]pyrazin-6-yl)phenyl)ethyl)-3-(6,6,6-trifluoro-5-methylhexan-3-yl)urea;

3-(1-(4,4-difluoro-6,6-dimethyltetrahydro-2H-pyran-2-yl)-2,2,2-trifluoroethyl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;

3-(1-cyclobutyl-2,2,2-trifluoroethyl)-1-ethyl-1-((S)-2,2,2-trifluoro-1-(5-methoxy-4-(8-methoxyimidazo[1,2-a]pyrazin-6-yl)pyridin-2-yl)ethyl)urea;

3-(1-cyclopropyl-2,2,2-trifluoroethyl)-1-ethyl-1-(2,2,2-trifluoro-1-(5-methoxy-4-(8-methoxyimidazo[1,2-a]pyrazin-6-yl)pyridin-2-yl)ethyl)urea;

3-(1-cyclopropyl-2,2-difluoroethyl)-1-ethyl-1-((S)-2,2,2-trifluoro-1-(5-methoxy-4-(8-methoxyimidazo[1,2-a]pyrazin-6-yl)pyridin-2-yl)ethyl)urea;

1-ethyl-1-(2,2,2-trifluoro-1-(5-methoxy-4-(8-methoxyimidazo[1,2-a]pyrazin-6-yl)pyridin-2-yl)ethyl)-3-((S)-1,1,1-trifluorobutan-2-yl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-(2-(trifluoromethyl)cyclobutyl)urea;

3-(1,1-difluorobutan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-(3,3,3-trifluoro-2-methylpropyl)urea;

(S)-1-ethyl-1-(2,2,2-trifluoro-1-(5-methoxy-4-(8-methoxyimidazo[1,2-a]pyrazin-6-yl)pyridin-2-yl)ethyl)-3-(1-(trifluoromethyl)cyclobutyl)urea;

1-ethyl-3-((S)-1,1,1,5,5,5-hexafluoropentan-2-yl)-1-(2,2,2-trifluoro-1-(7-(8-methoxyimidazo[1,2-a]pyrazin-6-yl)furo[3,2-b]pyridin-5-yl)ethyl)urea;

1-ethyl-3-((S)-1,1,1,5,5,5-hexafluoropentan-2-yl)-1-(2,2,2-trifluoro-1-(8-(8-methoxyimidazo[1,2-a]pyrazin-6-yl)imidazo[1,2-a]pyridin-6-yl)ethyl)urea;

1-ethyl-3-((S)-1,1,1,5,5,5-hexafluoropentan-2-yl)-1-(2,2,2-trifluoro-1-(5-(7-methoxypyrazolo[1,5-a]pyridin-5-yl)-6-(methylthio)pyridin-3-yl)ethyl)urea;

1-(cyclopropyl(5-methoxy-4-(8-methoxy-2-methylimidazo[1,2-a]pyrazin-6-yl)pyridin-2-yl)methyl)-1-ethyl-3-((S)-1,1,1,5,5,5-hexafluoropentan-2-yl)urea;

1-(2,2-difluoro-1-(5-methoxy-4-(8-methoxy-2-methylimidazo[1,2-a]pyrazin-6-yl)pyridin-2-yl)ethyl)-1-ethyl-3-((S)-1,1,1,5,5,5-hexafluoropentan-2-yl)urea;

3-((S)-3-cyclopropoxy-1,1,1-trifluoropropan-2-yl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;

1-cyclopropyl-3-((S)-1,1,1,5,5,5-hexafluoropentan-2-yl)-1-(2,2,2-trifluoro-1-(5-methoxy-4-(8-methoxy-2-methylimidazo[1,2-a]pyrazin-6-yl)pyridin-2-yl)ethyl)urea;

1-(2,2-difluoroethyl)-1-(2,2,2-trifluoro-1-(5-methoxy-4-(8-methoxy-[1,2,4]triazolo[1,5-a]pyrazin-6-yl)pyridin-2-yl)ethyl)-3-((R)-6,6,6-trifluorohexan-3-yl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-((R)-6,6,6-trifluorohexan-3-yl)urea;

N-ethyl-N'-[(2S)-1,1,1,5,5,5-hexafluoropentan-2-yl]-N-{2,2,2-trifluoro-1-[3-(8-methoxyimidazo[1,2-a]pyrazin-6-yl)phenyl]ethyl}urea;

1-ethyl-3-((S)-1,1,1,5,5,5-hexafluoropentan-2-yl)-1-((S)-2,2,2-trifluoro-1-(3-(imidazo[1,2-a]pyridin-6-yl)-4-methoxyphenyl)ethyl)urea;

3-((R)-1-(cyanomethyl)piperidin-3-yl)-1-ethyl-1-((R)-1-(3-(8-methoxyimidazo[1,2-a]pyrazin-6-yl)phenyl)ethyl)urea;

(R)-3-(2-cyanopropan-2-yl)-1-ethyl-1-(1-(3-(8-methoxyimidazo[1,2-a]pyrazin-6-yl)phenyl)ethyl)urea;

1-ethyl-3-(1-(3-methyl-1,2,4-oxadiazol-5-yl)ethyl)-1-((S)-2,2,2-trifluoro-1-(5-methoxy-4-(8-methoxyimidazo[1,2-a]pyrazin-6-yl)pyridin-2-yl)ethyl)urea;

1-ethyl-3-((1R,2R)-2-methyl-2-(trifluoromethyl)cyclopropyl)-1-((S)-2,2,2-trifluoro-1-(5-methoxy-4-(8-methoxyimidazo[1,2-a]pyrazin-6-yl)pyridin-2-yl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-((S)-1,1,1-trifluoro-3,3-dimethylbutan-2-yl)urea;

(S)-1-ethyl-3-isopropyl-1-(2,2,2-trifluoro-1-(5-methoxy-4-(8-methoxyimidazo[1,2-a]pyrazin-6-yl)pyridin-2-yl)ethyl)urea;

(S)-1-ethyl-1-(2,2,2-trifluoro-1-(5-methoxy-4-(8-methoxyimidazo[1,2-a]pyrazin-6-yl)pyridin-2-yl)ethyl)-3-(3-(2,2,2-trifluoroethyl)cyclobutyl)urea;

1-ethyl-3-((1R,2R)-1-methyl-2-(trifluoromethyl)cyclopropyl)-1-((S)-2,2,2-trifluoro-1-(5-methoxy-4-(8-methoxyimidazo[1,2-a]pyrazin-6-yl)pyridin-2-yl)ethyl)urea;

(S)-3-cyclopropyl-1-ethyl-1-(2,2,2-trifluoro-1-(5-methoxy-4-(8-methoxyimidazo[1,2-a]pyrazin-6-yl)pyridin-2-yl)ethyl)urea;

3-(1-(4,4-difluorotetrahydro-2H-pyran-2-yl)-2,2,2-trifluoroethyl)-1-ethyl-1-((R)-1-(3-(8-methoxyimidazo[1,2-a]pyrazin-6-yl)phenyl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-(1,1,1-trifluoro-4-oxopentan-2-yl)urea;

3-((S)-4-cyano-1,1,1-trifluorobutan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-((S)-1,1,1-trifluoro-4-(methylsulfonyl)butan-2-yl)urea;

3-(1-cyanobutyl)-1-ethyl-1-((R)-1-(3-(8-methoxyimidazo[1,2-a]pyrazin-6-yl)phenyl)ethyl)urea;

(S)-1-ethyl-1-(2,2,2-trifluoro-1-(5-methoxy-4-(8-methoxyimidazo[1,2-a]pyrazin-6-yl)pyridin-2-yl)ethyl)-3-(3-(trifluoromethyl)cyclobutyl)urea;

1-ethyl-3-((1S,2R)-2-methyl-2-(trifluoromethyl)cyclopropyl)-1-((S)-2,2,2-trifluoro-1-(5-methoxy-4-(8-methoxyimidazo[1,2-a]pyrazin-6-yl)pyridin-2-yl)ethyl)urea;

3-(3,3-difluorobutan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea;

3-(1,1-difluoropropan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea;

3-(2,2-difluorocyclopropyl)-1-ethyl-1-((S)-2,2,2-trifluoro-1-(5-methoxy-4-(8-methoxyimidazo[1,2-a]pyrazin-6-yl)pyridin-2-yl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-(1,1,1-trifluoro-3-(2-oxooxazolidin-3-yl)propan-2-yl)urea;

1-ethyl-3-((2S)-1,1,1,5,5,5-hexafluoro-4-methoxypentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-(4,4,4-trifluoro-1-(oxetan-2-yl)butyl)urea;

1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(1,1,1-trifluoro-3-(tetrahydrofuran-2-yl)propan-2-yl)urea;

1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(2,2,2-trifluoro-1-(tetrahydro-2H-pyran-3-yl)ethyl)urea;

1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(2,2,2-trifluoro-1-(tetrahydro-2H-pyran-4-yl)ethyl)urea;

1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(5,5,5-trifluoro-1-methoxypentan-2-yl)urea;

1-ethyl-3-((S)-1,1,1,5,5,5-hexafluoropentan-2-yl)-1-(2,2,2-trifluoro-1-(6-methoxy-5-(8-methoxyimidazo[1,2-a]pyrazin-6-yl)pyridin-3-yl)ethyl)urea;

1-ethyl-3-((S)-1,1,1,5,5,5-hexafluoropentan-2-yl)-1-((R)-1-(5-methoxy-4-(7-methoxypyrazolo[1,5-c]pyrimidin-5-yl)pyridin-2-yl)ethyl)urea;

1-ethyl-1-((R)-1-(3-(8-methoxyimidazo[1,2-a]pyrazin-6-yl)phenyl)ethyl)-3-(1,1,1,4,4-pentafluorobutan-2-yl)urea;

3-(1-(4,4-difluoro-1-methylpiperidin-2-yl)-2,2,2-trifluoroethyl)-1-ethyl-1-((R)-1-(3-(7-methoxypyrazolo[1,5-a]pyridin-5-yl)phenyl)ethyl)urea;

1-ethyl-1-((R)-1-(3-(8-methoxyimidazo[1,2-a]pyrazin-6-yl)phenyl)ethyl)-3-(1,1,1-trifluoro-5-oxohexan-2-yl)urea;

1-ethyl-1-((R)-1-(3-(8-methoxyimidazo[1,2-a]pyrazin-6-yl)phenyl)ethyl)-3-(2,2,6,6,6-pentafluorohexan-3-yl)urea;

3-((1R)-1-(4,4-difluorotetrahydro-2H-pyran-2-yl)propyl)-1-ethyl-1-((R)-1-(3-(8-methoxyimidazo[1,2-a]pyrazin-6-yl)phenyl)ethyl)urea;

3-(3-(1-ethoxycyclopropyl)-1,1,1-trifluoropropan-2-yl)-1-ethyl-1-((R)-1-(3-(8-methoxyimidazo[1,2-a]pyrazin-6-yl)phenyl)ethyl)urea;

1-((R)-1-(3-(8-methoxyimidazo[1,2-a]pyrazin-6-yl)phenyl)ethyl)-1-methyl-3-((R)-6,6,6-trifluorohexan-3-yl)urea;
1-((R)-1-(3-(8-methoxyimidazo[1,2-a]pyrazin-6-yl)phenyl)ethyl)-1-propyl-3-((R)-6,6,6-trifluorohexan-3-yl)urea;
1-isopropyl-1-((R)-1-(3-(8-methoxyimidazo[1,2-a]pyrazin-6-yl)phenyl)ethyl)-3-((R)-6,6,6-trifluorohexan-3-yl)urea;
1-(2,2-difluoroethyl)-3-((S)-1,1,1,5,5,5-hexafluoropentan-2-yl)-1-(1-(3-(8-methoxyimidazo[1,2-a]pyrazin-6-yl)phenyl)ethyl)urea;
1-ethyl-1-(2,2,2-trifluoro-1-(6-methoxy-5-(8-methoxyimidazo[1,2-a]pyrazin-6-yl)pyridin-3-yl)ethyl)-3-((S)-1,1,1-trifluoropropan-2-yl)urea;
1-ethyl-3-((S)-1,1,1,5,5,5-hexafluoropentan-2-yl)-1-(1-(2-(8-methoxyimidazo[1,2-a]pyrazin-6-yl)pyrimidin-4-yl)ethyl)urea;
1-ethyl-3-((S)-1,1,1,5,5,5-hexafluoropentan-2-yl)-1-(1-(6-(8-methoxyimidazo[1,2-a]pyrazin-6-yl)pyridazin-4-yl)ethyl)urea;
1-ethyl-1-((R)-1-(3-(8-methoxyimidazo[1,2-a]pyrazin-6-yl)phenyl)ethyl)-3-(6,6,6-trifluorohex-1-yn-3-yl)urea;
1-ethyl-1-((S)-2,2,2-trifluoro-1-(3-(8-methoxyimidazo[1,2-a]pyrazin-6-yl)phenyl)ethyl)-3-(2,2,2-trifluoro-1-(3-fluorophenyl)ethyl)urea;
1-ethyl-3-(1-methyl-6-(trifluoromethyl)piperidin-3-yl)-1-((S)-2,2,2-trifluoro-1-(3-(8-methoxyimidazo[1,2-a]pyrazin-6-yl)phenyl)ethyl)urea;
(R)-1,3-diethyl-1-(1-(3-(8-methoxyimidazo[1,2-a]pyridin-6-yl)phenyl)ethyl)urea;
3-((1S)-1-(3,3-difluorocyclohexyl)-2,2,2-trifluoroethyl)-1-ethyl-1-((R)-1-(3-(8-methoxyimidazo[1,2-a]pyrazin-6-yl)phenyl)ethyl)urea;
1-ethyl-3-((S)-1,1,1,5-tetrafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;
1-ethyl-3-((S)-1,1,1,5,5-pentafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;
1-ethyl-3-((S)-1,1,1,5,6,6-hexafluorohex-5-en-2-yl)-1-((S)-2,2,2-trifluoro-1-(5-methoxy-4-(8-methoxy-2-methylimidazo[1,2-a]pyrazin-6-yl)pyridin-2-yl)ethyl)urea;
3-((S)-3-cyclopropyl-1,1,1-trifluoropropan-2-yl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;
3-(4-cyclopropyl-1,1,1-trifluorobutan-2-yl)-1-ethyl-1-((R)-1-(3-(8-methoxyimidazo[1,2-a]pyrazin-6-yl)phenyl)ethyl)urea;
1-ethyl-1-((R)-1-(3-(8-methoxyimidazo[1,2-a]pyrazin-6-yl)phenyl)ethyl)-3-(1,1,1-trifluorohept-6-yn-2-yl)urea;
1-ethyl-3-((S)-1,1,5,5,5-pentafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;
1-ethyl-3-((S)-1,1,5,5-tetrafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;
1-ethyl-1-((S)-2,2,2-trifluoro-1-(5-methoxy-4-(8-methoxy-[1,2,4]triazolo[1,5-a]pyrazin-6-yl)pyridin-2-yl)ethyl)-3-((S)-1,1,5-trifluoropentan-2-yl)urea;
1-ethyl-1-(2,2,2-trifluoro-1-(5-methoxy-4-(8-methoxyimidazo[1,2-a]pyrazin-6-yl)pyridin-2-yl)ethyl)-3-((S)-1,1,1-trifluoropent-4-en-2-yl)urea;
1-ethyl-1-((R)-1-(3-(8-methoxyimidazo[1,2-a]pyrazin-6-yl)phenyl)ethyl)-3-((S)-1,1,1-trifluoro-4-methylpent-3-en-2-yl)urea;
1-ethyl-1-((S)-2,2,2-trifluoro-1-(5-methoxy-4-(8-methoxyimidazo[1,2-a]pyrazin-6-yl)pyridin-2-yl)ethyl)-3-(1,1,1-trifluorobut-3-yn-2-yl)urea;
3-((R)-6,6-difluorohexan-3-yl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;
1-ethyl-1-(2,2,2-trifluoro-1-(5-methoxy-4-(8-methoxyimidazo[1,2-a]pyrazin-6-yl)pyridin-2-yl)ethyl)-3-((R)-1,1,1-trifluoropentan-3-yl)urea;
3-(1-cyclopropyl-3,3,3-trifluoropropyl)-1-ethyl-1-(2,2,2-trifluoro-1-(5-methoxy-4-(8-methoxyimidazo[1,2-a]pyrazin-6-yl)pyridin-2-yl)ethyl)urea;
3-(1-cyclopropyl-4-fluorobutyl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;
1-ethyl-1-((S)-2,2,2-trifluoro-1-(5-methoxy-4-(8-methoxy-2-methylimidazo[1,2-a]pyrazin-6-yl)pyridin-2-yl)ethyl)-3-((E)-6,6,6-trifluorohex-4-en-3-yl)urea;
1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(1-(2-(trifluoromethyl)cyclopropyl)propyl)urea;
3-((S)-1-cyclopropyl-4,4-difluorobutyl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;
1-((R)-1-(3-(8-(difluoromethoxy)imidazo[1,2-a]pyridin-6-yl)phenyl)ethyl)-1-ethyl-3-((R)-6,6,6-trifluorohexan-3-yl)urea;
1-ethyl-1-((R)-1-(3-(7-methoxyimidazo[1,2-a]pyridin-6-yl)phenyl)ethyl)-3-(6,6,6-trifluorohexan-3-yl)urea;
1-((R)-1-(3-(8-(difluoromethyl)imidazo[1,2-a]pyridin-6-yl)phenyl)ethyl)-1-ethyl-3-((R)-6,6,6-trifluorohexan-3-yl)urea;
1-ethyl-1-((R)-1-(3-(8-(methoxymethyl)imidazo[1,2-a]pyridin-6-yl)phenyl)ethyl)-3-((R)-6,6,6-trifluorohexan-3-yl)urea;
1-((R)-1-(3-(7-chloropyrazolo[1,5-a]pyridin-5-yl)phenyl)ethyl)-1-ethyl-3-((R)-6,6,6-trifluorohexan-3-yl)urea;
1-ethyl-1-((R)-1-(3-(7-(methoxymethyl)imidazo[1,2-a]pyridin-6-yl)phenyl)ethyl)-3-(6,6,6-trifluorohexan-3-yl)urea;
1-ethyl-1-((R)-1-(3-(8-(methylthio)imidazo[1,2-a]pyrazin-6-yl)phenyl)ethyl)-3-((R)-6,6,6-trifluorohexan-3-yl)urea;
1-((R)-1-(3-(8-ethoxyimidazo[1,2-a]pyridin-6-yl)phenyl)ethyl)-1-ethyl-3-((R)-6,6,6-trifluorohexan-3-yl)urea;
1-ethyl-1-((R)-1-(4-methoxy-3-(8-methylimidazo[1,2-a]pyridin-6-yl)phenyl)ethyl)-3-((R)-6,6,6-trifluorohexan-3-yl)urea;
1-((R)-1-(3-(8-aminoimidazo[1,2-a]pyridin-6-yl)-4-methoxyphenyl)ethyl)-1-ethyl-3-((R)-6,6,6-trifluorohexan-3-yl)urea;
1-ethyl-1-((R)-1-(4-methoxy-3-(1H-pyrrolo[2,3-b]pyridin-5-yl)phenyl)ethyl)-3-((R)-6,6,6-trifluorohexan-3-yl)urea;
1-ethyl-1-((R)-1-(3-(imidazo[1,2-a]pyrimidin-6-yl)phenyl)ethyl)-3-(6,6,6-trifluorohexan-3-yl)urea;
1-ethyl-1-((R)-1-(3-(7-methylimidazo[1,2-a]pyridin-6-yl)phenyl)ethyl)-3-(6,6,6-trifluorohexan-3-yl)urea;
1-((R)-1-(3-(3-chloro-8-methoxyimidazo[1,2-a]pyridin-6-yl)phenyl)ethyl)-1-ethyl-3-((S)-1,1,1,5,5,5-hexafluoropentan-2-yl)urea;
1-((R)-1-(3-(2-chloro-8-methoxyimidazo[1,2-a]pyridin-6-yl)phenyl)ethyl)-1-ethyl-3-((S)-1,1,1,5,5,5-hexafluoropentan-2-yl)urea;
1-ethyl-3-((S)-1,1,1,5,5,5-hexafluoropentan-2-yl)-1-((R)-1-(3-(8-methoxy-[1,2,4]triazolo[1,5-a]pyridin-6-yl)phenyl)ethyl)urea;
1-((R)-1-(3-(3-aminoimidazo[1,2-a]pyridin-6-yl)phenyl)ethyl)-1-ethyl-3-((S)-1,1,1,5,5,5-hexafluoropentan-2-yl)urea;
1-((R)-1-(3-(3,5-dichloro-8-methoxyimidazo[1,2-a]pyridin-6-yl)phenyl)ethyl)-1-ethyl-3-((S)-1,1,1,5,5,5-hexafluoropentan-2-yl)urea;

1-((R)-1-(3-(7-chloroimidazo[1,2-a]pyridin-6-yl)phenyl)ethyl)-1-ethyl-3-((R)-6,6,6-trifluorohexan-3-yl)urea;

1-ethyl-3-((S)-1,1,1,5,5,5-hexafluoropentan-2-yl)-1-((S)-2,2,2-trifluoro-1-(5-methoxy-4-(8-methoxyimidazo[1,2-a]pyridin-6-yl)pyridin-2-yl)ethyl)urea;

1-ethyl-1-((S)-1-(4-(8-ethylimidazo[1,2-a]pyrazin-6-yl)-5-methoxypyridin-2-yl)-2,2,2-trifluoroethyl)-3-((S)-1,1,1,5,5,5-hexafluoropentan-2-yl)urea;

1-ethyl-3-((S)-1,1,1,5,5,5-hexafluoropentan-2-yl)-1-((S)-2,2,2-trifluoro-1-(5-methoxy-4-(8-methoxy-5-methylimidazo[1,2-a]pyrazin-6-yl)pyridin-2-yl)ethyl)urea;

1-ethyl-3-((S)-1,1,1,5,5,5-hexafluoropentan-2-yl)-1-((R)-1-(5-methoxy-4-(4-methoxybenzo[d]oxazol-6-yl)pyridin-2-yl)ethyl)urea;

1-ethyl-1-((R)-1-(4-(7-ethylpyrazolo[1,5-a]pyridin-5-yl)-5-methoxypyridin-2-yl)ethyl)-3-((S)-1,1,1,5,5,5-hexafluoropentan-2-yl)urea;

1-ethyl-3-((S)-1,1,1,5,5,5-hexafluoropentan-2-yl)-1-((S)-2,2,2-trifluoro-1-(5-methoxy-4-(8-methylimidazo[1,2-a]pyrazin-6-yl)pyridin-2-yl)ethyl)urea;

1-ethyl-3-((S)-1,1,1,5,5,5-hexafluoropentan-2-yl)-1-((S)-2,2,2-trifluoro-1-(5-methoxy-4-(4-methoxy-1-methyl-1H-benzo[d]imidazol-6-yl)pyridin-2-yl)ethyl)urea;

1-ethyl-3-((S)-1,1,1,5,5,5-hexafluoropentan-2-yl)-1-((S)-2,2,2-trifluoro-1-(5-methoxy-4-(7-methoxypyrazolo[1,5-a]pyrimidin-5-yl)pyridin-2-yl)ethyl)urea;

1-ethyl-3-((S)-1,1,1,5,5,5-hexafluoropentan-2-yl)-1-((S)-2,2,2-trifluoro-1-(4-(8-fluoro-[1,2,4]triazolo[1,5-a]pyridin-6-yl)-5-methoxypyridin-2-yl)ethyl)urea;

1-ethyl-3-((S)-1,1,1,5,5,5-hexafluoropentan-2-yl)-1-((S)-2,2,2-trifluoro-1-(5-methoxy-4-(4-methoxyimidazo[2,1-f][1,2,4]triazin-2-yl)pyridin-2-yl)ethyl)urea;

1-ethyl-3-((S)-1,1,1,5,5,5-hexafluoropentan-2-yl)-1-((S)-2,2,2-trifluoro-1-(5-methoxy-4-(8-methoxyimidazo[1,2-a]pyrazin-6-yl)pyridin-2-yl)ethyl)urea;

(R)-1-ethyl-1-(5-(imidazo[1,2-a]pyridin-6-yl)-2,4-dimethoxybenzyl)-3-(6,6,6-trifluorohexan-3-yl)urea;

1-ethyl-3-((S)-1,1,1,5,5,5-hexafluoropentan-2-yl)-1-((R)-1-(6-methoxy-5-(8-methoxyimidazo[1,2-a]pyrazin-6-yl)pyridazin-3-yl)ethyl)urea;

1-ethyl-3-((S)-1,1,1,5,5,5-hexafluoropentan-2-yl)-1-(2,2,2-trifluoro-1-(5-methoxy-4-(8-methoxyimidazo[1,2-a]pyrazin-6-yl)pyrimidin-2-yl)ethyl)urea;

1-ethyl-3-((S)-1,1,1,5,5,5-hexafluoropentan-2-yl)-1-(2,2,2-trifluoro-1-(5-methoxy-6-(8-methoxyimidazo[1,2-a]pyrazin-6-yl)pyrazin-2-yl)ethyl)urea;

1-ethyl-3-((S)-1,1,1,5,5,5-hexafluoropentan-2-yl)-1-(2,2,2-trifluoro-1-(5-methoxy-4-(8-methoxyimidazo[1,2-a]pyrazin-6-yl)-6-methylpyridin-2-yl)ethyl)urea;

1-(1-(4-(2-cyano-8-methoxyimidazo[1,2-a]pyridin-6-yl)-5-methoxypyridin-2-yl)-2,2,2-trifluoroethyl)-1-ethyl-3-((S)-1,1,1,5,5,5-hexafluoropentan-2-yl)urea;

1-ethyl-3-((S)-1,1,1,5,5,5-hexafluoropentan-2-yl)-1-((S)-2,2,2-trifluoro-1-(5-methoxy-4-(4-methoxythiazolo[4,5-c]pyridin-6-yl)pyridin-2-yl)ethyl)urea;

1-ethyl-3-((S)-1,1,1,5,5,5-hexafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;

1-ethyl-3-((S)-1,1,1,5,5,5-hexafluoropentan-2-yl)-1-(2,2,2-trifluoro-1-(5-methoxy-4-(8-methoxyimidazo[1,2-b]pyridazin-6-yl)pyridin-2-yl)ethyl)urea;

1-ethyl-3-((S)-1,1,1,5,5,5-hexafluoropentan-2-yl)-1-(2,2,2-trifluoro-1-(5-methoxy-4-(8-methoxyquinolin-6-yl)pyridin-2-yl)ethyl)urea;

1-(1-(4-(3-cyano-8-methoxyimidazo[1,2-a]pyrazin-6-yl)-5-methoxypyridin-2-yl)-2,2,2-trifluoroethyl)-1-ethyl-3-((S)-1,1,1,5,5,5-hexafluoropentan-2-yl)urea;

1-ethyl-3-((S)-1,1,1,5,5,5-hexafluoropentan-2-yl)-1-(2,2,2-trifluoro-1-(5-methoxy-4-(8-methoxyquinoxalin-6-yl)pyridin-2-yl)ethyl)urea;

1-ethyl-3-((S)-1,1,1,5,5,5-hexafluoropentan-2-yl)-1-((S)-2,2,2-trifluoro-1-(5-methoxy-4-(7-methoxy-1H-benzo[d]imidazol-5-yl)pyridin-2-yl)ethyl)urea;

1-ethyl-3-((S)-1,1,1,5,5,5-hexafluoropentan-2-yl)-1-(2,2,2-trifluoro-1-(6-methoxy-4-(8-methoxyimidazo[1,2-a]pyrazin-6-yl)pyridin-2-yl)ethyl)urea;

1-ethyl-3-((S)-1,1,1,5,5,5-hexafluoropentan-2-yl)-1-(2,2,2-trifluoro-1-(2-methoxy-5-(8-methoxyimidazo[1,2-a]pyrazin-6-yl)pyridin-3-yl)ethyl)urea;

1-ethyl-3-((S)-1,1,1,5,5,5-hexafluoropentan-2-yl)-1-((R)-1-(5-(8-methoxyimidazo[1,2-a]pyrazin-6-yl)-6-methylpyridin-3-yl)ethyl)urea;

1-ethyl-1-((R)-1-(6-methoxy-5-(8-methoxyimidazo[1,2-a]pyrazin-6-yl)pyridin-3-yl)ethyl)-3-((S)-1,1,1,5,5-pentafluorohexan-2-yl)urea;

1-ethyl-3-((S)-1,1,1,5,5,5-hexafluoropentan-2-yl)-1-(2,2,2-trifluoro-1-(5-methoxy-6-(8-methoxyimidazo[1,2-a]pyrazin-6-yl)pyridin-2-yl)ethyl)urea;

1-ethyl-3-((S)-1,1,1,5,5,5-hexafluoropentan-2-yl)-1-((S)-2,2,2-trifluoro-1-(4-(8-methoxyimidazo[1,2-a]pyrazin-6-yl)-5-methylpyridin-2-yl)ethyl)urea;

1-ethyl-3-((S)-1,1,1,5,5,5-hexafluoropentan-2-yl)-1-(2,2,2-trifluoro-1-(5-(8-methoxyimidazo[1,2-a]pyrazin-6-yl)pyridin-3-yl)ethyl)urea;

1-ethyl-1-((R)-1-(7-(imidazo[1,2-a]pyridin-6-yl)-2,3-dihydrobenzofuran-5-yl)ethyl)-3-((R)-6,6,6-trifluorohexan-3-yl)urea;

1-ethyl-1-((R)-1-(2-fluoro-5-(imidazo[1,2-a]pyridin-6-yl)-4-methoxyphenyl)ethyl)-3-((R)-6,6,6-trifluorohexan-3-yl)urea;

1-((R)-1-(4-bromo-3-(imidazo[1,2-a]pyridin-6-yl)phenyl)ethyl)-1-ethyl-3-((R)-6,6,6-trifluorohexan-3-yl)urea;

1-ethyl-3-((S)-1,1,1,5,5,5-hexafluoropentan-2-yl)-1-((R)-1-(6-methoxy-5-(8-methoxyimidazo[1,2-a]pyrazin-6-yl)pyridin-3-yl)ethyl)urea;

1-ethyl-3-((S)-1,1,1,5,5,5-hexafluoropentan-2-yl)-1-((R)-1-(5-methoxy-4-(7-methoxypyrazolo[1,5-a]pyridin-5-yl)pyridin-2-yl)ethyl)urea;

1-((R)-1-(3-(6-amino-5-methoxypyridin-3-yl)phenyl)ethyl)-1-ethyl-3-((S)-1,1,1,5,5,5-hexafluoropentan-2-yl)urea;

1-ethyl-3-((S)-1,1,1,5,5,5-hexafluoropentan-2-yl)-1-((R)-1-(5-methoxy-4-(8-methoxyimidazo[1,2-a]pyrazin-6-yl)pyridin-2-yl)ethyl)urea;

3-((S)-1-cyclopropyl-4,4,4-trifluorobutyl)-1-ethyl-1-((R)-1-(6-methoxy-5-(8-methoxyimidazo[1,2-a]pyrazin-6-yl)pyridin-3-yl)ethyl)urea;

1-ethyl-3-((S)-1,1,1,5,5,5-hexafluoropentan-2-yl)-1-((R)-1-(5-methoxy-4-(8-methoxy-3-methylimidazo[1,2-a]pyrazin-6-yl)pyridin-2-yl)ethyl)urea;

1-ethyl-3-((S)-1,1,1,5,5,5-hexafluoropentan-2-yl)-1-(1-(2-(8-methoxyimidazo[1,2-a]pyrazin-6-yl)pyridin-4-yl)ethyl)urea;

1-ethyl-3-((S)-1,1,1,5,5,5-hexafluoropentan-2-yl)-1-(1-(6-(8-methoxyimidazo[1,2-a]pyrazin-6-yl)pyrimidin-4-yl)ethyl)urea;

1-ethyl-3-((S)-1,1,1,5,5,5-hexafluoropentan-2-yl)-1-((R)-1-(4-(8-methoxyimidazo[1,2-a]pyrazin-6-yl)pyridin-2-yl)ethyl)urea;

1-((R)-1-(4-chloro-3-(8-methoxyimidazo[1,2-a]pyridin-6-yl)phenyl)ethyl)-1-ethyl-3-((R)-6,6,6-trifluorohexan-3-yl)urea;

1-(1-(5-chloro-4-(8-fluoroimidazo[1,2-a]pyridin-6-yl)pyridin-2-yl)ethyl)-1-ethyl-3-((S)-1,1,1,5,5,5-hexafluoropentan-2-yl)urea;
1-ethyl-1-(1-(4-(8-fluoroimidazo[1,2-a]pyridin-6-yl)-5-methoxypyridin-2-yl)ethyl)-3-((S)-1,1,1,5,5,5-hexafluoropentan-2-yl)urea;
3-(cyano(3,3-difluorocyclohexyl)methyl)-1-ethyl-1-((R)-1-(3-(8-methoxyimidazo[1,2-a]pyrazin-6-yl)phenyl)ethyl)urea;
N'-{3-[(dimethylsulfamoyl)amino]-1,1,1-trifluoropropan-2-yl}-N-ethyl-N-{(1R)-1-[3-(8-methoxyimidazo[1,2-a]pyrazin-6-yl)phenyl]ethyl}urea;
(R)-1-ethyl-1-(2-(3-(imidazo[1,2-a]pyridin-6-yl)phenyl)propan-2-yl)-3-(6,6,6-trifluorohexan-3-yl)urea;
1-ethyl-1-((R)-1-(3-(imidazo[1,2-a]pyridin-6-yl)-4-vinylphenyl)ethyl)-3-((R)-6,6,6-trifluorohexan-3-yl)urea;
1-ethyl-1-((R)-1-(3-(8-methoxyimidazo[1,2-a]pyrazin-6-yl)phenyl)ethyl)-3-((S)-1,1,1-trifluoro-4-methylpent-3-en-2-yl)urea;
2-(3-ethyl-3-((R)-1-(3-(8-methoxyimidazo[1,2-a]pyrazin-6-yl)phenyl)ethyl)ureido)-3,3,3-trifluoropropyl acetate;
2-(3-ethyl-3-((R)-1-(3-(8-methoxyimidazo[1,2-a]pyrazin-6-yl)phenyl)ethyl)ureido)-3,3,3-trifluoropropyl acetate;
2-(3-ethyl-3-((R)-1-(3-(8-methoxyimidazo[1,2-a]pyrazin-6-yl)phenyl)ethyl)ureido)-3,3,3-trifluoropropyl dimethylcarbamate;
3-(3-ethyl-3-((R)-1-(3-(8-methoxyimidazo[1,2-a]pyrazin-6-yl)phenyl)ethyl)ureido)-4,4,4-trifluoro-N,N-dimethylbutanamide;
1-ethyl-1-((R)-1-(3-(7-methoxyindolin-5-yl)phenyl)ethyl)-3-((R)-6,6,6-trifluorohexan-3-yl)urea;
1-ethyl-3-((S)-1,1,1,5,5,5-hexafluoropentan-2-yl)-1-((R)-1-(3-(2-hydroxy-8-methoxyimidazo[1,2-a]pyridin-6-yl)phenyl)ethyl)urea;
1-ethyl-3-((S)-1,1,1,5,5,5-hexafluoropentan-2-yl)-1-((R)-1-(3-(8-methoxy-2-(trifluoromethyl)imidazo[1,2-a]pyridin-6-yl)phenyl)ethyl)urea;
(S)-1-(2,2-difluoro-1-(5-methoxy-4-(8-methoxyimidazo[1,2-a]pyrazin-6-yl)pyridin-2-yl)vinyl)-1-ethyl-3-(1,1,1,5,5,5-hexafluoropentan-2-yl)urea;
1-ethyl-3-((S)-1,1,1,5,5,5-hexafluoropentan-2-yl)-1-((R)-1-(5-(8-methoxy-imidazo[1,2-a]pyrazin-6-yl)-1-methyl-6-oxo-1,6-dihydropyridin-3-yl)ethyl)urea; and
1-ethyl-3-((S)-1,1,1,5,5,5-hexafluoropentan-2-yl)-1-((R)-1-(6-hydroxy-5-(7-methoxypyrazolo[1,5-a]pyridin-5-yl)pyridin-3-yl)ethyl)urea;

or a pharmaceutically acceptable salt thereof.

Alternate embodiments of the present invention may also exclude any of the compounds which are recited in the list above.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, isopentyl, neopentyl, sec-pentyl, hexyl, and the like. A group which is designated as being independently substituted with substituents may be independently substituted with multiple numbers of such substituents.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes suitable for inclusion in the compounds of the invention include isotopes of hydrogen such as $^{2}H$ and $^{3}H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}C$ isotope. An embodiment of the present invention includes compounds that are substituted with an $^{18}F$ isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature.

The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the compounds disclosed in the following Examples and pharmaceutically acceptable salts thereof and individual enantiomers or diastereomers thereof.

The present invention is also directed to the use of the compounds disclosed herein as agonists of orexin receptor activity. The subject compounds and pharmaceutically acceptable salts thereof are useful in a method of agonizing orexin receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for agonizing orexin receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to agonize the orexin receptor in the subject. In an embodiment, the amount of compound can be an "effective amount", wherein the subject compound is administered in an amount that will elicit the biological or medical response of a tissue, system, animal or human that is being sought by the researcher, veterinarian, medical doctor or other clinician. An effective amount does not necessarily include considerations of toxicity and safety related to the administration of the compound. It is recognized that one skilled in the art may affect neurological and psychiatric disorders associated with orexin receptor activation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and or "administering a" compound should be understood to mean providing a compound of the invention or a prodrug of a compound of the invention to the subject.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R agonists may be readily determined without undue experimentation by methodology well known in the art. Both the OX1R and/or OX2R G-coupled protein receptors (GPCRs) couple through the Gαq signaling pathway, which ultimately promotes calcium mobilization via inositol triphosphate (IP3) production. The half-life of IP-3 is relatively short, being rapidly metabolized to inositol monophosphate (IP-1), which can be readily detected using a commercially available assay kit (IP-One; Cisbio; cat #621PAPEC) coupled with a cell line expressing the target receptor(s) of interest. The utility of the compounds in accordance with the present invention as orexin receptor OX1R and/or OX2R agonists may be determined utilizing this assay.

In a typical experiment, the OX1 and OX2 receptor agonist activity is determined in accordance with the following general experimental method. Chinese hamster ovary (CHO) cells expressing human OX1R and/or the human OX2R were grown in Iscove's modified DMEM containing glutaMAX™, 1% G418, 100 U/mL penicillin, 100 μg/mL streptomycin and 10% heat-inactivated qualified fetal bovine serum (FBS). The OX2R cells were seeded at 10,000 cells/well/50 μL and the OX1R cells were seeded at 20,000 cells/well/50 μL into 384-well white tissue culture plates (Greiner; cat #781080). All cell/media reagents were from GIBCO-Invitrogen Corp. The seeded cell plate(s) were incubated at 37° C. with 5% $CO_2$ and 85% humidity for 20-24 hours. On the day of the assay, assay-ready compound plates were prepared using an acoustic liquid handler (ECHO; Labcyte), which dispensed sufficient volume of test compound stock (10 mM in DMSO) or 100% DMSO to prepare 10 point, ½-log dilutions in a final volume of 202.5 nL/well in all test wells of a 384-well diamond plate (Labcyte). Following completion of assay-ready plates, importantly, the next three steps were performed with minimal delay: 1) 20 μl of 1× stimulation buffer was added to the compound plate using a Multidrop Combi (small cassette, Thermo Fisher Scientific cat #24073290); 2) culture medium was removed from the cell plate using the Bluewasher plate washer (gentle spin; BlueCatBio); 3) 14 μl of compound/stimulation buffer mixture was added to the cell plate using a Bravo liquid handler (Agilent) prior to incubating cell plates at 37° C. with 5% $CO_2$ and 85% humidity for 1 or 2 hours (OX1R and OX2R, respectively). During this incubation, IP-one detection reagents were prepared (38:1:1 lysis buffer:D2:AB-cryptate reagents). Six μL of mixed detection reagents were added to the cell plate using a Multidrop Combi (small cassette, Thermo Fisher Scientific cat #24073290) and incubated 60 minutes at room temperature in the dark. Fluorescence signal was detected using an Envision plate reader (Perkin Elmer) [LANCE/DELFIA Dual Enh (Em: APC 665; Ex: Cy5 620)].

For each compound, data were fit to a four parameter logistic fit (ActivityBase software) and the $EC_{50}$ was reported as the inflection point of the resulting curve. Percent effect for each test compound was determined as the percentage of sample raw value/mean max effect, where the mean max effect was derived from the mean raw value of 32 control wells per assay plate (using Orexin A (cat #003-30) at 1 μM for human OX1R and a reference compound at 1 uM with 100% activity previously established by comparison to Orexin A for human OX2R). The intrinsic orexin receptor agonist activity of a compound which may be used in the present invention may be determined by these assays.

All of the final compounds of the following examples had activity in agonizing the human orexin-2 receptor in the aforementioned IPOne assay with an $EC_{50}$ of about 0.01 nM to 5000 nM. Additional data is provided in the following Examples. Such a result is indicative of the intrinsic activity of the compounds in use as agonists of orexin-1 receptor and/or the orexin-2 receptor. In general, one of ordinary skill in the art would appreciate that a substance is considered to effectively agonize the orexin receptor if it has an $EC_{50}$ in the IPOne assay of less than about 50 μM, or more specifically less than about 1000 nM.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of disorders associated with orexin receptors, including one or more of the following conditions or diseases: narcolepsy, narcolepsy syndrome accompanied by narcolepsy-like symptoms, cataplexy in narcolepsy, excessive daytime sleepiness (EDS) in narcolepsy, hypersomnia, idiopathic hypersomnia, repeatability hypersomnia, intrinsic hypersomnia, hypersomnia accompanied by daytime hypersomnia, interrupted sleep, sleep apnea, wakefulness, nocturnal myoclonus, disturbances of consciousness, such as coma, REM sleep interruptions, jet-lag, excessive daytime sleepiness, shift workers' sleep disturbances, dyssomnias, sleep disorders, sleep disturbances, hypersomnia associated with depression, emotional/mood disorders, Alzheimer's disease or cognitive impairment, Parkinson's disease, Guillain-Barre syndrome, Kleine Levin syndrome, and sleep disorders which accompany aging; Alzheimer's sundowning; conditions associated with circadian rhythmicity as well as mental and physical disorders associated with travel across time zones and with rotating shift-work schedules; fibromyalgia; cardiac failure; diseases related to bone loss; sepsis; syndromes which are manifested by non-restorative sleep and muscle pain or sleep apnea which is associated with respiratory disturbances during sleep; conditions which result from a diminished quality of sleep; and other diseases related to general orexin system dysfunction.

Thus, in certain embodiments the present invention may provide methods for: treating or controlling narcolepsy, narcolepsy syndrome accompanied by narcolepsy-like symptoms, cataplexy in narcolepsy, excessive daytime sleepiness (EDS) in narcolepsy, hypersomnia, idiopathic hypersomnia, repeatability hypersomnia, intrinsic hypersomnia, hypersomnia accompanied by daytime hypersomnia, interrupted sleep, sleep apnea, disturbances of consciousness, REM sleep interruptions, jet-lag, shift workers' sleep disturbances, dyssomnias, night terror, insomnias associated with depression, emotional/mood disorders, Alzheimer's disease or cognitive impairment; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling insulin resistance syndrome; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling Guillain-Barre syndrome; treating or controlling Klein Levin syndrome; treating or controlling psychosis; treating or controlling dysthymic, mood, psychotic and anxiety disorders; treating side effects or complications due to anesthesia; reversal of anesthesia; reversal of anesthesia following surgery; treating or controlling depression, including major depression and major depression disorder; treating or controlling bipolar disorder; or treating, controlling, ameliorating or reducing the risk of schizophrenia, in a mammalian subject which comprises administering to the subject a compound of the present invention.

The compounds of the present invention may also potentially have utility in treating, preventing, ameliorating, controlling or reducing the risk of a variety of other disorders associated with orexin receptors, including one or more of the following conditions or diseases including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia; night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders overeating, anorexia, bulimia, cachexia, dysregulated appetite control, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, lung disease, abnormal heart rhythms and arrythmias, myocardial infarction, congestive heart failure, coronary heart disease, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; sudden death, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; treating or controlling Guillain-Barre syndrome; treating or controlling Klein Levin syndrome; treating or controlling psychosis; treating or controlling dysthymic, mood, psychotic and anxiety disorders; treating complications due to anesthesia; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seizures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize.

Generally, dosage levels of between 0.0001 to 100 mg/kg. of body weight daily are administered to the subject, e.g., humans, adolescent humans and elderly humans, to obtain effective agonism of orexin receptors. The dosage range will generally be about 0.5 mg to 10.0 g. per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered once or multiple times during the day. The compounds may be administered upon awaking or otherwise in the morning, or during waking hours. For example, the compounds may be administered about 1 hour after awakening, about 30 minutes after awakening or immediately after awakening.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with compounds which are known in the art to be useful for treating or controlling narcolepsy, including e.g., methylphenidate, amphetamine, pemoline, phenelzine, protriptyline, gamma-hydroxybutyric acid, sodium oxybate, or other oxybate salts, modafinil, armodafinil, caffeine, and salts thereof, and combinations thereof, and the like.

The compounds of the present invention may be administered in combination with compounds which are known in the art to be useful for preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, other orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, omortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, including, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-$NH_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activator receptor a agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579; (g) PPARδ agonists, such as those disclosed in WO97/28149; (h) PPAR a/S agonists, such as muraglitazar, and the compounds disclosed in U.S. Pat. No. 6,414, 002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001, 836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,Nle14]Bn(6-14) and [D-Phe6,Phe13]Bn (6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone 0 agonists, such as KB-2611 (KaroBioBMS); (38) FAS (fatty acid synthase) inhibitors, such as Cerulenin and $C_{75}$; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu (28,31)] NPY 24-36, TASP-V, and cyclo-(28/32)—Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®9), 3-methoxynaltrexone, naloxone, naltrexone; (57) 110 HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide., (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors, such as verubecestat; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; $GABA_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (1 Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, orexin receptor antagonists, such as suvorexant, other orexin agonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptable salts thereof.

In another embodiment, the subject compound may be employed in combination with an agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptable salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term “composition” is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein or are otherwise known in the art: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; AcCl: acetyl chloride; AcOH: acetic acid; ACN: acetonitrile; $B_2Pin_2$: bis(pinacolato)diboron; BPin: pinacolato boron; BAST: bis(2-methoxyethyl) aminosulfur trifluoride; Bn: benzyl; BnOH: benzyl alcohol; Boc: tert-butyloxy carbonyl; $Boc_2O$, Boc anhydride: di-tert-butyl decarbonate; BSA: bovine serum albumin; CbzCl: benzylchloroformate; CDI: carbonyl diimidazole; DAST: (diethylamino)sulfur trifluoride; DCM ($CH_2Cl_2$): dichloromethane; DCE: dichloroethane; DDQ: 2,3-dichloro-5,6-dicyano-1,4-benzoquinone; DEAD: diethylazodicarboxylate; DIBAL-H: diisobutylaluminium hydride; DIPEA: N,N-diisopropylethylamine; DMA, DMAc: dimethylacetamide; DMAP: 4-dimethylaminopyridine; DMF: N,N-dimethylformamide; DMP: Dess Martin periodinane; DMSO: dimethylsulfoxide; DPPA: diphenylphosphoryl azide; dppf: 1,1'-Fferrocenediyl-bis(diphenylphosphine); DMSO: dimethylsulfoxide; EDC: N-(3-Dimethylaminopropyl)-N'-ethylcarbodiimide; $Et_3N$: triethylamine; EtOAc: ethyl acetate; EtOH: ethanol; HCl: hydrogen chloride; HOAt: 1-hydroxy-7-aza-benzotriazole; HOBT: hydroxybenzotriazole hydrate; HPLC: high performance liquid chromatography; Hunig's base, DIEA: N,N-diisopropylethylamine; Grubbs II catalyst: (1,3-bis(2,4,6-trimethylphenyl)-2-imidazolidinylidene)dichloro-(phenylmethylene)(tricyclohexylpho sphine)ruthenium; HATU: 1-[bis(dimethylamino)-methylene]-1H-1,2,3-triazolo[4,5-b]pyridinium 3-oxid hexafluorophosphate, N-[(dimethylamino)-1H-1,2,3-triazolo-[4,5-b]pyridin-1-yl-methylene]-N-methylmethanaminium hexafluorophosphate N-oxide; Hoveyda Grubbs II catalyst: (1,3-bis-(2,4,6-trimethylphenyl)-2-imidazolidinylidene)dichloro(o-isopropoxyphenylmethylene)ruthenium, Dichloro[1,3-bis(2,4,6-trimethylphenyl)-2-imidazolidinylidene](2-isopropoxyphenylmethylene)ruthenium(II); IBX: 2-iodoxybenzoic acid; IPA, iPrOH: isopropyl alcohol; LC-MS: liquid chromatography mass spectroscopy; LDA: lithium diisoproylamide; LiHMDS: lithium hexamethyldisilazide; mCPBA: meta-chloro perbenzoic acid; MeOH: methanol; $MgSO_4$: magnesium sulfate; Ms: methanesulfonyl; MTBE: methyl tert-butyl ether; $NaHCO_3$: sodium bicarbonate; NaOH: sodium hydroxide; $nBu_3SnCl$: tributyltin chloride; n-BuLi: n-butyl lithium; NMM: N-methylmorpholine; NMR: nuclear magnetic resonance; Oxone: potassium peroxymonosulfate; $PCy_3$ Pd G2: chloro[(tricyclohexylphosphine)-2-(2'-aminobiphenyl)]-palladium(II); $Pd(dppf)Cl_2$: [1,1'-bis(diphenylphosphino)ferrocene]-dichloropalladium(II); $Pd(PPh_3)_2Cl_2$: bis(triphenylphosphine)-palladium(II) dichloride; $Pd(PPh_3)_4$: tetrakis(triphenyl-phosphine)palladium(0); $Pd_2dba_3$: tris (dibenzylideneacetone)dipalladium(0); PPTS: pyridinium p-toluenesulfonate; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; TBAF: tetrabutyl ammonium fluoride; TBDPSCl: tert-butyl(chloro)diphenyl-silane; TBSCl: tert-butyldimethylsilyl chloride; t-Bu: tert-butyl; TEA, $Et_3N$: triethylamine; TEMPO: 2,2,6,6-tetramethyl-1-piperidinyloxy; THF: tetrahydrofuran; TFA: trifluoracetic acid; TLC: thin layer chromatography; TMSCl: trimethylsilyl chloride; TsCl: p-toluenesulfonyl chloride; XPhos Pd G2: chloro(2-dicyclohexylphosphino-2',4',6'-triisopropyl-1,1'-biphenyl)[2-(2'-amino-1,1'-biphenyl)]-palladium(II); XPhos Pd G3: (2-dicyclohexylphosphino-2',4',6'-triisopropyl-1,1'-biphenyl)[2-(2'-amino-1,1'-biphenyl)]palladium(II) methanesulfonate; X-Phos: 2-(dicyclohexyl-phosphino)-2',4',6'-triisopropylbiphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediate A1: 6-bromo-8-methoxyimidazo[1,2-a]pyrazine

Intermediate A1

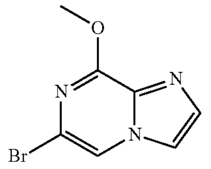

Into a 5-L 3-necked round-bottom flask purged and maintained with an inert atmosphere of nitrogen, was placed methanol (2.56 L), 6,8-dibromoimidazo[1,2-a]pyrazine (A1-1) (128 g, 462.23 mmol, 1 eq), a solution of sodium methanolate (32.5 g, 600.90 mmol, 1.30 eq) in MeOH (75.8 g). The resulting solution was stirred for 1 h at 70° C. in an oil bath. The reaction progress was monitored by LCMS. The resulting mixture was concentrated under vacuum. The resulting solution was diluted with 1.28 L of water. The solids were collected by filtration and washed by water (1.28 L×2). The solid was dried in an oven under reduced pressure. This resulted in the title compound. MS: 228/230 [M+1]. H-NMR (300 MHz, $CDCl_3$-$d_6$, ppm): δ 7.89 (s, 1H), 7.65 (d, J=1.1 Hz, 1H), 7.58 (d, J=1.1 Hz, 1H), 4.17 (s, 3H).

Intermediate A2: 6-bromo-8-methoxyimidazo[1,2-a]pyridine

Intermediate A2

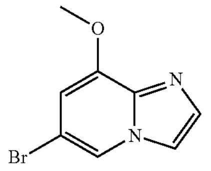

Step 1: 3-methoxypyridin-2-amine (A2-2)

A2-2

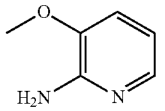

Into a 2-L round-bottom flask, was placed a solution of 3-methoxy-2-nitropyridine (A2-1) (135 g, 875.91 mmol, 1 eq) in MeOH (1.35 L), Pd/C (13.5 g, 10% wt). The flask was evacuated and flushed three times with nitrogen, followed by fulfilled with hydrogen balloon. The resulting solution was stirred 18 h at 40° C. The solids were filtered out. The filtrate was concentrated. This resulted in the title compound.

Step 2: 5-bromo-3-methoxypyridin-2-amine (A2-3)

A2-3

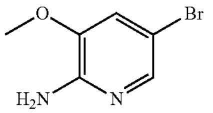

Into a 2-L 3-necked round-bottom flask purged and maintained with an inert atmosphere of nitrogen, was placed a solution of 3-methoxypyridin-2-amine (A2-2) (87 g, 700.80 mmol, 1 eq) in acetic acid (870 mL). This was followed by the addition of dibromide (134.4 g, 840.97 mmol, 1.2 eq) dropwise with stirring in 20 min at 30° C. The resulting solution was stirred for 3 h at ambient temperature. The resulting mixture was concentrated. The pH value of the residue was adjusted to 7 with saturated $NaHCO_3$. The resulting solution was extracted with of ethyl acetate (2×1 L). The organic phase was washed with of brine (2×1 L). The mixture was dried over anhydrous sodium sulfate, filtered, concentrated. This resulted in the title compound.

Step 3: 6-bromo-8-methoxyimidazo[1,2-a]pyridine (Intermediate A2)

Intermediate A2

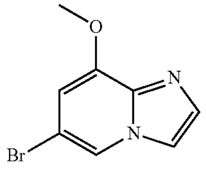

Into a 5-L 3-necked round-bottom flask purged and maintained with an inert atmosphere of nitrogen, was placed a solution of 5-bromo-3-methoxypyridin-2-amine (A2-3) (113 g, 556.54 mmol, 1 eq) in EtOH (2.3 L), a solution of 2-chloroacetaldehyde (52.4 g, 667.85 mmol, 1.2 eq) in water (78.6 g). The resulting solution was stirred for 5 h at 80° C. The resulting mixture was concentrated. The resulting mixture was slurry with 3 L of acetone. The solids were collected by filtration. The salt was freed saturated $NaHCO_3$ to afford the title compound. MS: 227 [M+1].

H-NMR (400 MHz, $CDCl_3$, ppm): δ 7.94 (d, J=1.6 Hz, 1H), 7.55 (dd, J=14.4, 1.2 Hz, 2H), 6.55 (d, J=1.5 Hz, 1H), 4.03 (s, 3H).

Intermediate A3: 5-bromo-7-methoxypyrazolo[1,5-a]pyridine

Intermediate A3

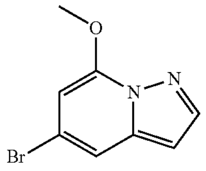

Step 1: amino diphenylphosphinate (A3-2)

A3-2

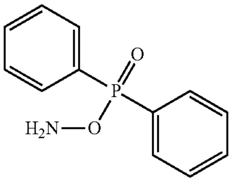

Into a 200-L pressure tank reactor, was placed $NH_2OH{\cdot}HCl$ (3670.9 g, 52825.09 mmol, 2.5 eq, 100%), $H_2O$ (50 L), dioxane (50 L). This was followed by the addition of $NaHCO_3$ (4437.7 g, 52825.09 mmol, 2.5 eq, 100%) in several batches at 0° C. The resulting solution was stirred for 30 min at 0° C. To this was added diphenylphosphinoyl chloride (A3-1)(5000 g, 21130.03 mmol, 1 eq, 100%) dropwise with stirring at 0° C. The resulting solution was allowed to react, with stirring, for an additional 2 h at 20° C. The solids were collected by filtration. The resulting solid was washed with of $H_2O$ (2×1 L), of 0.25 mol/L NaOH (aq) (2×1 L), petroleum (2×1 L). This resulted in the title compound.

Step 2: 1-amino-4-((tert-butoxycarbonyl)amino) pyridin-1-ium (A3-3)

A3-3

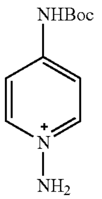

Into a 50-L pressure tank reactor, was placed tert-butyl 2-(pyridin-4-yl)acetate (1020 g, 5278.25 mmol, 1 eq, 100%), $CH_2Cl_2$ (24 L). This was followed by the addition of amino diphenylphosphinate (2461.8 g, 10556.29 mmol, 2.00 eq, 100%) (A3-2) dropwise with stirring at 25° C. The resulting solution was stirred 18 h at 25° C. The reaction was then quenched by the addition of 10 L of HI. The solids were collected by filtration and washed with 3×5 L $CH_2Cl_2$ (3×5 L), hexane (3×5 L), resulting in the title compound.

Step 3: ethyl 5-((tert-butoxycarbonyl)amino)pyrazolo[1,5-a]pyridine-3-carboxylate (A3-4)

A3-4

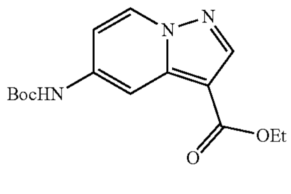

Into a 50-L pressure tank reactor, was placed 1-amino-4-((tert-butoxycarbonyl)amino)pyridin-1-ium (1700 g, 5174.62 mmol, 1 eq, 64%) (A3-3), DMF (25 L). This was followed by the addition of $K_2CO_3$ (1430.3 g, 10349.24 mmol, 2 eq, 100%) in several batches at 25° C. To this was added ethyl prop-2-ynoate (609.2 g, 6209.54 mmol, 1.2 eq, 100%) dropwise with stirring at 25° C. The resulting solution was stirred 18 h at 25° C. The residue was dissolved in 25 L of $H_2O$. The resulting solution was extracted with of ethyl acetate (3×2 L). The organic phase was washed with of $NaCl/H_2O$ (2×5 L). The mixture was dried over anhydrous sodium sulfate. The residue was applied onto a silica gel column (1% to 10% ethyl acetate/petroleum ether), and concentrated to give the title compound.

Step 4: ethyl 5-aminopyrazolo[1,5-a]pyridine-3-carboxylate (A3-5)

A3-5

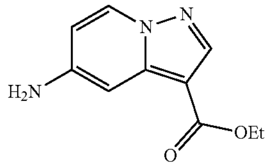

Into a 20-L 4-necked round-bottom flask, was placed ethyl 5-((tert-butoxycarbonyl)amino)pyrazolo[1,5-a]pyridine-3-carboxylate (A3-4), DCM (6.5 L). This was followed by the addition of TFA (717.0 g, 6288.19 mmol, 3.00 eq) in portions at 0° C. The resulting solution was stirred for 3 h at 0° C. The resulting mixture was concentrated under vacuum. This resulted in the title compound.

Step 5: ethyl 5-bromopyrazolo[1,5-a]pyridine-3-carboxylate (A3-6)

A3-6

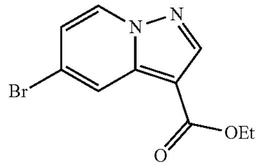

Into a 10-L 4-necked round-bottom flask purged and maintained with an inert atmosphere of nitrogen, was placed ethyl 5-bromopyrazolo[1,5-a]pyridine-3-carboxyl (A3-5) (535 g, 2607.00 mmol, 1 eq, 100%) in HBr (1.6 L). This was followed by the addition of $NaNO_2$ (197.9 g, 2867.70 mmol, 1.1 eq) in $H_2O$ (2 L) dropwise with stirring at 0° C. The resulting solution was stirred for 1 h at 0° C. To the mixture was added CuBr (561.0 g, 3910.49 mmol, 1.5 eq) in HBr (1.6 L) dropwise with stirring at 0° C. The resulting solution was allowed to react with stirring for an additional 2 h at 25° C. The resulting solution was extracted with of dichloromethane (3×1 L) and the organic layers combined. The resulting mixture was washed with of $NaCl/H_2O$ (3×5 L). The mixture was dried over anhydrous sodium sulfate. The residue was applied onto a silica gel column with (0-20% ethyl acetate/petroleum ether). This resulted in the title compound.

Step 6: 5-bromopyrazolo[1,5-a]pyridine (A3-7)

A3-7

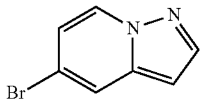

Into a 3-L 4-necked round-bottom flask, was placed ethyl 5-bromopyrazolo[1,5-a]pyridine-3-carboxylate (A3-6) (365 g, 1356.38 mmol, 1 eq, 100%), $H_2O$ (1.2 L, 100%), $H_2SO_4$ (600 mL, 11256346.9 mmol, 8298.80 eq, 100%). The resulting solution was stirred for 1 18 h at 110° C. The pH value of the solution was adjusted to 7 with NaOH (6 mol/L). The solids were collected by filtration. The residue was dissolved in 5 L of $H_2O$. The resulting solution was extracted with of dichloromethane (1 L×3) and the organic layers combined and concentrated under vacuum. The residue was applied onto a silica gel column (0-10% ethyl acetate/petroleum ether). This resulted in the title compound.

Step 7: 5-bromo-7-chloropyrazolo[1,5-a]pyridine (A3-8)

A3-8

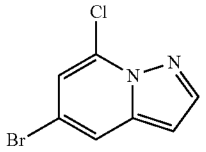

Into a 3-mL round-bottom flask purged and maintained with an inert atmosphere of nitrogen, was placed 5-bromopyrazolo[1,5-a]pyridine (A3-7) (160 g, 812.04 mmol, 1 eq, 100%), THF (1.6 L). The resulting solution was stirred for 2 h at −78° C. This was followed by the addition of LiHMDS (163.1 g, 974.45 mmol, 1.2 eq) dropwise with stirring at −78° C. To this was added $C_2Cl_6$ (228.0 g, 974.45 mmol, 1.2 eq) in THF (200 mL) dropwise with stirring at −78° C.

The resulting solution was allowed to react, with stirring, for an additional night at 25° C. The reaction was then quenched by the addition of 2 L of water/ice. The resulting solution was extracted with ethyl acetate (3×1 L) and the organic layers combined and dried over anhydrous sodium sulfate. The residue was applied onto a silica gel column (0-50% ethyl acetate/petroleum ether). This resulted in the title compound.

Step 8: 5-bromo-7-methoxypyrazolo[1,5-a]pyridine (Intermediate A3)

Intermediate A3

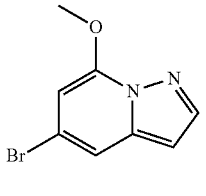

Into a 5-L 4-necked round-bottom flask, was placed 5-bromo-7-chloropyrazolo[1,5-a]pyridine (A3-8) (160 g, 691.20 mmol, 1 eq, 100%), $CH_{30}H$ (2 L). This was followed by the addition of $CH_3ONa$ (112.0 g, 2073.61 mmol, 3 eq) in $CH_3OH$ (500 mL) dropwise with stirring at 25° C. The resulting solution was stirred for 1 18 h at 50° C. The resulting mixture was concentrated under vacuum. The residue was applied onto a silica gel column (0-10% ethyl acetate/petroleum ether). This resulted in 135 of the title compound. MS: 229 [M+2]. H-NMR (300 MHz, $CDCl_3$, ppm): δ 7.97 (d, 1H), 7.38 (d, 1H), 6.47 (d, 1H), 6.20 (d, 1H), 4.15 (s, 3H).

Intermediate A4: (R)-1-(3-bromophenyl)-N-ethyl-ethan-1-amine

Intermediate A4

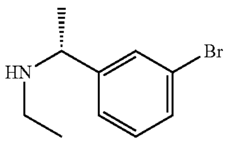

Step 1: (S,E)-N-(3-bromobenzylidene)-2-methylpropane-2-sulfinamide (A4-2)

A4-2

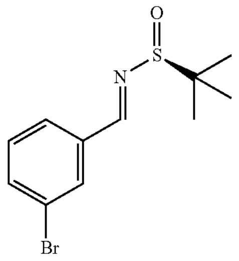

Into a 10-L 4-necked round-bottom flask purged and maintained with an inert atmosphere of nitrogen, was placed 3-bromobenzaldehyde (A4-1) (370 g, 1999.78 mmol, 1 eq), toluene (3700 mL), tetrakis(propan-2-yloxy)thallane (976.8 mL, 2.22 mmol), (S)-2-methylpropane-2-sulfinamide (290848.6 mg, 2399.74 mmol, 1.2 eq). The resulting solution was stirred for 6 h at 70° C. The reaction was then quenched by the addition of $NaHCO_3$. The solids were filtered out. The filtrate was extracted with ethyl acetate. The organic phase was washed with NaCl, dried over anhydrous magnesium sulfate and concentrated. This resulted in of the title compound.

Step 2: (S)—N—((R)-1-(3-bromophenyl)ethyl)-2-methylpropane-2-sulfinamide (A4-3)

A4-3

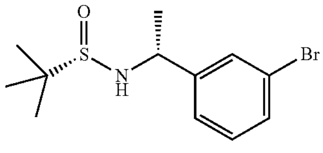

Into a 10-L 4-necked round-bottom flask purged and maintained with an inert atmosphere of nitrogen, was placed (S,E)-N-(3-bromobenzylidene)-2-methylpropane-2-sulfinamide (A4-2) (520 g, 1804.30 mmol, 1 eq), THF (5200 mL, 72.12 mmol, 0.04 eq). This was followed by the addition of $CH_3MgBr$ (1000 mL, 8679.68 mmol, 4.81 eq) dropwise with stirring at 0° C. The resulting solution was stirred for 4 h at 0° C. The reaction was then quenched by the addition of $NH_4Cl$. The solids were filtered out. The filtrate was extracted with ethyl acetate. The organic phase was washed with of NaCl, dried over anhydrous magnesium sulfate and concentrated. The residue was applied onto a silica gel column (0-50%, ethyl acetate/hexane). This resulted in the title compound.

Step 3: (R)-1-(3-bromophenyl)ethan-1-amine (A4-4)

A4-4

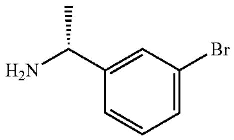

Into a 5000-mL 4-necked round-bottom flask purged and maintained with an inert atmosphere of nitrogen, was placed (S)—N—((R)-1-(3-bromophenyl)ethyl)-2-methylpropane-2-sulfinamide (A4-3) (412 g, 1 eq), MeOH (4120 mL), HCl-dioxane (4 M) (412 mL). The resulting solution was stirred for 2 h at ambient temperature. The resulting mixture was concentrated to afford the title compound.

Step 4: (R)-1-(3-bromophenyl)-N-ethylethan-1-amine (Intermediate A4)

Intermediate A4

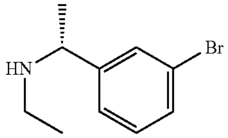

Into a 3000-mL 4-necked round-bottom flask purged and maintained with an inert atmosphere of nitrogen, was placed (R)-1-(3-bromophenyl)ethan-1-amine (A4-4) (230 g, 1149.55 mmol, 1 eq), trichloromethane (2300 mL), DIEA (297.1 g, 2299.09 mmol, 2.0 eq), acetaldehyde (50.6 g, 1149.55 mmol, 1.0 eq). The reaction mixture was stirred in 4 h. This was followed by the addition of sodium triacetoxyborohydride (609.1 g, 2873.86 mmol, 2.5 eq). The resulting solution was stirred for 6 h at ambient temperature. The reaction was then quenched by the addition of water. The resulting solution was diluted with of DCM, washed with 2M NaOH. The resulting solution was extracted with ethyl acetate, the organic phase was dried over anhydrous magnesium sulfate and concentrated. The residue was applied onto a silica gel column with (0-50%, ethyl acetate/petroleum ether). This resulted in the title compound.

Intermediate A5: (R)—N-ethyl-1-(3-(8-methoxyimidazo[1,2-a]pyrazin-6-yl)phenylethan-1-amine

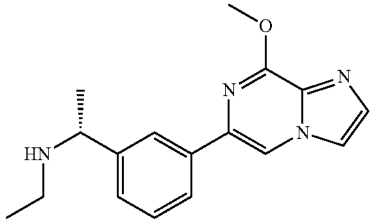 [SMILES: CCN[C@H](C)c1cccc(-c2cn3ccnc3c(OC)n2)c1]

Step 1: (R)—N-ethyl-1-(3-(4,4,5,5-tetramethyl-1,3,2-dioxaborolan-2-yl)phenyl)ethan-1-amine (A5-1

A5-1

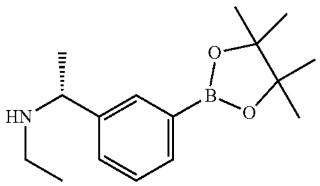

Into a 2000-mL 3-necked round-bottom flask purged and maintained with an inert atmosphere of nitrogen, was placed (R)-1-(3-bromophenyl)-N-ethylethan-1-amine (Intermediate A4) (130 g, 569.84 mmol, 1 eq), MeOH (1300 mL), DIEA (294.6 g, 2279.42 mmol, 4.00 eq), cataCXium A-Pd-G2 (38 g, 56.95 mmol, 0.10 eq), 4,4,5,5-tetramethyl-2-(4,4,5,5-tetramethyl-1,3,2-dioxaborolan-2-yl)-1,3,2-dioxaborolane (289.4 g, 1139.64 mmol, 2.00 eq). The resulting solution was stirred 18 h at 70° C. The reaction was then quenched by the addition of water. The resulting solution was extracted with ethyl acetate and the organic phase was dried over anhydrous magnesium sulfate and concentrated. This resulted in the title compound.

Step 2: (R)—N-ethyl-1-(3-(8-methoxyimidazo[1,2-a]pyrazin-6-yl)phenyl)ethan-1-amine (Intermediate A5)

Intermediate A5

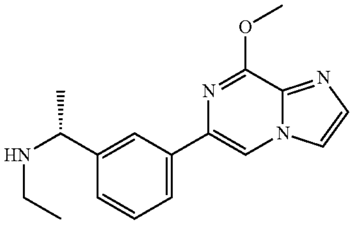

Into a 10-mL 2-necked round-bottom flask purged and maintained with an inert atmosphere of nitrogen, was placed (R)—N-ethyl-1-(3-(4,4,5,5-tetramethyl-1,3,2-dioxaborolan-2-yl)phenyl)ethan-1-amine (A5-1) (0.5 g, 1.82 mmol, 1 eq). This was followed by the addition of dioxane (5 mL), $K_3PO_4$ (1.9 g, 9.08 mmol, 5 eq), 6-bromo-8-methoxyimidazo[1,2- a]pyrazine (Intermediate A1) (0.5 g, 2.18 mmol, 1.2 eq), XPhos palladium(II) biphenyl-2-amine chloride (0.1 g, 0.18 mmol, 0.10 eq). The resulting solution was stirred 18 h at 75° C. The reaction was then quenched by the addition of water. The resulting solution was extracted with ethyl acetate, the organic phase was dried over anhydrous calcium chloride and concentrated. The residue was applied onto a silica gel column with (0-20%, MeOH/DCM). This resulted in the title compound.

Intermediate 6: (R)—N-ethyl-1-(3-(8-methoxyimidazo[1,2-a]pyridin-6-yl)phenyl)ethan-1-amine Intermediate A6

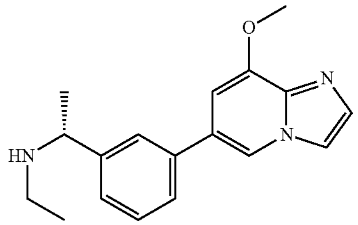

A5-1 was reacted with Intermediate A2 according to the procedure in step 2 of the synthesis of Intermediate A5. MS: 296.2 [M+1]. H-NMR: (300 MHz, DMSO-d6, ppm): δ 8.52 (d, J=1.4 Hz, 1H), 7.96 (d, J=1.1 Hz, 1H), 7.68 (s, 1H), 7.58 (d, J=7.8 Hz, 1H), 7.52 (d, J=1.2 Hz, 1H), 7.50-7.33 (m, 2H), 6.92 (s, 1H), 4.04 (s, 3H), 3.81 (d, J=6.5 Hz, 1H), 2.47-2.35 (m, 2H), 1.32 (d, J=6.6 Hz, 3H), 1.01 (t, J=7.1 Hz, 3H).

Intermediate 7: (R)—N-ethyl-1-(3-(7-methoxypyrazolo[1,5-a]pyridin-5-yl)phenyl)ethan-1-amine Intermediate A7

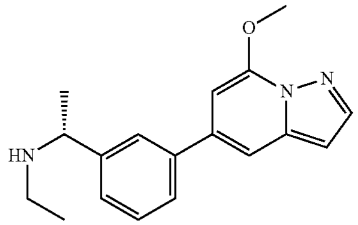

A5-1 was reacted with Intermediate A3 according to the procedure in step 2 of the synthesis of Intermediate A5. MS: 296.1 [M+1]. H-NMR (300 MHz, DMSO-d6, ppm): δ 8.02 (d, J=2.2 Hz, 1H), 7.78 (t, J=1.8 Hz, 1H), 7.73-7.58 (m, 2H), 7.51-7.35 (m, 2H), 6.65 (dd, J=6.0, 1.9 Hz, 2H), 3.82 (q, J=6.6 Hz, 1H), 3.32 (s, H), 2.51-2.32 (m, 1H), 1.32 (d, J=6.6 Hz, 3H), 1.01 (t, J=7.1 Hz, 3H).

Intermediate A8: imidazo[1,2-a]pyridin-6-ylboronic acid

Intermediate A8

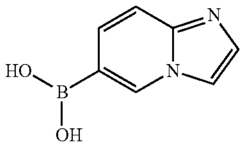

A 2 L three-necked round bottom flask was charged with 6-bromoimidazo[1,2-a]pyridine (60.0 g, 304 mmol, 1.0 eq) (A8-1) and this was dissolved in THF (600 mL) and cooled to −70° C. While under $N_2$, the triisopropyl borate (160 g, 853 mmol, 2.8 eq) was added at −70° C. and a white suspension formed. To this, n-BuLi (2.5 M, 384 mL, 3.15 eq) was added at −70° C. and the reaction contents were stirred for 30 min and a light yellow solution formed. This was warmed to −20° C. and stirred, under $N_2$, for 30 min. The reaction contents were poured into a flask containing saturated $NH_4Cl$ (3.0 L) and the solid was filtered and washed with water (500 mL) and acetonitrile (1.0 L) to afford the title compound, crude. H-NMR (400 MHz, DMSO-d6, ppm): δ 8.79 (s, 1H), 8.26 (s, 2H), 7.95 (s, 1H), 7.52-7.57 (m, 1H), 7.47-7.52 (m, 2H).

Intermediate A9: (R)—N-ethyl-1-(3-(imidazo[1,2-a]pyridin-6-yl)phenyl)ethan-1-amine Intermediate A9

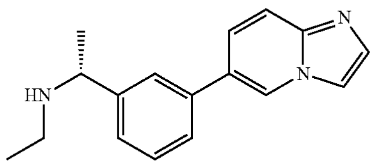

A 2 L three-necked round bottom flask was charged with (R)-1-(3-bromophenyl)-N-ethylethan-1-amine (Intermediate A4) (50.0 g, 189 mmol, 1.0 eq) and this was dissolved in dioxane (500 mL) and water (166 mL). To this, $K_2CO_3$ (121 g, 877 mmol, 4.0 eq) and imidazo[1,2-a]pyridin-6-ylboronic acid (Intermediate A8) (71.0 g, 438 mmol, 2.0 eq) were added in one portion. The reaction contents were de-gassed under vacuum and purged with nitrogen three times. $Pd(PPh_3)_4$ (25.3 g, 21.9 mmol, 0.1 eq) was added in one portion and the reaction contents were heated to 100° C. for 3 hrs. The contents were poured into water (1 L) and extracted with DCM (1.5 L×2), dried over $Na_2SO_4$ and filtered and concentrated under vacuum to afford an oil. This was purified via silica gel chromatography (0-10% MeOH/DCM with 0.2% $NH_3$—$H_2O$) to give the title compound. H-NMR (400 MHz, $CDCl_3$, ppm): δ 8.36 (s, 1H), 7.60-7.73 (m, 3H), 7.50-7.60 (m, 1H), 7.38-7.50 (m, 3H), 7.31-7.38 (m, 1H), 3.89 (q, J=6.6 Hz, 1H), 2.47-2.67 (m, 2H), 1.69-2.24 (m, 1H), 1.43 (d, J=6.6 Hz, 3H), 1.12 (t, J=7.2 Hz, 3H).

Intermediate A10: N-(4-methoxy-3-(8-methoxyimidazo[1,2-a]pyridin-6-yl)benzyl)ethylamine Intermediate A10

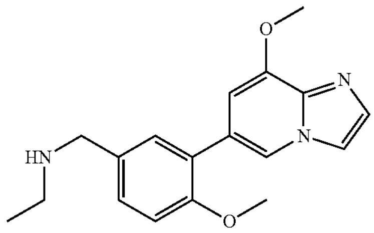

Step 1: 4-methoxy-3-(8-methoxyimidazo[1,2-a]pyridin-6-yl)benzaldehyde (A10-2)

A10-2

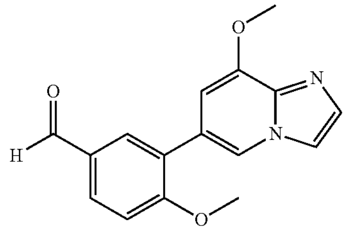

(5-formyl-2-methoxyphenyl)boronic acid (A10-1) was reacted with Intermediate A2 according to the procedure in step 2 of the synthesis of Intermediate A5. MS: 283.1 [M+1].

Step 2: N-(4-methoxy-3-(8-methoxyimidazo[1,2-a]pyridin-6-yl)benzyl)ethylamine (Intermediate A10)

Intermediate A10

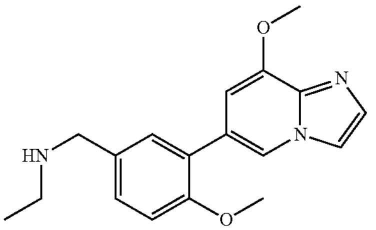

The 4-methoxy-3-(8-methoxyimidazo[1,2-a]pyridin-6-yl)benzaldehyde (A10-2) (0.3 g, 1.063 mmol) was dissolved in $CHCl_3$ (5.31 ml) and treated with ethylamine (2.0 M in THF) (1.063 ml, 2.125 mmol) and acetic acid (0.122 ml, 2.125 mmol) and stirred at ambient temperature for 18 h, then treated with sodium triacetoxyborohydride (0.563 g, 2.66 mmol) and stirred 1 h. This was diluted with $CH_2Cl_2$, washed with 2 M NaOH, dried by filtering through a hydrophobic frit and concentrated to give the title compound which was used crude. MS: 312.2 [M+1].

Intermediate A11: 2,2,2-trifluoro-1-(1-methylazetidin-3-yl)ethan-1-amine

Intermediate A11

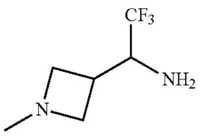

Step 1: tert-butyl (E)-3-(((tert-butylsulfinyl)imino)methyl)azetidine-1-carboxylate (A11-2) A11-2

A11-2

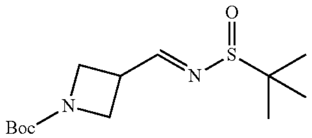

To a solution of tert-butyl 3-formylazetidine-1-carboxylate (A11-1) (900 mg, 4.86 mmol) and 2-methylpropane-2-sulfinamide (707 mg, 5.83 mmol) in anhydrous DCE (20 mL) were added magnesium sulfate (2924 mg, 24.30 mmol) and PPTS (61.1 mg, 0.243 mmol). TLC (petroleum ether: EtOAc=2:1) showed the starting material was consumed. TLC (petroleum ether:EtOAc=1:1) showed the product was formed. The resulting mixture was stirred at 50° C. under $N_2$ protection for 2 h. The crude product was purified by flash silica gel chromatography (0-30%, EtOAc/petroleum ether) to give the title compound.

Step 2: tert-butyl 3-(1-((tert-butylsulfonylamino)-2,2,2-trifluoroethyl)azetidine-1-carboxylate (A11-3)

A11-3

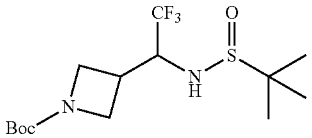

To a solution of tert-butyl (E)-3-(((tert-butylsulfinyl)imino)methyl)azetidine-1-carboxylate (A11-2) (1.4 g, 4.85 mmol) and tetrabutylammonium difluorotriphenylsilicate (6.55 g, 12.14 mmol) in anhydrous THF (80 mL) was added trimethyl(trifluoromethyl)silane (1.519 g, 10.68 mmol) slowly at −40° C. The resulting mixture was slowly warmed to 0° C. within 2 h. The reaction mixture was poured into water (100 mL), extracted with EtOAc (40 mL×3). The organic layer was washed with brine (30 mL), dried over $Na_2SO_4$, then filtered and concentrated. The crude product was purified by flash silica gel chromatography (0-50% EtOAc/petroleum ether) to give the title compound.

Step 3: 2-methyl-N-(2,2,2-trifluoro-1-(1-methylazetidin-3-yl)ethyl)propane-2-sulfinamide (A11-4)

A11-4

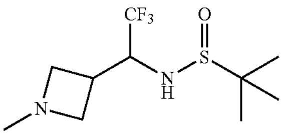

To a solution of tert-butyl 3-(1-((tert-butylsulfinyl)amino)-2,2,2-trifluoroethyl)azetidine-1-carboxylate (A11-3) (400 mg, 1.116 mmol) in anhydrous THF (10 mL) was added LAH (127 mg, 3.35 mmol) at 0° C. The resulting mixture was stirred at 70° C. for 1 h. TLC (petroleum ether:EtOAc=1:1) showed the starting material was consumed. The reaction mixture was diluted with THF (40 mL) and then $Na_2SO_4$ (25 g) was added. water was added into the stirred mixture drop-wise until no gas released and the mixture was continue stirring for 10 min. It is filtered and concentrated to give the title compound. It is used in the next step directly without further purification. MS: 273.2 [M+1].

Step 4: 2,2,2-trifluoro-1-(1-methylazetidin-3-yl) ethan-1-amine (Intermediate A11)

Intermediate A11

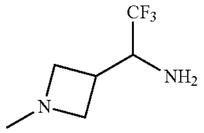

To a solution of 2-methyl-N-(2,2,2-trifluoro-1-(1-methylazetidin-3-yl)ethyl)propane-2-sulfinamide (A11-4) (250 mg, 0.918 mmol) in anhydrous MeOH (1 mL) was added MeOH/HCl (4M) (1 mL). The resulting mixture was stirred at 30° C. for 2 h. LCMS showed the starting material was consumed. The reaction mixture was concentrated to give crude title compound. It is used in the next step directly without further purification. MS: 169.0 [M+1].

Intermediate A12: 1-(3,3-difluorocyclohexyl)ethan-1-amine

Intermediate A12

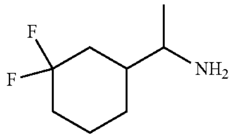

Step 1: 3-(1-nitroethyl)cyclohexan-1-one (A12-2)

A12-2

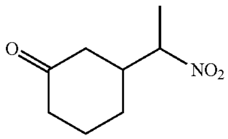

To a solution of cyclohex-2-en-1-one (A12-1) (60 g, 624 mmol) in DCM (600 mL) was added pyrrolidine (44.4 g, 624 mmol). Then nitroethane (46.9 g, 624 mmol) was added in the reaction mixture. The reaction mixture was stirred at 28° C. for 16 h. TLC showed the starting material was consumed and the new spots were formed. The reaction mixture was poured into $H_2O$ (700 mL) and separated the organic layer. Then the organic layer was washed successively with water (700 mL×2), aq. sat. $NaHCO_3$ (700 mL), brine (700 mL) and dried over $Na_2SO_4$. The organic phase was filtered and concentrated. The residue was purified by chromatography on silica gel (10-20%, ethyl acetate/petroleum ether) to give the title compound. H-NMR (400 MHz, $CDCl_3$, ppm): δ 4.55-4.46 (m, 1H), 2.50-2.40 (m, 2H), 2.37-2.23 (m, 2H), 2.18-2.09 (m, 2H), 1.97-1.91 (m, 1H),), 1.74-1.62 (m, 2H), 1.55 (dd, J=10.00, 3.60 Hz, 3H), 1.52-1.42 (m, 1H).

Step 2: 1,1-difluoro-3-(1-nitroethyl)cyclohexane (A12-3)

A12-3

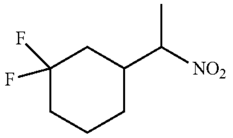

To a solution of 3-(1-nitroethyl)cyclohexan-1-one (A12-2) (71 g, 414.73 mmol) in DCM (700 mL) was added DAST (200 g, 1.24 mol) dropwise at −5° C. Then the reaction was warmed slowly to 30° C. for 16 h. The reaction was determined by TLC (petroleum ether:EtOAc=20:1), TLC showed the starting material was consumed. The resulting mixture was poured into ice-water (1000 mL) and extracted with DCM (2×400 mL). The combined organic layers were washed successively with water (700 mL), aq. sat. $NaHCO_3$ (700 mL), brine (700 mL) and dried over $Na_2SO_4$, then the organic phase was filtered and concentrated. The residue was purified by chromatography on silica gel (petroleum ether) to give the title compound. H-NMR (400 MHz, $CDCl_3$): δ 4.55-4.37 (m, 1H), 2.36-1.98 (m, 3H), 1.95-1.58 (m, 4H), 1.56-1.52 (m, 3H), 1.51-1.23 (m, 1H), 1.17-1.02 (m, 1H).

Step 3: 1-(3,3-difluorocyclohexyl)ethan-1-amine (A12-4)

A12-4

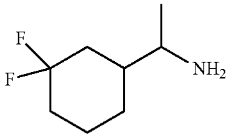

To a solution of 1,1-difluoro-3-(1-nitroethyl)cyclohexane (A12-3) (1 g, 5.18 mmol) in EtOAc (20 mL) was added Raney Ni (30 mg, 0.52 mmol). The resulting mixture was stirred at 30° C. under H2 (15 Psi) for 16 h. TLC showed the starting material was consumed and new spots were detected. The reaction mixture was filtered with EtOac (15 mL) and concentrated to give the title compound which was used without further purification.

Step 4: benzyl (1-(3,3-difluorocyclohexyl)ethyl)carbamate (A12-5)

A12-5

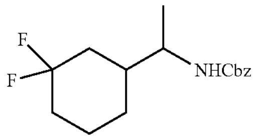

To a solution of 1-(3,3-difluorocyclohexyl)ethan-1-amine (A12-4) (72 g, 353 mmol) in EA (1200 mL) was added CbzCl (60.2 g, 353 mmol) and TEA (73.8 mL, 529 mmol). The resulting mixture was stirred at 34° C. for 16 h. TLC indicated new spots were detected. The reaction mixture was filtered and concentrated. This was purified via preparative HPLC on a C18 column (45-71% MeCN/water with 0.1% TFA modifier). The title compound was resolved via prep-SFC using the following conditions: OD column (250 mm×50 mm, 10 mm), 15% IPA (0.1% $NH_3 \cdot H_2O$), flow rate=180 mL/min. H-NMR (400 MHz, $CD_3OD$, ppm): δ 7.41-7.21 (m, 5H), 5.07 (s, 2H), 3.66-3.46 (m, 1H), 2.17-1.93 (m, 2H), 1.87-1.71 (m, 2H), 1.70-1.55 (m, 2H), 1.54-1.31 (m, 2H), 1.12 (d, J=6.8 Hz, 3H), 1.08-0.95 (m, 1H).

Step 5: 1-(3,3-difluorocyclohexyl)ethan-1-amine (Intermediate A12)

Intermediate A12

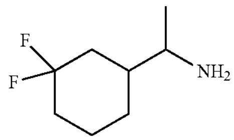

The benzyl (1-(3,3-difluorocyclohexyl)ethyl)carbamate (A12-51 (50 mg, 0.168 mmol) was dissolved in EtOH (841 μl) and treated with HCl (4.0 M in dioxane) (168 μl, 0.673 mmol) and 20% palladium hydroxide on carbon (23.62 mg, 0.034 mmol). This was subjected to a hydrogen (1 atm) and stirred at ambient temperature for 18 h. The reaction was deemed complete via LCMS. The reaction contents were filtered through an SPE cartridge containing celite and concentrated to give the title compound which was used without further purification.

Intermediate A13: (S)-1,1,1,5,5,5-hexafluoropentan-2-amine

Intermediate A13

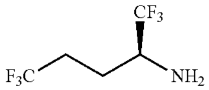

Step 1: 4,4,4-trifluorobutanol (A13-2)

A13-2

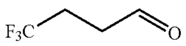

A three-necked flask was charged with $(COCl)_2$ (297.3 g, 2.34 mol, 205.0 mL, 1.5 eq) and this was dissolved in dry DCM (1.5 L). This was cooled to −70° C. and treated with DMSO (292.8 g, 3.75 mol, 292.8 mL, 2.4 eq) and the mixture was stirred for 30 min at −70° C. To this, 4,4,4-trifluorobutan-1-ol (A13-1) (200.0 g, 1.56 mol, 1.0 eq) in dry DCM (200 mL) was added to the mixture at −70° C. and this was stirred for 2 h. TLC (petroleum ether:Ethyl acetate=3:1, product Rf=0.7) showed the reaction was complete. Upon completion, the reaction contents were poured over water (5.0 L). The organic portion was washed with brine and dried over $Na_2SO_4$ and filtered to give the title compound as a solution in DCM and used directly in the next reaction.

Step 2: (R,E)-2-methyl-N-(4,4,4-trifluorobutylidene) propane-2-sulfinamide (A13-3)

A13-3

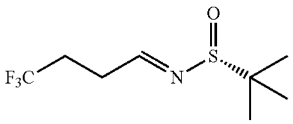

The 4,4,4-trifluorobutanal (A13-2) (196.0 g, 1.55 mol, 1.0 eq) in DCM (2.8 L) was cooled to 15° C. To this, (R)-2-methylpropane-2-sulfinamide (188.4 g, 1.55 mol, 1.0 eq), followed by $CuSO_4$ (744.4 g, 4.66 mol, 3.0 eq) and 4 angstrom molecular sieves (400.0 g). This was heated to 40° C. for 18 h while stirring under $N_2$. TLC (petroleum ether: Ethyl acetate=5:1, product $R_f$=0.35) showed the reaction was complete. The reaction contents were filtered and the filter cake was washed with DCM (5.0 L×2) and the filtrate was concentrated under vacuum. This was purified on silica gel (0-100%, EtOAc/petroleum ether) to afford the title compound. H-NMR (400 MHz, $CDCl_3$, ppm): δ 8.12 (s, 1H), 2.78-2.81 (m, 2H), 2.49-2.54 (m, 2H), 1.19 (s, 9H).

Step 3: (R)—N—((S)-1,1,1,5,5,5-hexafluoropentan-2-yl)-2-methylpropane-2-sulfinamide (A13-4)

A13-4

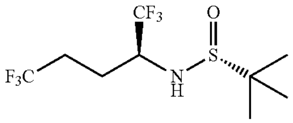

A flask was charged with (R,E)-2-methyl-N-(4,4,4-trifluorobutylidene)propane-2-sulfinamide (A13-3) (135.9 g, 0.59 mol, 1.0 eq) which was dissolved in THF (1.3 L) and this was cooled to 15° C. To this, tetrabutylammonium difluorotriphenylsilicate (320.0 g, 0.59 mol, 1.0 eq) was added. This was cooled to −30° C. and treated with $TMSCF_3$ (84.3 g, 0.59, 1.0 eq) dropwise over 0.5 h. The reaction contents were allowed to warm to 0° C. over the course of 2 h. TLC (petroleum ether:Ethyl acetate=5:1, product $R_f$=0.3) showed the reaction was complete. The reaction contents were filtered over celite and the filter cake was washed with EtOAc (1.0 L×2). The filtrate was washed with brine (1.0 L) and dried over $Na_2SO_4$, filtered and concentrated under reduced pressure. This was purified via silica gel (0-100%, EtOAc/petroleum ether) to afford the title compound. H-NMR (400 MHz, MeOD, ppm): δ 3.87-3.93 (m, 1H), 2.36-2.56 (m, 2H), 1.90-2.04 (m, 2H), 1.26 (s, 9H).

Step 4: (S)-1,1,1,5,5,5-hexafluoropentan-2-amine (Intermediate A13)

Intermediate A13

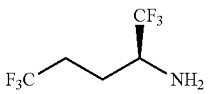

A three-necked flask was charged with (R)—N—((S)-1,1,1,5,5,5-hexafluoropentan-2-yl)-2-methylpropane-2-sulfinamide (A13-4) was cooled to 0° C. and treated with HCl (g)/Ethyl acetate (4 M, 417.7 mL, 10.0 eq) drop-wise to the mixture and this was warmed to 15° C. and stirred for 2 hrs. TLC (petroleum ether:ethyl acetate=3:1, product $R_f$=0) showed the reaction was complete. The reaction contents were concentrated under pressure to afford a solid. This was treated with petroleum ether (100 mL) and stirred at 15° C. for 1 h, then the mixture was filtered. The filter cake was washed with petroleum ether (100 mL×2) and dried under reduced pressure to give the title compound. H-NMR (400 MHz, MeOD, ppm): δ 4.27-4.32 (m, 1H), 2.45-2.52 (m, 2H), 2.18-2.21 (m, 1H), 2.12-2.18 (m, 1H).

Intermediate A14: (R)-6,6,6-trifluorohexan-3-amine

Intermediate A14

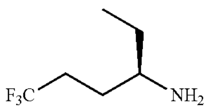

Step 1: 4,4,4-trifluoro-N-methoxy-N-methylbutanamide (A14-2)

A14-2

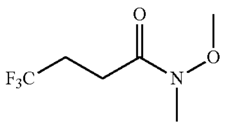

Into a 20-L 4-necked round-bottom flask purged and maintained with an inert atmosphere of nitrogen, was placed a solution of 4,4,4-trifluorobutanoic acid (A14-1) (443 g, 3.12 mol, 1.00 eq), EDCI (717.3 g, 3.74 mol, 1.20 eq), methoxy(methyl)amine hydrochloride (365 g, 3.74 mol, 1.20 eq) and DMAP (19 g, 155.52 mmol, 0.05 eq) in dichloromethane (9000 mL). The resulting solution was stirred for 16 h at 25° C. The reaction was then quenched by the addition of 8 L of citric acid solution. The resulting solution was extracted with 5 L of DCM and the organic layers combined. The resulting mixture was washed with of sodium chloride (3 L×2). The resulting mixture was washed with of sodium bicarbonate (4 L×2). The mixture was dried over anhydrous sodium sulfate and concentrated under vacuum to give the title compound.

Step 2: 6,6,6-trifluorohexan-3-one (A14-3)

A14-3

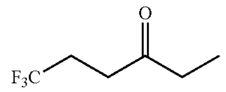

Into a 10-L 4-necked round-bottom flask purged and maintained with an inert atmosphere of nitrogen, was placed a solution of 4,4,4-trifluoro-N-methoxy-N-methylbutanamide (A14-2) (381 g, 2.06 mol, 1.00 eq) in dichloromethane (3810 mL). This was followed by the addition of bromo (ethyl)magnesium (2060 mL, 2.00 eq) dropwise at 0° C. in 60 min. The resulting solution was stirred for 3 h at 25° C. in a water bath. The reaction mixture was cooled to −5° C. with a water/ice bath. The reaction was then quenched by the addition of 10 L of 1 mol/L hydrogen chloride. The resulting solution was extracted with of dichloromethane (4 L×2) and the organic layers combined. The resulting mixture was washed with of sodium chloride (5.0 L×2). The mixture was dried over anhydrous sodium sulfate and concentrated under vacuum to give the title compound.

Step 3: (R,E)-2-methyl-N-(6,6,6-trifluorohexan-3-ylidene)propane-2-sulfinamide (A14-4)

A14-4

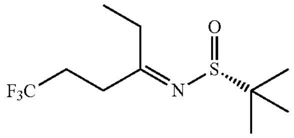

Into a 10-L, 4-necked round-bottom flask purged and maintained with an inert atmosphere of nitrogen, was placed a solution of 6,6,6-trifluorohexan-3-one (A14-3) (267 g, 1.73 mol, 1.00 eq), (R)-2-methylpropane-2-sulfinamide (630 g, 5.20 mol, 3.00 eq) and tetrapropoxytitanium (1231 g, 4.33 mol, 2.50 eq) in tetrahydrofuran (5500 mL). The resulting solution was stirred for 16 h at 80° C. in an oil bath. The reaction mixture was cooled to 25° C. with a water/ice bath. The reaction was then quenched by the addition of 5000 mL of aqueous $NH_4Cl$. The solids were filtered out. The filtrate was dried over anhydrous sodium sulfate and concentrated. The residue was applied onto a silica gel column (0-10%, ethyl acetate/petroleum ether) to give the title compound.

Step 4: (S)-2-methyl-N—((R)-6,6,6-trifluorohexan-3-yl)propane-2-sulfinamide (A14-5)

A14-5

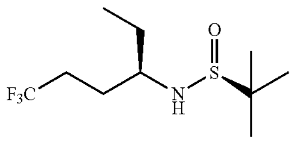

Into a 10-L 4-necked round-bottom flask purged and maintained with an inert atmosphere of nitrogen, was placed a solution of (R,E)-2-methyl-N-(6,6,6-trifluorohexan-3-ylidene)propane-2-sulfinamide (A14-4) (242.4 g, 942.03 mmol, 1.0 eq) in tetrahydrofuran (2500 mL). This was followed by the addition of $BH_3$ in THF (1 M, 2826 mL, 3.0 eq) at −78° C. in 1 h. The resulting solution was stirred for 3 h at −78° C. in a liquid nitrogen bath. The reaction was then quenched by the addition of 5000 mL of water. The resulting solution was extracted with of ethyl acetate (3.0 L×2) and the organic layers combined. The resulting mixture was washed with sodium chloride (2.0 L×2). The mixture was dried over anhydrous sodium sulfate and concentrated under vacuum. The resulting mixture was washed with 250 mL of n-heptane. The solids were collected by filtration, resulting in a mixture of diastereomers. Into a 2000-mL round-bottom flask purged and maintained with an inert atmosphere of nitrogen, this mixture was resolved via by flash-prep-HPLC with the following conditions: Combi-Flash-1 C18 silica gel (40-50%, $NH_4HCO_3$/MeCN) to give the title compound.

Step 5: (R)-6,6,6-trifluorohexan-3-amine (Intermediate A14)

Intermediate A14

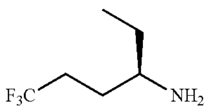

Into a 3000-mL round-bottom flask purged and maintained with an inert atmosphere of nitrogen, was placed (S)-2-methyl-N—((R)-6,6,6-trifluorohexan-3-yl)propane-2-sulfinamide (A14-5) (127.5 g, 1 eq), methanol (1000 mL), 4 M HCl (260 mL). The resulting solution was stirred for 2 h at 25° C. The resulting mixture was concentrated under vacuum. The resulting solid was washed with 500 ml of EtOEt and filtered to give the title compound. H-NMR (400 MHz, DMSO-d6, ppm): δ 8.25 (s, 3H), 3.12 (d, J=7.0 Hz, 1H), 2.54-2.36 (m, 2H), 1.84-1.71 (m, 2H), 1.67-1.55 (m, 2H), 0.92 (t, J=7.5 Hz, 3H).

Intermediate A15: 1,1,1-trifluoro-3-(2H-1,2,3-triazol-2-yl)propan-2-amine

Intermediate A15

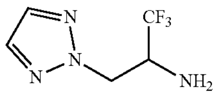

Step 1: 2-((tert-butoxycarbonyl)amino)-3,3,3-trifluoropropyl 4-methylbenzenesulfonate (15-1)

15-1

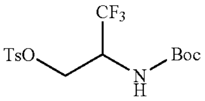

To a solution of compound tert-butyl (1,1,1-trifluoro-3-hydroxypropan-2-yl)carbamate (1.7 g, 7.42 mmol) in DCM (20 mL) were added TEA (2.252 g, 22.25 mmol) and TsCl (2.121 g, 11.13 mmol) at 0° C. The mixture was stirred at 15° C. for 15 h. TLC showed the starting material was consumed and new spots were detected. The reaction mixture was poured into water (30 mL), extracted with DCM (30 mL×3). The organic layer was washed with brine (30 mL), dried over $Na_2SO_4$. After filtration and concentration, the residue was purified by flash silica gel chromatography (ISCO®; 40 g SepaFlash® Silica Flash Column, eluent of 5-10% ethyl acetate/petroleum ether gradient@30 mL/min) to give the title compound.

Step 2: tert-butyl (1,1,1-trifluoro-3-(2H-1,2,3-triazol-2-yl)propan-2-yl)carbamate (15-2) and tert-butyl (1,1,1-trifluoro-3-(1H-1,2,3-triazol-1-yl)propan-2-yl)carbamate (15-3)

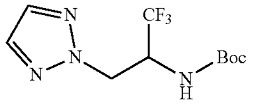

+

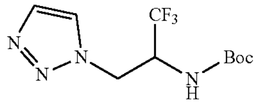

15-2 15-3

To a solution of compound 2-((tert-butoxycarbonyl)amino)-3,3,3-trifluoropropyl 4-methylbenzenesulfonate (31-1) (100 mg, 0.261 mmol) in anhydrous MeCN (3 mL) were added $Cs_2CO_3$ (255 mg, 0.783 mmol), 2H-1,2,3-triazole (36.0 mg, 0.522 mmol). And the resulting mixture was stirred at 80° C. under $N_2$ protection for 5 h. TLC showed new spots were found. The reaction mixture was filtered and concentrated in vacuo. Then the residue was purified by prep-TLC ($SiO_2$, EtOAc/petroleum ether=2:1) to give afford the separated compounds.

Step 3: tert-butyl (1,1,1-trifluoro-3-(2H-1,2,3-triazol-2-yl)propan-2-yl)carbamate (15-4)

15-4

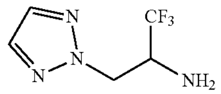

To a solution of compound tert-butyl (1,1,1-trifluoro-3-(2H-1,2,3-triazol-2-yl)propan-2-yl)carbamate (15-2) in 4 M HCl in MeOH (4 mL), and the resulting mixture was stirred at 20° C. under $N_2$ protection for 6 h. The mixture was concentrated in vacuo to give the crude product as a mixture of diastereomers. MS: 181.0 [M+1].

Intermediate A16: 1,1,1-trifluoro-3-(1H-1,2,3-triazol-1-yl)propan-2-amine

Intermediate A16

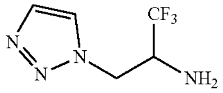

The title compound was prepared from tert-butyl (1,1,1-trifluoro-3-(1H-1,2,3-triazol-1-yl)propan-2-yl)carbamate (15-3) using the procedure outlined in step 3 in the synthesis of Intermediate A15.

Example 1-1 for Table 1: 1-ethyl-3-((S)-1,1,1,5,5,5-hexafluoropentan-2-yl)-1-((R)-1-(3-(imidazo[1,2-a]pyridin-6-yl)phenyl)ethyl)urea Example 1-1

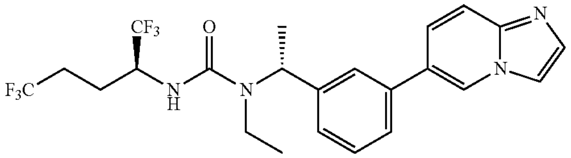

The (S)-1,1,1,5,5,5-hexafluoropentan-2-amine, HCl (327 mg, 1.413 mnol) (Intermediate A13) was dissolved in DCM (4711 μl) and treated with CDI (229 mg, 1.413 mmol) and TEA (525 μl, 3.77 mmol) and stirred at ambient temperature for 30 min, then treated with (R)—N-ethyl-1-(3-(imidazo[1,2-a]pyridin-6-yl)phenyl)ethylamine (Intermediate A9) and this mixture was stirred for 18 h at ambient temperature. This was diluted with DCM, washed with saturated $NaHCO_3$, dried ($Na_2SO_4$), filtered and evaporated to give the crude title compound. This was purified via reverse phase chromatography C18 (acetonitrile/water with 0.1% TFA as a modifier) to afford the title compound. MS: 487.3 [M+1].

The following compounds were prepared according to the general procedures herein and in an analogous manner to that used to synthesize the Examples above using the appropriate intermediates. The starting materials were either prepared as described in the intermediates section, commercial available, or prepared from commercially available reagents using conventional reactions well known in the art.

TABLE 1

| Ex. | Structure | Name | Exact Mass [M + H]+ |
|---|---|---|---|
| 1-2 | 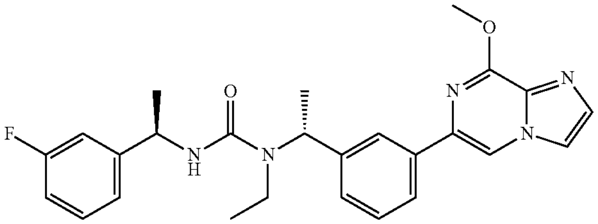 [SMILES: CCN(C(=O)N[C@H](C)c1cccc(F)c1)[C@H](C)c1cccc(-c2cn3ccnc3c(OC)n2)c1] | 1-ethyl-3-((R)-1-(3-fluorophenyl)ethyl)-1-((R)-1-(3-(8-methoxyimidazo[1,2-a]pyrazin-6-yl)phenyl)ethyl)urea | 484.4 |
| 1-3 | 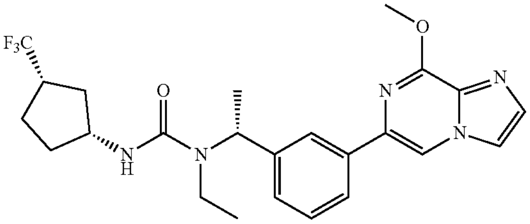 [SMILES: CCN(C(=O)N[C@@H]1CC[C@H](C(F)(F)F)C1)[C@H](C)c1cccc(-c2cn3ccnc3c(OC)n2)c1] | 1-ethyl-1-((R)-1-(3-(8-methoxyimidazo[1,2-a]pyrazin-6-yl)phenyl)ethyl)-3-((1R,3S)-3-(trifluoromethyl)cyclopentyl)urea | 476.3 |
| 1-4 | 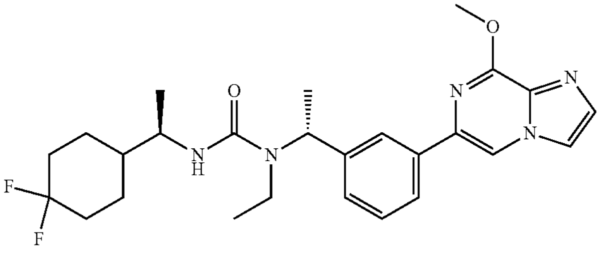 [SMILES: CCN(C(=O)N[C@H](C)C1CCC(F)(F)CC1)[C@H](C)c1cccc(-c2cn3ccnc3c(OC)n2)c1] | 3-((R)-1-(4,4-difluorocyclohexyl)ethyl)-1-ethyl-1-((R)-1-(3-(8-methoxyimidazo[1,2-a]pyrazin-6-yl)phenyl)ethyl)urea | 486.3 |
| 1-5 | 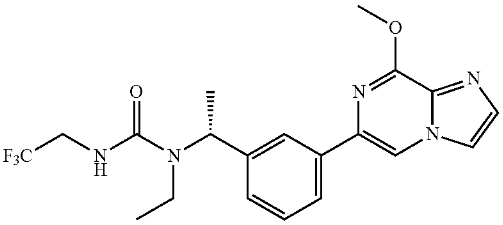 [SMILES: CCN(C(=O)NCC(F)(F)F)[C@H](C)c1cccc(-c2cn3ccnc3c(OC)n2)c1] | (R)-1-ethyl-1-(1-(3-(8-methoxyimidazo[1,2-a]pyrazin-6-yl)phenyl)ethyl)-3-(2,2,2-trifluoroethyl)urea | 444.3 |

TABLE 1-continued

| Ex. | Structure | Name | Exact Mass [M + H]+ |
|---|---|---|---|
| 1-6 | 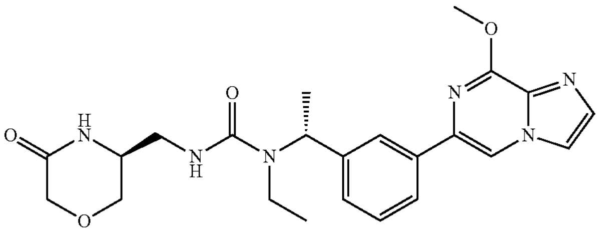 [SMILES: CCN(C(=O)NC[C@H]1COCC(=O)N1)[C@H](C)c1cccc(-c2cn3ccnc3c(OC)n2)c1] | 1-ethyl-1-((R)-1-(3-(8-methoxyimidazo[1,2-a]pyrazin-6-yl)phenyl)ethyl)-3-(((S)-5-oxomorpholin-3-yl)methyl)urea | 453.4 |
| 1-7 | 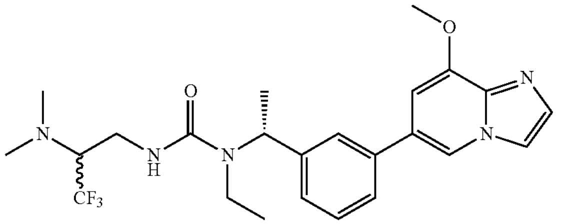 [SMILES: CCN(C(=O)NCC(N(C)C)C(F)(F)F)[C@H](C)c1cccc(-c2cc(OC)c3nccn3c2)c1] | 3-(2-(dimethylamino)-3,3,3-trifluoropropyl)-1-ethyl-1-((R)-1-(3-(8-methoxyimidazo[1,2-a]pyridin-6-yl)phenyl)ethyl)urea | 478.4 |
| 1-8 | 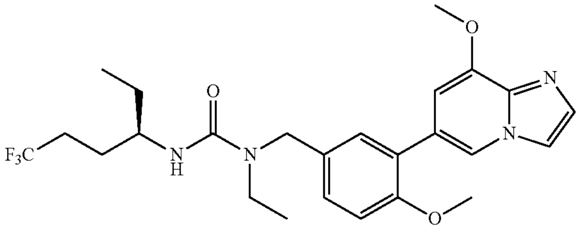 [SMILES: CC[C@H](CCC(F)(F)F)NC(=O)N(CC)Cc1ccc(OC)c(-c2cc(OC)c3nccn3c2)c1] | (R)-1-ethyl-1-(4-methoxy-3-(8-methoxyimidazo[1,2-a]pyridin-6-yl)benzyl)-3-(6,6,6-trifluorohexan-3-yl)urea | 493.3 |
| 1-9 | 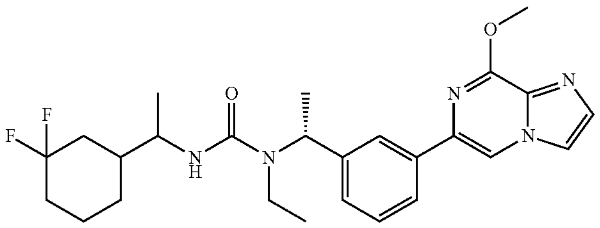 [SMILES: CCN(C(=O)NC(C)C1CCCC(F)(F)C1)[C@H](C)c1cccc(-c2cn3ccnc3c(OC)n2)c1] | 3-(1-(3,3-difluorocyclohexyl)ethyl)-1-ethyl-1-((R)-1-(3-(8-methoxyimidazo[1,2-a]pyrazin-6-yl)phenyl)ethyl)urea | 486.3 |
| 1-10 | 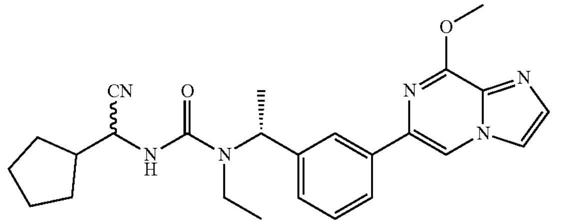 [SMILES: CCN(C(=O)NC(C#N)C1CCCC1)[C@H](C)c1cccc(-c2cn3ccnc3c(OC)n2)c1] | 3-(cyano(cyclopentyl)methyl)-1-ethyl-1-((R)-1-(3-(8-methoxyimidazo[1,2-a]pyrazin-6-yl)phenyl)ethyl)urea | 447.2 |
| 1-11 | 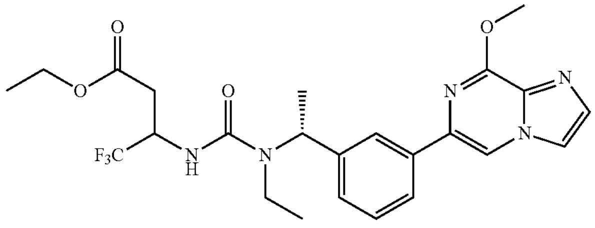 [SMILES: CCOC(=O)CC(NC(=O)N(CC)[C@H](C)c1cccc(-c2cn3ccnc3c(OC)n2)c1)C(F)(F)F] | ethyl 3-(3-ethyl-3-((R)-1-(3-(8-methoxyimidazo[1,2-a]pyrazin-6-yl)phenyl)ethyl)ureido)-4,4,4-trifluorobutanoate | 508.4 |

TABLE 1-continued

| Ex. | Structure | Name | Exact Mass [M + H]+ |
|---|---|---|---|
| 1-12 | 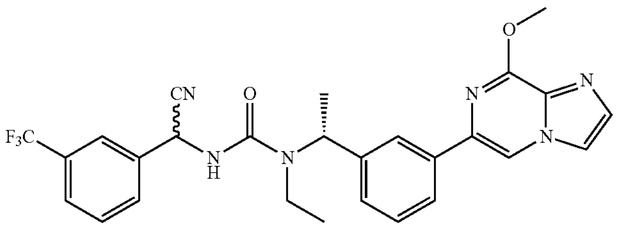 [SMILES: CCN(C(=O)NC(C#N)c1cccc(C(F)(F)F)c1)[C@H](C)c1cccc(-c2cn3ccnc3c(OC)n2)c1] | 3-(cyano(3-(trifluoromethyl)phenyl)methyl)-1-ethyl-1-((R)-1-(3-(8-methoxyimidazo[1,2-a]pyrazin-6-yl)phenyl)ethyl)urea | 523.2 |
| 1-13 | 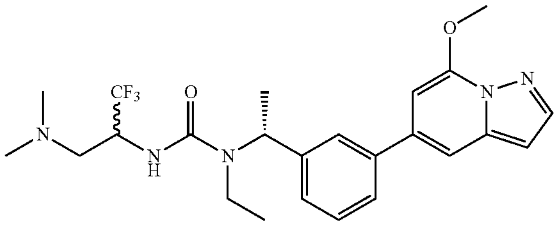 [SMILES: CCN(C(=O)NC(CN(C)C)C(F)(F)F)[C@H](C)c1cccc(-c2cc(OC)n3nccc3c2)c1] | 3-(3-(dimethylamino)-1,1,1-trifluoropropan-2-yl)-1-ethyl-1-((R)-1-(3-(7-methoxypyrazolo[1,5-a]pyridin-5-yl)phenyl)ethyl)urea | 478.3 |
| 1-14 | 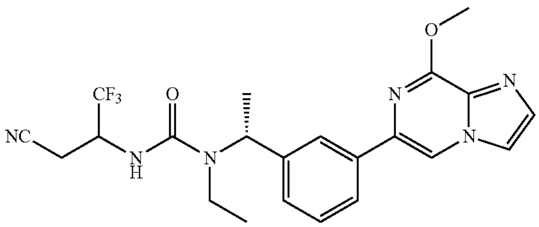 [SMILES: CCN(C(=O)NC(CC#N)C(F)(F)F)[C@H](C)c1cccc(-c2cn3ccnc3c(OC)n2)c1] | 3-(3-cyano-1,1,1-trifluoropropan-2-yl)-1-ethyl-1-((R)-1-(3-(8-methoxyimidazo[1,2-a]pyrazin-6-yl)phenyl)ethyl)urea | 461.3 |
| 1-15 | 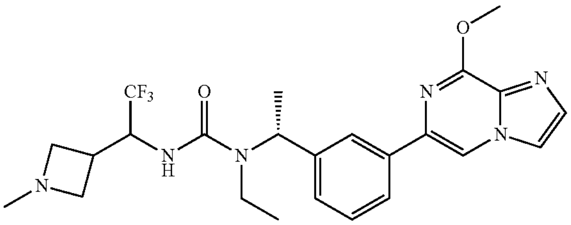 [SMILES: CCN(C(=O)NC(C1CN(C)C1)C(F)(F)F)[C@H](C)c1cccc(-c2cn3ccnc3c(OC)n2)c1] | 1-ethyl-1-((R)-1-(3-(8-methoxyimidazo[1,2-a]pyrazin-6-yl)phenyl)ethyl)-3-(2,2,2-trifluoro-1-(1-methylazetidin-3-yl)ethyl)urea | 491.4 |
| 1-16 | 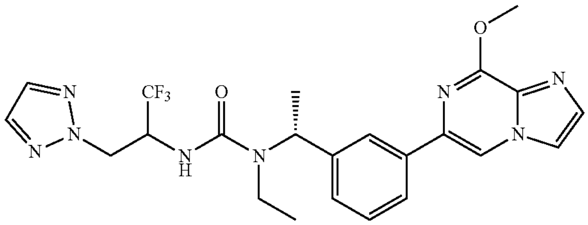 [SMILES: CCN(C(=O)NC(Cn1nccn1)C(F)(F)F)[C@H](C)c1cccc(-c2cn3ccnc3c(OC)n2)c1] | 1-ethyl-1-((R)-1-(3-(8-methoxyimidazo[1,2-a]pyrazin-6-yl)phenyl)ethyl)-3-(1,1,1-trifluoro-3-(2H-1,2,3-triazol-2-yl)propan-2-yl)urea | 503.2 |
| 1-17 | 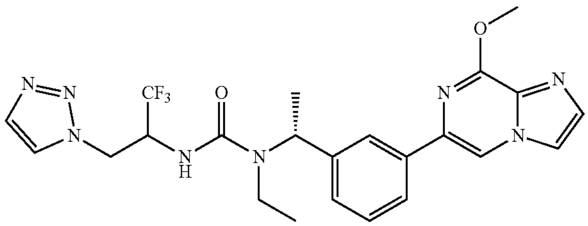 [SMILES: CCN(C(=O)NC(Cn1ccnn1)C(F)(F)F)[C@H](C)c1cccc(-c2cn3ccnc3c(OC)n2)c1] | 1-ethyl-1-((R)-1-(3-(8-methoxyimidazo[1,2-a]pyrazin-6-yl)phenyl)ethyl)-3-(1,1,1-trifluoro-3-(1H-1,2,3-triazol-1-yl)propan-2-yl)urea | 503.1 |

Intermediate B1: 8-methoxy-6-(4,4,5,5-tetramethyl-1,3,2-dioxaborolan-2-yl)imidazo[1,2-a]pyrazine Intermediate B1

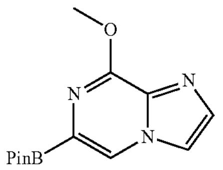

A flask was charged with the 6-bromo-8-methoxyimidazo[1,2-a]pyrazine (Intermediate A1) (240 g, 1.05 mol, 1.0 eq) and 4,4,4',4',5,5,5',5'-octamethyl-2,2'-bi(1,3,2-dioxaborolane) (320 g, 1.26 mol, 1.25 eq) and these were dissolved in dioxane (3.12 L). This was treated with and $CH_3COOK$ (310 g, 3.16 mol, 3.00 eq). Nitrogen was bubbled into the mixture for 10 min, then Pd(dppf)$Cl_2$·$CH_2Cl_2$ (8.59 g, 0.01 mol, 0.01 eq) was added to the reaction mixture. The mixture was heated to 90° C. and stirred for 4 h. TLC (petroleum ether:ethyl acetate=0:1, product $R_f$=0.10) showed the reaction was complete. The mixture was concentrated under reduced pressure to give the crude product. This was triturated with DCM (10 L) for 1 h. The suspension was filtered and filter cake was washed with DCM (5 L). The filtered solid was triturated with methyl tert-butyl ether (3.0 L) and filtered with the filter cake washed with methyl tert-butyl ether (500 mL) to afford the title compound.

Intermediate B2: N-ethyl-2,2,2-trifluoro-1-(5-methoxy-4-(8-methoxyimidazo[1,2-a]pyrazin-6-yl)pyridin-2-yl)ethan-1-amine Intermediate B2

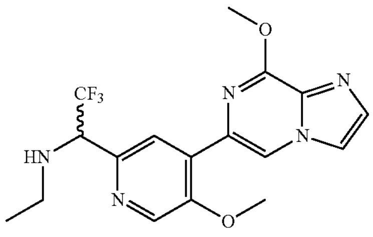

Step 1: 2-(hydroxymethyl)-5-methoxy-4H-pyran-4-one (32-2)

B2-2

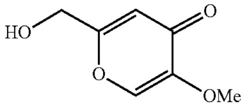

A flask was charged the 5-hydroxy-2-(hydroxymethyl)-4H-pyran-4-one (32-1) (500 g, 3.52 mol, 1 eq) which was dissolved in $H_2O$ (2.20 L) and treated with KOH (217 g, 3.87 mol, 1.10 eq) at ambient temperature. This was cooled to 5° C. and dimethyl sulfate (488 g, 3.87 mol, 345 mL, 1.1 eq) was added drop-wise over the course of 1.5 h while keeping temperature no warmer than 5° C. The reaction contents were heated to 70° C. and the suspension was stirred for 12 h. TLC (Dichloromethane:Methanol=5:1, product $R_f$=0.70) showed the reaction was completed. The reaction contents were filtered and the filter cake was washed with EtOH (1 L) and the solid was dried under vacuum to afford the title compound. H-NMR (400 MHz, DMSO-d6, ppm): δ 8.08 (s, 1H), 6.29 (s, 1H), 4.29 (s, 2H), 3.64 (s, 3H).

Step 2: 2-(hydroxymethyl)-5-methoxypyridin-4(1H)-one (32-3)

B2-3

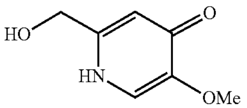

A 10 L sealed tube was charged with 2-(hydroxymethyl)-5-methoxy-4H-pyran-4-one (32-2) (1100 g, 7.05 mol, 1.0 eq) which was dissolved in MeOH (2.20 L) and treated with $NH_3·H_2O$ (3.00 kg, 31.7 mol, 3.30 L, 37% purity, 4.50 eq). The reaction contents were heated to 90° C. and stirred for 12 h. TLC (DCM:Methanol=5:1, product $R_f$=0.30) showed the reaction was completed. The reaction mixture was concentrated to give a residue as crude product. This was triturated with MeOH (1.5 L) for 1 h, then filtered to give a solid which was rinsed with MeOH (300 mL) to afford the title product. H-NMR (400 MHz, MeOD, ppm): δ 7.46 (s, 1H), 6.41 (s, 1H), 4.54 (s, 2H), 3.79 (s, 3H).

Step 3: 4-chloro-2-(chloromethyl)-5-methoxypyridine (B2-4)

B2-4

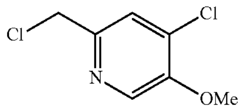

A flask was charged with 2-(hydroxymethyl)-5-methoxy-pyridin-4(1H)-one (B2-3) (430 g, 2.58 mol, 1.00 eq) which as treated with $POCl_3$ (2.0 L). This was heated to 100° C. and stirred for 5 h. TLC (petroleum ether:ethyl acetate=1:1, product $R_f$=0.70) showed the reaction was completed. The reaction contents were concentrated under vacuum to afford a residue as crude product. This was diluted with DCM (5.0 L) and quenched with aqueous $NaCO_3$ (30.0 L) such that the pH value of the organic layer was 7-8. The suspension was filtered and extracted with DCM (5.0 L×3). The organic layer was dried over $Na_2SO_4$, filtered and concentrated to give a solid as the title compound. H-NMR (400 MHz, $CDCl_3$, ppm): δ 8.21 (s, 1H), 7.48 (s, 1H), 4.59 (s, 2H), 4.00 (s, 3H).

Step 4: 4-chloro-5-methoxypicolinaldehyde (B2-5)

B2-5

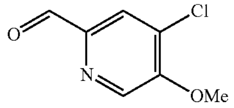

A flask was charged with 4-chloro-2-(chloromethyl)-5-methoxypyridine (B2-4) (430 g, 2.24 mol, 1.00 eq) and NMO (524 g, 4.48 mol, 2.00 eq) which were dissolved in ACN (2.50 L). The reaction contents were heated to 80° C. for 3 h while stirring under $N_2$. The reaction was monitored via LCMS. The reaction contents were cooled to ambient temperature and poured into a flask containing $H_2O$ (10.0 L) and extracted with EtOAc (5.0 L×2). The organic portion was washed with brine (3.0 L×3), dried over $Na_2SO_4$, filtered, and concentrated to afford the title compound. H-NMR (400 MHz, $CDCl_3$, ppm): δ 9.94 (s, 1H), 8.40 (s, 1H), 7.99 (s, 1H), 4.10 (s, 3H).

Step 5: 1-(4-chloro-5-methoxypyridin-2-yl)-2,2,2-trifluoroethan-1-ol (B2-6)

B2-6

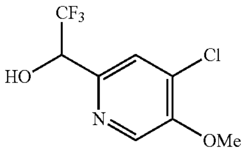

A flask was charged with the 4-chloro-5-methoxypicolinaldehyde (B2-5) (310 g, 1.81 mol, 1.0 eq) and dissolved in DMF (2.2 L) and treated with $CF_3SiMe_3$ (514 g, 3.61 mol, 2.0 eq) and $K_2CO_3$ (1000.70 mol, 0.40 eq). The reaction mixture was stirred at ambient temperature for 12 h. TLC (petroleum ether:ethyl acetate=1:1, product $R_f$=0.70) showed the reaction was completed. The reaction contents were poured into a flask containing HCl (1.0 M, 8.0 L) and the pH of the mixture was adjusted to pH 7-8 with addition of solid $NaHCO_3$. This was extracted with EtOAc (5.0 L×3) and washed with brine (5.0 L×3). The organic portion was dried over $Na_2SO_4$ and concentrated under reduced pressure to give a solid as the title compound. H-NMR (400 MHz, $CDCl_3$, ppm): δ 8.26 (s, 1H), 7.45 (s, 1H), 5.08 (s, 1H), 4.96 (s, 1H), 4.03 (s, 3H).

Step 6: 1-(4-chloro-5-methoxypyridin-2-yl)-2,2,2-trifluoroethan-1-one (B2-7)

B2-7

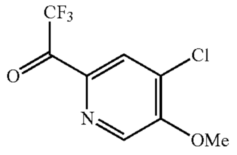

A flask was charged with 1-(4-chloro-5-methoxypyridin-2-yl)-2,2,2-trifluoroethan-1-ol (B2-6) which was dissolved in dioxane (2.50 L) and treated with $MnO_2$ (576 g, 5.96 mol, 4.0 eq). This was heated to 100° C. and stirred for 12 h. The reaction was deemed complete via LCMS. This was cooled to ambient temperature and filtered over celite. The filter cake was washed with EtOAc (10 L) and the filtrate was concentrated to afford the title compound as a solid. H-NMR (400 MHz, $CDCl_3$, ppm): δ 8.44 (s, 1H), 8.20 (s, 1H), 4.13 (s, 3H).

Step 7: 1-(4-chloro-5-methoxypyridin-2-yl)-N-eth-2,2,2-trifluoroethan-1-amine (B2-8)

B2-8

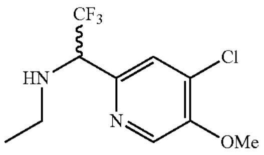

A flask was charged with 1-(4-chloro-5-methoxypyridin-2-yl)-2,2,2-trifluoroethan-1-one (B2-7) which was dissolved in DCM (1.3 L) and treated with $EtNH_2$ (158 g, 3.51 mol, 4.0 eq) and $TiCl_4$ (332 g, 1.75 mol, 2.0 eq). The reaction mixture was stirred at ambient temperature for 12 h. The reaction contents were treated with $NaBH_3CN$ (165 g, 2.63 mol, 3.0 eq) which was added in portions. The mixture was stirred at ambient temperature for 2 h and followed via TLC (petroleum ether:ethyl acetate=3:1, product $R_f$=0.60) until the starting material was fully consumed. The reaction contents were poured into a flask containing MeOH (5.0 L) and the solution was stirred for 0.5 h at ambient temperature. The pH of the reaction contents was adjusted to 10 via the addition of an aqueous solution of NaOH (5 M, 2.5 L). The mixture was filtered over celite and the filter cake was washed with DCM (10.0 L) and the filtrate was concentrated to give the crude product. This was purified via chromatography with silica gel (30-100%, EtOAc/petroleum ether) to afford the title compound. H-NMR (400 MHz, $CDCl_3$, ppm): δ 8.28 (s, 1H), 7.42 (s, 1H), 4.18 (q, J=14.4 Hz, 1H), 4.01 (s, 3H), 2.59-2.64 (m, 2H), 1.12 (t, J=7.2 Hz, 3H).

Step 8: N-ethyl-2,2,2-trifluoro-1-(5-methoxy-4-(8-methoxyimidazo[1,2-a]pyrazin-6-yl)pyridin-2-yl)ethan-1-amine (Intermediate B2)

Intermediate B2

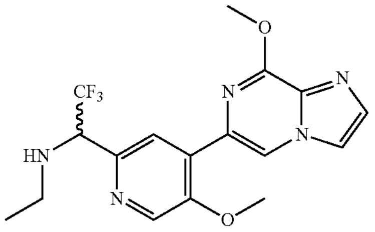

A flask was charged with 1-(4-chloro-5-methoxypyridin-2-yl)-N-ethyl-2,2,2-trifluoroethan-1-amine (B2-8) (135 g, 0.50 mol, 1.00 eq) and 8-methoxy-6-(4,4,5,5-tetramethyl-1,3,2-dioxaborolan-2-yl)imidazo[1,2-a]pyrazine (Intermediate B1) (152 g, 0.55 mol, 1.10 eq). These were dissolved in DME (2.0 L) and the mixture was purged with nitrogen for 10 min. To this, $K_3PO_4$ (2 M, 1.00 L, 3.00 eq) was added and the mixture was purged with nitrogen for 10 min. To this, XPhos Pd G2 (9.88 g, 0.01 mol, 0.10 eq) was added and the reaction contents were heated to 85° C. and stirred under nitrogen for 12 h. TLC (petroleum ether:ethyl acetate=1:1, product $R_f$=0.15) showed the reaction was completed. The reaction contents were filtered over a bed of celite and the filter cake was washed with EtOAc (5.0 L×3). The filtrate was treated with EtOAc (5.0 L×2) to extract and the combined organic portions were washed with water. The organic phase was concentrated under vacuum to afford crude product. This was purified using silica gel (30-100%, petroleum ether/EtOAc) to afford the title compound.

H-NMR (400 MHz, $CDCl_3$, ppm): δ 8.83 (s, 1H), 8.45 (s, 1H), 8.29 (s, 1H), 7.70 (s, 2H), 4.34 (q, J=7.6 Hz, 1H), 4.26 (s, 3H), 4.16 (s, 3H), 2.69-2.74 (m, 2H), 1.16 (t, J=7.6 Hz, 3H).

Intermediate B3: (S)—N-ethyl-2,2,2-trifluoro-1-(5-methoxy-4(8-methoxyimidazo[1,2-a]pyrazin-6-yl) pyridin-2-yl)ethan-1-amine Intermediate B3

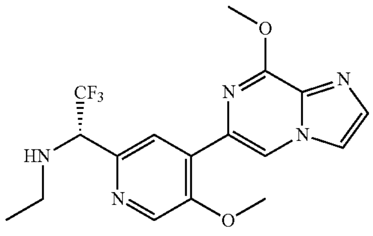

N-ethyl-2,2,2-trifluoro-1-(5-methoxy-4-(8-methoxyimidazo[1,2-a]pyrazin-6-yl)pyridin-2-yl)ethan-1-amine (Intermediate B2) was resolved via SFC using the following conditions: Daicel Chiralpak AS column (250 mm×50 mm, 10 um); mobile phase: 0.1% $NH_3$—$H_2O$ IPA with an isocratic gradient of 50%. The title compound was obtained as the 2nd eluting peak. H-NMR (400 MHz, $CDCl_3$, ppm): δ 8.82 (s, 1H), 8.43 (s, 1H), 8.27 (s, 1H), 7.69 (s, 2H), 4.31 (q, J=7.6 Hz, 1H), 4.26 (s, 3H), 4.12 (s, 3H), 2.67-2.71 (m, 2H), 2.43 (s, 1H), 1.15 (t, J=7.6 Hz, 3H). MS: 382.2 [M+1].

Intermediate B4: (S)—N-ethyl-2,2,2-trifluoro-1-(3-(4,4,5,5-tetramethyl-1,3,2-dioxaborolan-2-yl)phenyl) ethan-1-amine Intermediate B4

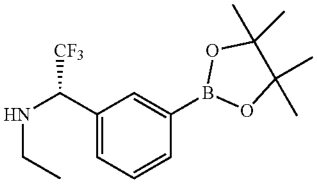

Step 1: 1-(3-bromophenyl)-2,2,2-trifluoroethan-1-one (B4-2)

B4-2

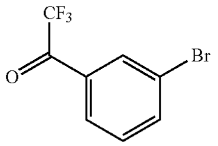

Into a 1 L 3-necked round-bottom flask purged and maintained with an inert atmosphere of nitrogen, was placed 1,3-dibromobenzene (B4-1) (50 g, 211.949 mmol, 1 equiv), THF (400 mL). This was followed by the addition of n-BuLi (85.6 mL, 214 mmol, 1.0 equiv, 2.5M) dropwise with stirring at −78° C. The resulting solution was stirred for 30 min at −78° C. To this was added ethyl 2,2,2-trifluoroacetate (41 g, 288.576 mmol, 1.36 eq) dropwise with stirring at −78° C. The resulting solution was stirred for 60 min at −78° C. The reaction was then quenched by the addition of 500 mL of aq. $NH_4Cl$. The resulting solution was extracted with ethyl acetate (2×600 mL) and the organic layers combined. The resulting mixture was washed with brine (500 mL). The mixture was dried over anhydrous $Na_2SO_4$ and concentrated under vacuum. The residue was applied onto a silica gel column (10-100%, ethyl acetate/petroleum ether. This resulted in the title compound.

Step 2: 1-(3-bromophenyl)-N-ethyl-2,2,2-trifluoroethan-1-amine (B4-3)

B4-3

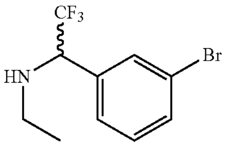

Into a 20 L 4-necked round-bottom flask purged and maintained with an inert atmosphere of nitrogen, was placed 1-(3-bromophenyl)-2,2,2-trifluoroethan-1-one (B4-2) (500 g, 1976.144 mmol, 1 eq), DCM (10 L), ethylamine (1970 mL, 2 M). This was followed by the addition of $TiCl_4$ (563 g, 2968.173 mmol, 1.50 eq) dropwise with stirring. To this was added $NaBH_3CN$ (249 g, 3962.318 mmol, 2.01 eq) in several batches. The resulting solution was stirred for 16 h at ambient temperature. The reaction was then quenched by the addition of 5 L of MeOH. The pH value of the solution was adjusted to 10 with 5 N NaOH. The solids were filtered out. The filtrate was dried over anhydrous $Na_2SO_4$ and concentrated under vacuum. The residue was applied onto a silica gel column (10-100%, ethyl acetate/petroleum ether) to afford the title compound.

Step 3: (S)-1-(3-bromophenyl)-N-ethyl-2,2,2-trifluoroethan-1-amine (B4-4)

B4-4

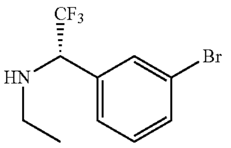

The crude 1-(3-bromophenyl)-N-ethyl-2,2,2-trifluoro-ethan-1-amine (B4-3) (200 g) was purified by Prep-SFC with the following conditions: CHIRALPAK IG column, 5×25 cm, 5 um; mobile phase, 100% hexane; detector, 210 nm. The second-eluting product produced the title compound.

Step 4: (S)—N-ethyl-2,2,2-trifluoro-1-(3-(4,4,5,5-tetramethyl-1,3,2-dioxaborolan-2-yl)phenyl)ethan-1-amine (Intermediate B4)

Intermediate B4

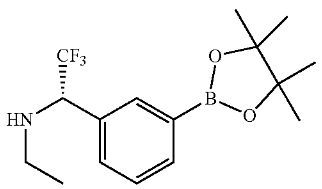

Into a 5 L 4-necked round-bottom flask purged and maintained with an inert atmosphere of nitrogen, was placed (S)-1-(3-bromophenyl)-N-ethyl-2,2,2-trifluoroethan-1-amine (B4-4) (80 g, 283.583 mmol, 1 eq), MeOH (2.4 L), 4,4,5,5-tetramethyl-2-(4,4,5,5-tetramethyl-1,3,2-dioxaborolan-2-yl)-1,3,2-dioxaborolane (144 g, 567.063 mmol, 2.00 eq), $CH_3COOK$ (84 g, 855.900 mmol, 3.02 eq), KF (50 g, 860.634 mmol, 3.03 eq), $Pd(PPh_3)_4$ (6.6 g, 5.712 mmol, 0.02 eq). The resulting solution was stirred for 2 h at ambient temperature. The resulting mixture was concentrated under vacuum. The resulting solution was diluted with 3 L of petroleum ether. The solids were filtered out. The filtrate was concentrated under vacuum. The residue was applied onto a silica gel column with (0-75%, ethyl acetate/petroleum) to afford the title compound. MS: 330.0 [M+1]. H-NMR: (400 MHz, Chloroform-d, ppm): δ 7.91-7.73 (m, 2H), 7.55 (d, J=7.7 Hz, 1H), 7.42 (t, J=7.5 Hz, 1H), 4.17 (q, J=7.5 Hz, 1H), 2.72-2.53 (m, 2H), 1.37 (s, 12H), 1.28 (s, 8H), 1.12 (t, J=7.1 Hz, 3H), 0.94-0.84 (m, 1H).

(S)-4-amino-5,5,5-trifluoropentanenitrile (Intermediate B5)

Intermediate B5

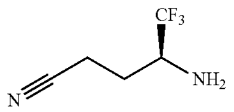

Step 1: 4-oxobutanenitrile (B5-2)

B5-2

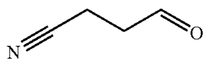

To a solution of 4,4-dimethoxybutanenitrile (B5-1) (20 g, 155 mmol) in water (200 mL) was added p-toluenesulfonic acid (5.33 g, 31.0 mmol), the resulting mixture was stirred at 100° C. for 4 h. TLC showed the reaction was completed and the new spot was found. The reaction mixture was extracted by EtOAc (3×60 mL), dried over $Na_2SO_4$. Then the organic phase was filtered and concentrated to give the title compound. H-NMR (400 MHz, $CDCl_3$, ppm): δ 9.80-9.67 (m, 1H), 2.86 (t, J=7.0 Hz, 2H), 2.58 (t, J=7.0 Hz, 2H).

Step 2: (R,E)-N-(3-cyanopropylidene)-2-methylpropane-2-sulfinamide (B5-3)

B5-3

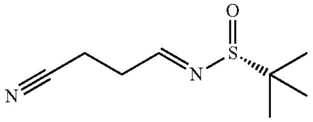

To a solution of 4-oxobutanenitrile (B5-2) (5 g, 60.2 mmol) in DCE (85 mL) were added (R)-(+)-2-methyl-2-propanesulfinamide (9.48 g, 78 mmol), PPTS (1.210 g, 4.81 mmol) and $MgSO_4$ (18.83 g, 156 mmol). The reaction mixture was stirred at 80° C. for 14 h. LCMS showed the desired MS was found. TLC showed the starting material disappeared and new spot was detected. The reaction mixture was filtered and concentrated, the crude product was purified by silica gel chromatography (50% ethyl acetate/petroleum ether to the title compound. H-NMR (400 MHz, $CDCl_3$, ppm): δ 8.16-8.06 (m, 1H), 2.91-2.84 (m, 2H), 2.80-2.59 (m, 2H), 1.20 (s, 9H).

Step 3: (R)—N—((S)-4-cyano-1,1,1-trifluorobutan-2-yl)-2-methylpropane-2-sulfinamide (B4-5)

B5-4

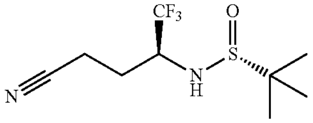

To a solution of (R,E)-N-(3-cyanopropylidene)-2-methylpropane-2-sulfinamide (B5-3) (4.46 g, 23.94 mmol) and tetrabutylammonium acetate (8.66 g, 28.7 mmol) in THF (80 mL) was added trimethyl(trifluoromethyl)silane (5.11 g, 35.9 mmol) at −40° C. for 2 h. Then the reaction mixture was warmed to 15° C. and stirred for 15 h. LCMS showed the desired MS was found. TLC showed the reaction was completed and a new spot was found. The reaction mixture was poured into water (100 mL) and extracted with EtOAc (3×100 mL), the combined organic layer was dried over $Na_2SO_4$, filtered and concentrated. The crude product was purified by silica gel chromatography (53%, ethyl acetate/petroleum ether) to give crude product. This was stirred in hexane (10 mL) for 10 min and the mixture was filtered to give the title compound. MS: 257.1 [M+1]. H-NMR (400 MHz, $CDCl_3$, ppm): δ 3.82-3.69 (m, 1H), 3.39 (br d, J=9.0 Hz, 1H), 2.71 (br d, J=7.3 Hz, 2H), 2.32-2.21 (m, 1H), 1.93-1.80 (m, 1H), 1.24 (s, 9H).

Step 4: (S)-4-amino-5,5,5-trifluoropentanenitrile (Intermediate B5)

Intermediate B5

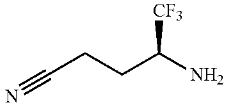

To a solution of (R)—N—((S)-4-cyano-1,1,1-trifluorobutan-2-yl)-2-methylpropane-2-sulfinamide (B4-5) (1.7 g, 6.63 mmol) in MeOH (34 mL) was added acetyl chloride (1.041 g, 13.27 mmol), and the mixture was stirred at 10° C. for 14 h. LCMS showed the reaction was completed (starting material disappeared). The reaction mixture was concentrated to give the crude product. The crude product was stirred in $Et_2O$ for 10 min, then the mixture was filtered to give the title compound. H-NMR (400 MHz, $CD_3OD$, ppm): δ 4.34-4.20 (m, 1H), 2.79 (dt, J=2.9, 7.5 Hz, 2H), 2.42-2.29 (m, 1H), 2.25-2.12 (m, 1H).

(2S)-1,1,1,5,5,5-hexafluoro-4-methoxypentan-2-amine (Intermediate B6)

Intermediate B6

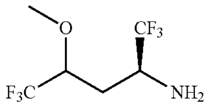

Step 1: 4,4,4-trifluoro-3-methoxybutanoic acid (B6-2)

B6-2

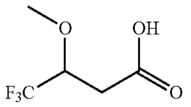

To a solution of methyl (E)-4,4,4-trifluorobut-2-enoate (B6-1) (20 g, 119 mmol) in MeOH (200 mL) was added sodium methoxide (9.64 g, 178 mmol), the mixture was stirred at 15° C. for 18 h, then NaOH (9.52 g, 238 mmol) and water (20 mL) were added to the above mixture and this was stirred at t 15° C. for 3 h. TLC showed the desired product was formed. The mixture was filtered, the filtrate was acidified with 10% HCl (100 mL), extracted with $Et_2O$ (3×200 mL). The organic phase was dried over $Na_2SO_4$, filtered and concentrated to give the title compound.

Step 2: methyl 4,4,4-trifluoro-3-methoxybutanoate (B6-3)

B6-3

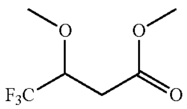

Thionyl chloride (44.6 g, 375 mmol) was added to MeOH (200 mL) at 0° C., after 5 min, 4,4,4-trifluoro-3-methoxybutanoic acid (B6-2) (21.5 g, 125 mmol) was added to the mixture and this was stirred at 15° C. for 8 h. TLC showed a new spot was found. The reaction mixture was poured into water (800 mL), extracted with $Et_2O$ (3×150 mL). The organic layer was dried over $Na_2SO_4$, filtered and concentrated to the crude title compound.

Step 3: 4,4,4-trifluoro-3-methoxybutanal (B6-4)

B6-4

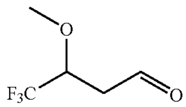

To a solution of methyl 4,4,4-trifluoro-3-methoxybutanoate (B6-3) (5 g, 26.9 mmol) in DCM (125 mL) was added DIBAL-H (29.5 mL, 29.5 mmol) (1 M in toluene) slowly at −78° C., the resulting mixture was stirred at −78° C. under $N_2$ protection for 1 h. TLC showed the desired product was found. The reaction mixture was poured into water (150 mL) and extracted with DCM (3×100 mL). The organic layer was washed with brine (100 mL), dried over $Na_2SO_4$ and filtered to give a solution of the title compound.

Step 4: (2S)-1,1,1,5,5,5-hexafluoro-4-methoxypentan-2-amine (Intermediate B6)

Intermediate B6

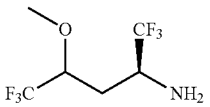

A solution of 4,4,4-trifluoro-3-methoxybutanal (B6-4) was converted to the title compound according to the procedures described in the synthesis of Intermediate B5, steps 2 through 4 with tetrabutylammonium difluorotriphenylsilicate in the place of tetrabutylammonium acetate. This was purified via preparative HPLC on a C18 column (45-71% MeCN/water with 0.1% TFA modifier to afford the title compound as separate diastereomers. First eluting peak: H-NMR (400 MHz, $CD_3OD$, ppm) δ 4.46-4.28 (m, 1H), 4.14-4.02 (m, 1H), 3.62 (s, 3H), 2.35-2.22 (m, 1H), 2.12-1.97 (m, 1H). MS: 226.1 [M+1]. Second eluting peak: H-NMR (400 MHz, $CD_3OD$, ppm) δ 4.35-4.21 (m, 1H), 4.07 (qd, J=6.2, 12.7 Hz, 1H), 3.62 (s, 3H), 2.19-2.08 (m, 2H). MS: 226.1 [M+1].

4,4,4-trifluoro-1-(oxetan-2-yl)butan-1-amine (Intermediate B7)

Intermediate B7

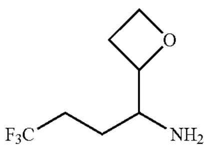

Step 1: 6,6,6-trifluorohex-1-en-3-ol (B7-2)

B7-2

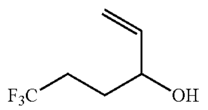

To a solution of 4,4,4-trifluorobutanal (B7-1) (9.8 g, 78 mmol) in DCM (120 mL) was added vinylmagnesium bromide (93 mL, 93 mmol) at 0° C., the mixture was stirred at 0° C. for 2 h. TLC showed the reaction was completed and a new spot was found. The reaction was checked by NMR and the NMR showed it is the desired product. The mixture was poured into saturated aqueous $NH_4Cl$, and extracted with DCM (120 mL). The combined organic layers were was dried over $Na_2SO_4$, then filtered and concentrated to give a solution of the title compound. The reaction mixture was direct moved to the next step without any purification. H-NMR (400 MHz, $CDCl_3$, ppm): δ 5.83 (ddd, J=6.1, 10.6, 17.1 Hz, 1H), 5.33-5.08 (m, 2H), 4.16 (br d, J=6.1 Hz, 1H), 2.33-2.06 (m, 2H), 1.82-1.63 (m, 2H).

Step 2: (((6,6,6-trifluorohex-1-en-3-yl)oxy)methyl) benzene (B7-3&

B7-3

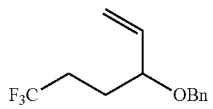

To a solution of 6,6,6-trifluorohex-1-en-3-ol (B7-2) (11.9 g, 77 mmol) in DMF (240 mL) was added NaH (4.63 g, 116 mmol) at 0° C. for 1 h. Then (bromomethyl)benzene (19.81 g, 116 mmol) was added. The reaction mixture was stirred at 10° C. for 14 h. TLC showed the reaction was completed, the reaction mixture was purified by silica gel chromatography (ISCO®; 80 g SepaFlash® Silica Flash Column, eluent of 7-11% ethyl acetate/petroleum ether gradient at 35 mL/min) to give the title compound. HNMR showed the desired product was formed. H-NMR (400 MHz, $CDCl_3$, ppm): δ 7.36-7.32 (m, 5H), 5.79-5.67 (m, 1H), 5.37-5.20 (m, 2H), 4.60 (d, J=11.7 Hz, 1H), 4.52-4.48 (m, 1H), 4.34 (d, J=11.7 Hz, 1H), 3.84-3.76 (m, 1H), 2.33-2.21 (m, 1H), 2.19-2.09 (m, 1H), 1.91-1.75 (m, 2H).

Step 3: 2-(1-(benzyloxy)-4,4,4-trifluorobutyl)oxirane (B7-4)

B7-4

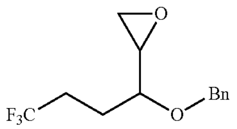

To a solution of (((6,6,6-trifluorohex-1-en-3-yl)oxy) methyl)benzene (B7-3) (4.8 g, 19.65 mmol) in DCM (120 mL) was added m-CPBA (6.78 g, 39.3 mmol) at 0° C. The mixture was stirred at 0° C. to 40° C. for 16 h. TLC (petroleum ether:EtOAc=10:1) showed the starting material was consumed and a new spot was detected. The reaction mixture was diluted with saturated $NaHCO_3$ (200 mL) and saturated $Na_2$S203 (200 mL), then extracted with DCM (3×150 mL). The combined organic phases were dried over anhydrous $Na_2SO_4$, filtered and concentrated. The residue was purified by flash silica gel chromatography (ISCO®; 80 g SepaFlash® Silica Flash Column, eluent of 5-7% EtOAc/petroleum ether gradient) to give the title compound.

Step 4: 2-(1-(benzyloxy)-4,4,4-trifluorobutyl)oxetane (B7-5)

B7-5

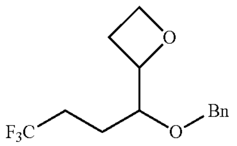

To a solution of potassium tert-butoxide (3.13 g, 27.9 mmol) in t-BuOH (76 mL) was added trimethylsulfoxonium iodide (6.13 g, 27.9 mmol) at 15° C., and the mixture was heated to 60° C. and a solution of (((6,6,6-trifluorohex-1-en-3-yl)oxy)methyl)benzene (B7-3) (2.9 g, 11.14 mmol) in t-BuOH (16 mL) was added to the above mixture. Then the mixture was stirred at 60° C. for 14 h. TLC showed the reaction was completed and the new spot was found. The reaction mixture was cooled to rt then quenched with $H_2O$ (100 mL). The aqueous layer was extracted with EtOAc (100 mL×3). The combined organic extracts were washed with saturated brine solution (100 mL) then dried over $Na_2SO_4$, filtered and concentrated. The residue was purified by flash silica gel chromatography (ISCO®; 80 g SepaFlash® Silica Flash Column, eluent of 15% EtOAc/petroleum ether gradient) to the title compound. H-NMR (400 MHz, $CDCl_3$, ppm): δ 7.43-7.23 (m, 5H), 4.96-4.76 (m, 2H), 4.74-4.61 (m, 2H), 4.59-4.49 (m, 1H), 3.72-3.62 (m, 1H), 2.77-2.45 (m, 2H), 2.37-2.06 (m, 2H), 1.81-1.57 (m, 2H).

Step 5: 4,4,4-trifluoro-1-(oxetan-2-yl)butan-1-ol (B7-6)

B7-6

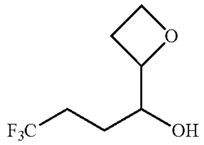

To a solution of 2-(1-(benzyloxy)-4,4,4-trifluorobutyl) oxetane (B7-5) (2.9 g, 10.57 mmol) in MeOH (60 mL) was added Pd—C (1.125 g, 1.057 mmol) and stirred at 50° C. under H2 (45 psi) for 4 h. The mixture was filtered and the filtrate was concentrated to give the title compound. The product was checked by HNMR. HNMR showed it was the desired product. H-NMR (400 MHz, $CDCl_3$, ppm): δ 4.80-4.57 (m, 2H), 4.53-4.39 (m, 1H), 3.78-3.58 (m, 1H), 3.15-2.95 (m, 1H), 2.75-2.55 (m, 1H), 2.52-2.27 (m, 2H), 2.21-2.06 (m, 1H), 1.62-1.42 (m, 2H).

Step 6: 4,4,4-trifluoro-1-(oxetan-2-yl)butyl methanesulfonate (B7-7)

B7-7

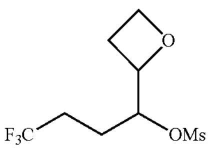

To a solution of 4,4,4-trifluoro-1-(oxetan-2-yl)butan-1-ol (B7-6) (1.4 g, 7.60 mmol) in DCM (30 mL) was added $Et_3N$ (3.18 mL, 22.81 mmol), then MsCl (0.889 mL, 11.40 mmol) was added to the mixture at 0° C. The mixture was stirred at 0° C.-15° C. for 2 h. TLC (petroleum ether:EtOAc=1:1) showed the starting material was consumed and a new spot was detected. The reaction mixture was quenched with $H_2O$ (50 mL). The aqueous layer was extracted with DCM (50 mL×3). The combined organic extracts were washed with saturated brine solution (30 mL) then dried over $Na_2SO_4$, filtered and concentrated to give a crude product as the title compound. The crude product was direct move to the next step without purification. H-NMR (400 MHz, $CDCl_3$, ppm): δ 4.89-4.74 (m, 2H), 4.72-4.63 (m, 1H), 4.58-4.43 (m, 1H), 3.20-3.09 (m, 3H), 2.80-2.61 (m, 1H), 2.82-2.41 (m, 1H), 2.39-2.17 (m, 2H), 1.87-1.68 (m, 2H).

Step 7: 2-(1-azido-4,4,4-trifluorobutyl)oxetane (B7-8)

B7-8

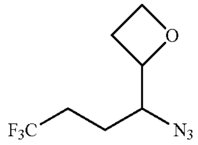

To a solution of 4,4,4-trifluoro-1-(oxetan-2-yl)butyl methanesulfonate (B7-7) (2 g, 7.63 mmol) in DMF (20 mL) was added sodium azide (0.992 g, 15.25 mmol) at 15° C. and the mixture was stirred at 60° C. for 3 h. TLC showed the reaction was completed and a new spot was found. The reaction mixture was poured into water (50 mL) and extracted with EtOAc (30 mL×3), the organic was washed by saturated brine (30 mL). The organic layer was dried over $Na_2SO_4$, filtered and concentrated. The residue was purified by flash silica gel chromatography (ISCO®; 20 g Sepa-Flash® SilicaFlash Column, eluent of 27% ethyl acetate/petroleum ether gradient at 35 mL/min) to give the title compound. H-NMR (400 MHz, $CDCl_3$, ppm): δ 4.86-4.75 (m, 1H), 4.73-4.66 (m, 1H), 4.64-4.55 (m, 1H), 3.70-3.41 (m, 1H), 2.78-2.51 (m, 2H), 2.38-2.10 (m, 2H), 1.76-1.54 (m, 2H).

Step 8: 4,4,4-trifluoro-1-(oxetan-2-yl)butan-1-amine (Intermediate B7)

Intermediate B7

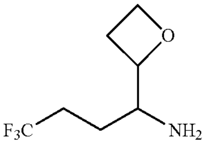

To a solution of 2-(1-azido-4,4,4-trifluorobutyl)oxetane (B7-8) (750 mg, 3.59 mmol) in MeOH (40 mL) was added Pd—C (382 mg, 0.359 mmol) and stirred at 20° C. under H2 (30 psi) for 4 h. The mixture was filtered and the filtrate was concentrated to give the title compound. HNMR showed it was the desired product. H-NMR (400 MHz, $CD_3OD$, ppm): δ 4.76 (br s, 2H), 4.62-4.44 (m, 2H), 4.39 (dtd, J=4.4, 6.0, 9.0 Hz, 1H), 2.84-2.74 (m, 1H), 2.61-2.35 (m, 2H), 2.33-2.22 (m, 1H), 2.17-2.04 (m, 1H), 1.67-1.50 (m, 1H), 1.37-1.24 (m, 1H).

Intermediate B8: (S)—N-ethyl-2,2,2-trifluoro-1-(3-(8-methoxyimidazo[1,2-a]pyrazin-6-yl)phenyl)ethan-1-amine Intermediate B8

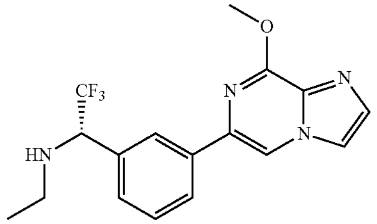

The (S)—N-ethyl-2,2,2-trifluoro-1-(3-(4,4,5,5-tetramethyl-1,3,2-dioxaborolan-2-yl)phenyl)ethan-1-amine (Intermediate B4) was converted to the title compound using the procedure in step 2 in the synthesis of Intermediate A5. MS: 351.2 [M+1].

Intermediate B9: (S)—N-ethyl-2,2,2-trifluoro-1-(3-(imidazo[1,2-a]pyridin-6-yl)-4-methoxyphenyl)ethan-1-amine Intermediate B9

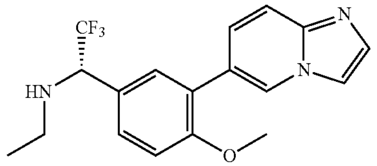

Step 1: 1-(3-bromo-4-methoxyphenyl)-N-ethyl-2,2,2-trifluoroethan-1-amine (B9-2)

B9-2

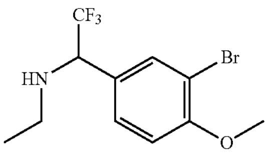

The 1-(3-bromo-4-methoxyphenyl)-2,2,2-trifluoroethan-1-one (B9-1) was converted to the title compound using the procedure in step 7 in the synthesis of Intermediate $B_2$. MS: 313.2 [M+1].

Step 2: N-ethyl-2,2,2-trifluoro-1-(3-(imidazo[1,2-a]pyridin-6-yl)-4-methoxyphenyl)ethan-1-amine (B9-3)

B9-3

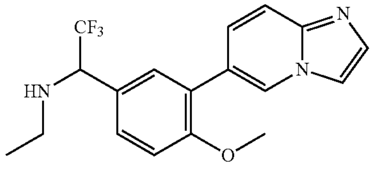

The 1-(3-bromo-4-methoxyphenyl)-N-ethyl-2,2,2-trifluoroethan-1-amine (B9-2) was converted to the title compound using the procedure in step 2 in the synthesis of Intermediate A5. MS: 350.1 [M+1].

Step 3: (S)—N-ethyl-2,2,2-trifluoro-1-(3-(imidazo[1,2-a]pyridin-6-yl)-4-methoxyphenyl)ethan-1-amine (Intermediate B9)

Intermediate B9

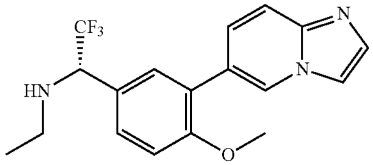

N-ethyl-2,2,2-trifluoro-1-(3-(imidazo[1,2-a]pyridin-6-yl)-4-methoxyphenyl)ethan-1-amine (B9-3) was resolved via Prep-SFC using the following conditions: IC column (2×25 cm), 25% isopropanol (0.2% NPA)/$CO_2$, 100 bar, 60 mL/min, 220 nM. The title compound eluted as the second peak. MS: 350.1 [M+1].

Intermediate B10: trans-2-methyl-2-(trifluoromethyl)cyclopropan-1-amine

Intermediate B10

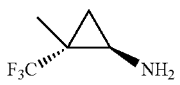

Step 1: ethyl 2-diazo-3,3,3-trifluoropropanoate (B10-2)

10-2

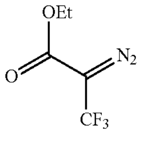

To a mixture of ethyl 3,3,3-trifluoro-2-oxopropanoate (10-1) (10 g, 64.1 mmol) in $CH_2Cl_2$ (80 mL) was added 4-methylbenzenesulfonhydrazide (12.29 g, 66.0 mmol). The resulting mixture was stirred at 20° C. under $N_2$ protection for 16 h. Pyridine (20.73 mL, 256 mmol) was added to the mixture. Then, $POCl_3$ (6.15 mL, 66.0 mmol) was added to the mixture dropwise. New spots were found on TLC. Then washed with $NH_4Cl$ (200 mL), extracted with DCM (50 mL×3), washed with $NaHCO_3$ (200 mL), washed with brine (100 mL). The organic layer was dried over $Na_2SO_4$, filtered and the filtrate was concentrated. The crude product was distillated under 80° C. to give the title compound.

Step 2: ethyl 2-(4-methoxyphenyl)-1-(trifluoromethyl)cyclopropane-1-carboxylate (10-3)

10-3

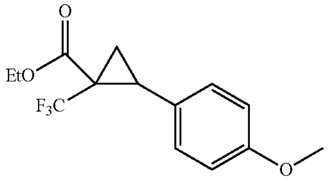

To a mixture of 1-methoxy-4-vinylbenzene (14.97 g, 112 mmol) and rhodium (ii) acetate dimer (1.644 g, 3.72 mmol) in DCM (100 mL) was added ethyl 2-diazo-3,3,3-trifluoropropanoate (B10-2) (12.5 g, 74.4 mmol) in DCM (20 mL) at 15° C. within 14 h. New spots were found on TLC. The mixture was filtered and the filtrate was concentrated. The crude product was purified by flash silica gel chromatography (ISCO®; 120 g SepaFlash® Silica Flash Column, eluent of 100% petroleum ether gradient) to give the title compound.

Step 3: trans-2-(4-methoxyphenyl)-1-(trifluoromethyl)cyclopropyl)methanol (10-4) and cis-2-(4-methoxyphenyl)-1-(trifluoromethyl)cyclopropyl)methanol (10-5)

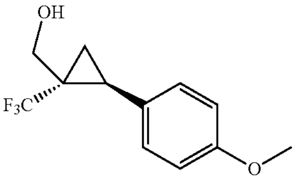

+

10-4

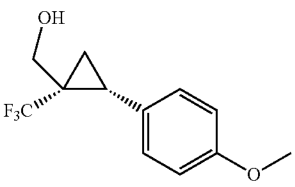

10-5

To a mixture of $LiAlH_4$ (0.889 g, 23.42 mmol) in THF (50 mL) was added ethyl 2-(4-methoxyphenyl)-1-(trifluoromethyl)cyclopropane-1-carboxylate (10-3) (5 g, 15.61 mmol) in THF (10 mL) at 0° C., the mixture was stirred at 0° C. under $N_2$ protection for 1 h. New spots were found on TLC. water (0.9 mL) was added to the mixture, 15% NaOH (0.9 mL) was added, then water (2.7 mL) was added as well. The mixture was dried over $MgSO_4$, filtered and the filtrate was concentrated. The crude product was purified by flash silica gel chromatography (ISCO®; 80 g SepaFlash® Silica Flash Column, eluent of 10% ETOAc gradient) to give the resolved title compounds.

Step 4: 1-((trans)-2-(bromomethyl)-2-(trifluoromethyl)cyclopropyl)-4-methoxybenzene (10-6)

10-6

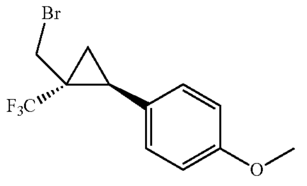

To a mixture of trans-2-(4-methoxyphenyl)-1-(trifluoromethyl)cyclopropyl)methanol (10-4) (1 g, 3.86 mmol) and triphenylphosphine (2.024 g, 7.72 mmol) in THF (15 mL) was added $CBr_4$ (1.919 g, 5.79 mmol). The mixture was stirred at 30° C. for 16 h. A new spot was found on TLC. Then washed with $H_2O$ (10 mL), extracted with EtOAc (20 mL×3), washed with brine (10 mL). The organic layer was dried over $Na_2SO_4$, filtered and the filtrate was concentrated. The residue was purified by flash silica gel chromatography (ISCO®; 12 g SepaFlash® Silica Flash Column, eluent of 100% petroleum ether gradient) to give the title compound.

Step 5: 1-methoxy-4-((trans)-2-methyl-2-(trifluoromethyl)cyclopropyl)benzene (10-7)

10-7

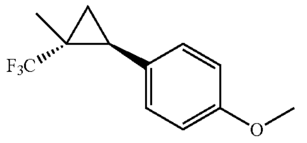

To a mixture of 1-((trans)-2-(bromomethyl)-2-(trifluoromethyl)cyclopropyl)-4-methoxybenzene (10-6) (5.8 g, 17.82 mmol) in DMSO (50 mL) was added $NaBH_4$ (1.349 g, 35.6 mmol), the resulting mixture was stirred at 70° C. under $N_2$ protection for 6 h. A new spot was found on TLC. Then washed with $H_2O$ (100 mL), extracted with EtOAc (50 mL×3), washed with brine (100 mL). The organic layer was dried over $Na_2SO_4$, filtered and the filtrate was concentrated. The residue was purified by flash silica gel chromatography (ISCO®; 40 g SepaFlash® Silica Flash Column, eluent of 100% PE gradient) to give the title compound. H-NMR (400 MHz, $CDCl_3$, ppm): δ 7.11 (d, J=8.1 Hz, 2H), 6.86 (d, J=8.6 Hz, 2H), 3.88-3.72 (m, 3H), 2.50 (dd, J=6.8, 9.3 Hz, 1H), 1.39 (dd, J=5.6, 9.5 Hz, 1H), 1.32-1.21 (m, 1H), 1.04-0.93 (m, 4H), 0.91-0.78 (m, 1H).

Step 6: trans-2-methyl-2-(trifluoromethyl)cyclopropane-1-carboxylic acid (10-8)

10-8

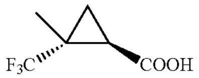

To a solution of 1-methoxy-4-((trans)-2-methyl-2-(trifluoromethyl)cyclopropyl)benzene (10-7) (1 g, 4.34 mmol) in $CCl_4$ (5 mL)/MeCN (5 mL)/water (5 mL) were added sodium periodate (9.29 g, 43.4 mmol) and rhodium (iii) chloride hydrate (0.049 g, 0.217 mmol) at 30° C. The mixture was stirred at 30° C. for 16 h. TLC analysis showed desired product. The reaction was diluted with $H_2O$ (20 mL) and extracted with EtOAc (20 mL×3), washed with brine (20 mL). The combined organic layers were dried over sodium sulfate, filtered and the filtrate was concentrated in vacuo. The residue was purified by flash silica gel chromatography (ISCO®; 40 g SepaFlash® Silica Flash Column, eluent of 50% EtOAc gradient) to give the title compound.

Step 7: benzyl ((trans)-2-methyl-2-(trifluoromethyl)cyclopropyl)carbamate (10-9)

10-9

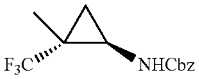

To a solution of trans-2-methyl-2-(trifluoromethyl)cyclopropane-1-carboxylic acid (10-8) (1.3 g, 7.73 mmol) in Toluene (20 mL) were added diphenylphosphoryl azide (1.995 mL, 9.28 mmol) and TEA (4.31 mL, 30.9 mmol) at 20° C. The mixture was stirred at 100° C. for 1 h. Then, benzyl alcohol (1.593 mL, 15.47 mmol) was added and stirred at 100° C. for 16 h. TLC showed desired product. The reaction was diluted with $H_2O$ (30 mL) and extracted with EtOAc (30 mL×3), washed with brine (20 mL). The combined organic layers were dried over sodium sulfate, filtered and the filtrate was concentrated in vacuo. The crude product was purified by flash silica gel chromatography (ISCO®; 40 g SepaFlash® Silica Flash Column, eluent of 20% EtOAc gradient) to give the title compound.

Step 8: trans-2-methyl-2-(trifluoromethyl)cyclopropan-1-amine (Intermediate B10)

Intermediate B10

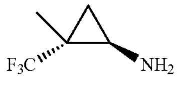

To a mixture of benzyl ((trans)-2-methyl-2-(trifluoromethyl)cyclopropyl)carbamate (10-9) (1.5 g, 3.84 mmol) (70% purity) in water (5 mL) was HCl (5 mL, 60.9 mmol) at 20° C. The mixture was stirred at 120° C. for 4 h. A new spot was found on TLC. The reaction was extracted with EtOAc (10 mL×3). The aqueous phase was concentrated to give the title compound. H-NMR (400 MHz, $CD_3OD$, ppm): δ 3.05 (dd, J=5.1, 8.6 Hz, 1H), 1.56-1.47 (m, 1H), 1.10 (t, J=5.7 Hz, 1H).

Intermediate B11: cis-2-methyl-2-(trifluoromethyl) cyclopropan-1-amine

Intermediate B11

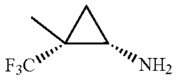

The cis-2-(4-methoxyphenyl)-1-(trifluoromethyl)cyclopropyl)methanol (10-5) was converted to the title compound via the procedure outlined in steps 4-8 in the synthesis of Intermediate B10. H-NMR (400 MHz, $CD_3OD$, ppm): δ 2.91-2.78 (m, 1H), 1.58-1.44 (m, 1H), 1.34-1.27 (m, 1H).

Intermediate B12: 5-(2-bromo-5-methoxypyridin-4-yl)-7-methoxypyrazolo[1,5-c]pyrimidine Intermediate B12

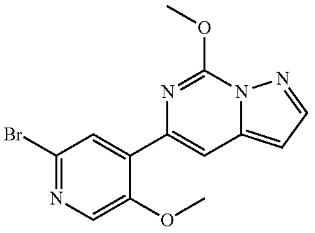

Step 1: 2-bromo-5-methoxyisonicotinaldehyde (12-2)

12-2

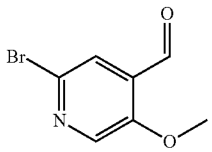

To a solution of 2-bromo-5-methoxypyridine (12-1) (10 g, 53.2 mmol) in THF (100 mL) was added lithium diisopropylamide (31.9 mL, 63.8 mmol) (2M in hexane) at −78° C. under $N_2$ and the solution was stirred at −78° C. for 1 h, then DMF (4.53 mL, 58.5 mmol) was added to the above solution at −78° C. The solution was stirred at −78° C. for 1 h. TLC showed the reaction completed. The mixture was quenched with water (100 mL) and extracted with EtOAc (100 mL×3), the combined organic layers were washed with brine (100 mL), dried over $Na_2SO_4$, filtered and concentrated in vacuo. The residue was purified by flash silica gel chromatography (ISCO®; 40 g SepaFlash® Silica Flash Column, eluent of 10% EtOAc gradient) to give the title compound. MS: 216.9 [M+1].

Step 2: 2-(2-bromo-5-methoxypyridin-4-yl)-2,3-dihydro-4H-pyran-4-one (12-3)

12-3

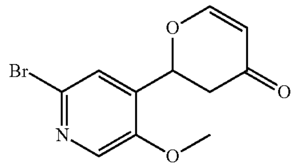

A solution of zinc chloride (1.741 mL, 1.741 mmol) (1 M in ether) was added to a solution of (E)-((4-methoxybuta-1,3-dien-2-yl)oxy)trimethylsilane (3 g, 17.41 mmol) and 2-bromo-5-methoxyisonicotinaldehyde (12-2) (4.51 g, 20.89 mmol) in toluene (100 mL) at 20° C. After stirring for 30 min, water (50 mL) and TFA (3 mL) were added, and the mixture was stirred vigorously for 20 min. TLC showed new spot was appeared. After concentration, the residue was partitioned between EtOAc (50 mL) and water (50 mL). The separated organic layer was washed with brine (50 mL), dried over $Na_2SO_4$, filtered. The filtrate was concentrated and purified by flash silica gel chromatography (ISCO®; 20 g SepaFlash® Silica Flash Column, eluent of 30% EtOAc gradient) give the title compound. MS: 283.9 [M+1].

Step 3: 2-(2-bromo-5-methoxypyridin-4-yl)-4H-pyran-4-one (12-4)

12-4

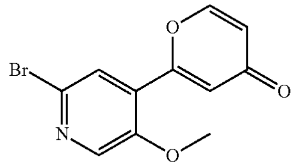

To a solution of 2-(2-bromo-5-methoxypyridin-4-yl)-2,3-dihydro-4H-pyran-4-one (12-3) (500 mg, 1.760 mmol) in toluene (5 mL) was added DDQ (799 mg, 3.52 mmol). The reaction was stirred at 90° C. for 16 h. TLC showed starting material was consumed and new spot was appeared. The mixture was filtered and concentrated. The crude was purified by flash silica gel chromatography (ISCO®; 8 g SepaFlash® Silica Flash Column, eluent of 30% EtOAc gradient) give the title compound. H-NMR (500 MHz, $CDCl_3$, ppm): δ 8.21 (s, 1H), 7.94-7.75 (m, 2H), 7.25 (d, J=2.3 Hz, 1H), 6.41 (dd, J=2.4, 6.0 Hz, 1H), 4.12 (s, 3H). MS: 283.9 [M+1].

Step 4: 5-(2-bromo-5-methoxypyridin-4-yl)pyrazolo [1,5-c]pyrimidine-7-thiol (12-5)

12-5

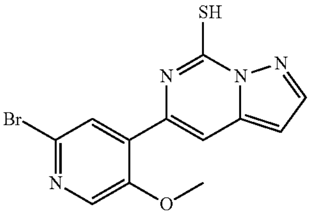

To a mixture of 2-(2-bromo-5-methoxypyridin-4-yl)-4H-pyran-4-one (12-4) (50 mg, 0.177 mmol) and hydrazinecarbothioamide (24.23 mg, 0.266 mmol) in MeOH (2 mL) was added HCl (4 N in MeOH) (0.02 mL) at 0° C. under $N_2$, then the mixture was stirred at 0° C. for 15 min, 20° C. for 15 min and 80° C. for 1 h. LCMS showed desired product was found. Combined batches were concentrated directly and purified by HPLC (Instrument EJ Method Column Boston Green ODS (150×30 m, 5 um, 30-50% CAN/water with 0.1% TFA as a modifier) to afford the title compound. MS: 336.9 [M+1].

Step 5: 5-(2-bromo-5-methoxypyridin-4-yl)-7-(methylthio)pyrazolo[1,5-c]pyrimidine (12-6)

12-6

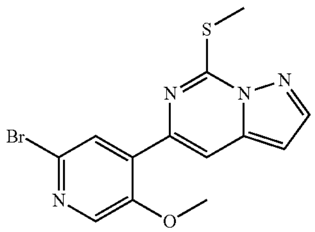

To a mixture of 5-(2-bromo-5-methoxypyridin-4-yl)pyrazolo[1,5-c]pyrimidine-7-thiol (12-5)(250 mg, 0.741 mmol) and sodium hydroxide (148 mg, 3.71 mmol) in MeOH (8 mL) and $H_2O$ (4 mL) was added iodomethane (0.232 mL, 3.71 mmol). Then the mixture was stirred at 15° C. for 1 h. LCMS showed the desired compound was found. The mixture was filtered and the filter cake was collected to give the title compound, which was used next step directly. MS: 352.9 [M+1].

Step 6: 5-(2-bromo-5-methoxypyridin-4-yl)-7-(methylsulfonyl)pyrazolo[1,5-c]pyrimidine (12-7)

12-7

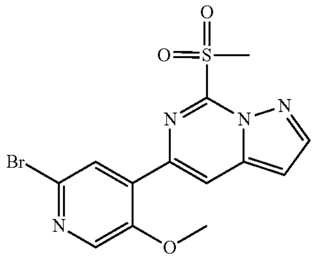

To a solution of 5-(2-bromo-5-methoxypyridin-4-yl)-7-(methylthio)pyrazolo[1,5-c]pyrimidine (12-6) (220 mg, 0.626 mmol) in DCM (3 mL) was added m-CPBA (463 mg, 1.879 mmol) and the mixture was stirred at 15° C. for 3 h. LCMS showed desired product was found. Saturated solution of $Na_2SO_3$ (10 mL) was added and the mixture was extracted with DCM (5 mL×3). The organic layer was washed with brine, dried with $Na_2SO_4$ and the solvent removed under vacuum. The crude was purified by TLC (DCM:MeOH=1 5:1) to give the title compound. MS: 384.8 [M+1].

Step 7: 5-(2-bromo-5-methoxypyridin-4-yl)-7-methoxypyrazolo[1,5-c]pyrimidine (Intermediate B12)

Intermediate B12

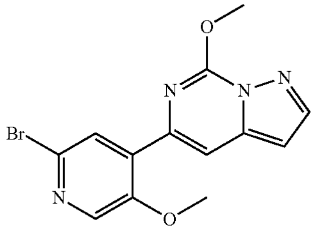

To a solution of 5-(2-bromo-5-methoxypyridin-4-yl)-7-(methylsulfonyl)pyrazolo[1,5-c]pyrimidine (12-7) (90 mg, 0.235 mmol) in MeOH (3 mL) was added sodium methoxide (19.03 mg, 0.352 mmol) was added and the mixture was stirred at 15° C. for 2 h. LCMS showed desired compound was found. The mixture was quenched with water (2 mL) and filtered. The filter cake was collected and purified by TLC (DCM/MeOH=20:1) to give the title compound. H-NMR (500 MHz, $CDCl_3$, ppm): δ 8.31-8.24 (m, 1H), 8.16 (s, 1H), 8.13 (s, 1H), 8.07 (d, J=2.0 Hz, 1H), 6.64 (d, J=2.1 Hz, 1H), 4.32 (s, 3H), 4.00 (s, 3H). MS: 336.9 [M+1].

Intermediate B13: 1-(4,4-difluoro-1-methylpiperidin-2-yl)-2,2,2-trifluoroethan-1-amine Intermediate B13

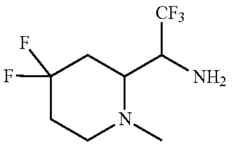

Step 1: tert-butyl 4,4-difluoropiperidine-1-carboxylate (B13-2)

B13-2

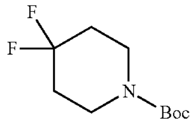

To a solution of tert-butyl 4-oxopiperidine-1-carboxylate (B13-1) (50 g, 251 mmol) in anhydrous DCM (300 mL) was added DAST (99 mL, 753 mmol) at −40° C. The resulting mixture was stirred at 22° C. under $N_2$ protection for 2 h. TLC (petroleum ether:EtOAc=5:1) showed the starting material was consumed. The reaction mixture was poured into ice water (500 mL), extracted with DCM (500 mL×3). The organic layer was washed with saturated aq. $NaHCO_3$ (500 mL), dried over $Na_2SO_4$, then filtered and concentrated. The crude product was purified by flash silica gel chromatography (ISCO®; 120 g Biotage® Silica Flash Column, Eluent of 15% EtOAc/petroleum ether gradient) to give the title compound. H-NMR (400 MHz, $CDCl_3$, ppm): δ 3.53 (br s, 4H), 1.91 (br s, 4H), 1.53-1.32 (m, 9H).

Step 2: tert-butyl 4,4-difluoro-2-formylpyridine-1-carboxylate (B13-3)

B13-3

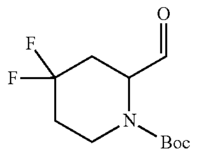

To a solution of tert-butyl 4,4-difluoropiperidine-1-carboxylate (B13-2) (11 g, 49.7 mmol) in $Et_2O$ (462 mL) was added TMEDA (10.40 g, 89 mmol). Then s-butyllithium (1.3 M in cyclohexane) (68.8 mL, 89 mmol) was dropped dropwise at −78° C. for 1 h under $N_2$. After stirred for 1 h at −78° C., DMF (7.27 g, 99 mmol) was added and stirred for 30 min. TLC showed starting material was consumed completely and a new spot was formed. The resulting mixture was poured into aqueous saturated $NH_4Cl$ (300 mL) and extracted with $Et_2O$ (300 mL×3). The organic layer was washed with brine (300 mL), dried over $Na_2SO_4$. After filtration and concentration, the residue was purified by flash silica gel chromatography (ISCO®; 120 g SepaFlash® Silica Flash Column, eluent of 5-27% ethyl acetate/petroleum ether gradient) to give the title compound. H-NMR (400 MHz, $CDCl_3$, ppm): δ 9.54 (d, J=1.5 Hz, 1H), 4.90-4.56 (m, 1H), 4.20-3.83 (m, 1H), 3.17 (br s, 1H), 2.67-2.52 (m, 1H), 2.28-2.05 (m, 1H), 2.00-1.75 (m, 2H), 1.45 (br s, 9H).

Step 3: tert-butyl 2-(E)-(((R)-tert-butylsulfinyl) imino)methyl)-4,4-difluoropiperidine-1-carboxylate (B13-4)

B13-4

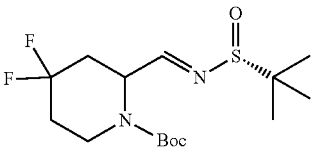

To a solution of tert-butyl 4,4-difluoro-2-formylpiperidine-1-carboxylate (B13-3) (8.6 g, 34.5 mmol) in DCE (100 mL) were added (R)-2-methylpropane-2-sulfinamide (6.27 g, 51.8 mmol), magnesium sulfate (41.5 g, 345 mmol) and PPTS (0.867 g, 3.45 mmol). The reaction mixture was stirred at 80° C. for 24 h. TLC showed a new spot was detected. The reaction mixture was filtered. The filtrate was concentrated and purified by flash silica gel chromatography (ISCO®; 120 g SepaFlash® Silica Flash Column, eluent of 0-23% ethyl acetate/petroleum ether gradient@35 mL/min) to give the title compound. H-NMR (400 MHz, $CDCl_3$, ppm): δ 7.98-7.86 (m, 1H), 5.28 (br d, J=6.5 Hz, 1H), 4.27-4.12 (m, 1H), 3.28-2.99 (m, 1H), 2.65 (br s, 1H), 2.46-2.19 (m, 1H), 1.96 (br dd, J=5.1, 12.4 Hz, 1H), 1.49 (s, 9H), 1.23 (d, J=9.8 Hz, 9H)

Step 4: tert-butyl 2-(1-(((R)-tert-butylsulfinyl) amino)-2,2,2-trifluoroethyl)-4,4-difluoropiperidine-1-carboxylate (B13-5)

B13-5

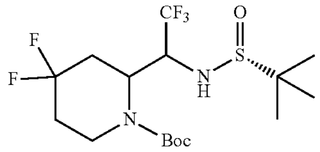

To a solution of 3 (7 g, 19.86 mmol) and TMAF (2.77 g, 29.8 mmol) in anhydrous DCM (150 mL) was added $TMSCF_3$ (8.47 g, 59.6 mmol) slowly at −30° C. The resulting mixture was slowly warmed to −20° C. within 2 h. LCMS showed desired mass was detected. TLC showed desired MS was found. The reaction mixture was poured into aq. $NH_4Cl$ (100 mL), extracted with EtOAc (100 mL×3). The organic layer was washed with brine (100 mL), dried over $Na_2SO_4$, then filtered and concentrated. The residue was purified by flash silica gel chromatography (ISCO®; 120 g SepaFlash® Silica Flash Column, eluent of 5-20% ethyl acetate/petroleum ether gradient) to give the title compound. MS: 423.4 [M+1].

Step 5: (R)—N-(1-(4,4-difluoro-1-methylpiperidin-2-yl)-2,2,2-trifluoroethyl)-2-methylpropane-2-sulfinamide (13-6)

B13-6

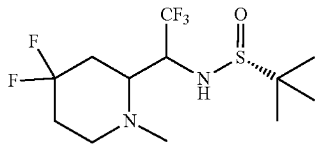

To a solution of tert-butyl 2-(1-(((R)-tert-butylsulfinyl) amino)-2,2,2-trifluoroethyl)-4,4-difluoropiperidine-1-carboxylate (B13-5) (6 g, 4.26 mmol) in anhydrous THF (50 mL) was added LAH (0.647 g, 17.04 mmol). The resulting mixture was stirred at 75° C. for 16 h. TLC (PE:EtOAc=1:1) showed the starting material was consumed. water (20 drops) was added into the stirred mixture and kept stirring for 5 min. The reaction mixture was diluted with THF (50 mL) and then $Na_2SO_4$ (25 g) was added. It's filtered and concentrated. The residue was purified by flash silica gel chromatography (ISCO®; 120 g SepaFlash® Silica Flash Column, eluent of 15-30% ethyl acetate/petroleum ether gradient) to give 5 (1 g, 2.97 mmol, 69.8% yield) as a solid. H-NMR (400 MHz, $CDCl_3$, ppm): δ 4.24 (br s, 1H), 4.11 (br t, J=7.0 Hz, 1H), 2.97 (br d, J=11.7 Hz, 1H), 2.69 (br d, J=12.1 Hz, 1H), 2.55 (br t, J=12.1 Hz, 1H), 2.35 (s, 3H), 2.20-1.83 (m, 4H), 1.25 (s, 9H). MS: 337.0 [M+1].

Step 6: 1-(4,4-difluoro-1-methylpiperidin-2-yl)-2,2,2-trifluoroethan-1-amine (Intermediate B13)

Intermediate B13

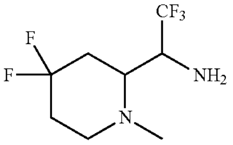

A solution of (R)—N-(1-(4,4-difluoro-1-methylpiperidin-2-yl)-2,2,2-trifluoroethyl)-2-methylpropane-2-sulfinamide (0.7 g, 2.081 mmol) (B13-6) in 4M HCl-MeOH (5 mL) was stirred at 20° C. for 2 h. LCMS showed desired mass observed. The resulting mixture was concentrated to give the crude title compound, which was used in next step without further purification. H-NMR (500 MHz, $CD_3OD$, ppm): δ 4.60-4.47 (m, 1H), 4.00 (br dd, J=1.3, 12.9 Hz, 1H), 3.78-3.69 (m, 1H), 3.60-3.46 (m, 1H), 3.05 (s, 3H), 2.63-2.28 (m, 4H). MS: 233.0 [M+1].

Intermediate B14: 5-amino-6,6,6-trifluorohexan-2-one

Intermediate B14

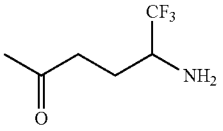

Step 1: ethyl 4-oxopentanoate (B14-2)

B14-2

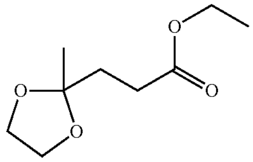

To a solution of ethane-1,2-diol (7.15 g, 115 mmol) and ethyl 4-oxopentanoate (B14-1) (10 g, 77 mmol) in toluene (300 mL) were added p-toluenesulfonic acid (0.225 g, 1.306 mmol), the mixture was stirred at 130° C. for 12 h. TLC (petroleum ether:EtOAc=3:1) showed new spots were found. The reaction mixture was poured into sat. $NaHCO_3$ (300 mL) and extracted with EtOAc (200 mL×3). The combined organic layers were washed with brine (200 mL), dried over $Na_2SO_4$. After filtration and concentration, the residue was purified by flash silica gel chromatography (ISCO®; 80 g SepaFlash® Silica Flash Column, eluent of 10% ethyl acetate/petroleum ether gradient@35 mL/min) to give the title compound. H-NMR (400 MHz, $CDCl_3$, ppm): δ 3.95-3.85 (m, 4H), 3.70-3.60 (m, 3H), 2.36 (t, J=7.7 Hz, 2H), 2.00-1.93 (m, 2H), 1.33-1.26 (m, 3H)

Step 2: 342-methyl-1,3-dioxolan-2-yl)propanal (B14-3)

B14-3

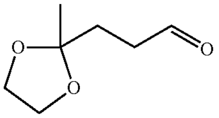

To a solution of ethyl 4-oxopentanoate (B14-2) (5 g, 28.7 mmol) in DCM (50 mL) was added 1 M solution of DIBAL-H (43.1 mL, 43.1 mmol) in toluene at −78° C., the resulting mixture was stirred at −78° C. under $N_2$ protection for half an h. TLC (petroleum ether:EtOAc=3:1) showed the starting material was consumed and a new spot was detected. The reaction was poured into water (50 mL), extracted with DCM (50 mL×3). The combined organic phases were washed with brine (100 mL), and dried over $Na_2SO_4$. The organic layer was filtered and concentrated to give the crude product as the title compound, which was used to next step without further purification.

Step 3: (E)-2-methyl-N-(3-(2-methyl-1,3-dioxolan-2-yl)propylidene)propane-2-sulfinamide (B14-4)

B14-4

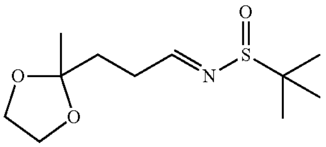

To a solution of 3-(2-methyl-1,3-dioxolan-2-yl)propanal (B14-3) (3.1 g, 21.50 mmol) in DCE (80 mL) added 2-methylpropane-2-sulfinamide (1.303 g, 10.75 mmol), PPTS (0.270 g, 1.075 mmol), $MgSO_4$ (3.88 g, 32.3 mmol). The reaction mixture was stirred at 80° C. for 8 h. LCMS showed the desired mass was found. TLC (petroleum ether: EtOAc=2:1) showed the starting material was consumed and a new spot was detected. The reaction mixture was filtered to the crude product, the crude product was purified by flash silica gel chromatography (ISCO®; 20 g SepaFlash® Silica Flash Column, Eluent of 25% EtOAc/petroleum ether gradient) to give the title compound. H-NMR (400 MHz, $CDCl_3$) δ 8.08 (t, J=4.4 Hz, 1H), 3.98-3.88 (m, 4H), 2.65-2.56 (m, 2H), 2.01-1.94 (m, 2H), 1.35-1.29 (m, 3H), 1.19-1.13 (m, 9H). MS: 247.6 [M+1].

Step 4: 2-methyl-N-(1,1,1-trifluoro-4-(2-methyl-1,3-dioxolan-2-yl)butan-2-yl)propane-2-sulfinamide (B14-5)

B14-5

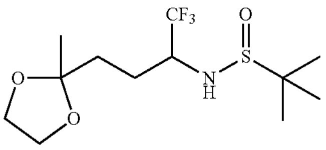

To a solution of (E)-2-methyl-N-(3-(2-methyl-1,3-dioxolan-2-yl)propylidene)propane-2-sulfinamide (B14-4) (500 mg, 2.021 mmol) and tetrabutylammonium difluorotriphenylsilicate (2728 mg, 5.05 mmol) in THF (20 mL) was added (trifluoromethyl)trimethylsilane (1437 mg, 10.11 mmol) at −40° C. The reaction mixture was stirred at −40° C. for 1 h. TLC (petroleum ether:EtOAc=1:1) showed the starting material was consumed and a new spot was detected. The reaction was poured into water (30 mL), extracted with EtOAc (30 mL×3). The combined organic phases were washed with brine (50 mL), and dried over $Na_2SO_4$. After filtration and concentration, the residue was purified by flash silica gel chromatography (ISCO®; 4 g SepaFlash® Silica Flash Column, eluent of 31% ethyl acetate/petroleum ether gradient@35 mL/min) to give the title compound. H-NMR 1011053-064-1 (400 MHz, $CDCl_3$) δ 4.03-3.92 (m, 4H), 3.80-3.71 (m, 1H), 2.02-1.91 (m, 2H), 1.75 (br s, 1H), 1.65-1.55 (m, 1H), 1.37-1.30 (m, 3H), 1.26-1.22 (m, 9H).

Step 5: 5-amino-6,6,6-trifluorohexan-2-one (Intermediate B14)

Intermediate B14

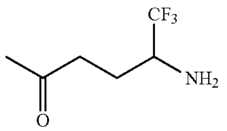

To a solution of 2-methyl-N-(1,1,1-trifluoro-4-(2-methyl-1,3-dioxolan-2-yl)butan-2-yl)propane-2-sulfinamide (B14-5) (70 mg, 0.221 mmol) in MeOH (3 mL) was added ACETYL CHLORIDE (34.6 mg, 0.441 mmol), and the mixture was stirred at 20° C. for 2 h. TLC (petroleum ether:EtOAc=1:1) showed the starting material was consumed. The reaction was concentrated to give the title compound, which was used to next step without further purification.

Intermediate B15: (1R)-1-(4,4-difluorotetrahydro-2H-pyran-2-yl)propan-1-amine Intermediate B15

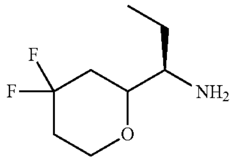

Step 1: benzyl (R)-(1-(methoxy(methyl)amino)-1-oxobutan-2-yl)carbamate (B15-2)

B15-2

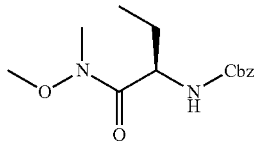

To a solution of (R)-2-(((benzyloxy)carbonyl)amino)butanoic acid (B15-1) (2 g, 8.43 mmol) in DCM (20 mL) were added triethylamine (3.41 g, 33.7 mmol) and HATU (4.81 g, 12.64 mmol) and stirred at 25° C. for 30 min. N,O-dimethylhydroxylamine hydrochloride (1.233 g, 12.64 mmol) was added to the above solution and stirred at 25° C. for 2 h. TLC (petroleum ether:EtOAc=1:1) showed the reaction was completed. The reaction mixture was poured into water (50 mL), extracted with EtOAc (50 mL×3). The organic layer was washed with brine (50 mL), dried over $Na_2SO_4$ and filtered. The filtrate was concentrated and purified by flash silica gel chromatography (ISCO®; 20 g SepaFlash® Silica Flash Column, eluent of 0-20% ethyl acetate/petroleum ether gradient@45 mL/min) to give the title compound.

Step 2: benzyl (R)-(1-oxobutan-2-yl)carbamate (B15-3)

B15-3

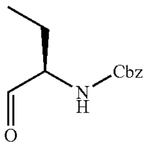

To a solution of benzyl (R)-(1-(methoxy(methyl)amino)-1-oxobutan-2-yl)carbamate (B15-2) (2 g, 7.13 mmol) in THF (20 mL) was added $LiAlH_4$ (0.812 g, 21.40 mmol) at 0° C. and stirred at 0° C. for 1 h. TLC (petroleum ether:EtOAc=3:1) showed the reaction was complete. The reaction mixture was poured into water (50 mL), extracted with EtOAc (40 mL×3). The organic layer was washed with brine (50 mL), dried over $Na_2SO_4$ and filtered. The filtrate was concentrated and purified by flash silica gel chromatography (ISCO®; 12 g SepaFlash® Silica Flash Column, eluent of 0-35% ethyl acetate/petroleum ether gradient@30 mL/min) to give the title compound.

Step 3: benzyl ((1R)-1-(4-hydroxytetrahydro-2H-pyran-2-yl)propylcarbamate (B15-4)

B15-4

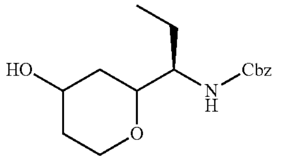

To a stirred solution of but-3-en-1-ol (0.163 g, 2.260 mmol) and benzyl (R)-(1-oxobutan-2-yl)carbamate (B15-3) (1 g, 4.52 mmol) in DCM (10 mL) was added TFA (1.480 mL, 19.21 mmol) at 0° C. Then the solution was warmed to 20° C. slowly and stirred at 20° C. for 14 h. The solvent was concentrated in vacuo, and the residue was taken up in MeOH (10 mL) and added $K_2CO_3$ (1.562 g, 11.30 mmol), the mixture was stirred at 20° C. for 2 h. TLC (petroleum ether:EtOAc=1:1) showed the reaction was complete. The mixture was filtered and concentrated to give crude product. The crude product was purified by flash silica gel chromatography (ISCO®; 20 g SepaFlash® Silica Flash Column, eluent of 0-45% ethyl acetate/petroleum ether gradient) to give the title compound.

Step 4: benzyl ((1R)-1-(4-oxotetrahydro-2H-pyran-2-yl)propyl)carbamate (B15-5)

B15-5

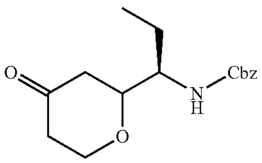

To a solution of benzyl ((1R)-1-(4-hydroxytetrahydro-2H-pyran-2-yl)propyl)carbamate (B15-4) (700 mg, 2.386 mmol) in DCM (2 mL) was added DMP (1012 mg, 2.386 mmol) and stirred at 20° C. for 3 h. TLC (petroleum ether:EtOAc=1:1) showed the reaction was complete. The reaction mixture was filtered and concentrated to give crude product. The crude product was purified by (ISCO®; 12 g SepaFlash® Silica Flash Column, eluent of 0-30% ethyl acetate/petroleum ether gradient@30 mL/min) to give the title compound.

Step 5: benzyl ((1R)-1-(4,4-difluorotetrahydro-2H-pyran-2-yl)propylcarbamate (B15-6)

B15-6

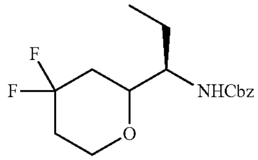

To a solution of benzyl ((1R)-1-(4-oxotetrahydro-2H-pyran-2-yl)propyl)carbamate (B15-5) (430 mg, 1.476 mmol) in DCM (5 mL) was added DAST (0.390 mL, 2.95 mmol) slowly at −40° C. and stirred at −40° C. to 20° C. for 3 h. TLC (petroleum ether:EtOAc=3:1) showed the reaction was complete. The reaction mixture was poured into water (10 mL), extracted with EtOAc (20 mL×3). The organic layer was washed with brine (10 mL), dried over $Na_2S04$ and filtered. The filtrate was concentrated and purified by flash silica gel chromatography (ISCO®; 12 g SepaFlash® Silica Flash Column, eluent of 10-15% ethyl acetate/petroleum ether gradient) to give the title compound.

Step 6: (1R)-1-(4,4-difluorotetrahydro-2H-pyran-2-yl)propan-1-amine (Intermediate B15)

Intermediate B15

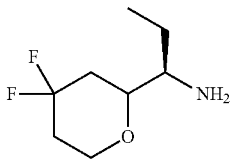

To a solution of benzyl ((1R)-1-(4,4-difluorotetrahydro-2H-pyran-2-yl)propyl)carbamate (B15-6) (370 mg, 1.181 mmol) in MeOH (10 mL) was added Pd/C (126 mg, 1.181 mmol) and stirred at 20° C. under H2 (50 psi) for 15 h. LCMS showed the reaction was complete. The reaction mixture was filtered and concentrated to give crude product as the title compound.

Intermediate B15: 3-(1-ethoxycyclopropyl)-1,1,1-trifluoropropan-2-amine

Intermediate B15

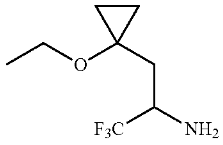

Step 1: 1-(2,2-diethoxyethyl)cyclopropan-1-01 (B15-2)

B15-2

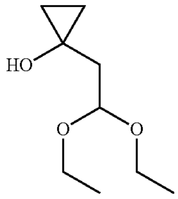

A solution of ethylmagnesium bromide (49.9 mL, 150 mmol) in THF (100 mL) were added to a solution of ethyl 3,3-diethoxypropanoate (B15-1) (9.5 g, 49.9 mmol) and tetraisopropoxytitanium (2.84 g, 9.99 mmol) in THF (100 mL) at 0° C. over a period of 3 h with stirring. Then the mixture was stirred at 18° C. for 12 h. TLC (petroleum ether:EtOAc=3:1) showed that new spots were found. The reaction mixture was poured into $NH_4Cl$ (100 mL), extracted with DCM (300 mL×3). The combined organic phases were dried over $Na_2SO_4$, then filtered and concentrated. The residue was purified by flash silica gel chromatography (ISCO®; 120 g SepaFlash® Silica Flash Column, eluent of 9% EtOAc gradient) to give the title compound.

Step 2: 1-(2,2-diethoxyethyl)-1-ethoxycyclopropane (B15-3)

B15-3

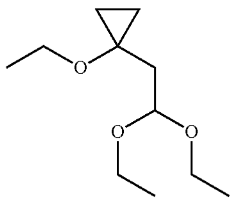

To a mixture of 1-(2,2-diethoxyethyl)cyclopropan-1-ol (B15-2) (2 g, 11.48 mmol) and iodoethane (3.58 g, 22.96 mmol) in DMF (30 mL) was added NaH (0.459 g, 11.48 mmol) at 0° C. The solution was stirred at 0° C. for 0.5 h. TLC (petroleum ether:EtOAc=3:1) showed the reaction completed. The mixture was quenched with water (150 mL) and extracted with EtOAc (50 mL×3). The combined organic layers were washed with brine (100 mL), dried over $Na_2SO_4$, then filtered and concentrated in vacuo. The residue was purified by flash silica gel chromatography (ISCO®; 40 g SepaFlash® Silica Flash Column, eluent of 17% EtOAc gradient) to give the title compound.

Step 3: 2-(1-ethoxycyclopropyl)acetaldehyde (B15-4)

B15-4

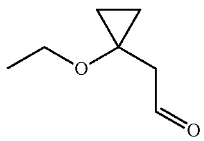

To a mixture of 1-(2,2-diethoxyethyl)-1-ethoxycyclopropane (B15-3) (750 mg, 3.71 mmol) in THF (1 mL) was added hydrogen chloride (1 mL, 2.00 mmol, 2M) at 0° C. and the solution was stirred at 0° C. for 30 min. TLC (petroleum ether:EtOAc=5:1) showed the reaction completed. The mixture was quenched with water (15 mL) and extracted with EtOAc (20 mL×3). The combined organic layers were washed with brine (10 mL), dried over $Na_2SO_4$, filtered and concentrated to give the title compound, which was used in next step that without further purification.

Step 4: 3-(1-ethoxycyclopropyl)-1,1,1-trifluoropropan-2-amine (Intermediate B15)

Intermediate B15

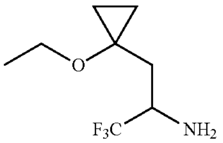

The title compound was prepared by following the procedures outlined in steps 3-5 in the synthesis of Intermediate B14. MS: 198.0 [M+1].

Intermediate B16: 1-(4,4-difluorotetrahydro-2H-pyran-2-yl)-2,2,2-trifluoroethan-1-amine Intermediate B16

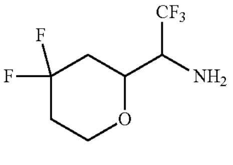

Step 1: 2-((benzyloxy)methyl)-2,3-dihydro-4H-pyran-4-one (B16-2)

B16-2

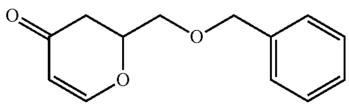

A flame-dried flask was charged with a solution of lithium methoxide (0.063 g, 1.665 mmol) in DMF (4.0 mL) and this was cooled to 0° C. and treated with the 1-methoxy-3-trimethylsiloxy-1,3-butadiene (4.70 mL, 24.14 mmol) as a solution in DMF (12 mL), then 2-(benzyloxy)acetaldehyde (B16-1) (2.339 mL, 16.65 mmol) was added as a solution in DMF (24 mL). The reaction contents were held at −4° C. for 18 h. This was quenched with sat. $NH_4Cl$ (5 mL). EtOAc (10 mL) was added and the organic portion was washed with sat. brine (5 mL) followed by water (5 mL). The organic layer was dried ($Na_2SO_4$), filtered and concentrated to an oil. This was dissolved in ether (40.0 mL), cooled to 0° C. and treated with TFA (7.5 mL) slowly and stirred for 1 h. The TFA mixture was poured into a flask containing sat. $NaHCO_3$ (50 mL). This was diluted with DCM (100 mL), washed with sat. brine (50 mL), dried ($Na_2SO_4$), filtered and concentrated to give an oil. This was purified via chromatography (silica gel, 0-50% 3:1 EtOAc:EtOH/hexanes) to afford the title compound. MS: 219.2 [M+1].

Step 2: 2-((benzyloxy)methyl)tetrahydro-4H-pyran-4-one (B16-3)

B16-3

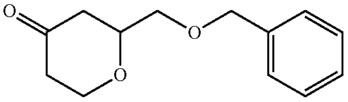

The 2-((benzyloxy)methyl)-2,3-dihydro-4H-pyran-4-one (B16-2) (1.0 g, 4.58 mmol) was dissolved in ethyl acetate (22.91 mL) and treated with TEA (1.916 mL, 13.75 mmol) followed by 10% palladium on carbon (0.244 g, 0.229 mmol) and inundated with H2 via a balloon (1 atm) and stirred at ambient temperature for 18 h. This was filtered through a bed of celite and concentrated to give an oil. This was purified via chromatography (silica gel, 0-30% EtOAc/hexanes) to afford the title compound. MS: 221.3 [M+1].

Step 3: 2-((benzyloxy)methyl)-4,4-difluorotetrahydro-2H-pyran (B16-4)

B16-4

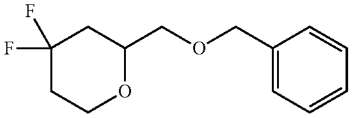

The 2-((benzyloxy)methyl)tetrahydro-4H-pyran-4-one (B16-3) (0.962 g, 4.37 mmol) was dissolved in DCM (21.84 mL) and treated with DAST (2.308 mL, 17.47 mmol) and stirred at ambient temperature for 18 h. The reaction contents were concentrated under vacuum to give an oil. This was purified via chromatography (silica gel, 0-30% 3:1 EtOAc:EtOH/hexanes) to afford the title compound.

Step 4: (4,4-difluorotetrahydro-2H-pyran-2-yl)methanol (B16-5)

B16-5

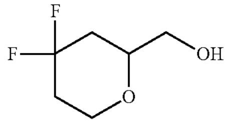

The 2-((benzyloxy)methyl)-4,4-difluorotetrahydro-2H-pyran (B16-4) (0.250 g, 1.032 mmol) was dissolved in THF (10.32 mL) and treated with 10% palladium on carbon (0.220 g, 0.206 mmol). This was inundated with hydrogen (2.080 mg, 1.032 mmol) at 40 psi and shaken via a Parr shaker for 18 h. This was filtered through a bed of celite and washed with ether and concentrated, carefully (keeping vacuum under 50 mbar) to give the title compound.

Step 5: 4,4-difluorotetrahydro-2H-pyran-2-carbaldehyde (B16-6)

B16-6

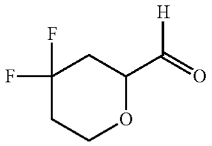

A flame-dried vial was charged with oxalyl chloride (2.0 M in DCM) (0.619 mL, 1.238 mmol) which was dissolved in DCM (1 mL) and cooled to −78° C. To this, DMSO (0.168 mL, 2.373 mmol) was added drop-wise. The mixture was stirred, −78° C., for 15 min, then treated with (4,4-difluorotetrahydro-2H-pyran-2-yl)methanol (B16-5) (0.157 g, 1.032 mmol) in DCM (1 mL) was added slowly via syringe and this was stirred, −78° C. for 30 min. TEA (0.662 mL, 4.75 mmol) was added and the ice bath was removed and the contents were stirred at ambient temperature for 45 min. This was diluted with $CH_2Cl_2$ (25 mL), washing with sat. $NaHCO_3$ (25 mL) followed by sat. $NH_4Cl$ (25 mL) and water (25 mL), and dried ($Na_2SO_4$), filtered and concentrated carefully under vacuum (>50 mbar) to give the title compound.

Step 6: 1-(4,4-difluorotetrahydro-2H-pyran-2-yl)-2,2,2-trifluoroethan-1-amine (Intermediate B16)

Intermediate B16

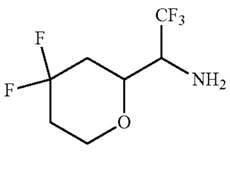

The title compound was prepared by following the procedures outlined in steps 3-5 in the synthesis of Intermediate B13. MS: 220.3 [M+1].

Intermediate B17: 4-amino-5,5,5-trifluoropentan-2-one

Intermediate B17

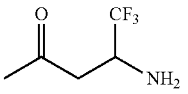

Step 1: 2-methyl-N-(1,1,1-trifluoro-4-oxopentan-2-yl)propane-2-sulfinamide (B17-2)

B17-2

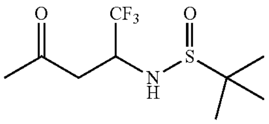

(E)-2-methyl-n-(2,2,2-trifluoroethylidene)propane-2-sulfinamide (B17-1) (0.250 g, 1.243 mmol) was dissolved in DCM (6.21 mL), cooled to −78° C. and treated with isopropenyloxytrimethylsilane (0.194 g, 1.491 mmol) followed by titanium tetrachloride (1.0 M in DCM) (0.497 mL, 0.497 mmol) and stirred, −78° C., under $N_2$ for 15 min. This was treated with water (20 mL) and extracted with 3:1 $HCCl_3$:IPA (50 mL×3), and dried by filtering through a hydrophobic frit and evaporating to give the title compound which was used without further purification. MS: 261.2 [M+1].

Step 2: 4-amino-5,5,5-trifluoropentan-2-one (Intermediate B17)

Intermediate B17

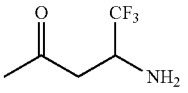

The 2-methyl-N-(1,1,1-trifluoro-4-oxopentan-2-yl)propane-2-sulfinamide (B17-2) (50 mg, 0.193 mmol) was dissolved in MeOH (964 μl) and treated with HCl (4.0 M in dioxane) (63.3 μl, 0.771 mmol) and stirred, at ambient temperature for 18 h. The contents of the reaction was concentrated under a stream of nitrogen to afford the title compound which was used without further purification.

Intermediate B18: (S)-1,1,1-trifluoro-4-(methylsulfonyl)butan-2-amine

Intermediate B18

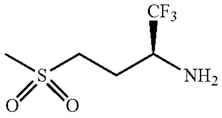

Step 1: (R)-2-methyl-N—((S)-1,1,1-trifluoro-4-(methylthio)butan-2-yl)propane-2-sulfinamide (B18-2)

B18-2

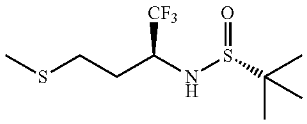

The title compound was prepared from 3-(methylthio) propanal (B18-1) by following the procedures outlined in steps 2-3 in the synthesis of Intermediate B5. MS: 278.2 [M+1].

Step 2: (R)-2-methyl-N—((S)-1,1,1-trifluoro-4-(methylsulfonyl)butan-2-yl)propane-2-sulfinamide (B18-3)

B18-3

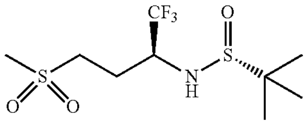

The (R)-2-methyl-N—((S)-1,1,1-trifluoro-4-(methylthio) butan-2-yl)propane-2-sulfinamide (B18-2) (0.340 g, 1.226 mmol) was dissolved in DCM (9.43 mL) and treated with m-CPBA (70-75% in water) (0.604 g, 2.452 mmol) and stirred at ambient temperature 4 hrs. This was diluted with $CH_2Cl_2$ (20 mL), washed with water (20 mL) followed by sat. NaCl (20 mL), dried ($Na_2SO_4$), filtered and evaporated to give an oil. This was purified via chromatography (silica, 0-100%, 3:1 EtOAc:EtOH/hexanes, 40 mL/min, 19 min) to afford the title compound. MS: 310.3 [M+1].

Step 3: (S)-1,1,1-trifluoro-4-(methylsulfonyl)butan-2-amine (Intermediate B18)

Intermediate B18

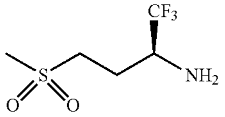

The (R)-2-methyl-N—((S)-1,1,1-trifluoro-4-(methylsulfonyl)butan-2-yl)propane-2-sulfinamide (B18-3) (0.138 g, 0.446 mmol) was dissolved in MeOH (2.230 mL) and treated with HCl (4.0 M in dioxane) (0.446 mL, 1.784 mmol) and stirred at ambient temperature for 2 h. The contents of the reaction was concentrated under a stream of nitrogen to afford the title compound which was used without further purification.

Intermediate B19: 3-(2-amino-3,3,3-trifluoropropyl)oxazolidin-2-one

Intermeditate B19

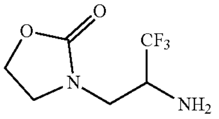

Step 1: 2-((tert-butoxycarbonyl)amino)-3,3,3-trifluoropropyl 4-methylbenzenesulfonate (B19-2)

B19-2

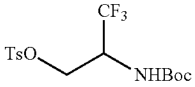

The tert-butyl (1,1,1-trifluoro-3-hydroxypropan-2-yl)carbamate (B19-1) (1.0 g, 4.36 mmol) was dissolved in DCM (11.76 mL), cooled to 0° C. and treated with Tosyl-$C_1$ (1.240 mL, 6.54 mmol) and stirred, 0-15° C. for 7 hrs. This was diluted with DCM (20 mL), washing with sat. brine (20 mL), dried ($Na_2SO_4$), filtered and evaporated to give an oil. This was purified via reverse phase chromatography (C18 column, 35-60% $CH_3CN$/water with 0.1% TFA) to afford the title compound. MS: 384.3 [M+1].

Step 2: tert-butyl (1,1,1-trifluoro-3-(2-oxooxazolidin-3-yl)propan-2-yl)carbamate (B19-3)

B19-3

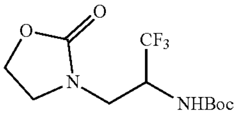

A sealable vial was charged with 2-((tert-butoxycarbonyl) amino)-3,3,3-trifluoropropyl 4-methylbenzenesulfonate (B19-2) (98 mg, 0.256 mmol) which was dissolved in DMF (1278 µl) and treated with Cesium carbonate (250 mg, 0.767 mmol) and 2-oxazolidone (44.5 mg, 0.511 mmol). The vial was capped and the reaction contents were heated to 70° C. and stirred for 4 hrs. This was diluted with EtOAc (10 mL), washed with water (10 mL), dried ($Na_2SO_4$), filtered and evaporated to give an oil. This was purified via chromatography (silica, 0-50%, 3:1 EtOAc:EtOH/hexanes) to give the title compound. MS: 299.2 [M+1].

Step 3: 3-(2-amino-3,3,3-trifluoropropyl)oxazolidin-2-one (Intermediate B19)

Intermediate B19

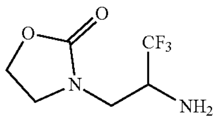

The tert-butyl (1,1,1-trifluoro-3-(2-oxooxazolidin-3-yl)propan-2-yl)carbamate (B19-3) (46.8 mg, 0.157 mmol) was dissolved in 4 M HCl in dioxane (4615 μl) and stirred at ambient temperature for 4 h. This was concentrated under vacuum to give the title compound and used without further purification.

Intermediate B20: (8-methoxy-2-methylimidazo[1,2-a]pyrazin-6-yl)boronic acid Intermediate B20

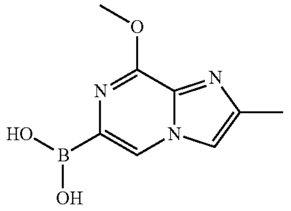

6-bromo-8-methoxy-2-methylimidazo[1,2-a]pyrazine (B20-1) (200 mg, 0.793 mmol), bis(pinacolato)diboron (254 mg, 1.000 mmol), potassium acetate (234 mg, 2.380 mmol), and [1,1'-bis(diphenylphosphino)ferrocene]dichloropalladium(II), complex with dichloromethane (32.4 mg, 0.040 mmol) were combined in degassed dioxane (8 mL) and heated at 90° C. for 3 h. The reaction was filtered through a pad of celite and concentrated to afford the title compound. MS: 208.1 [M+1].

Intermediate B21: N-ethyl-2,2,2-trifluoro-1-(5-methoxy-4-(8-methoxy-2-methylimidazo[1,2-a]pyrazin-yl)pyridin-2-yl)ethan-1-amine Intermediate B21

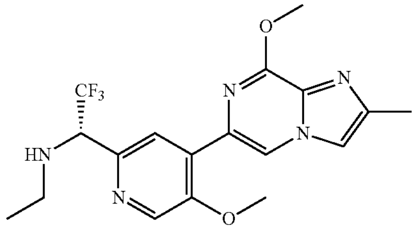

Step 1: 1-(4-bromo-5-methoxypyridin-2-yl)-2,2,2-trifluoroethan-1-ol (B21-2)

B21-2

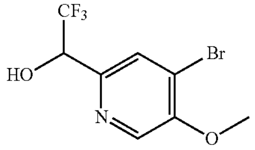

To a solution of 4-bromo-5-methoxypicolinaldehyde (B21-1) (5.00 g, 23.14 mmol) in DMF (50 mL) at ambient temperature was added (trifluoromethyl)trimethylsilane (6.84 mL, 46.3 mmol), followed by potassium carbonate (0.640 g, 4.63 mmol), and the solution was stirred for 18 h. The mixture was quenced by the slow addition of 1 M HCl (25 mL) and stirred for 1 h. The mixture was poured onto water (50 mL) and extracted with $Et_2O$ (6×30 mL). The combined organics were dried over $Na_2SO_4$, filtered, and concentrated to afford the title compound. MS: 286.0, 288.0 [M+1].

Step 2: 1-(4-bromo-5-methoxypyridin-2-yl)-2,2,2-trifluoroethane-1,1-diol (B21-3)

B21-3

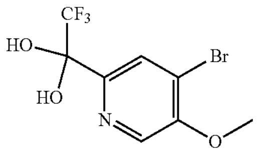

A suspension of 1-(4-bromo-5-methoxypyridin-2-yl)-2,2,2-trifluoroethan-1-ol (B21-2) (6.62 g, 23.14 mmol) and manganese dioxide (10.06 g, 116 mmol) in dioxane (100 mL) was stirred at 100° C. for 50 h. Additional manganese dioxide (2.00 g) was added after 24 h. The mixture was filtered hot though a pad of silica gel, rinsing with EtOAc (3×50 mL). The filtrates were concentrated and dried to afford the title compound. MS: 302.0, 304.0 [M+]).

Step 3: 1-(4-bromo-5-methoxypyridin-2-yl)-N-ethyl-2,2,2-trifluoroethan-1-amine (B21-4)

B21-4

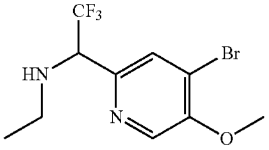

A 1 M solution of titanium(IV) chloride in toluene (42.6 mL, 42.6 mmol) was added dropwise over 30 min to a solution of 1-(4-bromo-5-methoxypyridin-2-yl)-2,2,2-trifluoroethane-1,1-diol (B21-3) (6.43 g, 21.29 mmol) in toluene (100 mL). A 2 M solution of ethylamine in THF (53.2 mL, 106 mmol) was then added dropwise and the flask sealed and stirred at 90° C. for 18 h. The solution was cooled to ambient temperature and solid sodium cyanoborohydride (4.01 g, 63.9 mmol) was added and stirring continued for 1 h at ambient temperature. The solution was quenched by the slow addition of MeOH until hydrogen evolution ceased, then neutralized with the slow addition of 50% aqueous NaOH until the pH >7. The resulting mixture was filtered through a pad of celite, rinsing with EtOAc (3×75 mL). The filtrates were concentrated and the crude purified by column chromatography on silica gel (120 g Isco gold column), eluting with hexanes:EtOAc/EtOH (3:1) 100:0 to 0:100 to afford the title compound. MS: 313.1, 315.1 [M+1].

Step 4: N-ethyl-2,2,2-trifluoro-1-(5-methoxy-4-(8-methoxy-2-methylimidazo[1,2-a]pyrazin-6-yl)pyridin-2-yl)ethan-1-amine (Intermediate B21)

Intermediate B21

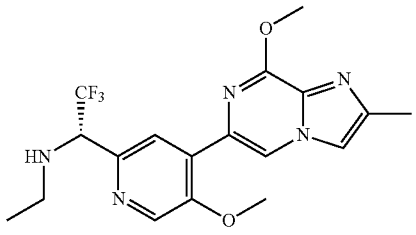

A solution of 1-(4-bromo-5-methoxypyridin-2-yl)-N-ethyl-2,2,2-trifluoroethan-1-amine (B21-4) (3.0 g, 9.58 mmol), (8-methoxy-2-methylimidazo[1,2-a]pyrazin-6-yl) boronic acid (Intermediate B20) (2.82 g, 13.61 mmol), and 1 M aqueous potassium phosphate (19.16 mL, 19.16 mmol) in dioxane (100 mL) was degassed. Chloro(2-dicyclohexylphosphino-2',4',6'-tri-i-propyl-1,1'-biphenyl)(2'-amino-1,1'-biphenyl-2-yl)palladium(II) (0.754 g, 0.958 mmol) was added and the mixture was heated at 55° C. for 3.5 h. The reaction mixture was filtered through a pad of celite, concentrated, and purified by column chromatography on silica gel (330 g Isco gold column), eluting with Hexanes:EtOAc/EtOH (3:1) 100:0 to 0:100 to afford the title compound. MS: 396.3 [M+1]. The enantiomers were separated by SFC chiral chromatography on an ES Industries AS-H column (30 mm×250 mm; 5 micron), eluting with 15% MeOH (0.1% DEA) in $CO_2$ at 80 mL/min (100 bar).

Intermediate B22: 1-(5-bromo-6-methoxypyridin-3-yl)-N-ethyl-2,2,2-trifluoroethan-1-amine Intermediate B22

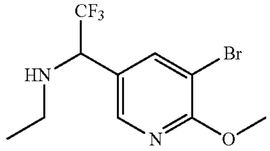

The title compound was prepared from 5-bromo-6-methoxynicotinaldehyde (B22-1) via the procedures outlined in steps 1-4 in the synthesis of Intermediate B21. MS: 313.0, 313.5 [M+1].

Intermediate B23: N-ethyl-2,2,2-trifluoro-1-(6-methoxy-5-(8-methoxyimidazo[1,2-a]pyrazin-6-yl)pyridin-3-yl)ethan-1-amine Intermediate B23

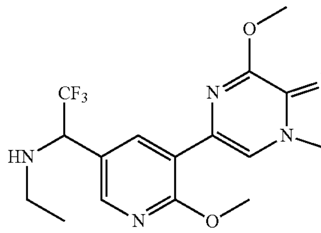

To a solution of 1-(5-bromo-6-methoxypyridin-3-yl)-N-ethyl-2,2,2-trifluoroethan-1-amine (Intermediate B22) (120 mg, 0.383 mmol) in dioxane (2 mL) and water (0.5 mL) was added potassium carbonate (106 mg, 0.766 mmol), 8-methoxy-6-(4,4,5,5-tetramethyl-1,3,2-dioxaborolan-2-yl) imidazo[1,2-a]pyrazine (Intermediate B1) (89 mg, 0.460 mmol) and $PdCl_2$(dppf) (28.0 mg, 0.038 mmol), the mixture was stirred at 90° C. for 2 h. LCMS showed the desired mass was formed and TLC (petroleum ether:EtOAc=0:1) showed the new spots were formed. The mixture was poured into water (10 mL), extracted with EtOAc (3 mL×3). The combined organic phases were washed with brine (10 mL), and dried over $Na_2SO_4$. After filtration and concentration, the residue was purified by prep-TLC (petroleum ether: EtOAc=0:1) to give the title compound. MS: 382.0 [M+1]. H-NMR (400 MHz, $CDCl_3$, ppm): δ 8.79 (s, 1H), 8.68 (d, J=2.0 Hz, 1H), 8.17 (d, J=2.3 Hz, 1H), 7.67 (d, J=4.3 Hz, 2H), 5.29 (s, 1H), 4.28-4.21 (m, 3H), 4.18-4.10 (m, 3H), 2.72-2.58 (m, 2H), 1.13 (t, J=7.0 Hz, 3H). Intermediate B24: 7-methoxy-5-(4,4,5,5-tetramethyl-1,3,2-dioxaborolan-2-yl) pyrazolo[1,5-a]pyridine Intermediate B24

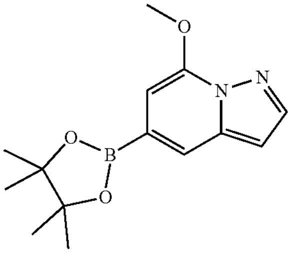

The title compound was prepared from 5-bromo-7-methoxypyrazolo[1,5-a]pyridine (Intermediate A3) using the procedure outlined in step 2 in the synthesis of Intermediate B1. MS: 275.2 [M+1].

Intermediate B25: (8-methoxy-[1,2,4]triazolo[1,5-a] pyrazin-6-yl)boronic acid

Intermediate B25

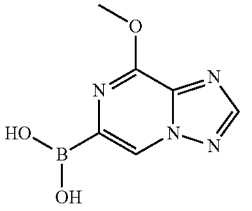

Step 1: 6-bromo-8-methoxy-[1,2,4]triazolo[1,5-a] pyrazine (B25-2)

B25-1

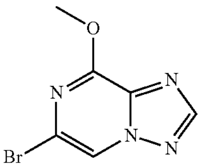

The title compound was prepared from 6-bromo-8-chloro-[1,2,4]triazolo[1,5-a]pyrazine (B25-1) using the procedure outlined in step 1 of the synthesis of Intermediate B1. H-NMR (500 MHz, $DCC_3$, ppm): δ 8.45-8.28 (m, 2H), 4.32-4.14 (m, 3H). MS: 230.8 [M+1].

Step 2: (8-methoxy-[1,2,4]triazolo[1,5-a]pyrazin-6-yl)boronic acid (Intermediate B25)

Intermediate B25

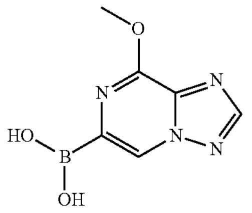

6-bromo-8-methoxy-[1,2,4]triazolo[1,5-a]pyrazine (B25-2) (500 mg, 2.183 mmol), hypodiboric acid (587 mg, 6.55 mmol), and cataCXium A-Pd-G2 (73.0 mg, 0.109 mmol) were combined in a screw cap vial. The vial was capped with a septum cap then degassed (3× pump/$N_2$). To this was added MeOH (10 mL) and DIEA (1.15 mL, 6.58 mmol). The gas inlet was removed then the mixture was heated to 50° C. After 2 h LC/MS indicates reaction complete. The mixture was cooled to ambient temperature, diluted with MeOH, filtered through a pad of celite washing with MeOH, and concentrated. The material was taken up in $Et_2O$ and sonicated until it turned over to a solid. The solid was collected by filtration, washed with $Et_2O$, then dried under vacuum. The solid was taken up in a small amount of $H_2O$ and sonicated for 2 min. The resulting solid was collected by filtration, washed with a small amount of $H_2O$, then air dried. The solid was taken up in MeOH and transferred to a round bottom flask then the mixture was concentrated to provide the title compound. MS: 195.1 [M+1].

Intermediate B26: N-ethyl-2,2,2-trifluoro-1-(7-(8-methoxyimidazo[1,2-a]pyrazin-6-yl)furo[3,2-b]pyridin-5-yl)ethan-1-amine Intermediate B26

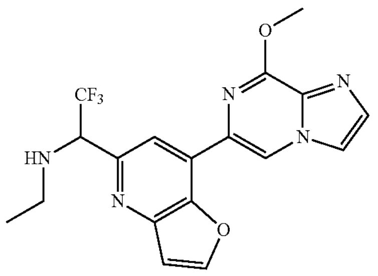

Step 1: 5-Methyl-2-(trimethylsilyl)furo[3,2-b]pyridine (B26-2)

B26-2

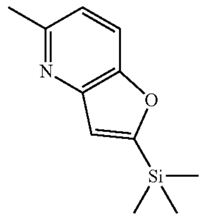

A solution of 2-iodo-6-methylpyridin-3-ol (B26-1) (3.1 g, 13.19 mmol) in a mixture of 1,4-dioxane (30 mL) and TEA (30 mL) was degassed (3× pump/$N_2$). To this was added ethynyltrimethylsilane (2.4 mL, 17.10 mmol), $(PPh_3)_2PdCl_2$ (0.463 g, 0.660 mmol), and CuI (0.126 g, 0.660 mmol). The mixture was degassed (3× pump/$N_2$) then heated to 45° C. for 18 h. The resulting mixture was cooled to ambient temperature then diluted with EtOAc. The mixture was filtered through a pad of Celite® washing with EtOAc then the filtrate was concentrated. The crude product was subjected to silica gel chromatography (ISCO® RediSep-Rf-80 g, 0-25% EtOAc/heptane, 15 minute gradient) to give the title compound. H-NMR (500 MHz, $CDCl_3$, ppm): δ 7.63 (d, J=8.4 Hz, 1H), 7.06 (d, J=0.9 Hz, 1H), 7.04 (d, J=8.4 Hz, 1H), 2.65 (s, 3H), 0.36 (s, 9H). MS: 206.1 [M+1].

Step 2: 5-Methyl-2-(trimethylsilyl)furo[3,2-b]pyridine 4-oxide (B26-3)

B26-3

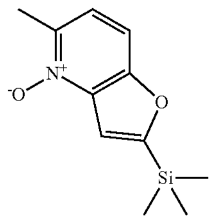

To a solution of 5-methyl-2-(trimethylsilyl)furo[3,2-b]pyridine (B26-2) (2.63 g, 12.81 mmol) in DCM (60 mL) was added m-CPBA (2.98 g, 17.29 mmol) at ambient temperature. After 4 h TEA (5.4 mL, 38.7 mmol) was added. After 5 min the mixture was concentrated. The crude product was subjected to silica gel chromatography (ISCO® RediSep-Rf-80 g, 0-100% 3:1 EtOAc:EtOH/heptane, 15 minute gradient) to give the title compound. H-NMR (500 MHz, $CDCl_3$, ppm): δ 7.39 (s, 1H), 7.38 (d, J=8.7 Hz, 1H), 7.13 (d, J=8.4 Hz, 1H), 2.63 (s, 3H), 0.37 (s, 9H). MS: 222.1 [M+1].

Step 3: 7-Chloro-5-methyl-2-(trimethylsilyl)furo[3,2-b]pyridine (B26-4)

B26-4

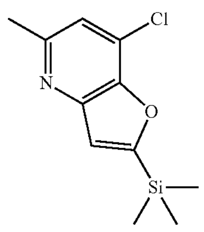

To a solution of 5-methyl-2-(trimethylsilyl)furo[3,2-b] pyridine 4-oxide (B26-3) (2.975 g, 13.44 mmol) in $CH_3CN$ (60 mL) was added $POCl_3$ (3.8 mL, 40.8 mmol) then the mixture was heated to reflux 18 h. The resulting mixture was cooled to ambient temperature then quenched by slow addition of saturated aqueous $NaHCO_3$. After the quench was complete the mixture was diluted with saturated aqueous $NaHCO_3$ then extracted with DCM (3×). The combined organic layers were dried ($MgSO_4$) then filtered through a short plug of silica gel washing with DCM. The filtrate was concentrated to give the title compound as an amber oil which was used as is in the next step. MS: 240.1 [M+1].

Step 4: 7-Chloro-5-methyl-2-(trimethylsilyl)furo[3,2-b]pyridine 4-oxide (B26-5)

B26-5

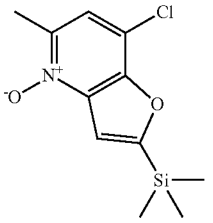

To a solution of crude 7-chloro-5-methyl-2-(trimethylsilyl)furo[3,2-b]pyridine (B26-4) (2.58 g, 10.76 mmol) in DCM (50 mL) was added m-CPBA (2.51 g, 14.55 mmol) at ambient temperature. After 2 h TEA (4.50 mL, 32.3 mmol) was added. After 5 min the mixture was concentrated. The crude product was subjected to silica gel chromatography (ISCO® RediSep-Rf-80 g, 0-100% 3:1 EtOAc:EtOH/heptane, 15 minute gradient) to give the title compound as a solid. MS: 256.0 [M+1].

Step 5: (7-Chlorofuro[3,2-b]pyridin-5-yl)methanol (B26-6)

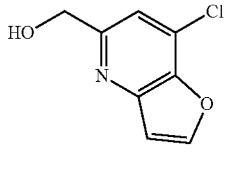 [SMILES: OCc1cc(Cl)c2occc2n1]

7-Chloro-5-methyl-2-(trimethylsilyl)furo[3,2-b]pyridine 4-oxide (B26-6) (2.39 g, 9.34 mmol) was taken up in $Ac_2O$ (45 mL) then the mixture was heated to 100° C. After 90 min the mixture was cooled to ambient temperature then concentrated. The residue was taken up in heptane then concentrated (2×) to give an amber oil. The oil was taken up in 45 mL of EtOH. To this was added 2M aqueous NaOH (14.1 mL, 28.2 mmol) at ambient temperature. After 90 min the mixture was concentrated. The residue was taken up in saturated aqueous $NH_4Cl$ then the mixture was extracted with EtOAc (3×). The combined organic layers were dried ($MgSO_4$), filtered, then the filtrate concentrated. The crude product was subjected to silica gel chromatography (ISCO® RediSep-Rf-80 g, 0-100% EtOAc/heptane, 15 minute gradient) to give the title compound. H-NMR (500 MHz, $CDCl_3$, ppm): δ 7.91 (d, J=2.3 Hz, 1H), 7.27 (s, 1H), 7.00 (d, J=2.3 Hz, 1H), 4.85 (d, J=5.1 Hz, 2H), 3.47 (t, J=5.3 Hz, 1H). MS: 183.9 [M+1].

Step 6: 7-Chlorofuro[3,2-b]pyridine-5-carbaldehyde (B26-7)

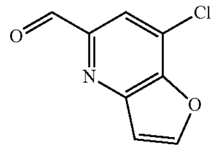 [SMILES: O=Cc1cc(Cl)c2occc2n1]

To a solution of (7-chlorofuro[3,2-b]pyridin-5-yl)methanol (B26-6) (1.32 g, 7.19 mmol) in $CHCl_3$ (35 mL) was added $MnO_2$ (3.13 g, 35.9 mmol) then the mixture was heated to reflux 18 h. The resulting mixture was cooled to ambient temperature then filtered through a pad of Celite® washing with $CHCl_3$. The filtrate was concentrated to give the title compound as a solid which was used as is in the next step. MS: 182.0 [M+1].

Step 7: 1-(7-Chlorofuro[3,2-b]pyridin-5-yl)-2,2,2-trifluoroethan-1-ol (B26-8)

B26-8

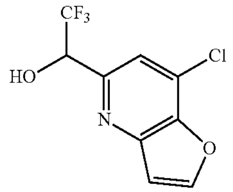

To a solution of 7-chlorofuro[3,2-b]pyridine-5-carbaldehyde (499 mg, 2.75 mmol) (B26-7) in DMF (10 mL) was added $K_2CO_3$ (76 mg, 0.550 mmol) then $TMSCF_3$ (0.82 mL, 5.55 mmol) at ambient temperature. After stirring 18 h 1 M HCl (10 mL) was added slowly and the mixture stirred at ambient temperature for 2.5 h. The resulting mixture was diluted with $H_2O$ then extracted with $Et_2O$ (3×). The combined organic layers were washed with brine then dried ($MgSO_4$) then filtered then the filtrate was concentrated to give the title compound as an orange oil which was used as is in the next step. MS: 252.0 [M+1].

Step 8: 1-(7-Chlorofuro[3,2-b]pyridin-5-yl)-2,2,2-trifluoroethane-1,1-diol (B26-9)

B26-9

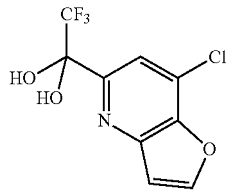

To a solution of crude 1-(7-chlorofuro[3,2-b]pyridin-5-yl)-2,2,2-trifluoroethan-1-ol (B26-8) (692 mg, 2.75 mmol) in EtOAc (20 mL) was added IBX (3.4 g, 5.50 mmol) then the mixture was heated to 80° C. 18 h. The resulting mixture was cooled to ambient temperature then diluted with EtOAc. The resulting mixture was filtered through a pad of Celite® washing with EtOAc then the filtrate was concentrated. The crude product was subjected to silica gel chromatography (ISCO® RediSep-Rf-80 g, 0-25% EtOAc/heptane, 15 minute gradient) to give the title compound. MS: 268.0 [M+1].

Step 9: 1-(7-Chlorofuro[3,2-b]pyridin-5-yl)-N-ethyl-2,2,2-trifluoroethan-1-amine (B26-10)

B26-10

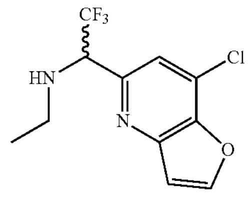

A screw cap vial was charged with 1-(7-chlorofuro[3,2-b]pyridin-5-yl)-2,2,2-trifluoroethane-1,1-diol (B26-9) (50 mg, 0.187 mmol) and toluene (0.8 mL). To this solution was added 1 M $TiCl_4$ (0.38 mL, 0.380 mmol) in toluene slowly at ambient temperature. After the addition was complete 2M ethylamine (0.47 mL, 0.940 mmol) in THF was added slowly at ambient temperature. During the addition the orange-red solution became a suspension. The vial was capped then the mixture heated to 90° C. 18 h. The resulting mixture was cooled to ambient temperature before sodium cyanoborohydride (36 mg, 0.573 mmol) and 0.4 mL MeOH was added. Stirring was continued at ambient temperature for 90 min then the mixture was quenched by addition of it to saturated $NaHCO_3$. The resulting mixture was diluted with $H_2O$ then extracted with DCM (3×). The combined organic layers were dried ($MgSO_4$) then filtered through a pad of Celite® washing with DCM. The filtrate was concentrated. The crude product was subjected to silica gel chromatography (ISCO® RediSep-Rf-12 g, 0-25% EtOAc/heptane, 10 minute gradient) to give the title compound as a clear oil. NMR: H-NMR (500 MHz, $CDCl_3$, ppm): δ 7.96 (d, J=2.2 Hz, 1H), 7.42 (s, 1H), 7.07 (d, J=2.2 Hz, 1H), 4.35 (q, J=7.3 Hz, 1H), 2.75-2.59 (m, 2H), 2.38 (s, 1H), 1.15 (t, J=7.1 Hz, 3H). MS: 279.1 [M+1].

Step 10: N-Ethyl-2,2,2-trifluoro-1-(7-(8-methoxyimidazo[1,2-a]pyrazin-6-yl)furo[3,2-b]pyridin-5-yl)ethan-1-amine (Intermediate B26)

Intermediate B26

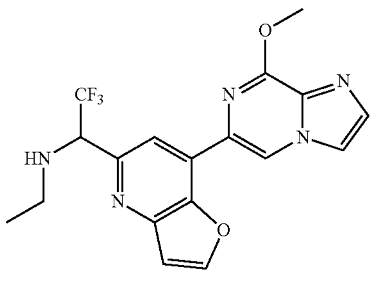

1-(7-Chlorofuro[3,2-b]pyridin-5-yl)-N-ethyl-2,2,2-trifluoroethan-1-amine (B26-9) (37 mg, 0.133 mmol), tetrahydroxydiboron (36 mg, 0.402 mmol), and CataCXium® A Pd G2 (5 mg, 7.48 μmol) were combined in a 10 mL round-bottom flask then the flask was sealed with a septa. The mixture was degassed (3× pump/$N_2$). Degassed MeOH (0.6 mL) and degassed DIEA (0.070 mL, 0.398 mmol) were added. The gas inlet was removed then the mixture heated to 50° C. After 3 h the mixture was removed from the heat and cooled to ambient temperature. The gas inlet was replaced. To this was added degassed 1 M $K_3PO_4$ (0.4 mL, 0.400 mmol) followed by 6-bromo-8-methoxyimidazo[1,2-a]pyrazine (Intermediate A1) (34 mg, 0.149 mmol) and CataCXium® A Pd G2 (5 mg, 7.48 μmol) under $N_2$. The gas inlet was removed then the mixture was heated to 50° C. 18 h. The resulting mixture was cooled to ambient temperature then diluted with EtOAc then filtered through a pad of Celite® washing with EtOAc. The filtrate was concentrated. The crude product was subjected to silica gel chromatography (ISCO® RediSep-Rf-12 g, 0-100% EtOAc/heptane, 15 minute gradient) to give the title compound. H-NMR (500 MHz, $CDCl_3$, ppm): δ 9.07 (s, 1H), 8.27 (s, 1H), 8.03 (d, J=2.3 Hz, 1H), 7.80 (d, J=1.0 Hz, 1H), 7.76 (d, J=1.0 Hz, 1H), 7.16 (d, J=2.3 Hz, 1H), 4.49 (q, J=7.5 Hz, 1H), 4.35 (s, 3H), 2.83-2.67 (m, 2H), 2.58 (s, 1H), 1.18 (t, J=7.1 Hz, 3H). MS: 392.2 [M+1].

Intermediate B27: N-Ethyl-2,2,2-trifluoro-1-(8-(8-methoxyimidazo[1,2-a]pyrazin-6-yl)imidazo[1,2-a]pyridin-6-yl)ethan-1-amine Intermediate B27

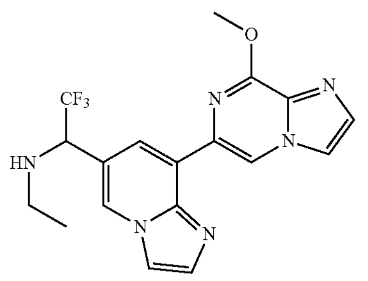

Step 1: 8-Chloro-6-(3,3,3-trifluoroprop-1-en-2-yl)imidazo[1,2-a]pyridine (B27-2)

B27-1

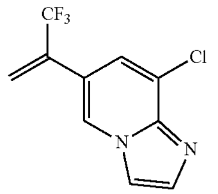

6-Bromo-8-chloroimidazo[1,2-a]pyridine (B27-1) (770 mg, 3.33 mmol), $PdCl_2$(dppf) (122 mg, 0.166 mmol), DME (10 mL) and 1 M $K_3PO_4$ (6.65 mL, 6.65 mmol) were charged into a 50 mL round bottom flask then the flask was sealed with a rubber septum. The mixture was degassed (3× pump/$N_2$). 4,4,6-trimethyl-2-(3,3,3-trifluoroprop-1-en-2-yl)-1,3,2-dioxaborinane (886 mg, 3.99 mmol) was added via syringe. The gas inlet was removed then the mixture was heated to 60° C. 18 h. The resulting mixture was cooled to ambient temperature then diluted with EtOAc then filtered through a pad of Celite® washing with EtOAc. The filtrate was concentrated. The crude product was subjected to silica gel chromatography (ISCO® RediSep-Rf-80 g, 0-50% EtOAc/heptane, 15 minute gradient) to give the title compound as a solid. H-NMR (500 MHz, $CDCl_3$, ppm): δ 8.22 (s, 1H), 7.76-7.73 (m, 1H), 7.71 (s, 1H), 7.38 (s, 1H), 6.12 (s, 1H), 5.93-5.89 (m, 1H).

Step 2: 1-(8-Chloroimidazo[1,2-a]pyridin-6-yl)-2,2,2-trifluoroethane-1,1-diol (B27-3)

B27-3

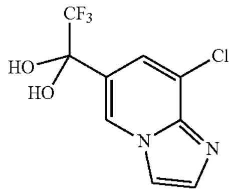

8-Chloro-6-(3,3,3-trifluoroprop-1-en-2-yl)imidazo[1,2-a]pyridine (B27-2) (465 mg, 1.886 mmol) was taken up in tert-BuOH (8 mL). To this was added $H_2O$ (2 mL), sodium periodate (1.21 g, 5.66 mmol), then a 2.5 wt % solution of osmium tetroxide (1.2 mL, 0.096 mmol) in tert-BuOH at ambient temperature. After 3 h another addition of a 2.5 wt % solution of osmium tetroxide (1.2 mL, 0.096 mmol) in tert-BuOH was made and stirring continued at ambient temperature 18 h. The resulting mixture was diluted with $H_2O$ then extracted with DCM (3×). The combined organic layers were dried ($MgSO_4$) then filtered then the filtrate was concentrated. The crude product was subjected to silica gel chromatography (ISCO® RediSep-Rf-40 g, 0-100% EtOAc/heptane, 15 minute gradient) to give the title compound as a solid. MS: 267.0 [M+1].

Step 3: 1-(8-Chloroimidazo[1,2-a]pyridin-6-yl)-N-ethyl-2,2,2-trifluoroethan-1-amine (B27-4)

B27-4

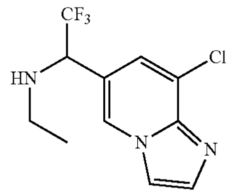

1-(8-Chloroimidazo[1,2-a]pyridin-6-yl)-2,2,2-trifluoroethan-1-one (B27-3) (413 mg, 1.661 mmol) was taken up in DCM (10 mL). To this was added 2M ethylamine (1.7 mL, 3.40 mmol) in THF followed by 1 M $TiCl_4$ (4.2 mL, 4.20 mmol) in DCM at ambient temperature. After stirring 18 h sodium cyanoborohydride (209 mg, 3.32 mmol) was added and stirring continued at ambient temperature. After 2 h the mixture was quenched by slow addition of 2 M NaOH until the mixture was basic. The resulting mixture was filtered through a tall pad of Celite® washing the DCM then concentrated. The crude product was subjected to silica gel chromatography (ISCO® RediSep-Rf-40 g, 0-75% EtOAc/heptane, 15 minute gradient) to give the title compound as a clear oil. MS: 278.1 [M+1].

Step 4: N-Ethyl-2,2,2-trifluoro-1-(8-(8-methoxyimidazo[1,2-a]pyrazin-6-yl)imidazo[1,2-a]pyridin-6-yl)ethan-1-amine (Intermediate B27)

Intermediate B27

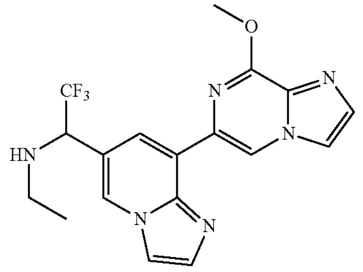

1-(8-Chloroimidazo[1,2-a]pyridin-6-yl)-N-ethyl-2,2,2-trifluoroethan-1-amine (B27-4) (25 mg, 0.090 mmol), 8-methoxy-6-(4,4,5,5-tetramethyl-1,3,2-dioxaborolan-2-yl)imidazo[1,2-a]pyrazine (30 mg, 0.109 mmol), and $DTBPFPdCl_2$ (3 mg, 4.60 μmol) were combined in a screw cap vial. To this was added DME (1 mL) and 1 M $K_3PO_4$ (0.270 mL, 0.270 mmol). $N_2$ was bubbled though the mixture for 1 minute. The vial was capped then heated to 85° C. 18 h. The resulting mixture was cooled to ambient temperature then concentrated. The crude material was taken up in DMSO (1.0 mL), filtered using a 0.45 μm PTFE syringe filter, then purified by preparative reversed-phase HPLC (30×100 mm Phenomenex AXIA-Gemini-NX (0.1% TFA), 5-50% $CH_3CN$/water over 18 min at 50 mL/min). Fractions containing product were pooled then concentrated to give the title compound. MS: 391.2 [M+1].

Intermediate B28: N-Ethyl-2,2,2-trifluoro-1-(5-(7-methoxypyrazolo[1,5-a]pyridin-5-yl)-6-(methylthio)pyridin-3-yl)ethan-1-amine Intermediate B28

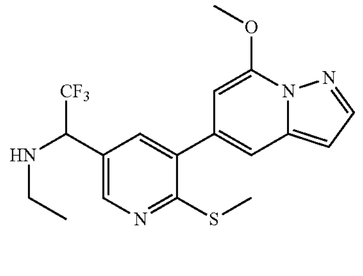

Step 1: Methyl 5-bromo-6-(methylthio)nicotinate (B28-2)

B28-2

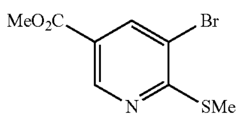

Methyl 5-bromo-6-chloronicotinate (B28-1) (1 g, 3.99 mmol) and NaSMe (0.560 g, 7.98 mmol) were combined in DMF (10 mL) and stirred at ambient temperature 18 h. The resulting mixture was diluted with 40 mL $H_2O$. The resulting solid was collected by filtration, washed with $H_2O$, then air dried. H-NMR (500 MHz, $CDCl_3$, ppm): δ 8.99 (d, J=1.9 Hz, 1H), 8.28 (d, J=1.8 Hz, 1H), 3.95 (s, 3H), 2.61 (s, 3H). MS: 262, 264 [M+1].

Step 2: (5-Bromo-6-(methylthio)pyridin-3-yl)methanol (B28-3)

B28-3

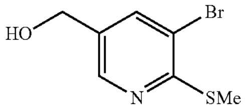

To a solution of methyl 5-bromo-6-(methylthio)nicotinate (B28-2) (875 mg, 3.34 mmol) in THF (15 mL) was added 2M $LiBH_4$ (2.6 mL, 5.20 mmol) in THF slowly at ambient temperature. After stirring 18 h the mixture was quenched with 15 mL 1 M NaOH. After stirring for 10 min the mixture was diluted with $H_2O$ then extracted with EtOAc (3×). The combined organic layers were dried ($MgSO_4$) then filtered then the filtrate was concentrated to give the title compound which was used as is in the next step. MS: 234, 236 [M+1].

Step 3: 5-Bromo-6-(methylthio)nicotinaldehyde (B28-4)

B28-4

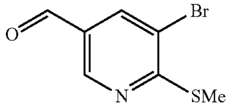

A solution of oxalyl chloride (0.52 mL, 5.94 mmol) in DCM (12 mL) was cooled to −78° C. To this was added DMSO (0.84 mL, 11.84 mmol) slowly. After 15 min a solution of (5-bromo-6-(methylthio)pyridin-3-yl)methanol (B28-3) (689 mg, 2.94 mmol) in 3 mL DCM was added slowly. After 30 min TEA (2.5 mL, 17.94 mmol) was added slowly. After 15 min the cooling bath was removed and the mixture warmed to ambient temperature. After 90 min the mixture was diluted with $H_2O$ then extracted with DCM (3×). The combined organic layers were dried ($MgSO_4$) then filtered then the filtrate was concentrated. The crude product was subjected to silica gel chromatography (ISCO® RediSep-Rf-40 g, 0-25% EtOAc/heptane, 15 minute gradient) to give the title compound. MS: 232, 234 [M+1].

Step 4: 1-(5-Bromo-6-(methylthio)pyridin-3-yl)-2,2,2-trifluoroethan-1-ol (B28-5)

B28-5

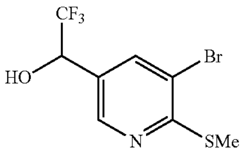

A round bottom flask was charged with CsF (34 mg, 0.224 mmol). The flask was flame dried under vacuum then allowed to cool to ambient temperature under $N_2$. 5-Bromo-6-(methylthio)nicotinaldehyde (B28-4) (510 mg, 2.197 mmol) and DME (10 mL) were added. After stirring for 1 minute $TMSCF_3$ (0.650 mL, 4.39 mmol) was added slowly at ambient temperature. After stirring 18 h the mixture was diluted with 10 mL 1 M HCl and stirred at ambient temperature. After 30 min the mixture was diluted with $H_2O$ then extracted with EtOAc (3×). The combined organic layers were washed with saturated $NaHCO_3$ then dried ($MgSO_4$) then filtered then the filtrate was concentrated to give the title compound which was used as in the next step. MS: 302, 304 [M+1].

Step 5: 1-(5-Bromo-6-(methylthio)pyridin-3-yl)-2,2,2-trifluoroethane-1,1-diol (B28-6)

B28-6

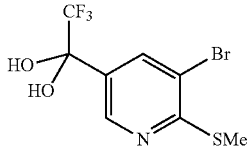

A round bottom flask was charged with DCM (15 mL) and oxalyl chloride (0.48 mL, 5.48 mmol) then the mixture was cooled to −78° C. To this was added DMSO (0.77 mL, 10.85 mmol) dropwise. After 15 min a solution of 1-(5-bromo-6-(methylthio)pyridin-3-yl)-2,2,2-trifluoroethan-1-ol (B28-5) (815 mg, 2.70 mmol) in 5 mL DCM was added slowly. After 1 h TEA (2.3 mL, 16.50 mmol) was added slowly. After 30 min the cooling bath was removed, and the mixture warmed to ambient temperature. After 90 min the mixture was diluted with $H_2O$ then extracted with DCM (3×). The combined organic layers were dried ($MgSO_4$) then filtered then the filtrate was concentrated. The crude product was subjected to silica gel chromatography (ISCO® RediSep-Rf-40 g, 0-25% EtOAc/heptane, 15 minute gradient) to give the title compound. MS: 318, 320 [M+1].

Step 6: 1-(5-Bromo-6-(methylthio)pyridin-3-yl)-N-ethyl-2,2,2-trifluoroethan-1-amine (B28-7)

B28-7

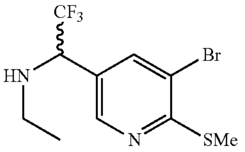

To a solution of 1-(5-bromo-6-(methylthio)pyridin-3-yl)-2,2,2-trifluoroethan-1-one (B28-6) (387 mg, 1.290 mmol) in DCM (8 mL) was added 2 M ethylamine (1.3 mL, 2.60 mmol) in THF followed by slow addition of 1 M $TiCl_4$ (3.3 mL, 3.30 mmol) in DCM at ambient temperature. After stirring 18 h sodium cyanoborohydride (162 mg, 2.58 mmol) was added all at once as a solid with stirring at ambient temperature. After 3 h the mixture was quenched by slow addition of 2 M NaOH until gas evolution ceased and the mixture was basic. The resulting slurry was filtered through a pad of Celite® washing with DCM and $H_2O$. The filtrate layers were separated and the aqueous layer extracted with DCM (3×). The combined organic layers were dried ($Na_2SO_4$) then filtered then the filtrate was concentrated. The crude product was subjected to silica gel chromatography (ISCO® RediSep-Rf-24 g, 0-25% EtOAc/heptane, 15 minute gradient) to give the title compound. H-NMR (500 MHz, $CDCl_3$, ppm): δ 8.42 (d, J=1.5 Hz, 1H), 7.83 (s, 1H), 4.15 (q, J=7.1 Hz, 1H), 2.69-2.59 (m, 2H), 2.58 (s, 3H), 1.13 (t, J=7.1 Hz, 3H). MS: 328, 331 [M+1].

Step 7: N-Ethyl-2,2,2-trifluoro-1-(5-(7-methoxy-pyrazolo[1,5-a]pyridin-5-yl)-6-(methylthio)pyridin-3-yl)ethan-1-amine (Intermediate B28)

Intermediate B28

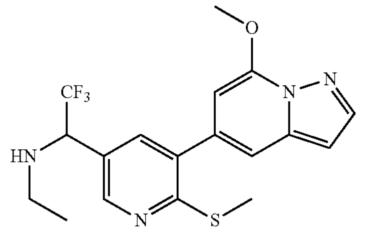

1-(5-Bromo-6-(methylthio)pyridin-3-yl)-N-ethyl-2,2,2-trifluoroethan-1-amine (B28-7) (130 mg, 0.395 mmol), 7-methoxy-5-(4,4,5,5-tetramethyl-1,3,2-dioxaborolan-2-yl)pyrazolo[1,5-a]pyridine (Intermediate B24) (130 mg, 0.474 mmol), and $DTBPFPdCl_2$ (26 mg, 0.040 mmol) were combined in THF (2 mL). To this was added 1 M $K_3PO_4$ (0.790 mL, 0.790 mmol). The mixture was degassed (3× pump/$N_2$) then heated to 60° C. 18 h. The resulting mixture was cooled to ambient temperature then diluted with EtOAc then filtered through a pad of Celite® washing with EtOAc. The filtrate was concentrated. The crude product was subjected to silica gel chromatography (ISCO® RediSep-Rf-24 g, 0-100% EtOAc/heptane, 15 minute gradient) to give the title compound.: H-NMR (500 MHz, $CDCl_3$) δ 8.52 (d, J=2.0 Hz, 1H), 8.06 (d, J=2.1 Hz, 1H), 7.59 (s, 1H), 6.61 (d, J=2.2 Hz, 1H), 6.24 (d, J=1.3 Hz, 1H), 4.27-4.22 (m, 1H), 4.21 (s, 3H), 2.68 (tt, J=11.3, 5.6 Hz, 2H), 2.57 (s, 3H), 1.15 (t, J=7.1 Hz, 3H). MS: 397.2 [M+1].

Intermediate B29: N-(cyclopropyl(5-methoxy-4-(8-methoxy-2-methylimidazo[1,2-a]pyrazin-6-yl)pyridin-2-yl)methyl)ethylamine Intermediate B29

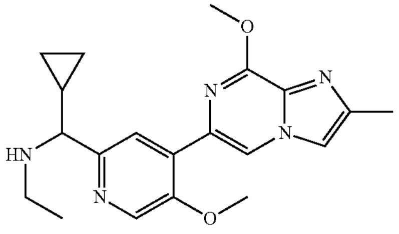

Step 1: (4-Chloro-5-methoxypyridin-2-yl)(cyclopropyl)methanol (B29-2)

B29-1

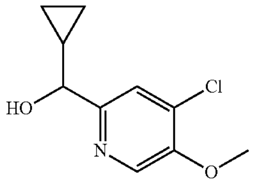

A solution of 4-chloro-5-methoxypicolinaldehyde (B2-5) (250 mg, 1.457 mmol) in THF (5 mL) was cooled to −78° C. To this was added 1 M cyclopropylmagnesium bromide (1.9 mL, 1.900 mmol) in 2-MeTHF slowly. After 30 min the cooling bath was removed and the mixture warmed to ambient temperature. After 30 min the mixture was diluted with saturated aqueous $NH_4Cl$ then extracted with EtOAc (3×). The combined organic layers were dried ($MgSO_4$) then filtered then the filtrate was concentrated. The crude product was subjected to silica gel chromatography (ISCO® RediSep-Rf-40 g, 0-100% EtOAc/heptane, 15 minute gradient) to give the title compound. H-NMR (500 MHz, $CDCl_3$, ppm): δ 8.22 (s, 1H), 7.47 (s, 1H), 4.06 (d, J=8.0 Hz, 1H), 4.02 (s, 3H), 4.00 (s, 1H), 1.12 (tq, J=7.9, 4.1, 3.0 Hz, 1H), 0.64 (d, J=8.4 Hz, 2H), 0.62-0.49 (m, 2H). MS: 214.1 [M+1].

Step 2: (4-Chloro-5-methoxypyridin-2-yl)cyclopropyl)methanone (B29-3)

B29-3

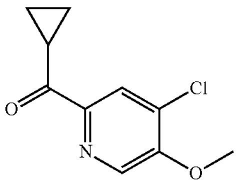

To a solution of (4-chloro-5-methoxypyridin-2-yl)(cyclopropyl)methanol (B29-3) (235 mg, 1.100 mmol) in EtOAc (5 mL) was added IBX (616 mg, 2.200 mmol) then the mixture was heated to 80° C. 18 h. The reaction was deemed incomplete by LC/MS then IBX (616 mg, 2.200 mmol) was added and heating was continued. After 4 h the mixture was cooled to ambient temperature then diluted with EtOAc then filtered through a pad of silica gel washing with EtOAc. The filtrate was concentrated. The crude product was subjected to silica gel chromatography (ISCO® RediSep-Rf-40 g, 0-50% EtOAc/heptane, 15 minute gradient) to give the title compound. MS: 212.1 [M+1].

Step 3: N-((4-Chloro-5-methoxypyridin-2-yl)(cyclopropyl)methyl)ethylamine (B29-4)

B29-4

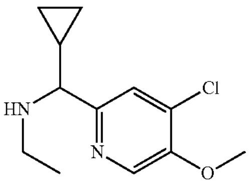

(4-Chloro-5-methoxypyridin-2-yl)(cyclopropyl)methanone (B29-3) (233 mg, 1.1 mmol) and $MgSO_4$ (265 mg, 2.200 mmol) were combined in EtOH (6 mL) in a microwave vial. To this was added 2M ethylamine (2.75 mL, 5.50 mmol) in THF, AcOH (0.315 mL, 5.50 mmol), then sodium cyanoborohydride (138 mg, 2.200 mmol). The vial was capped then heated to 90° C. by conventional heating 18 h. The resulting mixture was cooled to ambient temperature then concentrated. The residue was taken up in $H_2O$ and the pH adjusted to 9. The resulting mixture was diluted with $H_2O$ then extracted with DCM (3×). The combined organic layers were dried ($MgSO_4$) then filtered then the filtrate was concentrated. The crude product was subjected to silica gel chromatography (ISCO® RediSep-Rf-24 g, 0-100% 3:1 EtOAc:EtOH/heptane, 15 minute gradient) to give the title compound. H-NMR (500 MHz, $CDCl_3$, ppm): δ 8.23 (s, 1H), 7.45 (s, 1H), 4.01 (s, 3H), 2.95 (d, J=8.9 Hz, 1H), 2.62 (dq, J=11.5, 7.1 Hz, 1H), 2.49 (dq, J=11.4, 7.2 Hz, 1H), 1.14-1.02 (m, 4H), 0.70-0.62 (m, 1H), 0.47-0.27 (m, 3H). MS: 241. [M+1].

Step 4: N-(cyclopropyl(5-methoxy-4-(8-methoxy-2-methylimidazo[1,2-a]pyrazin-6-yl)pyridin-2-yl)methyl)ethylamine (Intermediate B29)

Intermediate B29

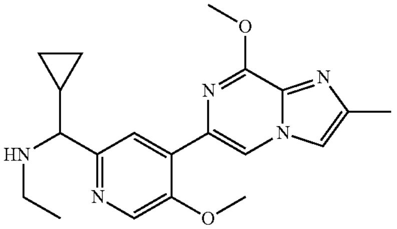

A screw cap vial was charged with N-((4-chloro-5-methoxypyridin-2-yl)(cyclopropyl)methyl)ethylamine (B29-4) (37 mg, 0.154 mmol) and (8-methoxy-2-methylimidazo[1,2-a]pyrazin-6-yl)boronic acid (Intermediate B20) (95 mg, 0.461 mmol). To this was added DME (1 mL) and 1 M $K_3PO_4$ (1 mL, 1.000 mmol). $N_2$ was bubbled though the mixture for 2 min then X-Phos Pd G2 (13 mg, 0.017 mmol) was added. $N_2$ was bubbled though the mixture for 1 minute. The vial was capped then heated to 85° C. 18 h. The resulting mixture was cooled to ambient temperature then diluted with EtOAc then filtered through a pad of Celite® washing with EtOAc. The filtrate was concentrated to give the title compound which was used as is in the next step. MS: 368.2 [M+1].

Intermediate B30: N-ethyl-22-difluoro-1-(5-methoxy-4-(8-methoxy-2-methylimidazo[1,2-a]pyrazin-6-yl)pyridin-2-yl)ethan-1-amine Intermediate B30

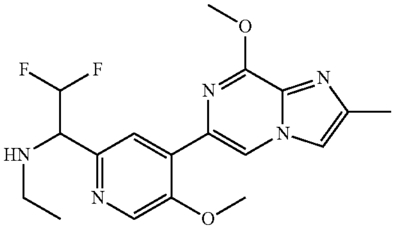

Step 1: 1-(4-Chloro-5-methoxypyridin-2-yl)-2,2-difluoroethan-1-ol (B30-2)

B30-2

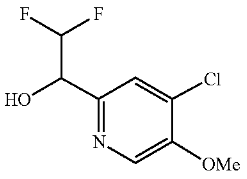

To a solution of 4-chloro-5-methoxypicolinaldehyde (B2-5) (250 mg, 1.457 mmol) in DMF (5 mL) was added CsF (45 mg, 0.296 mmol) then (difluoromethyl)trimethylsilane (0.4 mL, 2.93 mmol) at ambient temperature. After 3 h 1 M HCl (5 mL) was added. After 15 min the mixture was diluted with $H_2O$ then extracted with $Et_2O$ (3×). The combined organic layers were washed with $H_2O$ and brine then dried ($MgSO_4$) then filtered through a pad of silica gel washing with $Et_2O$. The filtrate was concentrated to give the title compound as a light orange oil which solidified slowly under vacuum and was used as is in the next step. MS: 224.1 [M+1].

Step 2: 1-(4-Chloro-5-methoxypyridin-2-yl)-N-ethyl-2,2-difluoroethan-1-amine (B30-3)

B30-3

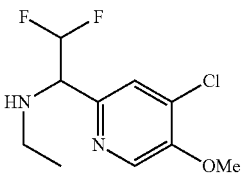

A solution of 1-(4-chloro-5-methoxypyridin-2-yl)-2,2-difluoroethan-1-ol (B30-2) (237 mg, 1.060 mmol) in DCM (5 mL) was cooled to 0° C. To this was added 2,6-lutidine (0.19 mL, 1.631 mmol) then $Tf_2O$ (0.24 mL, 1.421 mmol). After 1 h the mixture was warmed to ambient temperature then concentrated to give crude 1-(4-chloro-5-methoxypyridin-2-yl)-2,2-difluoroethyl trifluoromethanesulfonate which was used immediately as is in the next step. Crude 1-(4-chloro-5-methoxypyridin-2-yl)-2,2-difluoroethyl trifluoromethanesulfonate (377 mg, 1.06 mmol) was taken up in 2 M ethylamine (6 mL, 1.060 mmol) in THF. The solution was transferred to a screw cap vial. The vial was capped then heated to 70° C. After 1 h the mixture was cooled to ambient temperature then concentrated. The crude product was subjected to silica gel chromatography (ISCO® RediSep-Rf-24 g, 0-100% EtOAc/heptane, 15 minute gradient) to give the title compound. H-NMR (500 MHz, $CDCl_3$, ppm): δ 8.29 (s, 1H), 7.44 (s, 1H), 5.95 (td, J=56.2, 4.3 Hz, 1H), 4.03 (s, 3H), 3.98 (td, J=11.9, 4.3 Hz, 1H), 2.69-2.55 (m, 2H), 1.13 (t, J=7.1 Hz, 3H). MS: 251.1 [M+1].

Step 3: N-ethyl-2,2-difluoro-1-(5-methoxy-4-(8-methoxy-2-methylimidazo[1,2-a]pyrazin-6-yl)pyridin-2-yl)ethan-1-amine (Intermediate B30)

Intermediate B30

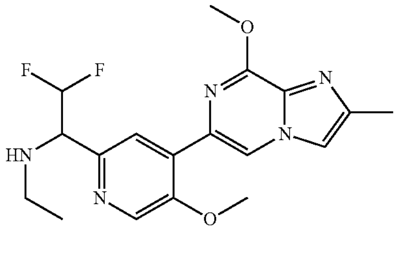

A screw cap vial was charged with 1-(4-chloro-5-methoxypyridin-2-yl)-N-ethyl-2,2-difluoroethan-1-amine (B30-3) (40 mg, 0.160 mmol) and 8-methoxy-2-methyl-6-(4,4,5,5-tetramethyl-1,3,2-dioxaborolan-2-yl)imidazo[1,2-a]pyrazine (Intermediate B20) (115 mg, 0.399 mmol). To this was added DME (1.5 mL) and 1 M $K_3PO_4$ (0.48 mL, 0.480 mmol). $N_2$ was bubbled though the mixture for 2 min then X-Phos Pd G2 (13 mg, 0.017 mmol) was added. $N_2$ was bubbled though the mixture for 1 minute. The vial was capped then heated to 85° C. 18 h. The resulting mixture was cooled to ambient temperature then diluted with EtOAc then filtered through a pad of Celite® washing with EtOAc. The filtrate was concentrated. The crude product was subjected to silica gel chromatography (ISCO® RediSep-Rf-12 g, 0-100% 3:1 EtOAc:EtOH/heptane, 15 minute gradient) to give the title compound. MS: 378.2 [M+1].

Intermediate B31: (S)-3-Cyclopropoxy-1,1,1-trifluoropropan-2-amine hydrochloride Intermediate B31

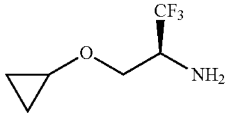

Step 1: (R)—N-(2-cyclopropoxyethylidene)-2-methylpropane-2-sulfinamide (B31-2)

B31-2

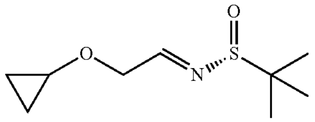

A solution of oxalyl chloride (0.86 mL, 9.83 mmol) in DCM (25 mL) was cooled to −78° C. To this was added DMSO (1.4 mL, 19.73 mmol) slowly. After 15 min a solution of 2-cyclopropoxyethan-1-ol (500 mg, 4.90 mmol) in 2 mL DCM was added. After 30 min TEA (4.1 mL, 29.4 mmol) was added slowly. After the addition was complete the cooling bath was removed and the mixture warmed to ambient temperature. After 90 min the mixture was diluted with $H_2O$ then extracted with DCM (3×). The combined organic layers were dried ($MgSO_4$) then filtered through a tall pad of silica gel washing with DCM, The filtrate was concentrated to give 2-cyclopropoxyacetaldehyde as an amber liquid which was used as is in the next step. To a solution of crude 2-cyclopropoxyacetaldehyde (283 mg, 2.83 mmol) in DCM (10 mL) was added (R)-2-methylpropane-2-sulfinamide (411 mg, 3.39 mmol), PPTS (71.0 mg, 0.283 mmol), then $MgSO_4$ (1.7 g, 14.12 mmol). The mixture was stirred at ambient temperature 18 h. The resulting mixture was filtered through a pad of Celite® washing with DCM then the filtrate was concentrated. The crude product was subjected to silica gel chromatography (ISCO® RediSep-Rf-24 g, 0-25% EtOAc/heptane, 15 minute gradient) to give the title compound. H-NMR (500 MHz, $CDCl_3$, ppm): δ 8.13 (t, J=3.3 Hz, 1H), 4.46-4.41 (m, 2H), 3.48 (tt, J=6.0, 3.0 Hz, 1H), 1.23 (s, 9H), 0.72-0.63 (m, J=3.1 Hz, 2H), 0.53 (qt, J=7.2, 3.6 Hz, 2H).

Step 2: (R)—N—((S)-3-cyclopropoxy-1,1,1-trifluoropropan-2-yl)-2-methylpropane-2-sulfinamide (B31-3)

B31-3

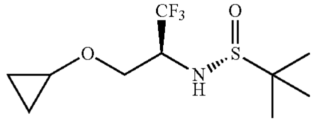

A solution of (R)—N-(2-cyclopropoxyethylidene)-2-methylpropane-2-sulfinamide (187 mg, 0.920 mmol) and tetrabutylammonium acetate (333 mg, 1.104 mmol) in THF (5 mL) was cooled to 0° C. To this was added $TMSCF_3$ (0.41 mL, 2.77 mmol) slowly. The mixture was allowed to warm as the bath warmed to ambient temperature over 3 h. The mixture was quenched with 10 drops of $H_2O$. The resulting mixture was diluted with EtOAc then filtered through a pad of Celite® washing with EtOAc then the filtrate was concentrated. The crude product was subjected to silica gel chromatography (ISCO® RediSep-Rf-24 g, 0-50% EtOAc/heptane, 15 minute gradient) to give the title compound. MS: 274.1 [M+1].

Step 3: (S)-3-Cyclopropoxy-1,1,1-trifluoropropan-2-amine (Intermediate B31)

Intermediate B31

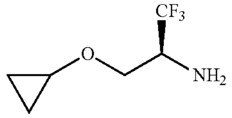

To a solution of (R)—N—((S)-3-cyclopropoxy-1,1,1-trifluoropropan-2-yl)-2-methylpropane-2-sulfinamide (80 mg, 0.293 mmol) in MeOH (1.5 mL) was added 4M HCl (0.37 mL, 1.480 mmol) in dioxane at ambient temperature. After 1 h LC/MS indicated that starting material was consumed. The mixture was concentrated. The residue was taken up in DCM/heptane and concentrated (2×) to give the title compound which was used without further purification.

Intermediate B32: N-(2,2,2-trifluoro-1-(5-methoxy-4-(8-methoxy-2-methylimidazo[1,2-a]pyrazin-6-yl)pyridin-2-yl)ethyl)cyclopropanamine Intermediate B32

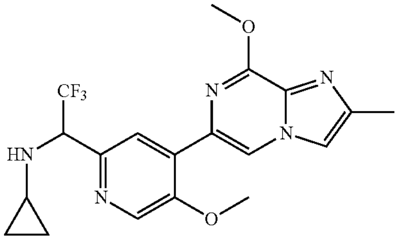

Step 1: 1-(4-Chloro-5-methoxypyridin-2-yl)-2,2,2-trifluoroethan-1-ol (B32-2)

B32-2

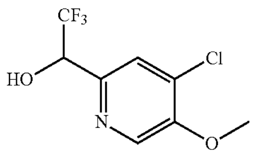

To a solution of 4-chloro-5-methoxypicolinaldehyde (B2-5) (1 g, 5.83 mmol) in DMF (20 ml) was added $K_2CO_3$ (0.161 g, 1.166 mmol) then $TMSCF_3$ (1.75 ml, 11.84 mmol) at ambient temperature. After 2 h 1 M HCl (20 ml) was added and the mixture stirred at ambient temperature for 90 min. The resulting mixture was diluted with $H_2O$ then extracted with $Et_2O$ (3×). The combined organic layers were washed with $H_2O$ and brine then dried ($MgSO_4$) then filtered then the filtrate was concentrated to give the title compound a solid which was used as is in the next step. MS: 242.0 [M+1].

Step 2: N-(1-(4-Chloro-5-methoxypyridin-2-yl)-2,2,2-trifluoroethyl)cyclopropanamine (B32-3)

B13-3

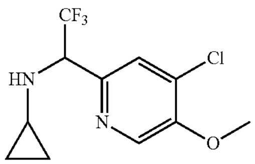

A solution of 1-(4-chloro-5-methoxypyridin-2-yl)-2,2,2-trifluoroethan-1-ol (B32-2) (250 mg, 1.035 mmol) in DCM (5 ml) was cooled to 0° C. To this was added 2,6-lutidine (0.185 ml, 1.588 mmol) then $Tf_2O$ (0.23 ml, 1.361 mmol). After 1 h the mixture was warmed to ambient temperature then concentrated to give crude 1-(4-chloro-5-methoxypyridin-2-yl)-2,2,2-trifluoroethyl trifluoromethanesulfonate which was used immediately as is in the next step. Crude 1-(4-chloro-5-methoxypyridin-2-yl)-2,2,2-trifluoroethyl trifluoromethanesulfonate (387 mg, 1.035 mmol) was taken up in THF (5 ml) and transferred to a screw cap vial. To this was added cyclopropanamine (0.72 ml, 10.39 mmol). The vial was capped then heated to 70° C. After 2 h the mixture was cooled to ambient temperature then concentrated. The crude product was subjected to silica gel chromatography (ISCO® RediSep-Rf-24 g, 0-100% EtOAc/heptane, 15 minute gradient) to give the title compound as a clear oil. H-NMR (500 MHz, $CDCl_3$) δ 8.32 (s, 1H), 7.42 (s, 1H), 4.32-4.22 (m, 1H), 4.04 (s, 3H), 3.03 (d, J=9.4 Hz, 1H), 2.13 (d, J=4.9 Hz, 1H), 0.46 (tq, J=8.6, 4.0 Hz, 4H). MS: 281.1 [M+1].

Step 3: N-(2,2,2-trifluoro-1-(5-methoxy-4-(8-methoxy-2-methylimidazo[1,2-a]pyrazin-6-yl)pyridin-2-yl)ethyl)cyclopropanamine (Intermediate B32)

Intermediate B32

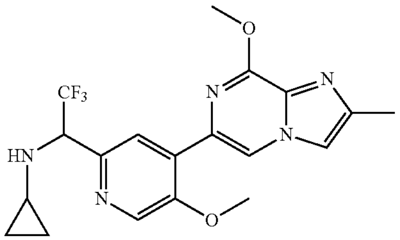

A screw cap vial was charged with N-(1-(4-chloro-5-methoxypyridin-2-yl)-2,2,2-trifluoroethyl)cyclopropanamine (B32-3) (40 mg, 0.143 mmol) and 8-methoxy-2-methyl-6-(4,4,5,5-tetramethyl-1,3,2-dioxaborolan-2-yl)imidazo[1,2-a]pyrazine (Intermediate B20) (103 mg, 0.356 mmol). To this was added DME (1.5 ml) and 1 M $K_3PO_4$ (0.43 mL, 0.430 mmol). $N_2$ was bubbled though the mixture for 2 min then X-Phos Pd G2 (11 mg, 0.014 mmol) was added. $N_2$ was bubbled though the mixture for 1 minute. The vial was capped then heated to 85° C. 18 h. The resulting mixture was cooled to ambient temperature then diluted with EtOAc then filtered through a pad of Celite® washing with EtOAc. The filtrate was concentrated. The crude product was subjected to silica gel chromatography (ISCO® RediSep-Rf-12 g, 0-100% EtOAc/heptane, 15 minute gradient) to give the title compound as a solid. MS: 408.2 [M+1].

Intermediate B33: N-(2,2-Difluoroethyl)-2,2,2-trifluoro-1-(5-methoxy-4-(8-methoxy-[1,2,4]triazolo[1,5-a]pyrazin-6-yl)pyridin-2-yl)ethan-1-amine Intermediate B33

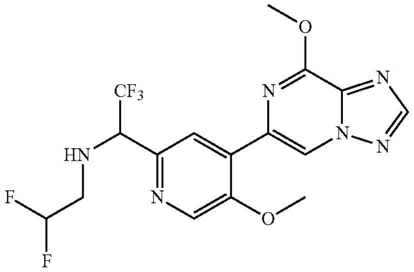

Step 1: 1-(4-Chloro-5-methoxypyridin-2-yl)-2,2,2-trifluoroethane-1,1-diol (B33-2)

B33-3

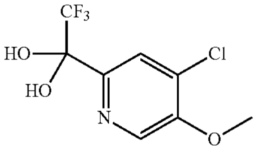

To a solution of crude 1-(4-chloro-5-methoxypyridin-2-yl)-2,2,2-trifluoroethan-1-ol (B2-6) (1.42 g, 5.88 mmol) in EtOAc (30 ml) was added IBX (7.31 g, 11.76 mmol) then the mixture was heated to 80° C. 18 h. The resulting mixture was cooled to ambient temperature then filtered then the filtrate was concentrated. The residue was taken up in 40 ml DCM. To this was added 1:1:1 saturated $Na_2S_2O_3$:$NaHCO_3$:$H_2O$ (45 ml) with rapid stirring at ambient temperature. After 90 min the mixture was diluted with $H_2O$ then extracted with DCM (3×). The combined organic layers were dried ($MgSO_4$) then filtered then the filtrate was concentrated to give the title compound which was used as is in the next step. MS: 258.1 [M+1].

Step 2: 1-(4-Chloro-5-methoxypyridin-2-yl)-N-(2,2-difluoroethyl)-2,2,2-trifluoroethan-1-amine (B33-3)

B33-3

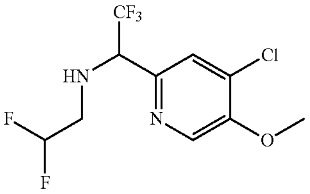

A screw cap vial was charged with crude 1-(4-chloro-5-methoxypyridin-2-yl)-2,2,2-trifluoroethane-1,1-diol (B33-2) (200 mg, 0.776 mmol) and toluene (4 ml). To this was added 1 M $TiCl_4$ (1.56 ml, 1.560 mmol) in toluene slowly at ambient temperature. After the addition was complete 2,2-difluoroethan-1-amine (0.28 ml, 3.97 mmol) was added at ambient temperature. The vial was capped then heated to 90° C. 18 h. The mixture was cooled to ambient temperature before sodium cyanoborohydride (146 mg, 2.329 mmol) and then 2 mL MeOH were added. After 3 h the mixture was quenched by addition of it to saturated $NaHCO_3$. The resulting slurry was diluted with DCM then filtered through a pad of Celite® washing with DCM. The filtrate layers were separated and the aqueous extracted with DCM (2×). The combined organic layers were dried ($MgSO_4$) then filtered then the filtrate was concentrated. The crude product was subjected to silica gel chromatography (ISCO® RediSep-Rf-12 g, 0-25% EtOAc/heptane, 15 minute gradient) to give the title compound. H-NMR (500 MHz, $CDCl_3$, ppm): δ 8.31 (s, 1H), 7.42 (s, 1H), 5.85 (tt, J=56.2, 4.3 Hz, 1H), 4.24 (p, J=7.3 Hz, 1H), 4.05 (s, 3H), 3.02 (dddq, J=29.0, 14.5, 10.6, 4.6 Hz, 2H), 2.82 (q, J=7.3 Hz, 1H). MS: 305.1 [M+1].

Step 3: N-(2,2-Difluoroethyl)-2,2,2-trifluoro-1-(5-methoxy-4-(8-methoxy-[1,2,4]triazolo[1,5-a]pyrazin-6-yl)pyridin-2-yl)ethan-1-amine (Intermediate B33)

Intermediate B33

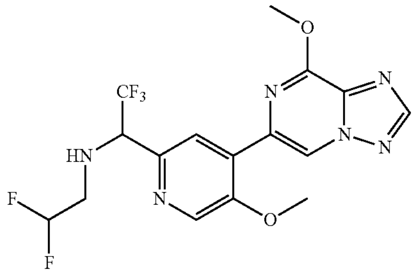

A screw cap vial was charged with 1-(4-chloro-5-methoxypyridin-2-yl)-N-(2,2-difluoroethyl)-2,2,2-trifluoro-ethan-1-amine (B33-3) (60 mg, 0.197 mmol) and (8-methoxy-[1,2,4]triazolo[1,5-a]pyrazin-6-yl)boronic acid (Intermediate B25) (50 mg, 0.258 mmol). To this was added DME (1.5 ml) and 1 M $K_3PO_4$ (0.59 mL, 0.590 mmol). $N_2$ was bubbled though the mixture for 2 min then X-Phos Pd G2 (16 mg, 0.020 mmol) was added. $N_2$ was bubbled though the mixture for 1 minute. The vial was capped then heated to 85° C. 18 h. The resulting mixture was cooled to ambient temperature then diluted with EtOAc then filtered through a pad of Celite® washing with EtOAc. The filtrate was concentrated. The crude product was subjected to silica gel chromatography (ISCO® RediSep-Rf-12 g, 0-50% EtOAc/heptane, 10 minute gradient) to give the title compound as a solid. H-NMR (500 MHz, $CDCl_3$, ppm): δ 9.30 (s, 1H), 8.50 (s, 1H), 8.47 (s, 1H), 8.29 (s, 1H), 6.06-5.68 (m, 1H), 4.41 (p, J=7.4 Hz, 1H), 4.33 (s, 3H), 4.18 (s, 3H), 3.17-3.01 (m, 2H), 2.94 (q, J=7.5 Hz, 1H). MS: 419.2 [M+1].

Intermediate 34: N-ethyl-1-(5-methoxy-4-(7-methoxypyrazolo[1,5-c]pyrimidin-5-yl)pyridin-2-yl)ethan-1-amine Intermediate B34

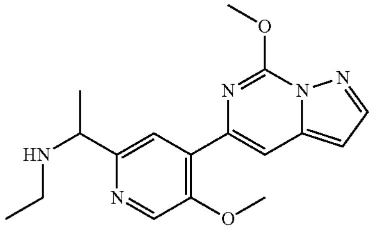

Step 1: 1-(5-methoxy-4-(7-methoxypyrazolo[1,5-c]pyrimidin-5-yl)pyridin-2-yl)ethan-1-one (B34-2)

B34-2

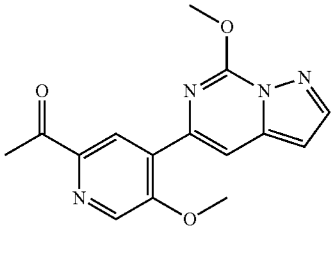

A solution of 5-(2-bromo-5-methoxypyridin-4-yl)-7-methoxypyrazolo[1,5-c]pyrimidine (Intermediate B12) (52 mg, 0.155 mmol) in dioxane (2 mL) was degassed. Tributyl (1-ethoxyvinyl)tin (0.079 mL, 0.233 mmol) and tetrakis (triphenylphosphine)palladium (17.93 mg, 0.016 mmol) were added and the mixture was heated at 100° C. for 3 h. Additional tributyl(1-ethoxyvinyl)tin (0.079 mL, 0.233 mmol) was added and heating was continued for 16 h. The mixture was cooled to ambient temperature and 10% HCl (1 mL) was added and stirring continued for 2 h at ambient temperature. The mixture was poured onto aqueous sat. $NaHCO_3$ (10 mL) and extracted with EtOAc (3×20 mL). The combined organics were dried over $Na_2SO_4$, filtered, and concentrated in vacuo. The crude was purified by column chromatography on silica gel (40 g ISCO gold column), eluting with hexanes:EtOAc/EtOH mix (3:1) 100:0 to 0:100 to afford the title compound. MS: 299.3 [M+1].

Step 2: N-ethyl-1-(5-methoxy-4-(7-methoxypyrazolo[1,5-c]pyrimidin-5-yl)pyridin-2-yl)ethan-1-amine (Intermediate B34)

Intermediate B34

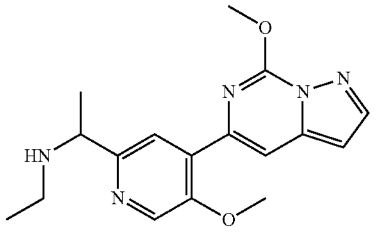

A solution of 1-(5-methoxy-4-(7-methoxypyrazolo[1,5-c]pyrimidin-5-yl)pyridin-2-yl)ethan-1-one (28 mg, 0.094 mmol), 2 M ethylamine in THF (0.235 mL, 0.469 mmol), acetic acid (0.027 mL, 0.469 mmol), and magnesium sulfate (12.43 mg, 0.103 mmol) in EtOH (1 ML) was heated at 50° C. for 1 h. The mixture was cooled and sodium cyanoborohydride (11.80 mg, 0.188 mmol) was added and the mixture was reheated to 50° C. for 3 h. The mixture was cooled, filtered, and concentrated. The crude product was purified by column chromatography on silica gel (24 g ISCO gold column), eluting with hexanes:MeOH/$NH_4$OH mix (100:1) 100:0 to 80:20 to afford the title compound. MS: 328.3 [M+1].

Intermediate B35: (R)-1-(3-(8-methoxyimidazo[1,2-a]pyrazin-6-yl)phenyl)-N-methylethan-1-amine Intermediate B35

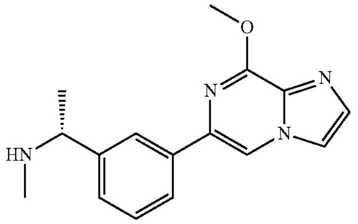

Step 1: tert-butyl (R)-(1-(3-(4,4,5,5-tetramethyl-1,3,2-dioxaborolan-2-yl)phenyl)ethyl)carbamate (B35-2)

B35-2

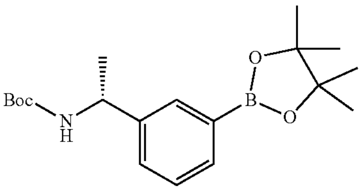

To a solution of (R)-tert-butyl (1-(3-bromophenyl)ethyl) carbamate (B35-1) (5.4 g, 17.99 mmol) in dioxane (100 ml) were added 4,4,4',4',5,5,5',5'-octamethyl-2,2'-bi(1,3,2-dioxaborolane) (5.48 g, 21.59 mmol), POTASSIUM ACETATE (4.41 g, 45.0 mmol) and $PdCl_2$(dppf) (1.316 g, 1.799 mmol), then the solution was stirred at 90° C. for 2 h. TLC (petroleum ether:EtOAc=10:1) showed new spots were formed. Then the reaction mixture poured into water (200 mL), extracted with EtOAc (60 mL×3). The organic layer washed with saturated brine and dried over $Na_2SO_4$, filtered and concentrated. The residue was purified by flash silica gel chromatography (ISCO®; 40 g SepaFlash® Silica Flash Column, eluent of 6% EtOAc gradient) to give the title compound. MS: 231.0 [M+1].

Step 2: tert-butyl (R)-(1-(3-(8-methoxyimidazo[1,2-a]pyrazin-6-yl)phenyl)ethyl)carbamate (B35-3)

B35-3

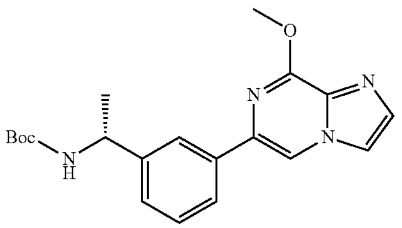

To a solution of 6-bromo-8-methoxyimidazo[1,2-a]pyrazine (Intermediate A1) (1 g, 4.39 mmol) and (R)-tert-butyl (1-(3-(4,4,5,5-tetramethyl-1,3,2-dioxaborolan-2-yl)phenyl) ethyl)-carbamate (B35-2) (1.523 g, 4.39 mmol) was added dioxane (20 ml) and water (4 ml). To this was added $K_2CO_3$ (1.212 g, 8.77 mmol) and [1,1'-BIS(DIPHENYLPHOSPHINO)-FERROCENE]-DICHLOROPALLADIUM(II) (0.321 g, 0.439 mmol), the resulting mixture was stirred at 90° C. under $N_2$ protection for 2 h. TLC (petroleum ether: EtOAc=0:1) showed that new spots were found and LCMS showed the desired product was formed. The reaction mixture was poured into water (20 mL) and extracted with EtOAc (15 mL×3). The combined organic layers were washed with brine (20 mL), dried over $Na_2SO_4$, filtered and concentrated. The crude product was purified by flash silica gel chromatography (ISCO®; 8 g SepaFlash® Silica Flash Column, eluent of 100% EtOAc gradient) to give the title compound. MS: 396.3 [M+1].

Step 3: (R)-1-(3-(8-methoxyimidazo[1,2-a]pyrazin-6-yl)phenyl)-N-methylethan-1-amine (Intermediate B35)

Intermediate B35

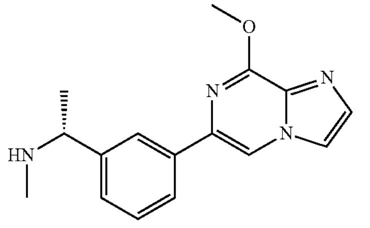

To a solution of tert-butyl (R)-(1-(3-(8-methoxyimidazo[1,2-a]pyrazin-6-yl)phenyl)ethyl)carbamate (B35-3) (100 mg, 0.271 mmol) in THF (1.5 mL) was added LAH (20.60 mg, 0.543 mmol), the mixture was stirred at 60° C. for 3 h. LCMS showed starting material was consumed and desired mass observed. The reaction mixture was poured into water (3 mL), extracted with EtOAc (3 mL×3). The organic layer was dried over $Na_2SO_4$, filtered. The filtrate was concentrated to the title compound, which was used to next step without further purification. MS: 283.2 [M+1].

Intermediate B36: (R)—N-(1-(3-(8-methoxyimidazo[1,2-a]pyrazin-6-yl)phenyl)ethyl)propan-1-amine Intermediate B36

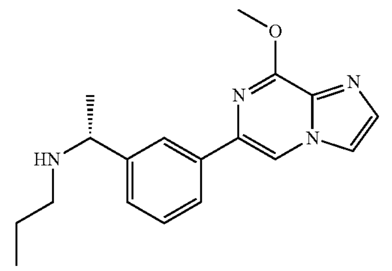

Step 1: (R)-1-(3-(8-methoxyimidazo[1,2-a]pyrazin-6-yl)phenyl)ethan-1-amine (B36-1)

B36-1

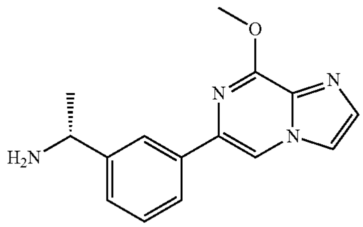

To a solution of tert-butyl (R)-(1-(3-(8-methoxyimidazo[1,2-a]pyrazin-6-yl)phenyl)ethyl)carbamate (B35-3) (700 mg, 1.900 mmol) in DCM (5 mL) and TFA (5 mL), the mixture was stirred at 25° C. for 1 h. The LCMS showed the starting material was consumed and desired mass observed.

The reaction mixture was poured into water (10 mL), extracted with EtOAc (10 mL×3). The organic layer was dried over $Na_2SO_4$ and filtered. The filtrate was concentrated to the title compound, which was used to next step without further purification. MS: 269.1 [M+1].

Step 2: (R)—N-(1-(3-(8-methoxyimidazo[1,2-a]pyrazin-6-yl)phenyl)ethyl)propan-1-amine (Intermediate B36)

Intermediate B36

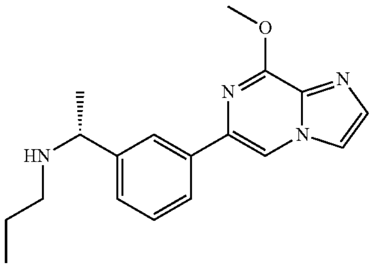

To a solution of (R)-1-(3-(8-methoxyimidazo[1,2-a]pyrazin-6-yl)phenyl)ethan-1-amine (B36-1) (100 mg, 0.373 mmol) and propionaldehyde (21.65 mg, 0.373 mmol) in MeOH (2 mL) was added $NaBH_3CN$ (23.42 mg, 0.373 mmol), the mixture was stirred at 30° C. for 8 h. The LCMS showed desired mass observed. The reaction mixture was filtered. The filtrate was concentrated to give the title compound, which was used to next step without further purification. MS: 311.3 [M+1].

Intermediate B37: (R)—N-(1-(3-(8-methoxyimidazo[1,2-a]pyrazin-6-yl)phenyl)ethyl)propan-2-amine Intermediate B37

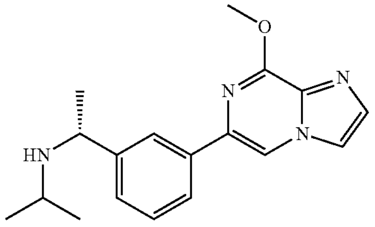

The title compound was prepared from (R)-1-(3-(8-methoxyimidazo[1,2-a]pyrazin-6-yl)phenyl)ethan-1-amine (B36-1) and acetone using the procedure outlined in step 2 in the synthesis of Intermediate B36. MS: 311.2 [M+1].

Intermediate B38: 2,2-difluoro-N-(1-(3-(8-methoxy-imidazo[1,2-a]pyrazin-6-yl)phenyl)ethyl)ethan-1-amine Intermediate B38

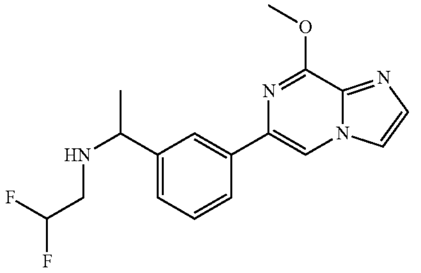

Step 1: 1-(3-(8-methoxyimidazo[1,2-a]pyrazin-6-yl) phenyl)ethan-1-one (B38-1)

B38-1

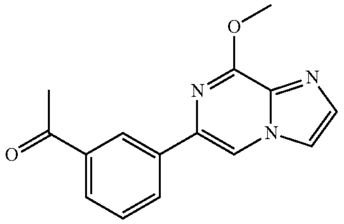

To a solution of 6-bromo-8-methoxyimidazo[1,2-a]pyrazine (Intermediate A1) (227 mg, 0.995 mmol) in dioxane (4 mL) and water (1 mL) was added (3-acetylphenyl) boronic acid (196 mg, 1.194 mmol) and $Na_2CO_3$ (264 mg, 2.489 mmol), then $Pd(dppf)Cl_2$ (72.8 mg, 0.100 mmol) was added. The reaction mixture was stirred at 90° C. for 15 h. LCMS showed the desired MS was formed. The reaction mixture was poured into water (10 mL), extracted withe EtOAc (10 mL×3). The combined organic layers were dried over $Na_2SO_4$, filtered and concentrated to the title compound, which was used in next step that without further purification. MS: 268.1 [M+1].

Step 2: 2,2-difluoro-N-(1-(3-(8-methoxyimidazo[1,2-a]pyrazin-6-yl)phenyl)ethyl)ethan-1-amine (Intermediate B38)

Intermediate B38

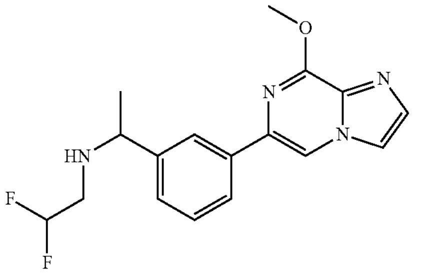

To a solution of 1-(3-(8-methoxyimidazo[1,2-a]pyrazin-6-yl)phenyl)ethan-1-one (B38-1) (200 mg, 0.748 mmol) in EtOH (2 mL) was added 2,2-difluoroethylamine (60.7 mg, 0.748 mmol), AcOH (4.28 μl, 0.075 mmol), $MgSO_4$ (225 mg, 1.871 mmol) and $NaBH_3CN$ (94 mg, 1.497 mmol) at 28° C., then stirred for 2 h at 90° C. LCMS showed the desired product was formed. The reaction mixture was filtered and concentrated to give the crude title compound, which was used in next step that without further purification. MS: 333.2 [M+1].

Intermediate B39: N-ethyl-1-(2-(8-methoxyimidazo [1,2-a]pyrazin-6-yl)pyrimidin-4-yl)ethan-1-amine Intermediate B39

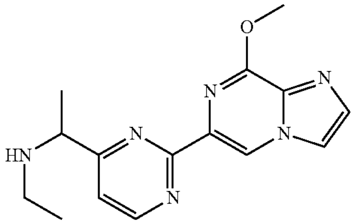

Step 1: 1-(2-(8-methoxyimidazo[1,2-a]pyrazin-6-yl) pyrimidin-4-yl)ethan-1-one (B39-1)

B39-1

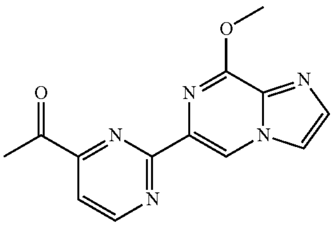

To a solution of (8-methoxy-6-(4,4,5,5-tetramethyl-1,3,2-dioxaborolan-2-yl)imidazo[1,2-a]pyrazine (Intermediate B1) (616 mg, 3.19 mmol) in dioxane (10 mL) and water (3 mL) were added $K_2CO_3$ (1324 mg, 9.58 mmol), 1-(2-chloropyrimidin-4-yl)ethan-1-one (500 mg, 3.19 mmol) and $PdCl_2(dppf)$ (117 mg, 0.160 mmol). The resulting mixture was stirred at 90° C. under $N_2$ protection for 3 h. TLC (petroleum ether:EtOAc=0:1) showed the starting material was consumed and new spots were found and LCMS showed the desired product was formed. The reaction mixture was concentrated and quenched with water (30 mL). The mixture was extracted with EtOAc (50 mL×3). The combined organic phases were washed with and brine (30 mL). The organic phases was dried over $Na_2SO_4$, filtered and concentrated. The crude product was purified by flash silica gel chromatography (ISCO®; 20 g SepaFlash® Silica Flash Column, eluent of 55% ethyl acetate/petroleum ether gradient@35 mL/min) to give the title compound. MS: 270.1 [M+1].

Step 2: N-ethyl-1-(2-(8-methoxyimidazo[1,2-a]pyrazin-6-yl)pyrimidin-4-yl)ethan-1-amine (Intermediate B39)

Intermediate B39

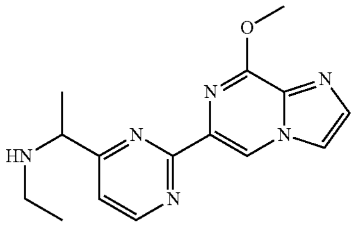

To a solution of 1-(2-(8-methoxyimidazo[1,2-a]pyrazin-6-yl)pyrimidin-4-yl)ethan-1-one (B39-1) (200 mg, 0.743 mmol) in ethanol (3 mL) was added ethylamine (67.0 mg, 1.486 mmol) at 25° C. dropwise. The mixture was stirred at 25° C. for 1 h. And then AcOH (0.021 mL, 0.371 mmol) and $NaBH_3CN$ (140 mg, 2.228 mmol) were added to the solution at 25° C. The mixture was stirred at 70° C. for 12 h. LCMS showed the desired product was found. The mixture was filtered and concentrated under reduced pressure to afforded the title compound as an oil. It was used to the next step without further purification. MS: 299.1 [M+1].

Intermediate B40: N-ethyl-1-(6-(8-methoxyimidazo[1,2-a]pyrazin-6-yl)pyridazin-4-yl)ethan-1-amine Intermediate B40

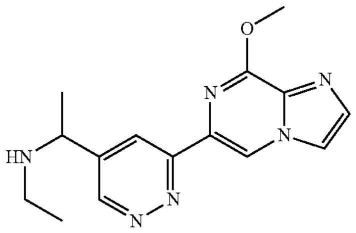

Step 1: 1-(6-chloropyridazin-4-yl)ethan-1-one (B40-1)

B40-1

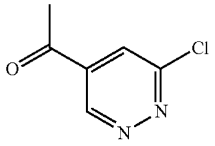

To a solution of methyl 6-chloropyridazine-4-carboxylate (4.9 g, 28.4 mmol) in THF (2 mL) was added methylmagnesium bromide (14.20 mL, 42.6 mmol as 3 M in 2-MeTHF) at −78° C. and stirred at −78° C. for 3 h. TLC (petroleum ether:EtOAc=2:1) showed the desired target was formed. The reaction mixture was poured into water (10 mL), extracted with EtOAc (20 mL×3). The organic layer was washed with brine (10 mL), dried over $Na_2SO_4$ and filtered. The filtrate was concentrated and purified flash silica gel chromatography (ISCO®; 20 SepaFlash® Silica Flash Column, eluent of 0-27% ethyl acetate/petroleum ether gradient) to give the title compound.

Step 2: N-ethyl-1-(6-(8-methoxyimidazo[1,2-a]pyrazin-6-yl)pyridazin-4-yl)ethan-1-amine (Intermediate B40)

Intermediate B40

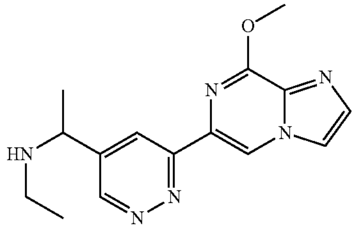

The title compound was prepared from Intermediate B1 and 1-(6-chloropyridazin-4-yl)ethan-1-one (B40-1) with using the procedures outlined in steps 1-2 in the synthesis of Intermediate B39 and used crude without further purification.

Intermediate B41: 6,6,6-trifluoro-5-methylhexan-3-amine

Intermediate B41

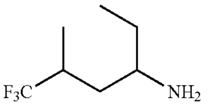

Step 1: 4,4,4-trifluoro-3-methylbutanal

B41-1

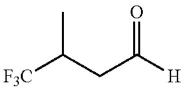

Ethyl 4,4,4-trifluoro-3-methylbutanoate (930 mg, 5.05 mmol) was dissolved in DCM (38 mL) and the solution was cooled to −78 C and treated with DIBAL-H 1.0 M (5555 μl, 5.56 mmol) added dropwise. The reaction was stirred at −78 C for 3 h. Work-up involved quenching with water (0.22 mL), 15% aq NaOH (0.22 mL) and water (0.56 mL). $MgSO_4$ was then added and the reaction was stirred at room temperature for 15 min. The reaction was then filtered and the crude material was partially concentrated down to afford a solution of the title compound which was used in the next step without purification.

Step 2: 6,6,6-trifluoro-5-methylhexan-3-amine (Intermediate B41)

Intermediate B41

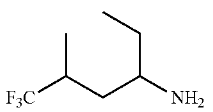

The title compound was prepared from 4,4,4-trifluoro-3-methylbutanal (B41-1) using the procedure outlined in steps 1-4 in the synthesis of Intermediate A11 using ethyl magnesium bromide in step 2. MS: 170.2 [M+1].

Intermediate B42: 1,1,1,5,5,5-hexafluoro-4-methylpentan-2-amine

Intermediate B42

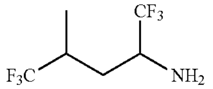

The title compound was prepared from 4,4,4-trifluoro-3-methylbutanal using the procedure outlined in steps 1-4 in the synthesis of Intermediate A11. This was used without further purification.

Intermediate B43: 1-(4,4-difluoro-6,6-dimethyltetrahydro-2H-pyran-2-yl)-2,2,2-trifluoroethan-1-amine Intermediate B43

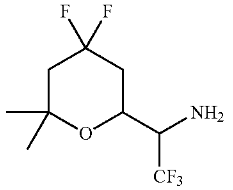

Step 1: ethyl 4,4-difluoro-6,6-dimethyltetrahydro-2H-pyran-2-carboxylate (B43-1)

B43-1

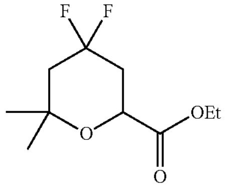

Ethyl 6,6-dimethyl-4-oxotetrahydro-2H-pyran-2-carboxylate (220 mg, 1.099 mmol) was dissolved in DCM (5.5 mL) and treated with DAST (871 µl, 6.59 mmol). The reaction was stirred at room temperature for 18 h. TLC showed formation of a less polar spot. Work-up involved quenching with sat aq $NaHCO_3$ (10 mL) and extracting with DCM (3×15 mL). The combined organic layers were washed with water (15 mL), dried ($MgSO_4$) and concentrated. The crude material was purified by ISCO flash column chromatography (0-40% EtOAc:hexanes) to afford the title compound. H-NMR (500 MHz, Chloroform-d, ppm). δ 4.35-4.29 (m, 1H), 4.20 (q, J=7.1 Hz, 2H), 2.32 (tdt, J=13.3, 4.6, 2.7 Hz, 1H), 2.04-1.95 (m, 1H), 1.93-1.84 (m, 1H), 1.84-1.76 (m, 1H), 1.73 (dd, J=14.0, 6.4 Hz, 1H), 1.35 (s, 3H), 1.28-1.24 (m, 6H).

Step 2: (4,4-difluoro-6,6-dimethyltetrahydro-2H-pyran-2-yl)methanol (43-2)

43-2

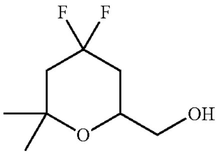

Ethyl 4,4-difluoro-6,6-dimethyltetrahydro-2H-pyran-2-carboxylate (195 mg, 0.877 mmol) was dissolved in THF (4 mL) and methanol (439 µl) and treated with $LiBH_4$ (1316 µl, 2.63 mmol) 2 M. The reaction was allowed to stir at room temperature for 2 h. TLC showed formation of a less polar spot. The reaction was quenched with sat aq $NH_4Cl$ (5 mL) and extracted with DCM (3×10 mL). The combined organic layers were washed with water (10 mL), dried ($MgSO_4$) and concentrated. The crude material was purified by ISCO flash column chromatography (0-60% EtOAc:hexanes) to the title compound. H-NMR (500 MHz, Chloroform-d, ppm): δ 3.87 (dq, J=8.8, 2.8 Hz, 1H), 3.68 (ddd, J=10.0, 6.2, 3.0 Hz, 1H), 3.53 (dt, J=11.5, 5.7 Hz, 1H), 2.43 (t, J=6.4 Hz, 1H), 2.04-1.92 (m, 2H), 1.81-1.74 (m, 1H), 1.74-1.65 (m, 1H), 1.29 (d, J=5.6 Hz, 6H).

Step 3: 4,4-difluoro-6,6-dimethyltetrahydro-2H-pyran-2-carbaldehyde (43-3)

43-3

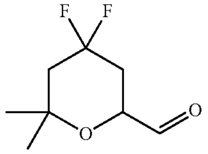

(4,4-difluoro-6,6-dimethyltetrahydro-2H-pyran-2-yl) methanol (127 mg, 0.705 mmol) was dissolved in DCM (388 µl) and the solution was cooled to 0 C and treated with TEMPO (1.101 mg, 7.05 µmol), potassium bromide (8.39 mg, 0.070 mmol) dissolved in water (194 µl) and sat aq $NaHCO_3$ (388 µl). Sodium hypochlorite 10% in water (435 µl, 0.705 mmol) was added dropwise over 30 min. The reaction was stirred at 0 C for 4 h. TLC showed formation of a more polar streak spot and no starting material left. The organic layer was separated from the aqueous and the aqueous layer was washed with DCM (2×5 mL). The organic layers were combined and used as a solution of the title compound in the next step without purification.

Step 4: 1-(4,4-difluoro-6,6-dimethyltetrahydro-2H-pyran-2-yl)-2,2,2-trifluoroethan-1-amine (Intermediate B43)

Intermediate B43

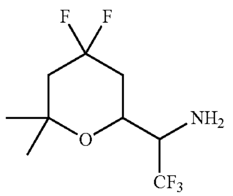

The title compound was prepared from 4,4,4-trifluoro-3-methylbutanal using the procedure outlined in steps 1-4 in the synthesis of Intermediate A11. This was used without further purification. MS: 248.2 [M+1].

Example 2-1 for Table 2: 1-ethyl-1-((S)-2,2,2-trifluoro-1-(5-methoxy-4-(8-methoxyimidazo[1,2-a]pyrazin-6-yl)pyridin-2-yl)ethyl)-3-((S)-1,1,1-trifluoropropan-2-yl)urea Example 2-1

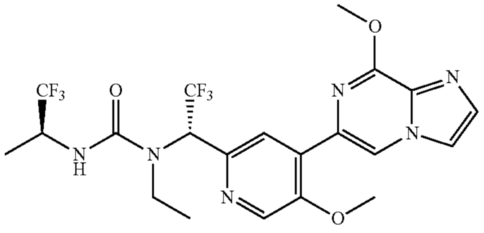

(S)-1,1,1-Trifluoropropan-2-amine (15.69 mg, 0.105 mmol) was dissolved in DCM (524 μl) and treated with sat. $NaHCO_3$ (524 μl) and triphosgene (10.27 mg, 0.035 mmol) and stirred at ambient temperature for 30 min. The organic portion of the reaction contents were dried ($Na_2SO_4$), filtered and treated with (S)—N-ethyl-2,2,2-trifluoro-1-(5-methoxy-4-(8-methoxyimidazo[1,2-a]pyrazin-6-yl)pyridin-2-yl)ethan-1-amine (Intermediate B3) (20 mg, 0.052 mmol) and stirred at 50° C. for 18 h. This was diluted with $CH_2Cl_2$, washed with sat. $NaHCO_3$, drying by filtering through a hydrophobic frit and evaporating to give a residue. This was purified via reverse phase chromatography (SunFire Prep C18 OBD column, 5 micron, 30×150 mm, 20-45% $CH_3CN$/water and 0.1% TFA as a modifier, 25 min, 50 mL/min) to afford the title compound. MS: 521.3 [M+1].

The following compounds were prepared according to the general procedures herein and in an analogous manner to that used to synthesize the Examples above using the appropriate intermediates. The starting materials were either prepared as described in the intermediates section, commercial available, or prepared from commercially available reagents using conventional reactions well known in the art.

TABLE 2

| Ex. | Structure | Name | Exact Mass [M + H]+ |
|---|---|---|---|
| 2-2 | 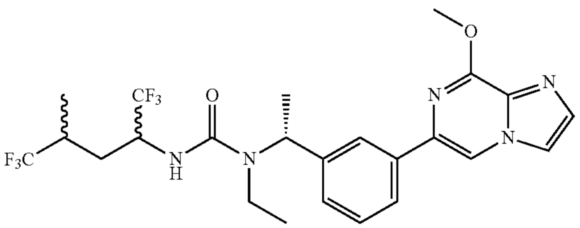 [SMILES: CCN(C(=O)NC(CC(C)C(F)(F)F)C(F)(F)F)[C@H](C)c1cccc(-c2cn3ccnc3c(OC)n2)c1] | 1-ethyl-3-(1,1,1,5,5,5-hexafluoro-4-methylpentan-2-yl)-1-((R)-1-(3-(8-methoxyimidazo[1,2-a]pyrazin-6-yl)phenyl)ethyl)urea | 532.3 |
| 2-3 | 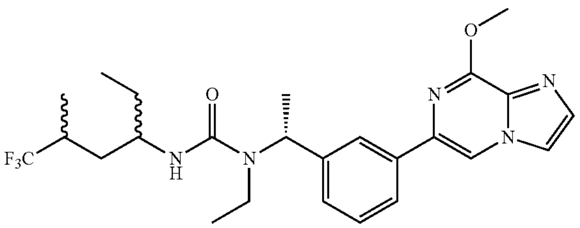 [SMILES: CCC(CC(C)C(F)(F)F)NC(=O)N(CC)[C@H](C)c1cccc(-c2cn3ccnc3c(OC)n2)c1] | 1-ethyl-1-((R)-1-(3-(8-methoxyimidazo[1,2-a]pyrazin-6-yl)phenyl)ethyl)-3-(6,6,6-trifluoro-5-methylhexan-3-yl)urea | 492.3 |

TABLE 2-continued

| Ex. | Structure | Name | Exact Mass [M + H]+ |
|---|---|---|---|
| 2-4 | 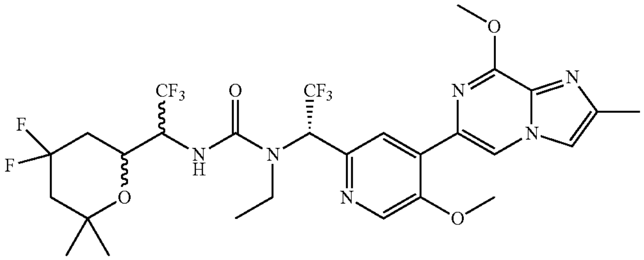 [SMILES: CCN(C(=O)NC(C1CC(F)(F)CC(C)(C)O1)C(F)(F)F)[C@@H](c1cc(-c2cn3cc(C)nc3c(OC)n2)c(OC)cn1)C(F)(F)F] | 3-(1-(4,4-difluoro-6,6-dimethyltetrahydro-2H-pyran-2-yl)-2,2,2-trifluoroethyl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea | 669.6 |
| 2-5 | 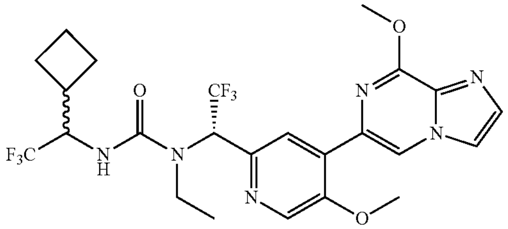 [SMILES: CCN(C(=O)NC(C1CCC1)C(F)(F)F)[C@@H](c1cc(-c2cn3ccnc3c(OC)n2)c(OC)cn1)C(F)(F)F] | 3-(1-cyclobutyl-2,2,2-trifluoroethyl)-1-ethyl-1-((S)-2,2,2-trifluoro-1-(5-methoxy-4-(8-methoxyimidazo[1,2-a]pyrazin-6-yl)pyridin-2-yl)ethyl)urea | 561.5 |
| 2-6 | 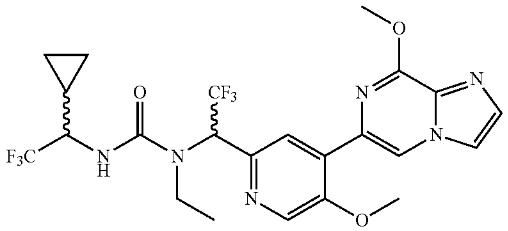 [SMILES: CCN(C(=O)NC(C1CC1)C(F)(F)F)C(c1cc(-c2cn3ccnc3c(OC)n2)c(OC)cn1)C(F)(F)F] | 3-(1-cyclopropyl-2,2,2-trifluoroethyl)-1-ethyl-1-(2,2,2-trifluoro-1-(5-methoxy-4-(8-methoxyimidazo[1,2-a]pyrazin-6-yl)pyridin-2-yl)ethyl)urea | 547.5 |
| 2-7 | 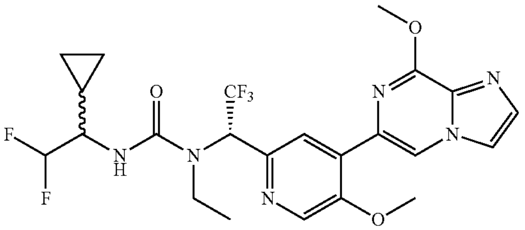 [SMILES: CCN(C(=O)NC(C(F)F)C1CC1)[C@@H](c1cc(-c2cn3ccnc3c(OC)n2)c(OC)cn1)C(F)(F)F] | 3-(1-cyclopropyl-2,2-difluoroethyl)-1-ethyl-1-((S)-2,2,2-trifluoro-1-(5-methoxy-4-(8-methoxyimidazo[1,2-a]pyrazin-6-yl)pyridin-2-yl)ethyl)urea | 529.3 |
| 2-8 | 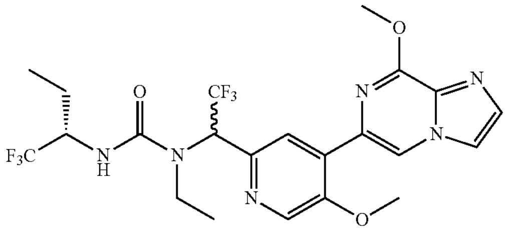 [SMILES: CC[C@H](NC(=O)N(CC)C(c1cc(-c2cn3ccnc3c(OC)n2)c(OC)cn1)C(F)(F)F)C(F)(F)F] | 1-ethyl-1-(2,2,2-trifluoro-1-(5-methoxy-4-(8-methoxyimidazo[1,2-a]pyrazin-6-yl)pyridin-2-yl)ethyl)-3-((S)-1,1,1-trifluorobutan-2-yl)urea | 535.3 |
| 2-9 | 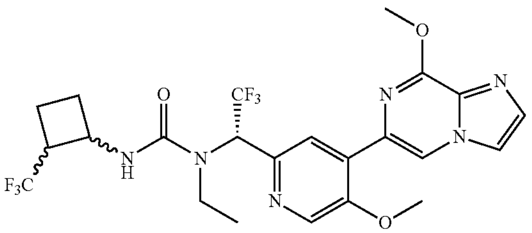 [SMILES: CCN(C(=O)NC1CCC1C(F)(F)F)[C@@H](c1cc(-c2cn3ccnc3c(OC)n2)c(OC)cn1)C(F)(F)F] | 1-ethyl-1-((S)-2,2,2-trifluoro-1-(5-methoxy-4-(8-methoxyimidazo[1,2-a]pyrazin-6-yl)pyridin-2-yl)ethyl)-3-(2-(trifluoromethyl)cyclobutyl)-urea | 547.3 |

TABLE 2-continued

| Ex. | Structure | Name | Exact Mass [M + H]+ |
|---|---|---|---|
| 2-10 | 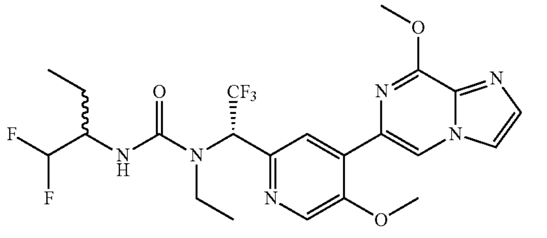 [SMILES: CCC(NC(=O)N(CC)[C@@H](c1cc(-c2cn3ccnc3c(OC)n2)c(OC)cn1)C(F)(F)F)C(F)F] | 3-(1,1-difluorobutan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea | 517.3 |
| 2-11 | 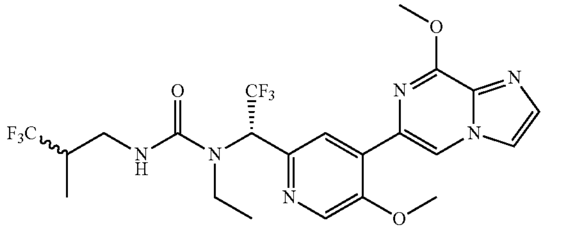 [SMILES: CCN(C(=O)NCC(C)C(F)(F)F)[C@@H](c1cc(-c2cn3ccnc3c(OC)n2)c(OC)cn1)C(F)(F)F] | 1-ethyl-1-((S)-2,2,2-trifluoro-1-(5-methoxy-4-(8-methoxyimidazo[1,2-a]pyrazin-6-yl)pyridin-2-yl)ethyl)-3-(3,3,3-trifluoro-2-methylpropyl)urea | 535.3 |
| 2-12 | 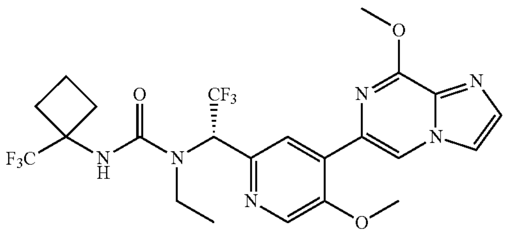 [SMILES: CCN(C(=O)NC1(C(F)(F)F)CCC1)[C@@H](c1cc(-c2cn3ccnc3c(OC)n2)c(OC)cn1)C(F)(F)F] | (S)-1-ethyl-1-(2,2,2-trifluoro-1-(5-methoxy-4-(8-methoxyimidazo[1,2-a]pyrazin-6-yl)pyridin-2-yl)ethyl)-3-(1-(trifluoromethyl)cyclobutyl)urea | 574.4 |
| 2-13 | 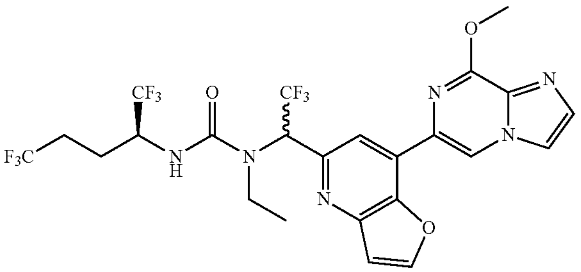 [SMILES: CCN(C(=O)N[C@@H](CCC(F)(F)F)C(F)(F)F)C(c1cc(-c2cn3ccnc3c(OC)n2)c2occc2n1)C(F)(F)F] | 1-ethyl-3-((S)-1,1,1,5,5,5-hexafluoropentan-2-yl)-1-(2,2,2-trifluoro-1-(7-(8-methoxyimidazo[1,2-a]pyrazin-6-yl)furo[3,2-b]pyridin-5-yl)ethyl)urea | 613.3 |
| 2-14 | 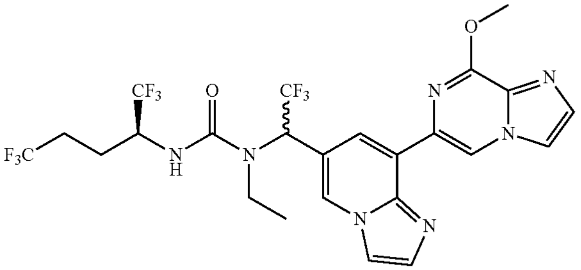 [SMILES: CCN(C(=O)N[C@@H](CCC(F)(F)F)C(F)(F)F)C(c1cc(-c2cn3ccnc3c(OC)n2)c2nccn2c1)C(F)(F)F] | 1-ethyl-3-((S)-1,1,1,5,5,5-hexafluoropentan-2-yl)-1-(2,2,2-trifluoro-1-(8-(8-methoxyimidazo[1,2-a]pyrazin-6-yl)imidazo[1,2-a]pyridin-6-yl)ethyl)urea | 612.4 |
| 2-15 | 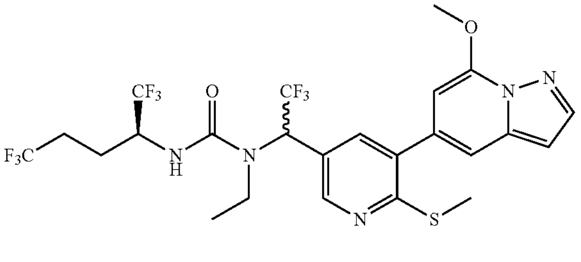 [SMILES: CCN(C(=O)N[C@@H](CCC(F)(F)F)C(F)(F)F)C(c1cnc(SC)c(-c2cc(OC)n3nccc3c2)c1)C(F)(F)F] | 1-ethyl-3-((S)-1,1,1,5,5,5-hexafluoropentan-2-yl)-1-(2,2,2-trifluoro-1-(5-(7-methoxypyrazolo[1,5-a]pyridin-5-yl)-6-(methylthio)pyridin-3-yl)ethyl)urea | 618.3 |

TABLE 2-continued

| Ex. | Structure | Name | Exact Mass [M + H]+ |
|---|---|---|---|
| 2-16 | 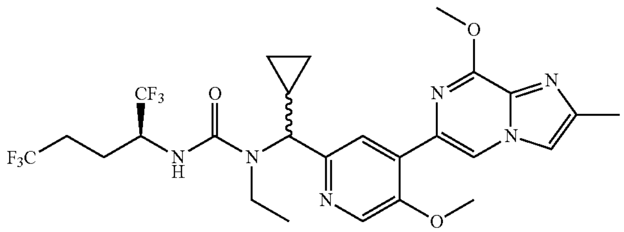 [SMILES: CCN(C(=O)N[C@@H](CCC(F)(F)F)C(F)(F)F)C(c1cc(-c2cn3cc(C)nc3c(OC)n2)c(OC)cn1)C1CC1] | 1-(cyclopropyl(5-methoxy-4-(8-methoxy-2-methylimidazo[1,2-a]pyrazin-6-yl)pyridin-2-yl)methyl)-1-ethyl-3-((S)-1,1,1,5,5,5-hexafluoropentan-2-yl)urea | 589.4 |
| 2-17 | 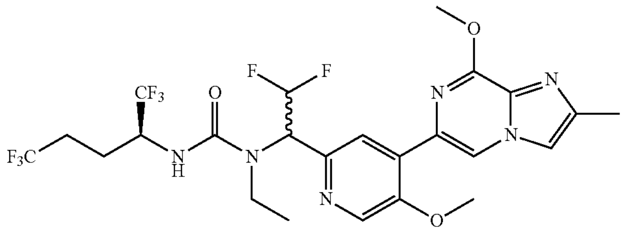 [SMILES: CCN(C(=O)N[C@@H](CCC(F)(F)F)C(F)(F)F)C(c1cc(-c2cn3cc(C)nc3c(OC)n2)c(OC)cn1)C(F)F] | 1-(2,2-difluoro-1-(5-methoxy-4-(8-methoxy-2-methylimidazo[1,2-a]pyrazin-6-yl)pyridin-2-yl)ethyl)-1-ethyl-3-((S)-1,1,1,5,5,5-hexafluoropentan-2-yl)urea | 599.3 |
| 2-18 | 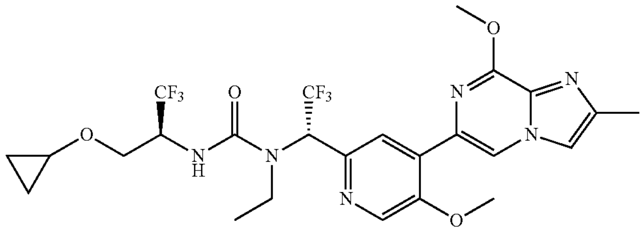 [SMILES: CCN(C(=O)N[C@@H](COC1CC1)C(F)(F)F)[C@@H](c1cc(-c2cn3cc(C)nc3c(OC)n2)c(OC)cn1)C(F)(F)F] | 3-((S)-3-cyclopropoxy-1,1,1-trifluoropropan-2-yl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea | 591.3 |
| 2-19 | 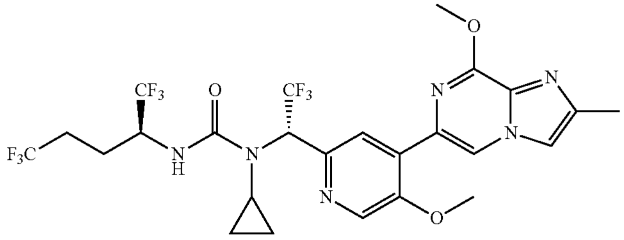 [SMILES: COc1cnc([C@H](N(C(=O)N[C@@H](CCC(F)(F)F)C(F)(F)F)C2CC2)C(F)(F)F)cc1-c1cn2cc(C)nc2c(OC)n1] | 1-cyclopropyl-3-((S)-1,1,1,5,5,5-hexafluoropentan-2-yl)-1-(2,2,2-trifluoro-1-(5-methoxy-4-(8-methoxy-2-methylimidazo[1,2-a]pyrazin-6-yl)pyridin-2-yl)ethyl)urea | 629.3 |
| 2-20 | 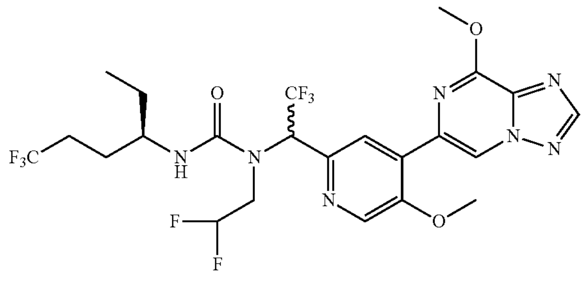 [SMILES: CC[C@H](CCC(F)(F)F)NC(=O)N(CC(F)F)C(c1cc(-c2cn3ncnc3c(OC)n2)c(OC)cn1)C(F)(F)F] | 1-(2,2-difluoroethyl)-1-(2,2,2-trifluoro-1-(5-methoxy-4-(8-methoxy-[1,2,4]triazolo[1,5-a]pyrazin-6-yl)pyridin-2-yl)ethyl)-3-((R)-6,6,6-trifluorohexan-3-yl)urea | 600.3 |
| 2-21 | 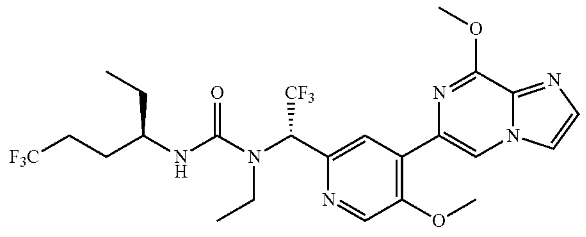 [SMILES: CC[C@H](CCC(F)(F)F)NC(=O)N(CC)[C@@H](c1cc(-c2cn3ccnc3c(OC)n2)c(OC)cn1)C(F)(F)F] | 1-ethyl-1-((S)-2,2,2-trifluoro-1-(5-methoxy-4-(8-methoxyimidazo[1,2-a]pyrazin-6-yl)pyridin-2-yl)ethyl)-3-((R)-6,6,6-trifluorohexan-3-yl)urea | 563.3 |

TABLE 2-continued

| Ex. | Structure | Name | Exact Mass [M + H]+ |
|---|---|---|---|
| 2-22 | 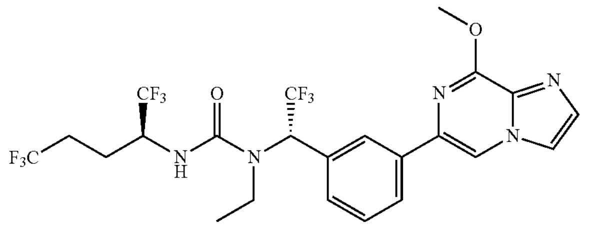 [SMILES: CCN(C(=O)N[C@@H](CCC(F)(F)F)C(F)(F)F)[C@@H](c1cccc(-c2cn3ccnc3c(OC)n2)c1)C(F)(F)F] | N-ethyl-N'-[(2S)-1,1,1,5,5,5-hexafluoropentan-2-yl]-N-{2,2,2-trifluoro-1-[3-(8-methoxyimidazo[1,2-a]pyrazin-6-yl)phenyl]ethyl}urea | 572.3 |
| 2-23 | 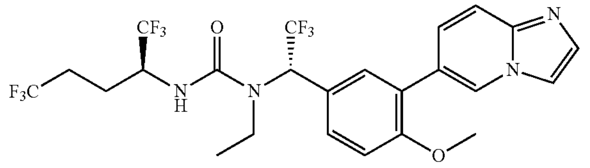 [SMILES: CCN(C(=O)N[C@@H](CCC(F)(F)F)C(F)(F)F)[C@@H](c1ccc(OC)c(-c2ccc3nccn3c2)c1)C(F)(F)F] | 1-ethyl-3-((S)-1,1,1,5,5,5-hexafluoropentan-2-yl)-1-((S)-2,2,2-trifluoro-1-(3-(imidazo[1,2-a]pyridin-6-yl)-4-methoxyphenyl)ethyl)urea | 571.0 |
| 2-24 | 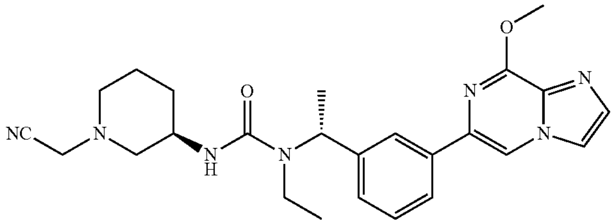 [SMILES: CCN(C(=O)N[C@@H]1CCCN(CC#N)C1)[C@H](C)c1cccc(-c2cn3ccnc3c(OC)n2)c1] | 3-((R)-1-(cyanomethyl)piperidin-3-yl)-1-ethyl-1-((R)-1-(3-(8-methoxyimidazo[1,2-a]pyrazin-6-yl)phenyl)ethyl)urea | 462.4 |
| 2-25 | 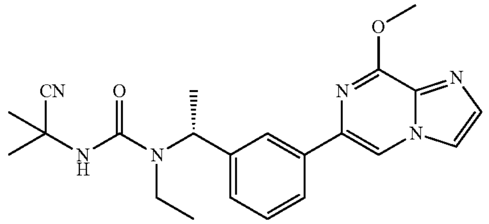 [SMILES: CCN(C(=O)NC(C)(C)C#N)[C@H](C)c1cccc(-c2cn3ccnc3c(OC)n2)c1] | (R)-3-(2-cyanopropan-2-yl)-1-ethyl-1-(1-(3-(8-methoxyimidazo[1,2-a]pyrazin-6-yl)phenyl)ethyl)urea | 407.4 |
| 2-26 | 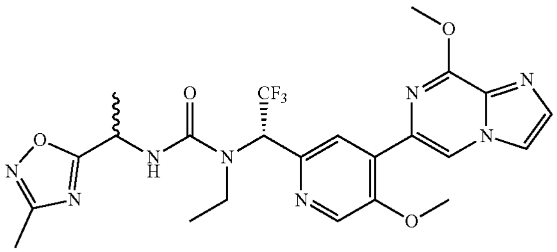 [SMILES: CCN(C(=O)NC(C)c1nc(C)no1)[C@@H](c1cc(-c2cn3ccnc3c(OC)n2)c(OC)cn1)C(F)(F)F] | 1-ethyl-3-(1-(3-methyl-1,2,4-oxadiazol-5-yl)ethyl)-1-((S)-2,2,2-trifluoro-1-(5-methoxy-4-(8-methoxyimidazo[1,2-a]pyrazin-6-yl)pyridin-2-yl)ethyl)urea | 435.3 |
| 2-27 | 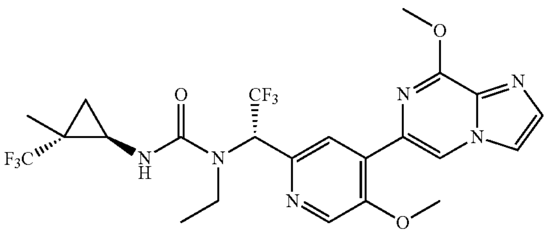 [SMILES: CCN(C(=O)N[C@@H]1C[C@@]1(C)C(F)(F)F)[C@@H](c1cc(-c2cn3ccnc3c(OC)n2)c(OC)cn1)C(F)(F)F] | 1-ethyl-3-((1R,2R)-2-methyl-2-(trifluoromethyl)-cyclopropyl)-1-((S)-2,2,2-trifluoro-1-(5-methoxy-4-(8-methoxyimidazo[1,2-a]pyrazin-6-yl)pyridin-2-yl)ethyl)urea | 547.2 |

TABLE 2-continued

| Ex. | Structure | Name | Exact Mass [M + H]+ |
|---|---|---|---|
| 2-28 | 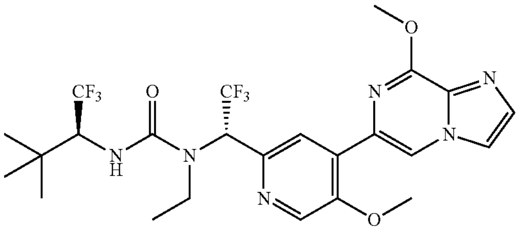 [SMILES: CCN(C(=O)N[C@@H](C(C)(C)C)C(F)(F)F)[C@@H](c1cc(-c2cn3ccnc3c(OC)n2)c(OC)cn1)C(F)(F)F] | 1-ethyl-1-((S)-2,2,2-trifluoro-1-(5-methoxy-4-(8-methoxyimidazo[1,2-a]pyrazin-6-yl)pyridin-2-yl)ethyl)-3-((S)-1,1,1-trifluoro-3,3-dimethylbutan-2-yl)urea | 563.3 |
| 2-29 | 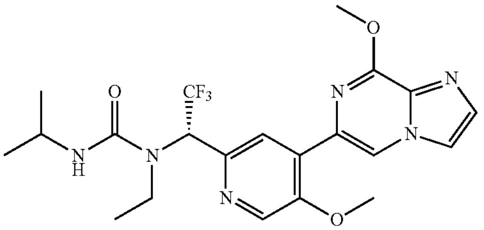 [SMILES: CCN(C(=O)NC(C)C)[C@@H](c1cc(-c2cn3ccnc3c(OC)n2)c(OC)cn1)C(F)(F)F] | (S)-1-ethyl-3-isopropyl-1-(2,2,2-trifluoro-1-(5-methoxy-4-(8-methoxyimidazo[1,2-a]pyrazin-6-yl)pyridin-2-yl)ethyl)urea | 467.3 |
| 2-30 | 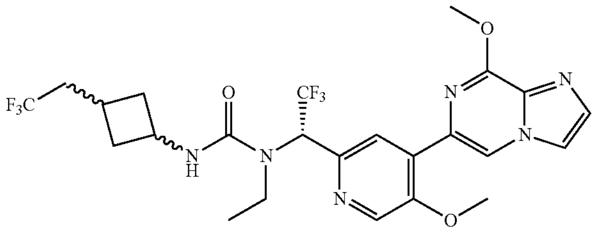 [SMILES: CCN(C(=O)NC1CC(CC(F)(F)F)C1)[C@@H](c1cc(-c2cn3ccnc3c(OC)n2)c(OC)cn1)C(F)(F)F] | (S)-1-ethyl-1-(2,2,2-trifluoro-1-(5-methoxy-4-(8-methoxyimidazo[1,2-a]pyrazin-6-yl)pyridin-2-yl)ethyl)-3-(3-(2,2,2-trifluoroethyl)cyclobutyl)urea | 561.3 |
| 2-31 | 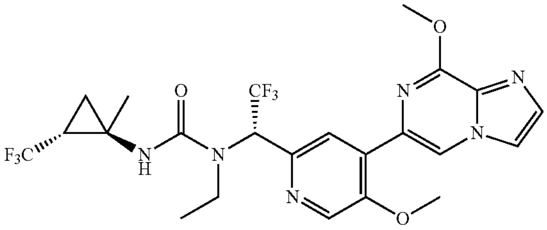 [SMILES: CCN(C(=O)N[C@]1(C)C[C@H]1C(F)(F)F)[C@@H](c1cc(-c2cn3ccnc3c(OC)n2)c(OC)cn1)C(F)(F)F] | 1-ethyl-3-((1R,2R)-1-methyl-2-(trifluoromethyl)cyclopropyl)-1-((S)-2,2,2-trifluoro-1-(5-methoxy-4-(8-methoxyimidazo[1,2-a]pyrazin-6-yl)pyridin-2-yl)ethyl)urea | 547.4 |
| 2-32 | 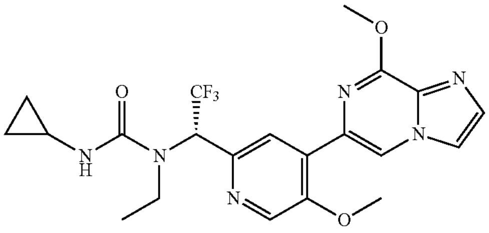 [SMILES: CCN(C(=O)NC1CC1)[C@@H](c1cc(-c2cn3ccnc3c(OC)n2)c(OC)cn1)C(F)(F)F] | (S)-3-cyclopropyl-1-ethyl-1-(2,2,2-trifluoro-1-(5-methoxy-4-(8-methoxyimidazo[1,2-a]pyrazin-6-yl)pyridin-2-yl)ethyl)urea | 465.4 |
| 2-33 | 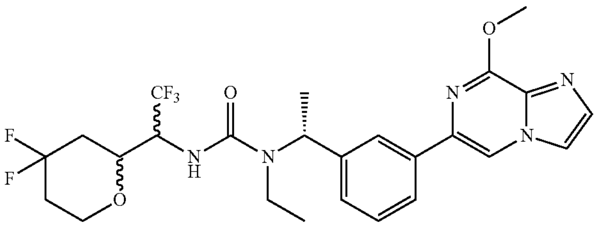 [SMILES: CCN(C(=O)NC(C1CC(F)(F)CCO1)C(F)(F)F)[C@H](C)c1cccc(-c2cn3ccnc3c(OC)n2)c1] | 3-(1-(4,4-difluorotetrahydro-2H-pyran-2-yl)-2,2,2-trifluoroethyl)-1-ethyl-1-((R)-1-(3-(8-methoxyimidazo[1,2-a]pyrazin-6-yl)phenyl)ethyl)urea | 542.3 |

TABLE 2-continued

| Ex. | Structure | Name | Exact Mass [M + H]+ |
|---|---|---|---|
| 2-34 | 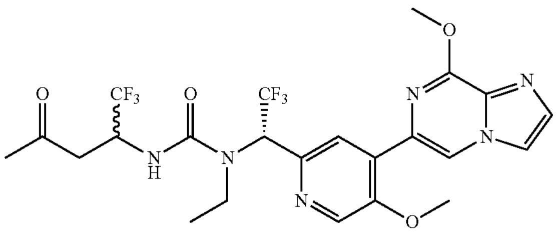 [SMILES: CCN(C(=O)NC(CC(C)=O)C(F)(F)F)[C@@H](c1cc(-c2cn3ccnc3c(OC)n2)c(OC)cn1)C(F)(F)F] | 1-ethyl-1-((S)-2,2,2-trifluoro-1-(5-methoxy-4-(8-methoxyimidazo[1,2-a]pyrazin-6-yl)pyridin-2-yl)ethyl)-3-(1,1,1-trifluoro-4-oxopentan-2-yl)urea | 563.2 |
| 2-35 | 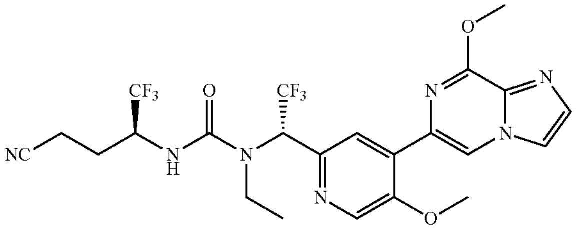 [SMILES: CCN(C(=O)N[C@@H](CCC#N)C(F)(F)F)[C@@H](c1cc(-c2cn3ccnc3c(OC)n2)c(OC)cn1)C(F)(F)F] | 3-((S)-4-cyano-1,1,1-trifluorobutan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea | 560.2 |
| 2-36 | 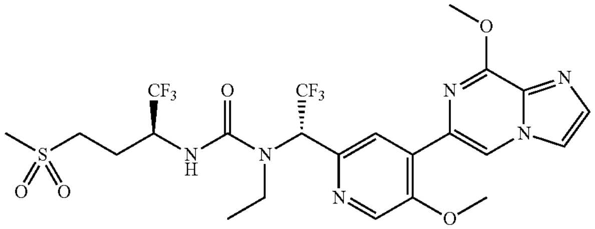 [SMILES: CCN(C(=O)N[C@@H](CCS(C)(=O)=O)C(F)(F)F)[C@@H](c1cc(-c2cn3ccnc3c(OC)n2)c(OC)cn1)C(F)(F)F] | 1-ethyl-1-((S)-2,2,2-trifluoro-1-(5-methoxy-4-(8-methoxyimidazo[1,2-a]pyrazin-6-yl)pyridin-2-yl)ethyl)-3-((S)-1,1,1-trifluoro-4-(methylsulfonyl)butan-2-yl)urea | 613.3 |
| 2-37 | 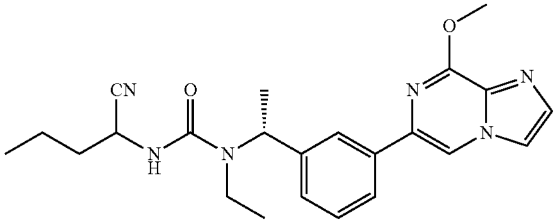 [SMILES: CCCC(C#N)NC(=O)N(CC)[C@H](C)c1cccc(-c2cn3ccnc3c(OC)n2)c1] | 3-(1-cyanobutyl)-1-ethyl-1-((R)-1-(3-(8-methoxyimidazo[1,2-a]pyrazin-6-yl)phenyl)ethyl)urea | 521.3 |
| 2-38 | 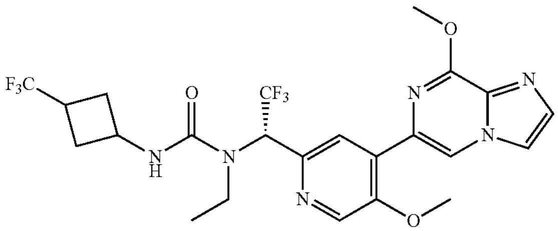 [SMILES: CCN(C(=O)NC1CC(C(F)(F)F)C1)[C@@H](c1cc(-c2cn3ccnc3c(OC)n2)c(OC)cn1)C(F)(F)F] | (S)-1-ethyl-1-(2,2,2-trifluoro-1-(5-methoxy-4-(8-methoxyimidazo[1,2-a]pyrazin-6-yl)pyridin-2-yl)ethyl)-3-(3-(trifluoromethyl)cyclobutyl)urea | 547.3 |
| 2-39 | 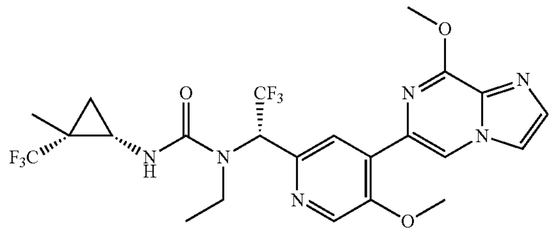 [SMILES: CCN(C(=O)N[C@H]1C[C@@]1(C)C(F)(F)F)[C@@H](c1cc(-c2cn3ccnc3c(OC)n2)c(OC)cn1)C(F)(F)F] | 1-ethyl-3-((1S,2R)-2-methyl-2-(trifluoromethyl)cyclopropyl)-1-((S)-2,2,2-trifluoro-1-(5-methoxy-4-(8-methoxyimidazo[1,2-a]pyrazin-6-yl)pyridin-2-yl)ethyl)urea | 547.2 |

TABLE 2-continued

| Ex. | Structure | Name | Exact Mass [M + H]+ |
|---|---|---|---|
| 2-40 | 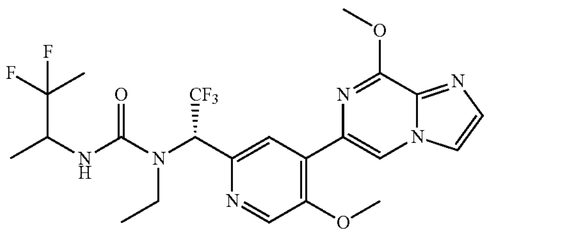 [SMILES: CCN(C(=O)NC(C)C(C)(F)F)[C@@H](c1cc(-c2cn3ccnc3c(OC)n2)c(OC)cn1)C(F)(F)F] | 3-(3,3-difluorobutan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea | 517.6 |
| 2-41 | 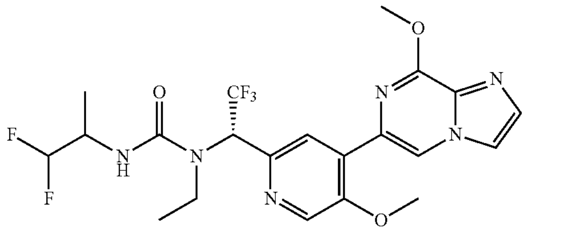 [SMILES: CCN(C(=O)NC(C)C(F)F)[C@@H](c1cc(-c2cn3ccnc3c(OC)n2)c(OC)cn1)C(F)(F)F] | 3-(1,1-difluoropropan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea | 503.2 |
| 2-42 | 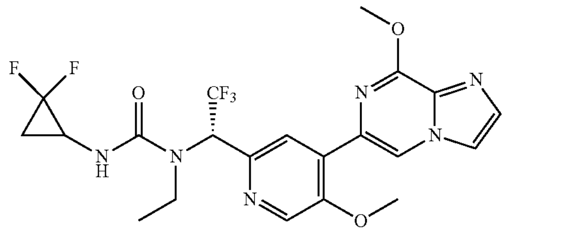 [SMILES: CCN(C(=O)NC1CC1(F)F)[C@@H](c1cc(-c2cn3ccnc3c(OC)n2)c(OC)cn1)C(F)(F)F] | 3-(2,2-difluorocyclopropyl)-1-ethyl-1-((S)-2,2,2-trifluoro-1-(5-methoxy-4-(8-methoxyimidazo[1,2-a]pyrazin-6-yl)pyridin-2-yl)ethyl)urea | 501.5 |
| 2-43 | 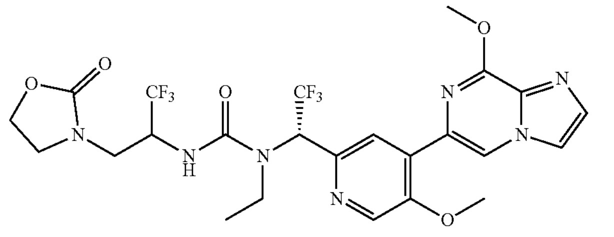 [SMILES: CCN(C(=O)NC(CN1CCOC1=O)C(F)(F)F)[C@@H](c1cc(-c2cn3ccnc3c(OC)n2)c(OC)cn1)C(F)(F)F] | 1-ethyl-1-((S)-2,2,2-trifluoro-1-(5-methoxy-4-(8-methoxyimidazo[1,2-a]pyrazin-6-yl)pyridin-2-yl)ethyl)-3-(1,1,1-trifluoro-3-(2-oxooxazolidin-3-yl)propan-2-yl)urea | 606.4 |
| 2-44 | 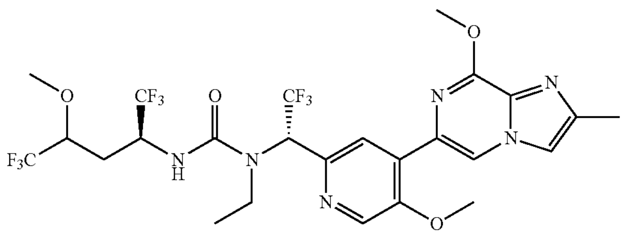 [SMILES: CCN(C(=O)N[C@@H](CC(OC)C(F)(F)F)C(F)(F)F)[C@@H](c1cc(-c2cn3cc(C)nc3c(OC)n2)c(OC)cn1)C(F)(F)F] | 1-ethyl-3-((2S)-1,1,1,5,5,5-hexafluoro-4-methoxypentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea | 648.5 |
| 2-45 | 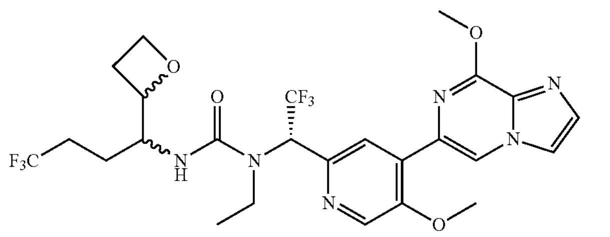 [SMILES: CCN(C(=O)NC(CCC(F)(F)F)C1CCO1)[C@@H](c1cc(-c2cn3ccnc3c(OC)n2)c(OC)cn1)C(F)(F)F] | 1-ethyl-1-((S)-2,2,2-trifluoro-1-(5-methoxy-4-(8-methoxyimidazo[1,2-a]pyrazin-6-yl)pyridin-2-yl)ethyl)-3-(4,4,4-trifluoro-1-(oxetan-2-yl)butyl)urea | 591.5 |

TABLE 2-continued

| Ex. | Structure | Name | Exact Mass [M + H]+ |
|---|---|---|---|
| 2-46 | 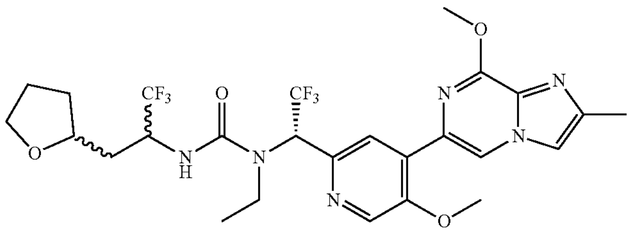 [SMILES: CCN(C(=O)NC(CC1CCCO1)C(F)(F)F)[C@@H](c1cc(-c2cn3cc(C)nc3c(OC)n2)c(OC)cn1)C(F)(F)F] | 1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(1,1,1-trifluoro-3-(tetrahydrofuran-2-yl)propan-2-yl)urea | 606.3 |
| 2-47 | 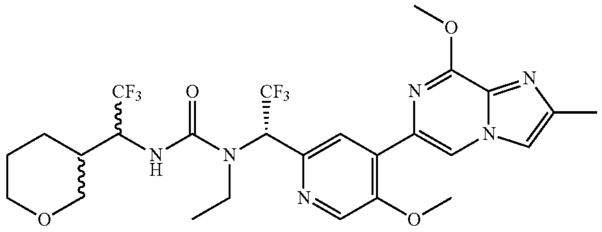 [SMILES: CCN(C(=O)NC(C1CCCOC1)C(F)(F)F)[C@@H](c1cc(-c2cn3cc(C)nc3c(OC)n2)c(OC)cn1)C(F)(F)F] | 1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(2,2,2-trifluoro-1-(tetrahydro-2H-pyran-3-yl)ethyl)urea | 606.3 |
| 2-48 | 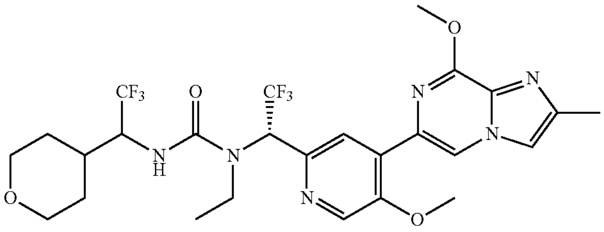 [SMILES: CCN(C(=O)NC(C1CCOCC1)C(F)(F)F)[C@@H](c1cc(-c2cn3cc(C)nc3c(OC)n2)c(OC)cn1)C(F)(F)F] | 1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(2,2,2-trifluoro-1-(tetrahydro-2H-pyran-4-yl)ethyl)urea | 606.3 |
| 2-49 | 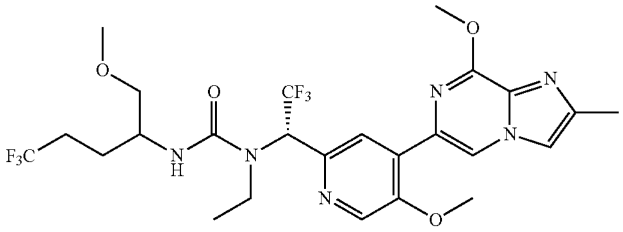 [SMILES: CCN(C(=O)NC(CCC(F)(F)F)COC)[C@@H](c1cc(-c2cn3cc(C)nc3c(OC)n2)c(OC)cn1)C(F)(F)F] | 1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(5,5,5-trifluoro-1-methoxypentan-2-yl)urea | 593.5 |
| 2-50 | 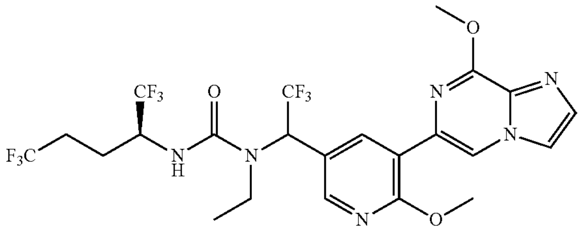 [SMILES: CCN(C(=O)N[C@@H](CCC(F)(F)F)C(F)(F)F)C(c1cnc(OC)c(-c2cn3ccnc3c(OC)n2)c1)C(F)(F)F] | 1-ethyl-3-((S)-1,1,1,5,5,5-hexafluoropentan-2-yl)-1-(2,2,2-trifluoro-1-(6-methoxy-5-(8-methoxyimidazo[1,2-a]pyrazin-6-yl)pyridin-3-yl)ethyl)urea | 604.3 |
| 2-51 | 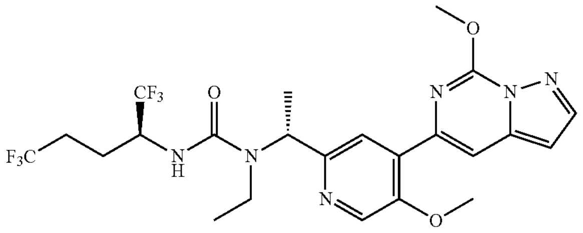 [SMILES: CCN(C(=O)N[C@@H](CCC(F)(F)F)C(F)(F)F)[C@H](C)c1cc(-c2cc3ccnn3c(OC)n2)c(OC)cn1] | 1-ethyl-3-((S)-1,1,1,5,5,5-hexafluoropentan-2-yl)-1-((R)-1-(5-methoxy-4-(7-methoxypyrazolo[1,5-c]pyrimidin-5-yl)pyridin-2-yl)ethyl)urea | 549.3 |

TABLE 2-continued

| Ex. | Structure | Name | Exact Mass [M + H]+ |
| --- | --- | --- | --- |
| 2-52 | 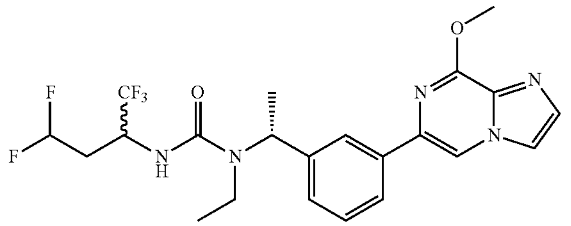 [SMILES: CCN(C(=O)NC(CC(F)F)C(F)(F)F)[C@H](C)c1cccc(-c2cn3ccnc3c(OC)n2)c1] | 1-ethyl-1-((R)-1-(3-(8-methoxyimidazo[1,2-a]pyrazin-6-yl)phenyl)ethyl)-3-(1,1,1,4,4-pentafluorobutan-2-yl)urea | 486.4 |
| 2-53 | 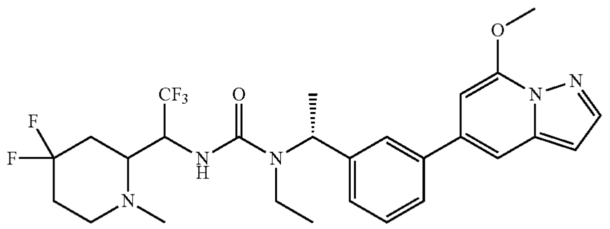 [SMILES: CCN(C(=O)NC(C1CC(F)(F)CCN1C)C(F)(F)F)[C@H](C)c1cccc(-c2cc(OC)n3nccc3c2)c1] | 3-(1-(4,4-difluoro-1-methylpiperidin-2-yl)-2,2,2-trifluoroethyl)-1-ethyl-1-((R)-1-(3-(7-methoxypyrazolo[1,5-a]pyridin-5-yl)phenyl)ethyl)urea | 554.2 |
| 2-54 | 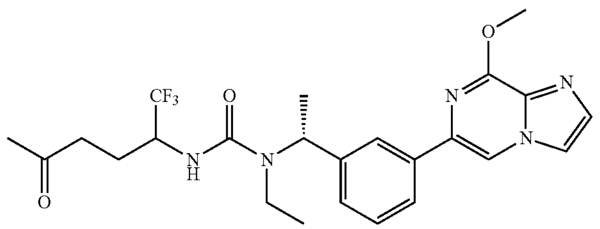 [SMILES: CCN(C(=O)NC(CCC(C)=O)C(F)(F)F)[C@H](C)c1cccc(-c2cn3ccnc3c(OC)n2)c1] | 1-ethyl-1-((R)-1-(3-(8-methoxyimidazo[1,2-a]pyrazin-6-yl)phenyl)ethyl)-3-(1,1,1-trifluoro-5-oxohexan-2-yl)urea | 492.1 |
| 2-55 | 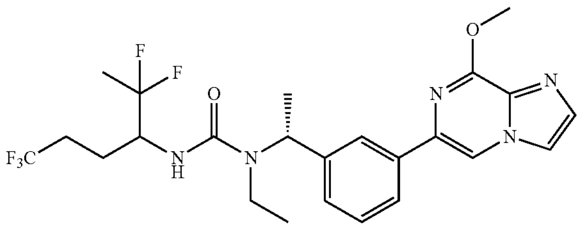 [SMILES: CCN(C(=O)NC(CCC(F)(F)F)C(C)(F)F)[C@H](C)c1cccc(-c2cn3ccnc3c(OC)n2)c1] | 1-ethyl-1-((R)-1-(3-(8-methoxyimidazo[1,2-a]pyrazin-6-yl)phenyl)ethyl)-3-(2,2,6,6,6-pentafluorohexan-3-yl)urea | 514.4 |
| 2-56 | 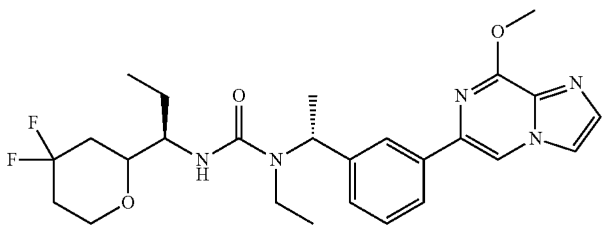 [SMILES: CC[C@@H](NC(=O)N(CC)[C@H](C)c1cccc(-c2cn3ccnc3c(OC)n2)c1)C1CC(F)(F)CCO1] | 3-((1R)-1-(4,4-difluorotetrahydro-2H-pyran-2-yl)propyl)-1-ethyl-1-((R)-1-(3-(8-methoxyimidazo[1,2-a]pyrazin-6-yl)phenyl)ethyl)urea | 502.3 |
| 2-57 | 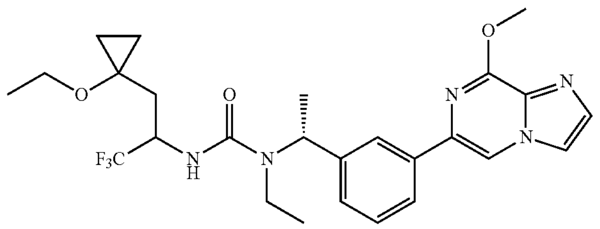 [SMILES: CCOC1(CC(NC(=O)N(CC)[C@H](C)c2cccc(-c3cn4ccnc4c(OC)n3)c2)C(F)(F)F)CC1] | 3-(3-(1-ethoxycyclopropyl)-1,1,1-trifluoropropan-2-yl)-1-ethyl-1-((R)-1-(3-(8-methoxyimidazo[1,2-a]pyrazin-6-yl)phenyl)ethyl)urea | 520.3 |

TABLE 2-continued

| Ex. | Structure | Name | Exact Mass [M + H]+ |
|---|---|---|---|
| 2-58 | 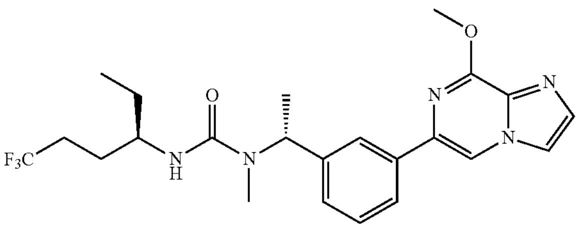 [SMILES: CC[C@H](CCC(F)(F)F)NC(=O)N(C)[C@H](C)c1cccc(-c2cn3ccnc3c(OC)n2)c1] | 1-((R)-1-(3-(8-methoxyimidazo[1,2-a]pyrazin-6-yl)phenyl)ethyl)-1-methyl-3-((R)-6,6,6-trifluorohexan-3-yl)urea | 464.3 |
| 2-59 | 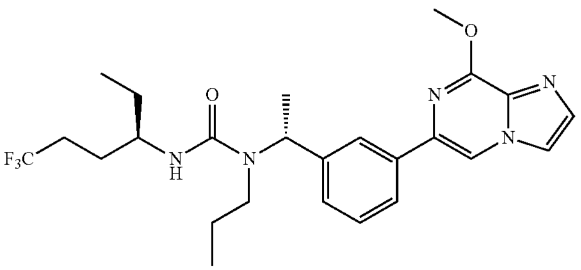 [SMILES: CCCN(C(=O)N[C@H](CC)CCC(F)(F)F)[C@H](C)c1cccc(-c2cn3ccnc3c(OC)n2)c1] | 1-((R)-1-(3-(8-methoxyimidazo[1,2-a]pyrazin-6-yl)phenyl)ethyl)-1-propyl-3-((R)-6,6,6-trifluorohexan-3-yl)urea | 492.2 |
| 2-60 | 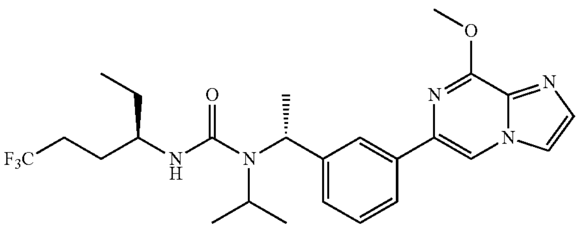 [SMILES: CC[C@H](CCC(F)(F)F)NC(=O)N(C(C)C)[C@H](C)c1cccc(-c2cn3ccnc3c(OC)n2)c1] | 1-isopropyl-1-((R)-1-(3-(8-methoxyimidazo[1,2-a]pyrazin-6-yl)phenyl)ethyl)-3-((R)-6,6,6-trifluorohexan-3-yl)urea | 492.4 |
| 2-61 | 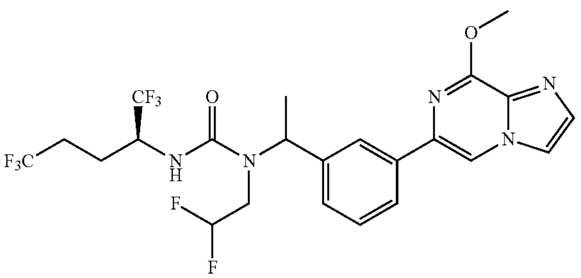 [SMILES: COc1nc(-c2cccc(C(C)N(CC(F)F)C(=O)N[C@@H](CCC(F)(F)F)C(F)(F)F)c2)cn2ccnc12] | 1-(2,2-difluoroethyl)-3-((S)-1,1,1,5,5,5-hexafluoropentan-2-yl)-1-(1-(3-(8-methoxyimidazo[1,2-a]pyrazin-6-yl)phenyl)ethyl)urea | 554.1 |
| 2-62 | 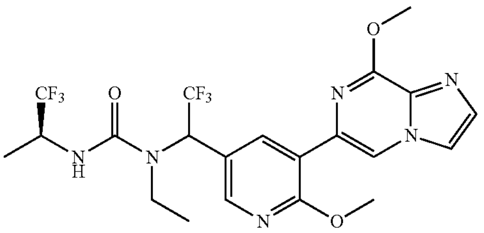 [SMILES: CCN(C(=O)N[C@@H](C)C(F)(F)F)C(c1cnc(OC)c(-c2cn3ccnc3c(OC)n2)c1)C(F)(F)F] | 1-ethyl-1-(2,2,2-trifluoro-1-(6-methoxy-5-(8-methoxyimidazo[1,2-a]pyrazin-6-yl)pyridin-3-yl)ethyl)-3-((S)-1,1,1-trifluoropropan-2-yl)urea | 521.0 |
| 2-63 | 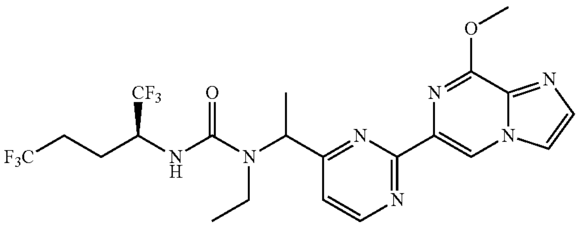 [SMILES: CCN(C(=O)N[C@@H](CCC(F)(F)F)C(F)(F)F)C(C)c1ccnc(-c2cn3ccnc3c(OC)n2)n1] | 1-ethyl-3-((S)-1,1,1,5,5,5-hexafluoropentan-2-yl)-1-(1-(2-(8-methoxyimidazo[1,2-a]pyrazin-6-yl)pyrimidin-4-yl)ethyl)urea | 520.0 |

TABLE 2-continued

| Ex. | Structure | Name | Exact Mass [M + H]+ |
|---|---|---|---|
| 2-64 | 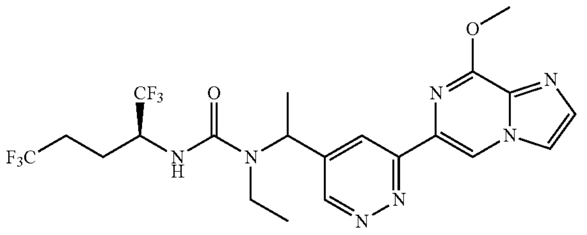 [SMILES: CCN(C(=O)N[C@@H](CCC(F)(F)F)C(F)(F)F)C(C)c1cnnc(-c2cn3ccnc3c(OC)n2)c1] | 1-ethyl-3-((S)-1,1,1,5,5,5-hexafluoropentan-2-yl)-1-(1-(6-(8-methoxyimidazo[1,2-a]pyrazin-6-yl)pyridazin-4-yl)ethyl)urea | 520.0 |
| 2-65 | 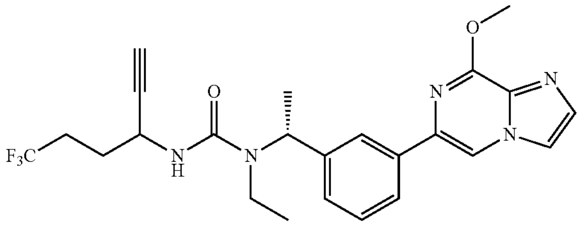 [SMILES: C#CC(CCC(F)(F)F)NC(=O)N(CC)[C@H](C)c1cccc(-c2cn3ccnc3c(OC)n2)c1] | 1-ethyl-1-((R)-1-(3-(8-methoxyimidazo[1,2-a]pyrazin-6-yl)phenyl)ethyl)-3-(6,6,6-trifluorohex-1-yn-3-yl)urea | 474.4 |
| 2-66 | 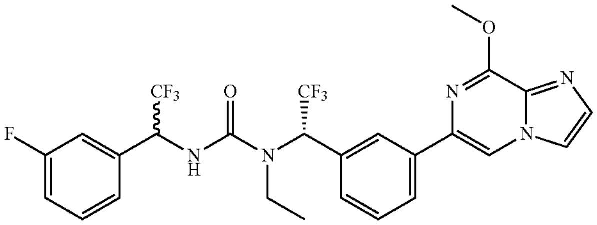 [SMILES: CCN(C(=O)NC(c1cccc(F)c1)C(F)(F)F)[C@@H](c1cccc(-c2cn3ccnc3c(OC)n2)c1)C(F)(F)F] | 1-ethyl-1-((S)-2,2,2-trifluoro-1-(3-(8-methoxyimidazo[1,2-a]pyrazin-6-yl)phenyl)ethyl)-3-(2,2,2-trifluoro-1-(3-fluorophenyl)ethyl)urea | 570.3 |
| 2-67 | 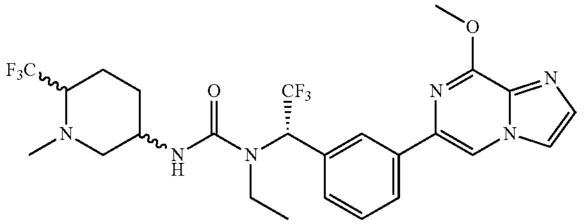 [SMILES: CCN(C(=O)NC1CCC(C(F)(F)F)N(C)C1)[C@@H](c1cccc(-c2cn3ccnc3c(OC)n2)c1)C(F)(F)F] | 1-ethyl-3-(1-methyl-6-(trifluoromethyl)piperidin-3-yl)-1-((S)-2,2,2-trifluoro-1-(3-(8-methoxyimidazo[1,2-a]pyrazin-6-yl)phenyl)ethyl)urea | 581.4 |
| 2-68 | 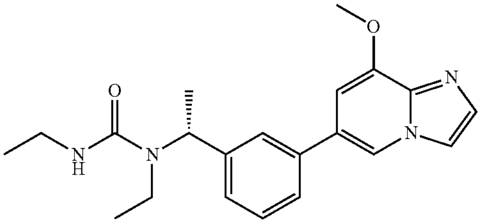 [SMILES: CCNC(=O)N(CC)[C@H](C)c1cccc(-c2cc(OC)c3nccn3c2)c1] | (R)-1,3-diethyl-1-(1-(3-(8-methoxyimidazo[1,2-a]pyridin-6-yl)phenyl)ethyl)urea | 367.3 |

Example 3-1 for Table 3: 3-((1S)-1-(3,3-difluorocyclohexyl)-2,2,2-trifluoroethyl)-1-ethyl-1-((R)-1-(3-(8-methoxyimidazo[1,2-a]pyrazin-6-yl)phenyl)ethyl) urea Example 3-1

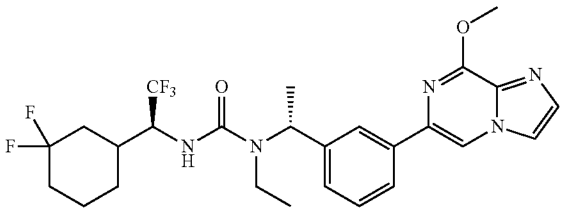

Step 1: 3,3-difluorocyclohexane-1-carbaldehyde $(C_{1-3})$

C1-3

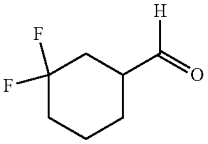

A flame-dried flask was charged with oxalyl chloride (2.0 M in DCM) (7.99 ml, 15.98 mmol) which was dissolved in DCM (13 mL) and cooled to −78° C. To this, DMSO (2.174 ml, 30.6 mmol) was added drop-wise. The mixture was stirred, −78° C., for 15 min, then treated with (3,3-difluorocyclohexyl)methanol (2.0 g, 13.32 mmol) in DCM (13 mL) was added slowly via syringe and this was stirred, −78° C. for 30 min. TEA (8.54 ml, 61.3 mmol) was added and the ice bath was removed and the contents were stirred, ambient temperature, for 45 min. This was diluted with $CH_2Cl_2$, washed with sat. $NaHCO_3$ followed by sat. $NH_4Cl$ and water, dried ($Na_2SO_4$), filtered and concentrated under vacuum (>50 mbar) to afford the title compound which was used without further purification.

Step 2: (R)—N—((E)-(3,3-difluorocyclohexyl) methylene)-2-methylpropane-2-sulfinamide (C1-2)

C1-2

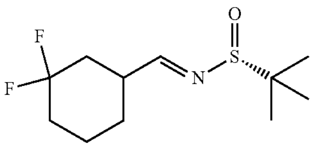

The 3,3-difluorocyclohexane-1-carbaldehyde (C1-3) (1.0 g, 6.75 mmol) was dissolved in DCM (11.25 ml) and treated with (R)-(+)-2-methyl-2-propanesulfinamide (1.063 g, 8.77 mmol), magnesium sulfate (2.112 g, 17.55 mmol) and PPTS (0.136 g, 0.540 mmol). The reaction contents were stirred at ambient temperature for 18 h. This was filtered through a bed of celite while washing the filter cake with DCM. The filtrate was concentrated to give an oil. This was purified via chromatography ($SiO_2$ 120 g RediSep column, 0-30% 3:1 EtOAc:EtOH/hexanes, 85 mL/min, 35 min) to give the title compound. MS: 252.3 [M+1].

Step 3: (R)—N-((1S)-1-(3,3-difluorocyclohexyl)-2,2,2-trifluoroethyl)-2-methylpropane-2-sulfinamide (C1-3)

C1-3

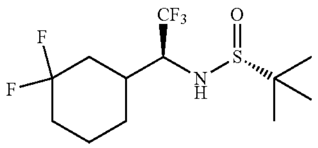

A flame-dried flask was charged with (R)—N—((E)-(3,3-difluorocyclohexyl)methylene)-2-methylpropane-2-sulfinamide (C1-2) (0.5 g, 1.989 mmol) and treated with THF (9.95 ml), cooled to −50° C. and treated with tetrabutylammonium fluoride (1.0 M in THF) (5.97 ml, 5.97 mmol) followed by (trifluoromethyl)trimethylsilane (1.191 ml, 7.96 mmol), added slowly. This was warmed to 0° C. and stirred for 2 h. This was quenched with sat. $NH_4Cl$, diluted with EtOAc and the organic portion was dried ($Na_2SO_4$), filtered and concentrated to give the crude product. This was purified via chromatography ($SiO_2$ 80 g RediSep column, 0-25% 3:1 EtOAc:EtOH/hexanes, 60 mL/min, 35 min) to afford the title compound. MS: 322.3 [M+1].

Step 4: (1S)-1-(3,3-difluorocyclohexyl)-2,2,2-trifluoroethan-1-amine (C1-4)

C1-4

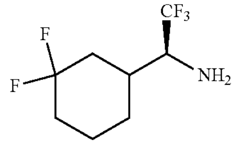

The (R)—N-((1S)-1-(3,3-difluorocyclohexyl)-2,2,2-trifluoroethyl)-2-methylpropane-2-sulfinamide (C1-3) was dissolved in MeOH (5.82 ml) and treated with HCl (4.0 M in dioxane) (0.873 ml, 3.49 mmol) and aged at ambient temperature for 2 h. The contents of the reaction was concentrated under a stream of nitrogen to afford the title compound which was used without further purification.

Step 4: 3-((1S)-1-(3,3-difluorocyclohexyl)-2,2,2-trifluoroethyl)-1-ethyl-1-((R)-1-(3-(8-methoxyimidazo[1,2-a]pyrazin-6-yl)phenyl)ethyl)urea (Example 3-1 for Table 3)

Example 3-1

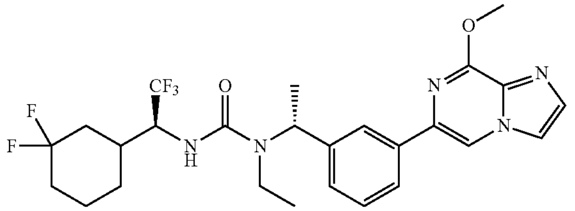

The title compound was prepared from (1S)-1-(3,3-difluorocyclohexyl)-2,2,2-trifluoroethan-1-amine (C1-4) and (R)—N-ethyl-1-(3-(8-methoxyimidazo[1,2-a]pyrazin-6-yl)phenyl)ethan-1-amine (Intermediate A5) using the procedure outlined in the synthesis of Example 2-1. The mixture of diastereomers were resolved via SFC using the following conditions: AD-H column (3×25 cm, 5 uM), 15% MeOH, flow rate=70 mL/min. The title compound eluted as the first peak. MS: 540.3 [M+1].

The following compounds were prepared according to the general procedures herein and in an analogous manner to that used to synthesize the Examples above using the appropriate alcohol starting materials that are commercially available and amines that have been previously described or that are commercially available. The starting materials were either prepared as described in the intermediates section, commercial available, or prepared from commercially available reagents using conventional reactions well known in the art. Examples 3-6 and 3-7 were prepared with racemic 2-methylpropane-2-sulfinamide and resolved via SFC.

TABLE 3

| Ex. | Structure | Name | Exact Mass [M + H]+ |
|---|---|---|---|
| 3-2 | 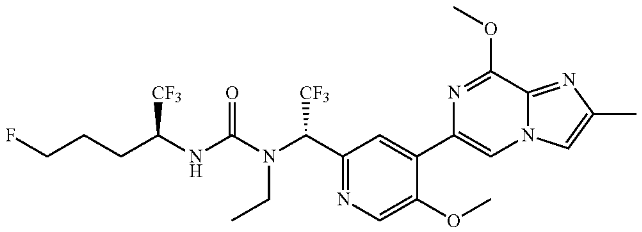 [SMILES: CCN(C(=O)N[C@@H](CCCF)C(F)(F)F)[C@@H](c1cc(-c2cn3cc(C)nc3c(OC)n2)c(OC)cn1)C(F)(F)F] | 1-ethyl-3-((S)-1,1,1,5-tetrafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea | 581.3 |
| 3-3 | 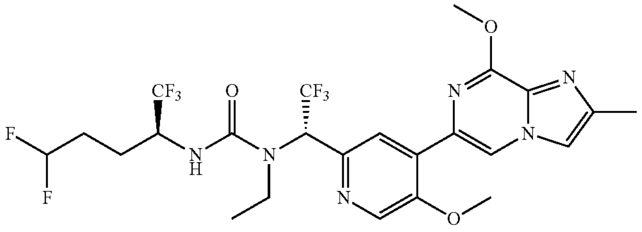 [SMILES: CCN(C(=O)N[C@@H](CCC(F)F)C(F)(F)F)[C@@H](c1cc(-c2cn3cc(C)nc3c(OC)n2)c(OC)cn1)C(F)(F)F] | 1-ethyl-3-((S)-1,1,1,5,5-pentafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea | 599.5 |
| 3-4 | 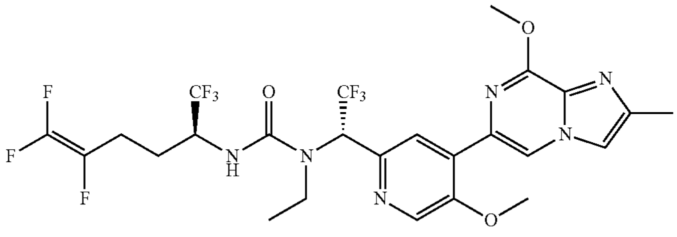 [SMILES: CCN(C(=O)N[C@@H](CCC(F)=C(F)F)C(F)(F)F)[C@@H](c1cc(-c2cn3cc(C)nc3c(OC)n2)c(OC)cn1)C(F)(F)F] | 1-ethyl-3-((S)-1,1,1,5,6,6-hexafluorohex-5-en-2-yl)-1-((S)-2,2,2-trifluoro-1-(5-methoxy-4-(8-methoxy-2-methylimidazo[1,2-a]pyrazin-6-yl)pyridin-2-yl)ethyl)urea | 629.5 |
| 3-5 | 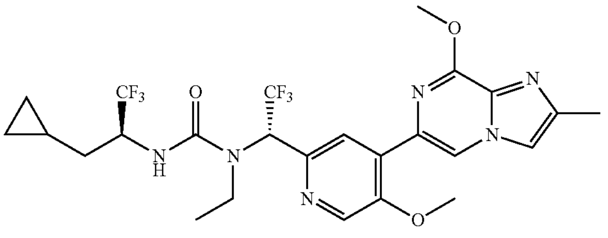 [SMILES: CCN(C(=O)N[C@@H](CC1CC1)C(F)(F)F)[C@@H](c1cc(-c2cn3cc(C)nc3c(OC)n2)c(OC)cn1)C(F)(F)F] | 3-((S)-3-cyclopropyl-1,1,1-trifluoropropan-2-yl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea | 575.2 |
| 3-6 | 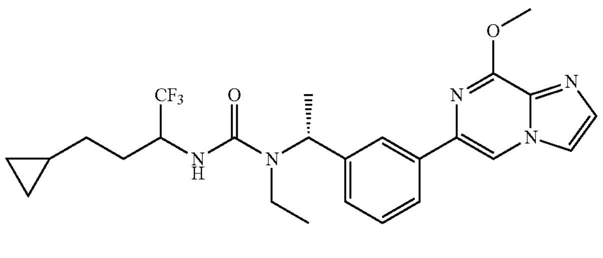 [SMILES: CCN(C(=O)NC(CCC1CC1)C(F)(F)F)[C@H](C)c1cccc(-c2cn3ccnc3c(OC)n2)c1] | 3-(4-cyclopropyl-1,1,1-trifluorobutan-2-yl)-1-ethyl-1-((R)-1-(3-(8-methoxyimidazo[1,2-a]pyrazin-6-yl)phenyl)ethyl)urea | 490.4 |

TABLE 3-continued

| Ex. | Structure | Name | Exact Mass [M + H]+ |
|---|---|---|---|
| 3-7 | 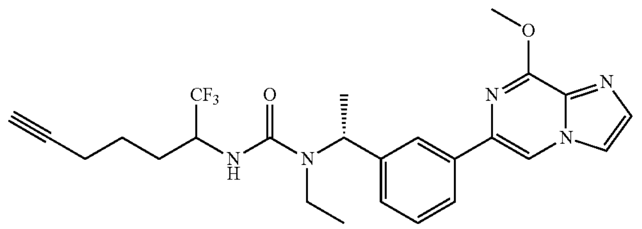 [SMILES: C#CCCCC(NC(=O)N(CC)[C@H](C)c1cccc(-c2cn3ccnc3c(OC)n2)c1)C(F)(F)F] | 1-ethyl-1-((R)-1-(3-(8-methoxyimidazo[1,2-a]pyrazin-6-yl)phenyl)ethyl)-3-(1,1,1-trifluorohept-6-yn-2-yl)urea | 488.2 |

Intermediate D1: (S)—N-ethyl-2,2,2-trifluoro-1-(5-methoxy-4-(8-methoxy-[1,2,4]triazolo[1,5-a]pyrazin-6-yl)pyridin-2-yl)ethan-1-amine Intermediate D1

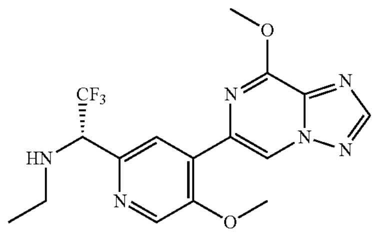

The racemic title compound was prepared from 1-(4-bromo-5-methoxypyridin-2-yl)-N-ethyl-2,2,2-trifluoroethan-1-amine (B21-4) and (8-methoxy-[1,2,4]triazolo[1,5-a]pyrazin-6-yl)boronic acid (Intermediate B25) using the procedure outlined in step 2 of synthesis of Intermediate A5. This enantiomers were resolved via prep SFC using the following conditions: AS-H column (2×25 cm), 15% MeOH/$CO_2$, 100 bar, flow rate=70 mL/min. The title compound eluted as the second peak. MS: 583.2 [M+1].

Example 4-1 for Table 4: 1-ethyl-3-((S)-1,1,5,5,5-pentafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea Example 4-1

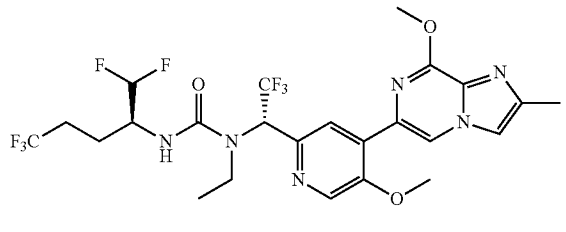

Step 1: (R)-2-methyl-N—((S)-1,1,5,5,5-pentafluoro-1-(phenylsulfonyl)pentan-2-yl)propane-2-sulfinamide (D2-1)

D2-1

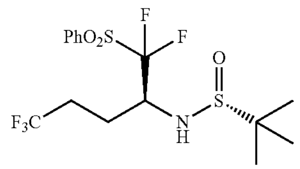

(R,E)-2-methyl-N-(4,4,4-trifluorobutylidene)propane-2-sulfinamide (A13-3) (379 mg, 1.653 mmol) was dissolved in THF (6.6 mL) and the solution was cooled to −78° C. The solution was treated with ((difluoromethyl)sulfonyl)benzene (236 μl, 1.653 mmol) and NaHMDS (1653 μl, 1.653 mmol) and stirred at −78° C. for 2 h. LCMS analysis showed formation of the desired product. Work-up involved quenching with sat. aq. $NH_4Cl$ (10 mL) and extracting with DCM (3×10 mL). The combined organic layers were washed with water (10 mL), dried ($MgSO_4$) and concentrated. The crude material was purified by ISCO flash column chromatography (0-60%, EtOAc:hexanes) to afford the title compound. MS: 422.2 [M+1].

Step 2: (R)-2-methyl-N—((S)-1,1,5,5,5-pentafluoropentan-2-yl)propane-2-sulfinamide (D2-2)

D2-2

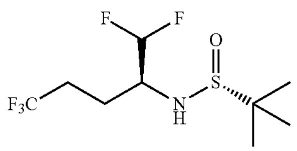

(R)-2-methyl-N—((S)-1,1,5,5,5-pentafluoro-1-(phenylsulfonyl)pentan-2-yl)propane-2-sulfinamide (D2-1) (398 mg, 0.944 mmol) was dissolved in DMF (12.8 mL) and treated with a solution of sodium acetate (1937 mg, 23.61 mmol) and acetic acid (1838 μl, 32.1 mmol) in water (3 mL). The reaction was placed in a water bath and magnesium (344 mg, 14.17 mmol) was added slowly. The water bath was removed after 10 min and the reaction was allowed to stir at room temperature for 15 h. Work-up involved quenching with water (3 mL) and extracting with EtOAc (3×10 mL).

The combined organic layers were washed with water (2×5 mL) and brine (2×5 mL), dried ($MgSO_4$) and concentrated. The crude material was purified by ISCO flash column chromatography (0-60% EtOAc:hexanes) to afford the title compound. H-NMR (500 MHz, Chloroform-d, ppm): δ 4.00 (d, J=8.2 Hz, 1H), 3.57-3.42 (m, 1H), 2.49 (dtq, J=21.6, 10.8, 4.7 Hz, 1H), 2.28 (dtt, J=20.2, 10.3, 4.6 Hz, 1H), 2.05 (s, 3H), 1.78 (dtd, J=15.0, 10.6, 4.8 Hz, 1H), 1.26 (s, 9H). MS: 282.3 [M+1].

Step 3: (S)-1,1,5,5,5-pentafluoropentan-2-amine (D2-3)

D2-3

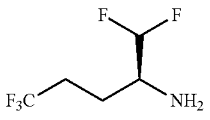

(R)-2-methyl-N—((S)-1,1,5,5,5-pentafluoropentan-2-yl) propane-2-sulfinamide (D2-2) (272 mg, 0.967 mmol) was dissolved in MeOH (4 mL) and treated with HCl (1.45 mL, 5.80 mmol) 4 N in dioxane. The reaction was stirred at ambient temperature for 1 h. LCMS analysis showed formation of the desired product. The reaction was concentrated and rotavaped twice with DCM to afford the title compound which was carried forward without purification. MS: 178.2 [M+1].

Step 4: 1-ethyl-3-((S)-1,1,5,5,5-pentafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea (Example 4-1 for Table 4)

Example 4-1

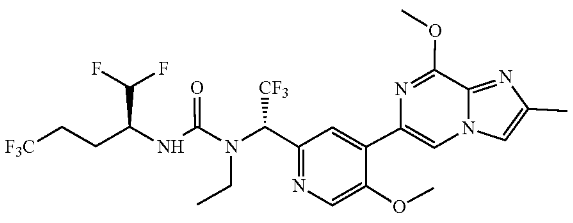

The title compound was prepared from (S)-1,1,5,5,5-pentafluoropentan-2-amine (D2-3) and (S)—N-ethyl-2,2,2-trifluoro-1-(5-methoxy-4(8-methoxy-2-methylimidazo[1,2-a]pyrazin-6-yl)pyridin-2-yl)ethan-1-amine (Intermediate 21) using the procedure outlined in the synthesis of Example 2-1. MS: 599.5 [M+1].

The following compounds were prepared according to the general procedures herein and in an analogous manner to that used to synthesize the Examples above using the appropriate intermediates. The starting materials were either prepared as described in the intermediates section, commercial available, or prepared from commercially available reagents using conventional reactions well known in the art.

TABLE 4

| Example | Structure | Name | Exact Mass [M + H]+ |
|---|---|---|---|
| 4-2 | 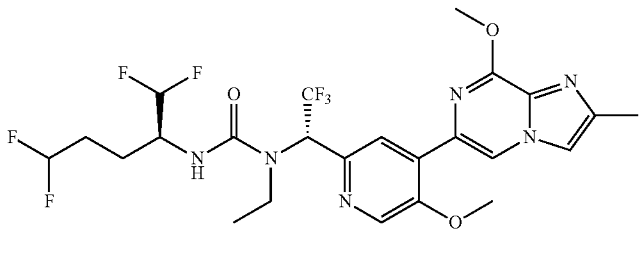 [SMILES: CCN(C(=O)N[C@@H](CCC(F)F)C(F)F)[C@@H](c1cc(-c2cn3cc(C)nc3c(OC)n2)c(OC)cn1)C(F)(F)F] | 1-ethyl-3-((S)-1,1,5,5-tetrafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea | 581.4 |
| 4-3 | 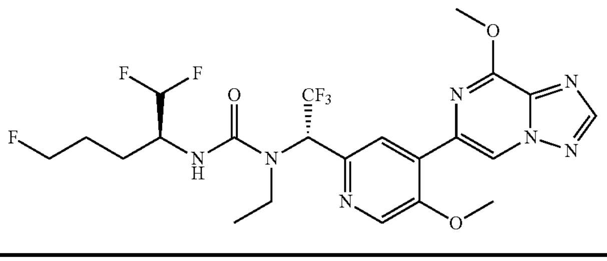 | 1-ethyl-1-((S)-2,2,2-trifluoro-1-(5-methoxy-4-(8-methoxy-[1,2,4]triazolo[1,5-a]pyrazin-6-yl)pyridin-2-yl)ethyl)-3-((S)-1,1,5-trifluoropentan-2-yl)urea | 550.5 |

Example 5-1 for Table 5: 1-ethyl-1-(2,2,2-trifluoro-1-(5-methoxy-4-(8-methoxyimidazo[1,2-a]pyrazin-6-yl)pyridin-2-yl)ethyl)-3-((S)-1,1,1-trifluoropent-4-en-2-yl)urea Example 5-1

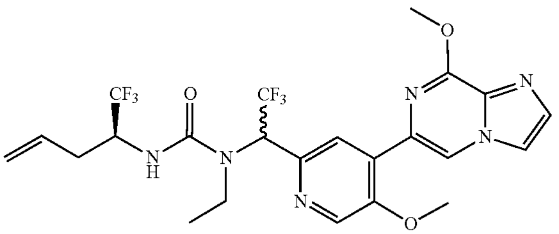

Step 1: (S)-2-methyl-N—((S)-1,1,1-trifluoropent-4-en-2-yl)propane-2-sulfinamide (E1-1)

E1-1

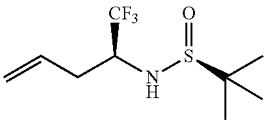

A flame-dried flask was charged with (S,E)-2-METHYL-N-(2,2,2-TRIFLUOROETHYLIDENE)PROPANE-2-SULFINAMIDE (0.174 ml, 0.994 mmol) which was dissolved in DCM (8.28 ml) and cooled to −60° C. To this, the ALLYLMAGNESIUM BROMIDE (1.0 M in diethyl ether) (2.485 ml, 2.485 mmol) was added and the contents were stirred, −60° C. for 45 min, then warmed slowly to −20° C. over the course of 75 min. The contents were quenched with sat. $NH_4Cl$ and warmed to ambient temperature and stirred for 20 min. DCM was added to extract, the organic portion was dried ($Na_2SO_4$), filtered and evaporated to tive an oil. This was purified via chromatography ($SiO_2$ 24 g RediSep column, 0-50% 3:1 EtOAc:EtOH/hexanes, 35 mL/min, 16 min) to afford the title compound. MS: 244.2 [M+1].

Step 2: (S)-1,1,1-trifluoropent-4-en-2-amine (E1-2)

E1-2

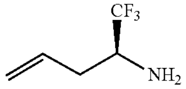

The (S)-2-methyl-N—((S)-1,1,1-trifluoropent-4-en-2-yl)propane-2-sulfinamide (5-1) (242 mg, 0.995 mmol) was dissolved in MeOH (3316 μl) and treated with HCl (4.0 M in dioxane) (408 μl, 4.97 mmol) and stirred at ambient temperature for 90 min. The contents of the reaction was concentrated under a stream of nitrogen to afford the title compound which was used without further purification.

Step 3: 1-ethyl-1-(2,2,2-trifluoro-1-(5-methoxy-4-(8-methoxyimidazo[1,2-a]pyrazin-6-yl)pyridin-2-yl)ethyl)-3-((S)-1,1,1-trifluoropent-4-en-2-yl)urea (Example 5-1 for Table 5)

Example 5-1

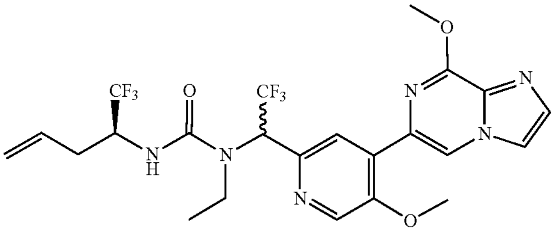

The title compound was prepared from (S)-1,1,1-trifluoropent-4-en-2-amine (E1-2) and N-ethyl-2,2,2-trifluoro-1-(5-methoxy-4-(8-methoxyimidazo[1,2-a]pyrazin-6-yl)pyridin-2-yl)ethan-1-amin (Intermediate B2) using the procedure outlined in the synthesis of Example 2-1. MS: 447.3 [M+1].

The following compounds were prepared according to the general procedures herein and in an analogous manner to that used to synthesize the Examples above using the appropriate intermediates. The starting materials were either prepared as described in the intermediates section, commercial available, or prepared from commercially available reagents using conventional reactions well known in the art. Examples 5-3 was prepared from the racemic (E)-2-methyl-N-(2,2,2-trifluoroethylidene)propane-2-sulfinamide.

TABLE 5

| Example | Structure | Name | Exact Mass [M + H]+ |
|---|---|---|---|
| 5-2 | 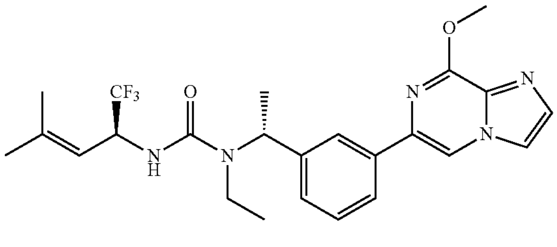 [SMILES: CCN(C(=O)N[C@@H](C=C(C)C)C(F)(F)F)[C@H](C)c1cccc(-c2cn3ccnc3c(OC)n2)c1] | 1-ethyl-1-((R)-1-(3-(8-methoxyimidazo[1,2-a]pyrazin-6-yl)phenyl)ethyl)-3-((S)-1,1,1-trifluoro-4-methylpent-3-en-2-yl)urea | 476.3 |

TABLE 5-continued

| Example | Structure | Name | Exact Mass [M + H]+ |
|---|---|---|---|
| 5-3 | 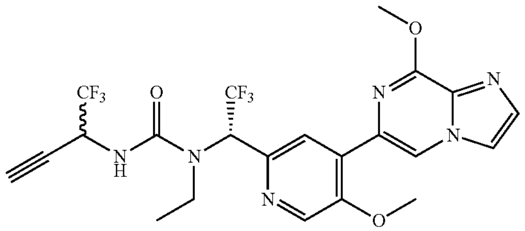 [SMILES: C#CC(NC(=O)N(CC)[C@@H](c1cc(-c2cn3ccnc3c(OC)n2)c(OC)cn1)C(F)(F)F)C(F)(F)F] | 1-ethyl-1-((S)-2,2,2-trifluoro-1-(5-methoxy-4-(8-methoxyimidazo[1,2-a]pyrazin-6-yl)pyridin-2-yl)ethyl)-3-(1,1,1-trifluorobut-3-yn-2-yl)urea | 531.5 |

Intermediate F1: (S)-1-cyclopropyl-4,4-difluorobutan-1-amine

Intermediate F1

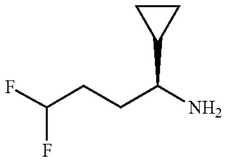

Step 1: 4,4-difluorobutanal (F1-1)

F1-1

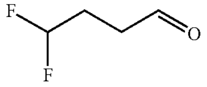

To a solution of 4,4-difluorobutan-1-ol (1.0 g, 9.08 mmol) in DCM (5 mL) was added TEMPO (0.014 g, 0.091 mmol) and KBr (0.108 g, 0.908 mmol) in water (2.5 mL) and aqueous sat. $NaHCO_3$ (5 mL) at 0° C. Sodium hypochlorite (10 wt % in water, 6.73 mL, 10.90 mmol) was added to the mixture dropwise at 0° C. over 15 min. The mixture was stirred at 0° C. for 1 h. The DCM layer was separated and the aqueous layer was washed with DCM (2×10 mL). The DCM layers were combined to afford the title compound which was used immediately in the next step without further purification.

Step 2: (S,E)-N-(4,4-difluorobutylidene)-2-methylpropane-2-sulfinamide (F1-2)

F1-2

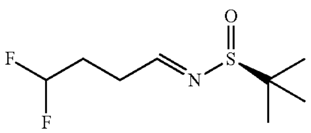

A solution of 4,4-difluorobutanal (F1-1) (0.982 g, 9.09 mmol) in DCM (15 mL) was treated with magnesium sulfate (2.84 g, 23.62 mmol), (S)-(−)-2-methyl-2-propanesulfinamide (1.346 mL, 9.99 mmol) and PPTS (0.183 g, 0.727 mmol). The reaction mixture was stirred at ambient temperature for 24 h and then filtered over a bed of celite and concentrated to give an oil. The crude was purified by column chromatography on silica gel (40 g ISCO gold column), eluting with Hexanes:EtOAc/EtOH mix (3:1) 100:0 to 50:50 to afford the title compound. MS: 212.2 [M+1].

Step 3: (S)—N—((S)-1-cyclopropyl-4,4-difluorobutyl)-2-methylpropane-2-sulfinamide (F1-3)

F1-2

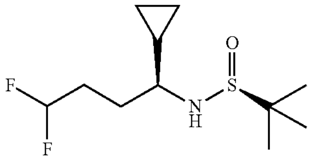

(S,E)-N-(4,4-Difluorobutylidene)-2-methylpropane-2-sulfinamide (F1-2) (110 mg, 0.521 mmol) was dissolved in DCM (2643 μl) and cooled to −78° C. and stirred under $N_2$. Cyclopropylmagnesium bromide (1.0 M in 2-methyltetrahydrofuran, 1041 μl, 1.041 mmol) was added and the reaction contents were stirred for 2 h at −78° C. for 2 h and then warmed to ambient temperature for 1 h. The reaction mixture was quenched by the addition of a few drops of MeOH. The reaction mixture was concentrated and purified by column chromatography on silica gel (40 g ISCO gold column), eluting with Hexanes:EtOAc/EtOH mix (3:1) 100:0 to 50:50 to afford the title compound. MS: 254.2 [M+1].

Step 4: (S)-1-cyclopropyl-4,4-difluorobutan-1-amine (Intermediate F1)

Intermediate F1

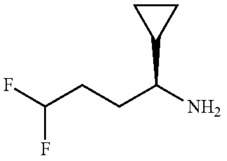

To a solution of (S)—N—((S)-1-cyclopropyl-4,4-difluorobutyl)-2-methylpropane-2-sulfinamide (F1-3) (110 mg, 0.434 mmol) in MeOH (0.5 mL) was added 4M HCl (0.217 mL, 0.868 mmol) in dioxane and the solution was aged for 1.5 h at ambient temperature. The reaction mixture was concentrated to afford the title compound. MS: 149.2 [M+1].

Example 6-1 for Table 6: 3-((R)-6,6-difluorohexan-3-yl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea Example 6-1 for Table 6

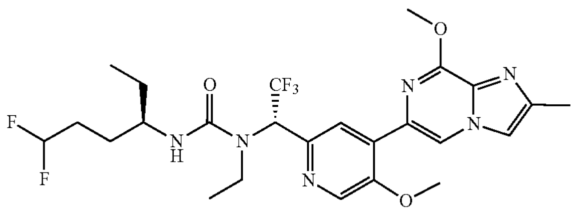

Step 1: (S)—N—((R)-6,6-difluorohexan-3-yl)-2-methylpropane-2-sulfinamide (F2-1)

F2-1

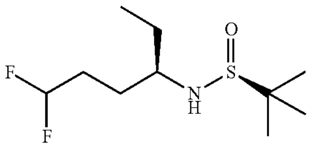

(S,E)-N-(4,4-difluorobutylidene)-2-methylpropane-2-sulfinamide (F1-2) (126 mg, 0.596 mmol) was dissolved in DCM (3 mL) and the solution was cooled to −78° C. The solution was treated with ethylmagnesium bromide 3.0 M (596 μl, 1.789 mmol) added dropwise and the reaction was stirred at −78° C. for 2 h. LCMS showed mostly starting material. The reaction was then allowed to warm slowly to −10° C. over 6 h. LCMS showed formation of the desired product and no starting material. Work-up involved quenching with sat aq $NH_4Cl$ (5 mL) and extracting with DCM (3×10 mL). The combined organic layers were washed with water (10 mL), dried ($MgSO_4$) and concentrated. The crude material was purified by ISCO flash column chromatography (0-60%, EtOAc:hexanes) to afford the title compound. H-NMR (500 MHz, Chloroform-d, ppm): δ 5.80 (tt, J=56.8, 4.3 Hz, 1H), 3.16 (dh, J=10.6, 6.2, 5.8 Hz, 1H), 3.02 (d, J=6.6 Hz, 1H), 1.98-1.77 (m, 2H), 1.76-1.50 (m, 4H), 1.20 (s, 9H), 0.94 (t, J=7.5 Hz, 3H). MS: 242.2 [M+1].

Step 2: (R)-6,6-difluorohexan-3-amine (F2-2)

F2-2

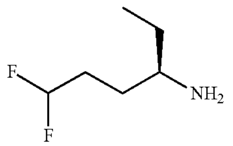

(R)—N—((R)-6,6-difluorohexan-3-yl)-2-methylpropane-2-sulfinamide (F2-1) 120 mg, 0.497 mmol) was dissolved in MeOH (2.1 mL) and treated with HCl (622 μl, 2.486 mmol) 4 M in dioxane. The reaction was stirred at room temperature for 2 h. LCMS analysis showed formation of the desired product. The reaction was concentrated to afford the title compound which was carried forward without purification.

Step 3: 3-((R)-6,6-difluorohexan-3-yl)-1-ethyl-1-(2,2,2-trifluoro-1-(5-methoxy-4-(8-methoxy-2-methylimidazo[1,2-a]pyrazin-6-yl)pyridin-2-yl)ethyl)urea (Example 6-1 for Table 6)

Example 6-1 for Table 6

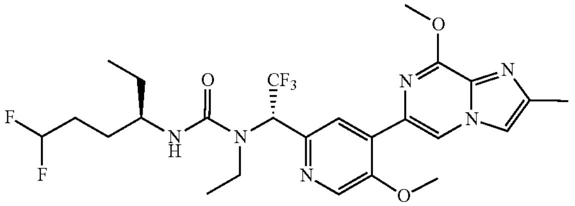

Title compound was prepared from (R)-6,6-difluorohexan-3-amine (F2-2) and N-ethyl-2,2,2-trifluoro-1-(5-methoxy-4-(8-methoxy-2-methylimidazo[1,2-a]pyrazin-6-yl)pyridin-2-yl)ethan-1-amine (Intermediate B21) using the procedure described in the synthesis of Example 2-1. MS: 559.5 [M+1].

The following compounds were prepared according to the general procedures herein and in an analogous manner to that used to synthesize the Examples above using the appropriate intermediates. The starting materials were either prepared as described in the intermediates section, commercial available, or prepared from commercially available reagents using conventional reactions well known in the art.

TABLE 6

| Example | Structure | Name | Exact Mass [M + H]+ |
|---|---|---|---|
| 6-2 | 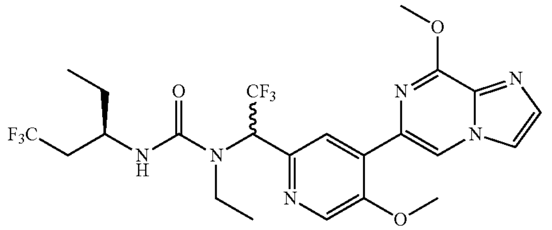 [SMILES: CC[C@H](CC(F)(F)F)NC(=O)N(CC)C(c1cc(-c2cn3ccnc3c(OC)n2)c(OC)cn1)C(F)(F)F] | 1-ethyl-1-(2,2,2-trifluoro-1-(5-methoxy-4-(8-methoxyimidazo[1,2-a]pyrazin-6-yl)pyridin-2-yl)ethyl)-3-((R)-1,1,1-trifluoropentan-3-yl)urea | 549.5 |

TABLE 6-continued

| Example | Structure | Name | Exact Mass [M + H]+ |
|---|---|---|---|
| 6-3 | 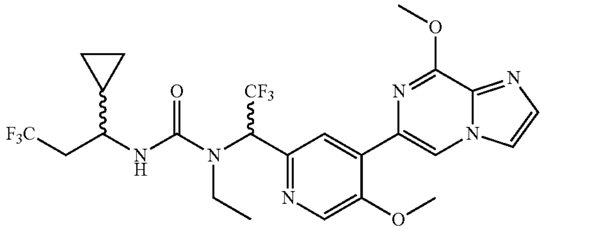 [SMILES: CCN(C(=O)NC(CC(F)(F)F)C1CC1)C(c1cc(-c2cn3ccnc3c(OC)n2)c(OC)cn1)C(F)(F)F] | 3-(1-cyclopropyl-3,3,3-trifluoropropyl)-1-ethyl-1-(2,2,2-trifluoro-1-(5-methoxy-4-(8-methoxyimidazo[1,2-a]pyrazin-6-yl)pyridin-2-yl)ethyl)urea | 561.5 |
| 6-4 | 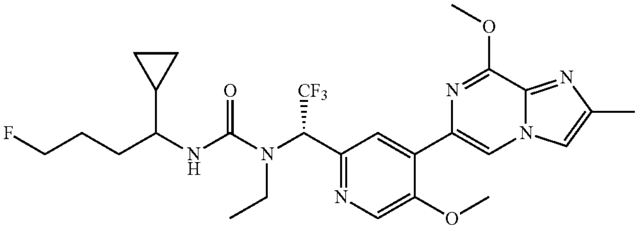 [SMILES: CCN(C(=O)NC(CCCF)C1CC1)[C@@H](c1cc(-c2cn3cc(C)nc3c(OC)n2)c(OC)cn1)C(F)(F)F] | 3-(1-cyclopropyl-4-fluorobutyl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea | 553.5 |
| 6-5 | 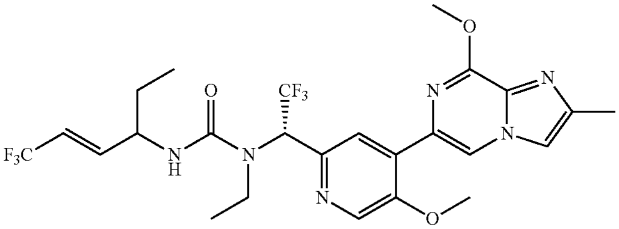 [SMILES: CCC(/C=C/C(F)(F)F)NC(=O)N(CC)[C@@H](c1cc(-c2cn3cc(C)nc3c(OC)n2)c(OC)cn1)C(F)(F)F] | 1-ethyl-1-((S)-2,2,2-trifluoro-1-(5-methoxy-4-(8-methoxy-2-methylimidazo[1,2-a]pyrazin-6-yl)pyridin-2-yl)ethyl)-3-((E)-6,6,6-trifluorohex-4-en-3-yl)urea | 575.5 |
| 6-6 | 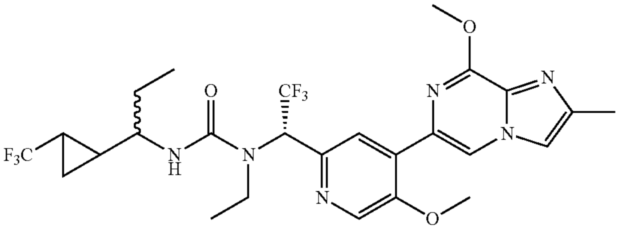 [SMILES: CCC(NC(=O)N(CC)[C@@H](c1cc(-c2cn3cc(C)nc3c(OC)n2)c(OC)cn1)C(F)(F)F)C1CC1C(F)(F)F] | 1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(1-(2-(trifluoromethyl)cyclopropyl)propyl)urea | 589.5 |
| 6-7 | 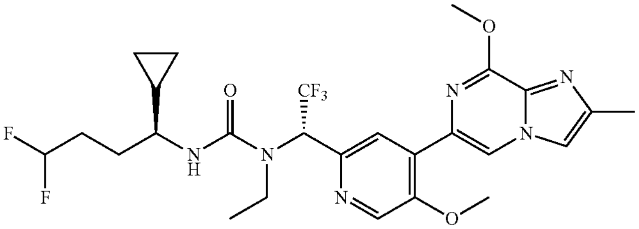 [SMILES: CCN(C(=O)N[C@@H](CCC(F)F)C1CC1)[C@@H](c1cc(-c2cn3cc(C)nc3c(OC)n2)c(OC)cn1)C(F)(F)F] | 3-((S)-1-cyclopropyl-4,4-difluorobutyl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea | 571.2 |

Intermediate G1: tert-butyl (R)-ethyl(1-(3-(4,4,5,5-tetramethyl-1,3,2-dioxaborolan-2-yl)phenyl)ethyl) carbamate Intermediate G1

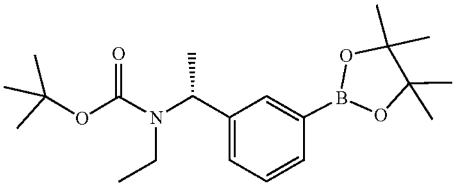

Step 1: tert-butyl (R)-(1-(3-bromophenyl)ethyl)(ethylcarbamate (G1-1)

G1-1

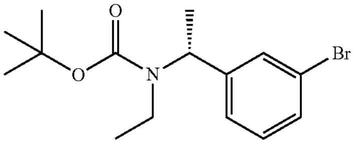

To a solution of tert-butyl (R)-(1-(3-bromophenyl)ethyl) carbamate (18 g, 60.0 mmol) in DMF (250 mL) was added NaH (3.60 g, 90 mmol) at 0° C. and stirred at 0° C. for 0.5 h under $N_2$ protection, and then iodoethane (10.29 g, 66.0 mmol) was added dropwise at 0° C. and stirred at 25° C. for 14 h. TLC (petroleum ether:EtOAc=10:1) showed the starting material disappeared and a new spot generated. The resulting mixture was poured into water (300 mL) and extracted with EtOAc (250 mL×4), the organic layers were combined and washed with brine (400 mL), dried over $Na_2SO_4$ and filtered. The filtrate was concentrated in vacuo. The residue was purified by flash silica gel chromatography (0-5%, EtOAc/petroleum ether) to give the title compound. MS: 328.1, 330.2 [M+1].

Step 2: tert-butyl (R)-ethyl(1-(3-(4,4,5,5-tetramethyl-1,3,2-dioxaborolan-2-yl)phenyl)ethyl)carbamate (Intermediate G1)

Intermediate G1

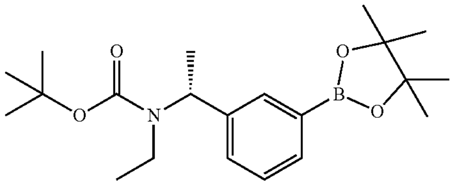

To a solution of tert-butyl (R)-(1-(3-bromophenyl)ethyl)(ethyl)carbamate (G1-1) (4 g, 12.19 mmol) in dioxane (40 ml) were added 4,4,4',4',5,5,5',5'-octamethyl-2,2'-bi(1,3,2-dioxaborolane) (3.71 g, 14.62 mmol), potassium acetate (3.59 g, 36.6 mmol), potassium acetate (3.59 g, 36.6 mmol) and $PdCl_2$(dppf) (0.892 g, 1.219 mmol). The mixture was stirred at 80° C. under $N_2$ for 3 h. TLC (petroleum ether:EtOAc=5:1) showed a new spot was found and LCMS showed desired product was formed. The reaction mixture was poured into water (50 mL), extracted with EtOAc (100 mL×3). The combined organic layers were washed with brine (20 mL), dried over $Na_2SO_4$ and filtered. The filtrate was concentrated and purified by Flash silica gel chromatography (ISCO®; 24 g SepaFlash® Silica Flash Column, eluent of 45% EtOAc/petroleum ether gradient) to afford the title compound. MS: 376.3 [M+1].

Intermediate G2: 6-bromo-8-(difluoromethoxy)imidazo[1,2-a]pyridine

Intermediate G2

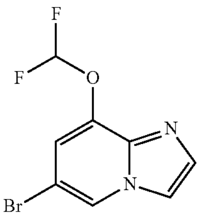

A solution of (R)-ethyl(1-(3-(4,4,5,5-tetramethyl-1,3,2-dioxaborolan-2-yl)phenyl)ethyl)carbamate (Intermediate G1) (200 mg, 0.802 mmol) was prepared in DMF (5 mL) and to this was added $Cs_2CO_3$ (784 mg, 2.405 mmol) and $CF_2ClCOOH$ (0.170 mL, 2.004 mmol). The reaction was stirred at 100° C. for 2 h. The reaction was detected by TLC and LCMS. The mixture was quenched with water (10 mL), extracted with EtOAc (20 mL×3), washed with brine (10 mL×3), dried over $Na_2SO_4$ and filtered. The filtrate was concentrated in vacuo and purified by prep-TLC ($SiO_2$, petroleum ether:EtOAc=2:1) to give the title compound. H-NMR (400 MHz, $CDCl_3$, ppm): δ 8.18 (d, J=1.8 Hz, 1H), 7.65 (s, 1H), 7.63 (d, J=1.3 Hz, 1H), 7.42 (t, J=73.6 Hz, 1H), 7.08 (s, 1H). MS: 262.9 [M+1].

Intermediate G3: 6-bromo-8-(methoxymethyl)imidazo[1,2-a]pyridine

Intermediate G3

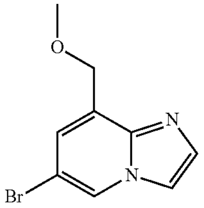

Step 1: methyl 6-bromoimidazo[1,2-a]pyridine-8-carboxylate (G3-1)

G3-1

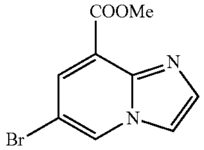

To a mixture of methyl 2-amino-5-bromonicotinate (500 mg, 2.164 mmol) in EtOH (5 mL) was added 2-chloroacetaldehyde (0.714 mL, 4.33 mmol) (40% purity). The mixture was stirred at 60° C. for 16 h under $N_2$. LCMS showed desired mass. Then the mixture was concentrated. Acetone (150 mL) was added to the mixture, and the mixture was stirred for 20 min. Then the mixture was filtered and the solid was concentrated to give the title compound, which was used in the next steps directly. MS: 256.7 [M+1].

Step 2: (6-bromoimidazo[1,2-a]pyridin-8-yl)methanol (G3-2)

G3-2

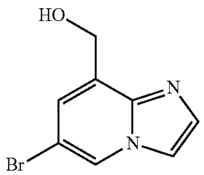

To a mixture of calcium chloride (870 mg, 7.84 mmol) and $NaBH_4$ (297 mg, 7.84 mmol) in THF (10 mL) was added methyl 6-bromoimidazo[1,2-a]pyridine-8-carboxylate (G3-

1) (200 mg, 0.784 mmol) in THF (2 mL) at 0° C. Then the mixture was stirred at 25° C. for 16 h. TLC and LCMS showed the starting material was consumed and the target product was found. To the mixture was added water (10 mL), which was extracted with DCM (20 mL×3). The combined organic layers were washed with brine (20 mL), dried over $MgSO_4$ and filtered. The filtrate was concentrated in vacuo to give the title compound, which was used for next step without further purification. MS: 228.7 [M+1].

Step 3: 6-bromo-8-(methoxymethyl)imidazo[1,2-a]pyridine (Intermediate G3)

Intermediate G3

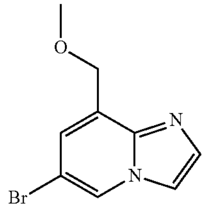

To a solution of methyl 6-bromoimidazo[1,2-a]pyridine-8-carboxylate (G3-1) (100 mg, 0.440 mmol) in DMF (2 mL) was added NaH (26.4 mg, 0.661 mmol) at 0° C. The mixture was stirred at 0° C. for 0.5 h. Then to the solution was added iodomethane (125 mg, 0.881 mmol) at 0° C., and the mixture was stirred at 25° C. for 1 h. LCMS showed the starting material was consumed completely and the product was detected. To the mixture was added water (10 mL), which was extracted with EtOAc (10 mL×3). The combined organic layers were washed with brine (10 mL), dried over $MgSO_4$ and filtered. The filtrate was concentrated in vacuo to give the residue, which was purified by prep-TLC ($SiO_2$, petroleum ether/EtOAc=0:1, v/v) to give the title compound. MS: 242.7 [M+1].

Intermediate G4: 6-bromo-7-(methoxymethyl)imidazo[1,2-a]pyridine

Intermediate G4

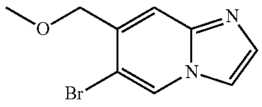

Step 1: methyl 2-amino-5-bromoisonicotinate (G4-1)

G4-1

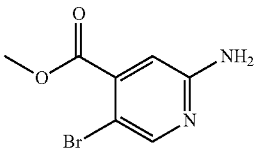

To a solution of methyl compound methyl 2-aminoisonicotinate (5 g, 32.9 mmol) in anhydrous acetonitrile (150 ml) was added NBS (5.85 g, 32.9 mmol), the resulting mixture was stirred at 0° C. under $N_2$ protection for 0.5 h. TLC (petroleum ether:ethyl acetate=3:1) showed the reaction was completed. The reaction mixture was concentrated, the residue was purified by flash silica gel chromatography ($SiO_2$, 0-25%, petroleum ether/ethyl acetate) to give the title compound. MS: 230.8, 232.7 [M+1].

Step 2: methyl 6-bromoimidazo[1,2-a]pyridine-7-carboxylate (G4-2)

G4-2

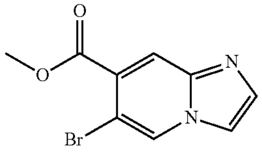

To a solution of 2-bromo-1,1-dimethoxyethane (5.06 g, 29.9 mmol) (5.06 g, 29.9 mmol) in water (20 ml) was added conc. HCl (1.572 ml, 19.15 mmol) at 20° C., the resulting mixture was stirred at 80° C. for 2 h. Then the mixture was cooled and sodium bicarbonate (3.22 g, 38.3 mmol) was added slowly. Finally, the mixture was diluted with EtOH (20 ml), methyl 2-amino-5-bromoisonicotinate (G4-1) (7.9 g, 23.93 mmol) was added and the result mixture was stirred at 80° C. for 8 h. TLC (petroleum ether:EtOAc=1:1) and LCMS showed the reaction was completed, the reaction mixture was concentrated. The residue was purified by flash silica gel chromatography ($SiO_2$, 0-50% EtOAc/petroleum ether) to give the title compound. MS: 256.7 [M+1].

Step 3: (6-bromoimidazo[1,2-a]pyridin-7-yl)methanol (G4-3)

G4-3

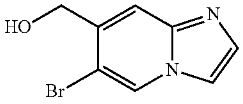

To a solution of methyl 6-bromoimidazo[1,2-a]pyridine-7-carboxylate (G4-2) (1 g, 3.92 mmol) in anhydrous EtOH (3 mL) was added $NaBH_4$ (0.445 g, 11.76 mmol) at 0° C. and stirred 4 h. Then the mixture was warmed to 20° C. and stirred for 12 h. LCMS showed the reaction was completed, the reaction mixture was concentrated (below 35° C.), the residue was purified by flash silica gel chromatography ($SiO_2$, 0-10% MeOH/DCM) to give the title compound. MS: 226.8 [M+1].

Step 4: 6-bromo-7-(methoxymethyl)imidazo[1,2-a]pyridine (Intermediate G4)

Intermediate G4

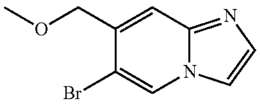

To a solution of (6-bromoimidazo[1,2-a]pyridin-7-yl) methanol (G4-3) (700 mg, 3.08 mmol) in anhydrous DMF (2 ml) was added NaH (185 mg, 4.62 mmol), the resulting mixture was stirred at 20° C. under $N_2$ protection for 1 h. Then Mel (0.212 ml, 3.39 mmol) was added into the mixture and the solution was stirred at 20° C. for 1 h. Water (5 mL) was added into the reaction mixture and the solution of the title compound in DMF and water was used in the next step directly without further purification. MS: 240.8, 242.8 [M+1].

Example 7-1 for Table 7: 1-((R)-1-(3-(8-(difluoromethoxy)imidazo[1,2-a]pyridin-6-yl)phenyl) ethyl)-1-ethyl-3-((R)-6,6,6-trifluorohexan-3-yl)urea Example 7-1

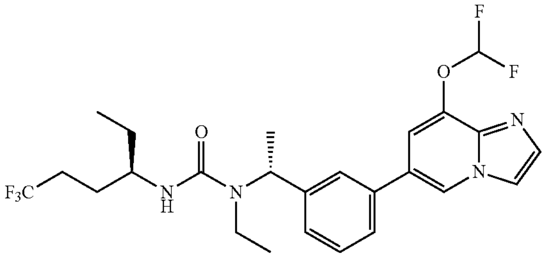

Step 1: tert-butyl (R)-(1-(3-(8-(difluoromethoxy) imidazo[1,2-a]pyridin-6-yl)phenyl)ethyl)(ethyl)carbamate (G5-1)

G5-1

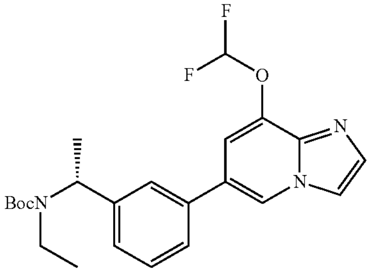

A flask was charged with 6-bromo-8-(difluoromethoxy) imidazo[1,2-a]pyridine (Intermediate G2)_(65 mg, 0.247 mmol), tert-butyl (R)-ethyl(1-(3-(4,4,5,5-tetramethyl-1,3,2-dioxaborolan-2-yl)phenyl)ethyl)carbamate (Intermediate G1) (111 mg, 0.297 mmol) and $Na_2CO_3$ (52.4 mg, 0.494 mmol) in 1,4-dioxane (2.5 mL) and water (0.5 mL) was added Pd(dppf)$Cl_2$ (18.08 mg, 0.025 mmol). The mixture was stirred at 90° C. for 16 h under $N_2$. LCMS showed starting material was consumed and desired mass was found. The mixture was quenched with water (5 mL), extracted with EtOAc (10 mL×3), washed with brine (10 mL), dried over $Na_2SO_4$ and filtered. The filtrate was concentrated in vacuo and purified by prep-TLC ($SiO_2$, petroleum ether: EtOAc=2:1) to give the title compound. MS: 432.2 [M+1].

Step 2: (R)-1-(3-(8-(difluoromethoxy)imidazo[1,2-a]pyridin-6-yl)phenyl)-N-ethylethan-(G5-2)

G5-2

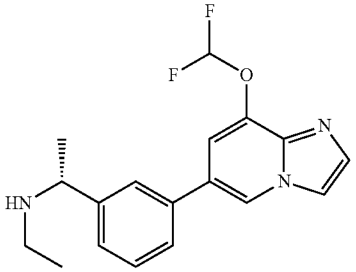

To the solution of tert-butyl (R)-(1-(3-(8-(difluoromethoxy)imidazo[1,2-a]pyridin-6-yl)phenyl)ethyl)(ethyl) carbamate (G5-1) (95 mg, 0.220 mmol) in DCM (3 mL) was added TFA (0.4 mL). The mixture was stirred at 20° C. for 2 h. The reaction was detected by LCMS. The mixture was concentrated in vacuo to give the title compound, which was used in the next step without further purification. MS: 332.1 [M+1].

Step 3: 1-((R)-1-(3-(8-(difluoromethoxy)imidazo[1,2-a]pyridin-6-yl)phenyl)ethyl)-1-ethyl-3-((R)-6,6,6-trifluorohexan-3-yl)urea (Example 7-1 for Table 7)

Example 7-1

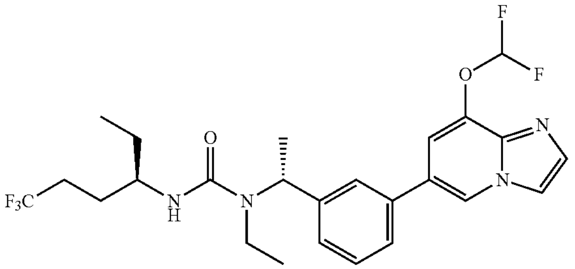

The title compound was prepared from (R)-6,6,6-trifluorohexan-3-amine (Intermediate A14) and (R)-1-(3-(8-(difluoromethoxy)imidazo[1,2-a]pyridin-6-yl)phenyl)N-ethylethan-1-amine (G52) using the procedure outlined in the synthesis of Example 2-1. MS: 513.2 [M+1].

The following compounds were prepared according to the general procedures herein and in an analogous manner to that used to synthesize the Examples above using the appropriate halogenated heterocycles and amines. The starting materials were either prepared as described in the intermediates section, commercial available, or prepared from commercially available reagents using conventional reactions well known in the art.

TABLE 7

| Example | Structure | Name | Exact Mass [M + H]+ |
|---|---|---|---|
| 7-2 | 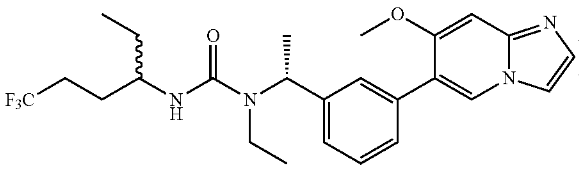 [SMILES: CCC(CCC(F)(F)F)NC(=O)N(CC)[C@H](C)c1cccc(-c2cn3ccnc3cc2OC)c1] | 1-ethyl-1-((R)-1-(3-(7-methoxyimidazo[1,2-a]pyridin-6-yl)phenyl)ethyl)-3-(6,6,6-trifluorohexan-3-yl)urea | 477.2 |
| 7-3 | 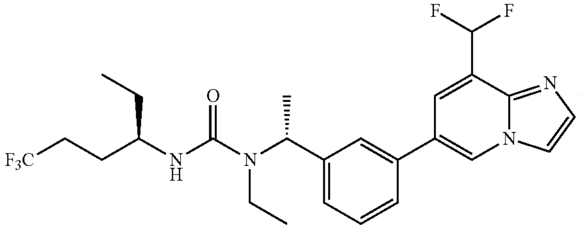 [SMILES: CC[C@H](CCC(F)(F)F)NC(=O)N(CC)[C@H](C)c1cccc(-c2cc(C(F)F)c3nccn3c2)c1] | 1-((R)-1-(3-(8-(difluoromethyl) imidazo [1,2-a]pyridin-6-yl)phenyl)ethyl)-1-ethyl-3-((R)-6,6,6-trifluorohexan-3-yl)urea | 497.0 |
| 7-4 | 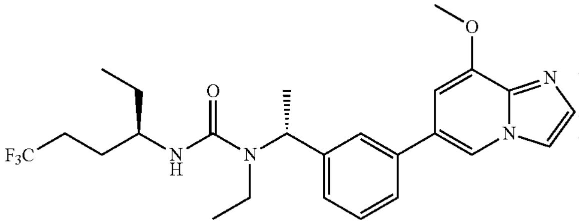 [SMILES: CC[C@H](CCC(F)(F)F)NC(=O)N(CC)[C@H](C)c1cccc(-c2cc(OC)c3nccn3c2)c1] | 1-ethyl-1-((R)-1-(3-(8-(methoxymethyl) imidazo[1,2-a]pyridin-6-yl)phenyl)ethyl)-3-((R)-6,6,6-trifluorohexan-3-yl)urea | 491.1 |
| 7-5 | 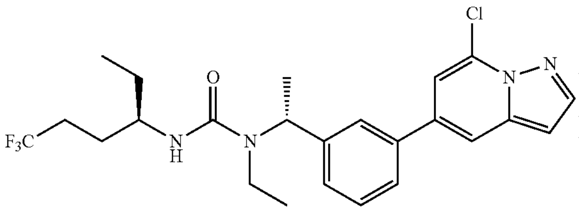 [SMILES: CC[C@H](CCC(F)(F)F)NC(=O)N(CC)[C@H](C)c1cccc(-c2cc(Cl)n3nccc3c2)c1] | 1-((R)-1-(3-(7-chloropyrazolo[1,5-a]pyridin-5-yl)phenyl)ethyl)-1-ethyl-3-((R)-6,6,6-trifluorohexan-3-yl)urea | 480.3 |
| 7-6 | 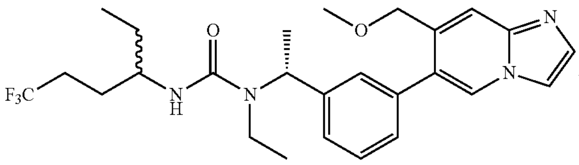 [SMILES: CCC(CCC(F)(F)F)NC(=O)N(CC)[C@H](C)c1cccc(-c2cn3ccnc3cc2COC)c1] | 1-ethyl-1-((R)-1-(3-(7-(methoxymethyl) imidazo[1,2-a]pyridin-6-yl)phenyl)ethyl)-3-(6,6,6-trifluorohexan-3-yl)urea | 491.2 |

Intermediate H1: 6-bromo-8-ethoxyimidazo[1,2-a]pyridine

Intermediate H1

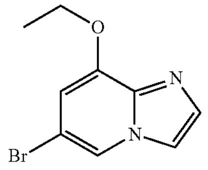

6-bromoimidazo[1,2-a]pyridin-8-ol (30 mg, 0.141 mmol) and CESIUM CARBONATE (92 mg, 0.282 mmol) were combined in DMF at ambient temperature. After stirring for 5 min, IODOETHANE (11.38 μl, 0.141 mmol) was added and the reaction was stirred at room temperature for 16 h. The reaction mixture was diluted with EtOAc (3 mL), filtered through a pad of celite washing with EtOAc, and concentrated in vacuo. The residue was purified by column chromatography ($SiO_2$, 12 g Isco Gold, 0-30% 3:1 EtOAc: EtOH/hexanes, 12 minute gradient) to give the title compound. MS: 241.1, 244.1 [M+1].

Intermediate H2: 6-bromo-2-chloro-8-methoxyimidazo[1,2-a]pyridine

Intermediate H2

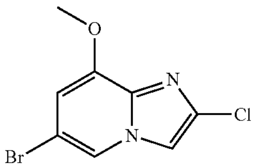

Ethyl bromoacetate (0.110 mL, 0.985 mmol) was added to 5-bromo-3-methoxypyridin-2-amine (200 mg, 0.985 mmol) and sodium bicarbonate (165 mg, 1.970 mmol) and the mixture was stirred at 80° C. for 18 h. The solvent was removed and the crude was dissolved in phosphorus oxychloride (1.836 mL, 19.70 mmol) and heated to 80° C. for 2 h. The phosphorus oxychloride was removed in vacuo and the mixture was partitioned between aqueous sat. $NaHCO_3$ (10 mL) and EtOAc (10 mL). The layers were separated and the aqueous was further extracted with EtOAc (3×10 mL). The combined organics were dried over $Na_2SO_4$, filtered, and concentrated in vacuo to afford the title compound. MS: 261.0, 263.0 [M+1].

Intermediate H3: 6-bromo-3,5-dichloro-8-methoxy-imidazo[1,2-a]pyridine

Intermediate H3

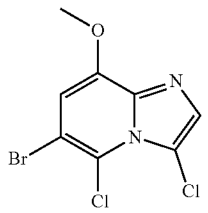

A solution of 6-bromo-8-methoxyimidazo[1,2-a]pyridine (317 mg, 1.40 mmol) and NCS (224 mg, 1.68 mmol) in ACN (5 mL) was heated at 65° C. for 4 hr. The mixture was concentrated and purified directly by column chromatography on silica gel (80 g ISCO gold column), eluting with Hexanes:EtOAc/EtOH mix (3:1) 100:0 to 0:100 to afford the title compound. MS: 297.0, 299.0 [M+1].

Intermediate H4: (R)-1-(3-bromo-4-methoxyphenyl)-N-ethylethan-1-amine

Intermediate H4

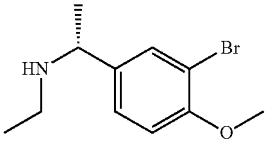

Step 1: (S,E)-N-(3-bromo-4-methoxybenzylidene)-2-methylpropane-2-sulfinamide (H4-1D

H4-1

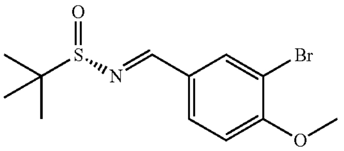

The 3-BROMO-4-METHOXYBENZALDEHYDE (1.0 g, 4.65 mmol) was dissolved in DCM (9.30 ml) and treated with (S)-(−)-2-METHYL-2-PROPANESULFINAMIDE (0.592 g, 4.88 mmol) and stirred, rt, for 10 days, then COPPER(II) SULFATE (1.633 g, 10.23 mmol) was added and the contents were stirred 18 h. The reaction mixture was filtered over a bed of celite, washing with DCM. This was concentrated under vacuum to give an oil. This was purified via chromatography ($SiO_2$, 80 g RediSep column, 0-60% 3:1 EtOAc:EtOH/hexanes, 60 mL/min, 35 min) to give the title compound. MS: 320.1, 321.1 [M+1].

Step 2: (S)—N—((R)-1-(3-bromo-4-methoxyphenyl)ethyl)-2-methylpropane-2-sulfinamide (H4-2)

H4-2

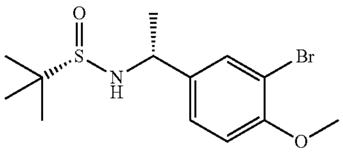

The (S,E)-N-(3-bromo-4-methoxybenzylidene)-2-methylpropane-2-sulfinamide (H4-1) (0.809 g, 2.54 mmol) was dissolved in THF (12.71 ml) and cooled to 0° C. and stirred, under $N_2$. To this, MeMgBr (4.0 eq, 10.16 mL) was added slowly via syringe. This was stirred, 0° C., 3 hr. LCMS showed conversion to product. This was quenched with sat. $NH_4Cl$, extracted with EtOAc. The organic portion was dried ($Na_2SO_4$), filtered and evaporated to give an oil. This was purified via chromatography ($SiO_2$ 80 g RediSep column, 0-2% MeOH/DCM, 60 mL/min, 35 min) to give the title compound. MS: 334.2, 337.2 [M+1].

Step 3: (S)—N—((R)-1-(3-bromo-4-methoxyphenyl)ethyl)-N-ethyl-2-methylpropane-2-sulfinamide

H4-3

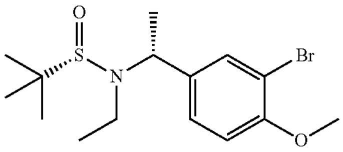

The (S)—N—((R)-1-(3-bromo-4-methoxyphenyl)ethyl)-2-methylpropane-2-sulfinamide (H4-2) (0.478 g, 1.430 mmol) was dissolved in DMF (7.15 ml) and treated with NaH (3.0 eq, 172 mg), stirred for rt for 5 min, then treated with EtI (2.4 eq, 276 μL) and stirred at ambient temperature for 18 h. This was diluted with EtOAc, washed with sat. brine, dried ($Na_2SO_4$), filtered and concentrated under vacuum to give the crude product. This was purified via chromatography ($SiO_2$, 40 g RediSep column, 0-10% MeOH/DCM, 40 mL/min, 19 min) to give the title compound. MS: 364.3, 365.3 [M+1].

Step 4: (R)-1-(3-bromo-4-methoxyphenyl)-N-ethyl-ethan-1-amine (Intermediate H4M

Intermediate H4

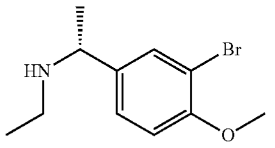

The (S)—N—((R)-1-(3-bromo-4-methoxyphenyl)ethyl)-N-ethyl-2-methylpropane-2-sulfinamide (H4-3) was dissolved in MeOH (2.380 ml) and treated with HCl (4.0 M in dioxane) (0.714 ml, 2.86 mmol) and stirred at ambient temperature for 18 h. The contents of the reaction was concentrated under vacuum to give the title compound. MS: 260.2, 261.2 [M+1].

Intermediate H5: 2-chloro-4-methoxyimidazo[2,1-f][1·2·4]triazine

Intermediate H5

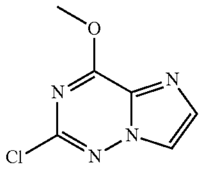

A solution of sodium methoxide (25 wt % in MeOH, 0.161 mL, 0.705 mmol) was added to a solution 2,4-dichloroimidazo[2,1-f][1,2,4]triazine (101 mg, 0.534 mmol) in THF (2 mL) and the mixture was stirred at ambient temperature for 1 h. The mixture was concentrated and purified by column chromatography on silica gel (24 g Isco Gold column), eluting with hexanes:EtOAc 100:0 to 0:100 to afford the title compound. MS: 185.0 [M+].

Example 8-1 for Table 8: 1-ethyl-1-((R)-1-(3-(8-(methylthio)imidazo[1,2-a]pyrazin-6-yl)phenyl)ethyl)-3-((R)-6,6,6-trifluorohexan-3-yl)urea Example 8-1

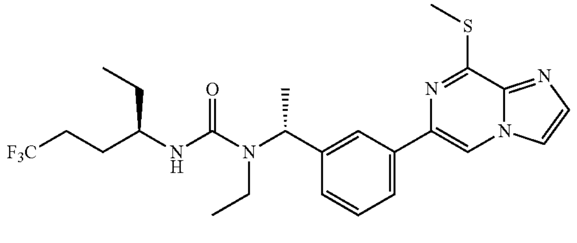

Step 1: 1-((R)-1-(3-bromophenyl)ethyl)-1-ethyl-3-((R)-6,6,6-trifluorohexan-3-yl)urea (H5-1)

H5-1

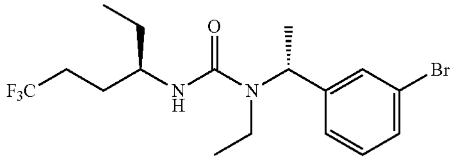

The title compound was prepared from (R)-1-(3-bromophenyl)-N-ethylethan-1-amine (Intermediate A4) and (R)-6,6,6-trifluorohexan-3-amine (Intermediate A14) using the procedure outlined in the synthesis of Example 1-1. MS: 411.2, 412.3 [M+1].

Step 2: 1-ethyl-1-((R)-1-(3-(4,4,5,5-tetramethyl-1,3,2-dioxaborolan-2-yl)phenyl)ethyl)-3-((R)-6,6,6-trifluorohexan-3-yl)urea (H5-2)

H5-2

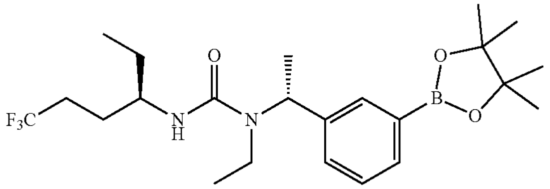

The title compound was prepared from 1-((R)-1-(3-bromophenyl)ethyl)-1-ethyl-3-((R)-6,6,6-trifluorohexan-3-yl)urea (H5-1) using the procedure outlined in step 1 of in the synthesis of Intermediate A5. MS: 457.5 [M+1].

Step 3: 1-ethyl-1-((R)-1-(3-(8-(methylthio)imidazo[1,2-a]pyrazin-6-yl)phenyl)ethyl)-3-((R)-6,6,6-trifluorohexan-3-yl (Example 8-1 for Table 8)

Example 8-1

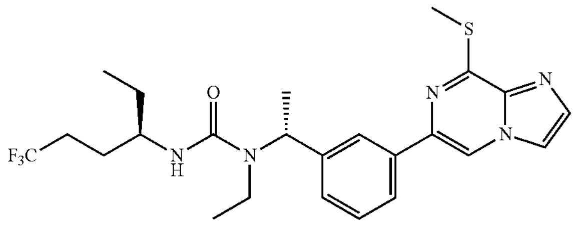

A sealable vial was charged with 1-ethyl-1-((R)-1-(3-(4,4,5,5-tetramethyl-1,3,2-dioxaborolan-2-yl)phenyl)ethyl)-3-((R)-6,6,6-trifluorohexan-3-yl)urea (H5-2) (29 mg, 0.064 mmol) and 6-bromo-8-(methylthio)imidazo[1,2-a]pyrazine (31.0 mg, 0.127 mmol) along with POTASSIUM CARBONATE (35.1 mg, 0.254 mmol) and these were dissolved in dioxane (381 μl) which had been sparged with nitrogen for 10 min. To this, water (42.4 μl) was added which also had been sparged with nitrogen for 10 min. 1,1'-BIS(DIPHE- NYLPHOSPHINO)-FERROCENE-PALLADIUM(II)DICHLORIDE DICHLOROMETHANE COMPLEX (5.19 mg, 6.35 μmol) was added and the reaction contents were heated to 80° C. and stirred for 18 h. This was diluted with EtOAc, washed with sat. $NaHCO_3$, dried by filtering through a hydrophobic frit and concentrated to give a residue. This was purified via reverse phase chromatography, multiple injections (SunFire Prep C18 OBD column, 5 micron, 30×150 mm, 5-70% $CH_3CN$/water with 0.1% TFA as a modifier, 25 min, 50 mL/min) to give the title compound. MS: 494.3 [M+1].

The following compounds were prepared according to the general procedures herein and in an analogous manner to that used to synthesize the Examples above using the appropriate halogenated heterocycles and amines. The starting materials were either prepared as described in the intermediates section, commercial available, or prepared from commercially available reagents using conventional reactions well known in the art.

TABLE 8

| Example | Structure | Name | Exact Mass [M + H]+ |
|---|---|---|---|
| 8-2 | 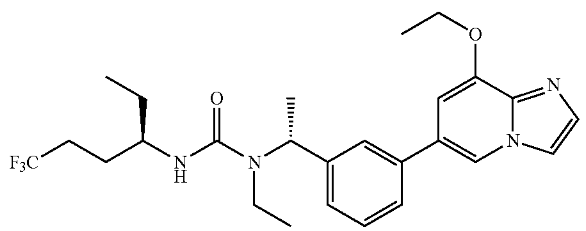 [SMILES: CCOc1cc(-c2cccc([C@@H](C)N(CC)C(=O)N[C@H](CC)CCC(F)(F)F)c2)cn2ccnc12] | 1-((R)-1-(3-(8-ethoxyimidazo[1,2-a]pyridin-6-yl)phenyl)ethyl)-1-ethyl-3-((R)-6,6,6-trifluorohexan-3-yl)urea | 491.4 |
| 8-3 | 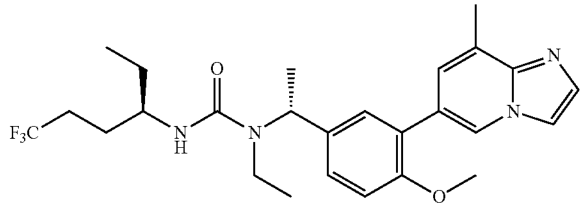 [SMILES: CC[C@H](CCC(F)(F)F)NC(=O)N(CC)[C@H](C)c1ccc(OC)c(-c2cc(C)c3nccn3c2)c1] | 1-ethyl-1-((R)-1-(4-methoxy-3-(8-methylimidazo[1,2-a]pyridin-6-yl)phenyl)ethyl)-3-((R)-6,6,6-trifluorohexan-3-yl)urea | 491.4 |
| 8-4 | 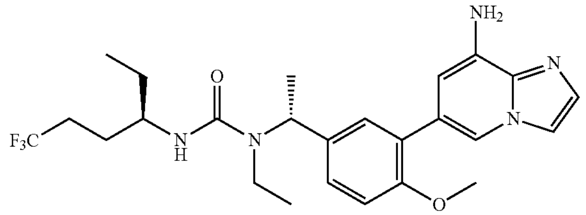 [SMILES: CC[C@H](CCC(F)(F)F)NC(=O)N(CC)[C@H](C)c1ccc(OC)c(-c2cc(N)c3nccn3c2)c1] | 1-((R)-1-(3-(8-aminoimidazo[1,2-a]pyridin-6-yl)-4-methoxyphenyl)ethyl)-1-ethyl-3-((R)-6,6,6-trifluorohexan-3-yl)urea | 492.3 |
| 8-5 | 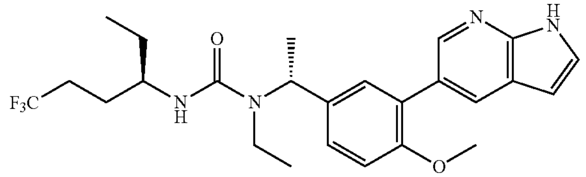 [SMILES: CC[C@H](CCC(F)(F)F)NC(=O)N(CC)[C@H](C)c1ccc(OC)c(-c2cnc3[nH]ccc3c2)c1] | 1-ethyl-1-((R)-1-(4-methoxy-3-(1H-pyrrolo[2,3-b]pyridin-5-yl)phenyl)ethyl)-3-((R)-6,6,6-trifluorohexan-3-yl)urea | 477.4 |
| 8-7 | 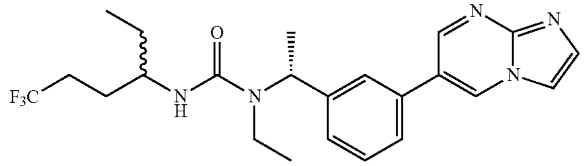 [SMILES: CCC(CCC(F)(F)F)NC(=O)N(CC)[C@H](C)c1cccc(-c2cnc3nccn3c2)c1] | 1-ethyl-1-((R)-1-(3-(imidazo[1,2-a]pyrimidin-6-yl)phenyl)ethyl)-3-(6,6,6-trifluorohexan-3-yl)urea | 448.1 |
| 8-8 | 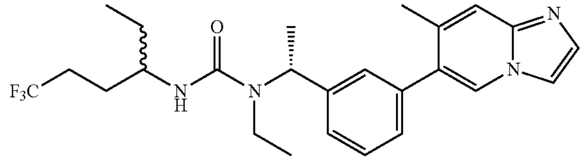 [SMILES: CCC(CCC(F)(F)F)NC(=O)N(CC)[C@H](C)c1cccc(-c2cn3ccnc3cc2C)c1] | 1-ethyl-1-((R)-1-(3-(7-methylimidazo[1,2-a]pyridin-6-yl)phenyl)ethyl)-3-(6,6,6-trifluorohexan-3-yl)urea | 461.5 |

TABLE 8-continued

| Example | Structure | Name | Exact Mass [M + H]+ |
| --- | --- | --- | --- |
| 8-9 | 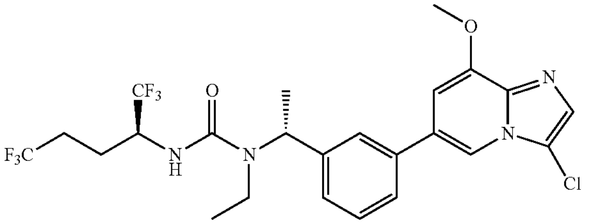 [SMILES: CCN(C(=O)N[C@@H](CCC(F)(F)F)C(F)(F)F)[C@H](C)c1cccc(-c2cc(OC)c3ncc(Cl)n3c2)c1] | 1-((R)-1-(3-(3-chloro-8-methoxyimidazo[1,2-a]pyridin-6-yl)phenyl)ethyl)-1-ethyl-3-((S)-1,1,1,5,5,5-hexafluoropentan-2-yl)urea | 551.5 |
| 8-10 | 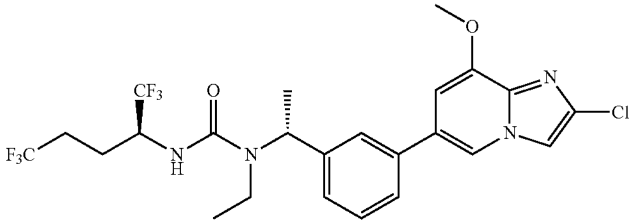 [SMILES: CCN(C(=O)N[C@@H](CCC(F)(F)F)C(F)(F)F)[C@H](C)c1cccc(-c2cc(OC)c3nc(Cl)cn3c2)c1] | 1-((R)-1-(3-(2-chloro-8-methoxyimidazo[1,2-a]pyridin-6-yl)phenyl)ethyl)-1-ethyl-3-((S)-1,1,1,5,5,5-hexafluoropentan-2-yl)urea | 551.5 |
| 8-11 | 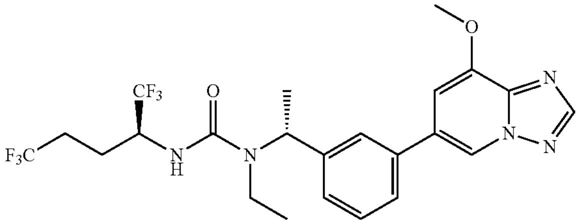 [SMILES: CCN(C(=O)N[C@@H](CCC(F)(F)F)C(F)(F)F)[C@H](C)c1cccc(-c2cc(OC)c3ncnn3c2)c1] | 1-ethyl-3-((S)-1,1,1,5,5,5-hexafluoropentan-2-yl)-1-((R)-1-(3-(8-methoxy-[1,2,4]triazolo[1,5-a]pyridin-6-yl)phenyl)ethyl) urea | 518.3 |
| 8-12 | 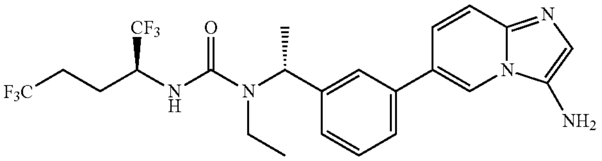 [SMILES: CCN(C(=O)N[C@@H](CCC(F)(F)F)C(F)(F)F)[C@H](C)c1cccc(-c2ccc3ncc(N)n3c2)c1] | 1-((R)-1-(3-(3-aminoimidazo[1,2-a]pyridin-6-yl)phenyl)ethyl)-1-ethyl-3-((S)-1,1,1,5,5,5-hexafluoropentan-2-yl)urea | 502.3 |
| 8-14 | 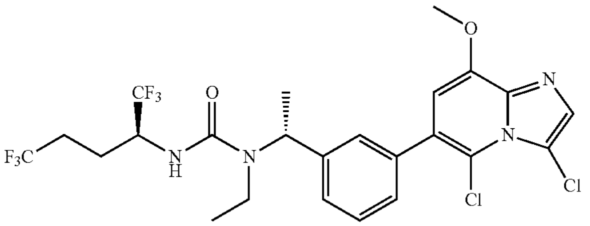 [SMILES: CCN(C(=O)N[C@@H](CCC(F)(F)F)C(F)(F)F)[C@H](C)c1cccc(-c2cc(OC)c3ncc(Cl)n3c2Cl)c1] | 1-((R)-1-(3-(3,5-dichloro-8-methoxyimidazo[1,2-a]pyridin-6-yl)phenyl)ethyl)-1-ethyl-3-((S)-1,1,1,5,5,5-hexafluoropentan-2-yl)urea | 585.5 |
| 8-15 | 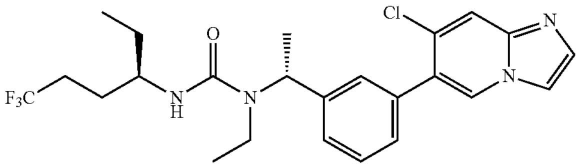 [SMILES: CC[C@H](CCC(F)(F)F)NC(=O)N(CC)[C@H](C)c1cccc(-c2cn3ccnc3cc2Cl)c1] | 1-((R)-1-(3-(7-chloroimidazo[1,2-a]pyridin-6-yl)phenyl)ethyl)-1-ethyl-3-((R)-6,6,6-trifluorohexan-3-yl)urea | 481.4 |

Intermediate I1: 6-bromo-8-ethylimidazo[1,2-a]pyrazine

Intermediate I1

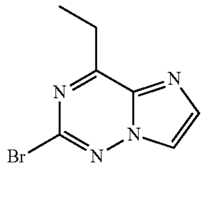

Step 1: 5-bromo-3-ethylpyrazin-2-amine (I1-1)

I1-1

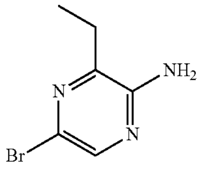

To a solution of 3,5-dibromopyrazin-2-amine (1 g, 3.95 mmol) and bis(triphenylphosphine)palladium(ii) dichloride (0.139 g, 0.198 mmol) in THF (10 mL) was added diethylzinc (3.95 mL, 3.95 mmol) (1.0 M in hexane) and stirred at 20° C. for 2 h. TLC (petroleum ether:EtOAc=1:1) and LCMS showed the reaction was completed. The reaction mixture was poured into water (30 mL), extracted with EtOAc (20 m Lx 3). The organic layer was washed with brine (20 mL), dried over $Na_2SO_4$ and filtered. The filtrate was concentrated and purified by flash silica gel chromatography (ISCO®; 12 g SepaFlash® Silica Flash Column, eluent of 0-20% ethyl acetate/petroleum ether gradient) to give the title compound.

Step 2: 6-bromo-8-ethylimidazo[1,2-a]pyrazine (Intermediate I1)

Intermediate I1

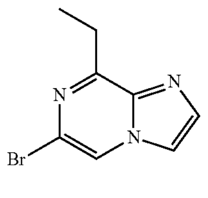

To a solution of 5-bromo-3-ethylpyrazin-2-amine (I1-1) (300 mg, 1.485 mmol) in 2-Propanol (5 mL) was added 2-chloroacetaldehyde (583 mg, 2.97 mmol, 40% w %) and stirred at 110° C. for 15 h. A solid was formed. The reaction was filtered and the filter cake was dissolved in water (20 mL), and then $NaHCO_3$ was added to adjusted pH=8. The mixture was extracted with EtOAc (30 mL×3). The organic layer was washed with brine (30 mL), dried over $Na_2SO_4$, filtered and concentrated. The crude product was dried to give the title compound. H-NMR (400 MHz, $CD_3OD$, ppm): δ 8.59 (s, 1H), 7.96 (d, J=1.0 Hz, 1H), 7.74 (d, J=1.0 Hz, 1H), 3.17 (q, J 10=7.6 Hz, 2H), 1.37 (t, J=7.6 Hz, 3H).

Intermediate 12: 6-bromo-8-methoxy-5-methylimidazo[1,2-a]pyrazine

Intermediate I2

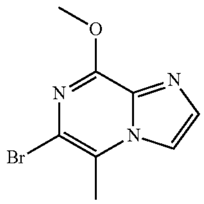

To a solution of 5-bromo-3-methoxy-6-methylpyrazin-2-amine (500 mg, 2.293 mmol) in water (10 mL) was added 2-chloroacetaldehyde (900 mg, 4.59 mmol) and stirred at 110° C. for 15 h. The reaction was poured into water (50 mL), and then $Na_2CO_3$ was added to adjusted pH=8. The mixture was extracted with EtOAc (50 mL×3). The organic layer was washed with brine (50 mL), dried over $Na_2SO_4$, filtered and concentrated to give the title compound. H-NMR (400 MHz, $CD_3OD$, ppm): δ 7.69 (d, J=1.2 Hz, 1H), 7.54 (d, J=1.2 Hz, 1H), 4.14 (s, 3H), 2.64 (s, 3H). MS: 241.8 [M+1].

Intermediate I3: 6-bromo-4-methoxybenzo[d]oxazole

Intermediate I3

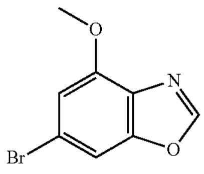

Step 1: 2-amino-5-bromobenzene-1,3-diol (13-1)

I3-1

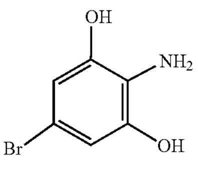

To a stirred and cooled (0° C.) suspension of 4-bromo-2,6-dimethoxyaniline (2 g, 8.62 mmol) in DCM (30 mL) was added $BBr_3$ (2.444 mL, 25.9 mmol) in DCM (20 mL). TLC showed a new spot was formed. The resulting mixture was allowed to warm to room temperature. After 1 h, the mixture was quenched into saturated aqueous sodium bicarbonate solution and was extracted with ethyl acetate (3×20 mL). The combined organic phases were washed with brine (20 mL), dried over sodium sulfate, filtered, and concentrated. Chromatographic purification of the crude product (silica gel column, 33% ethyl acetate/petroleum ether elute) afforded the title compound.

Step 2: 6-bromobenzo[d]oxazol-4-ol (I3-2)

I3-2

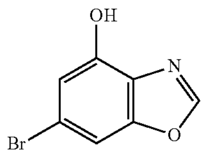

To a mixture of 2-amino-5-bromobenzene-1,3-diol (13-1) (1 g, 4.90 mmol), 4-methylbenzenesulfonic acid (0.084 g, 0.490 mmol) in toluene (20 mL) was added trimethoxymethane (5.20 g, 49.0 mmol) at 20° C., then the mixture was stirred at 70° C. under $N_2$ for 1 h, and concentrated in vacuo. TLC showed almost complete conversion to the desired product. The residue was purified by prep-TLC (petroleum ether:EtOAc=1:1) to give the title compound.

Step 3: 6-bromo-4-methoxybenzo[d]oxazole (Intermediate I3)

Intermediate I3

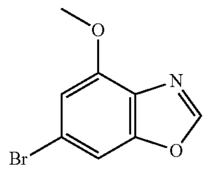

$K_2CO_3$ (1356 mg, 9.81 mmol) and MeI (1.023 mL, 16.35 mmol) were added to a solution of 6-bromobenzo[d]oxazol-4-ol (13-2) (700 mg, 3.27 mmol) in DMF (10 mL) at 30° C., and the mixture was stirred for 1 h at 30° C. TLC showed the starting material was consumed and desired product formed. Water (20 mL) was added to the reaction mixture and the product was extracted with ethyl acetate (20 mL×3). The organic layer was washed with brine (20 mL), and dried over sodium sulfate. A crude product obtained by evaporation under reduced pressure and purified by prep-TLC (petroleum ether:EtOAc=2:1) to give the title compound. H-NMR (400 MHz, $CD_3OD$, ppm): δ 8.39 (s, 1H), 7.50 (d, J=1.5 Hz, 1H), 7.11 (d, J=1.5 Hz, 1H), 4.04 (s, 3H).

Intermediate I4: 5-bromo-7-ethylpyrazolo[1,5-a]pyridine

Intermediate I4

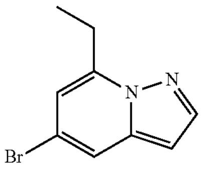

Step 1: 5-bromo-7-iodopyrazolo[1,5-a]pyridine (I4-1)

I4-1

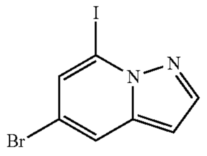

To a solution of 5-bromopyrazolo[1,5-a]pyridine (A3-7) (450 mg, 2.284 mmol) in THF (10 mL) was added n-BuLi (1.005 mL, 2.51 mmol) at −78° C. After the mixture was stirred −78° C. for 30 min, 1,2-diiodoethane (772 mg, 2.74 mmol) in THF (10 mL) was added slowly to above solution. Then the mixture was stirred −78° C. for another 30 min. LCMS showed the desired product was formed. The reaction mixture was poured into water (10 mL) and saturated $Na_2S203$ (3 mL) was added the quenched mixture. Then the mixture was extracted with EtOAc (10 mL×3). The combined organic phases were dried over $Na_2SO_4$ and filtered. The filtrate was concentrated and purified by reversed MPLC (Biotage; 20 g Agela, C18, 20-35 μm, Eluent of 5%-18% gradient of $MeCN/H_2O$ with 0.5% TFA as a modifier @30 mL/min) to afford the title compound. H-NMR (400 MHz, $CDCl_3$, ppm): δ 7.96 (s, 1H), 7.72 (s, 1H), 7.34 (s, 1H), 6.63 (s, 1H). MS: 322.9 [M+1].

Step 2: 5-bromo-7-iodopyrazolo[1,5-a]pyridine (Intermediate I4)

Intermediate I4

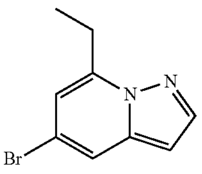

To a solution of 5-bromo-7-iodopyrazolo[1,5-a]pyridine (I4-1) (120 mg, 0.372 mmol) in THF (6 mL) was added $Pd(dppf)Cl_2$ (27.2 mg, 0.037 mmol) and diethylzinc (1 M in hexanes, 0.483 mL, 0.483 mmol). Then the mixture was stirred at 60° C. for 2 h. LCMS showed the desired product was formed. The reaction mixture was poured into water (5 mL), extracted with EtOAc (5 mL×3). The organic phases were dried over $Na_2SO_4$, filtered. The filtrate was concentrated and purified by prep-TLC ($SiO_2$, petroleum ether: EtOAc=10:1) to give the title compound. H-NMR (400 MHz, $CD_3OD$, ppm): δ 8.04 (s, 1H), 7.76 (s, 1H), 6.83 (s, 1H), 6.58 (s, 1H), 3.11 (q, J=11.2 Hz, 2H), 1.24 (t, J=11.2 Hz, 3H). MS: 224.9 [M+1].

Intermediate I5: 6-bromo-4-methoxy-1-methyl-1H-benzo[d]imidazole

Intermediate I5

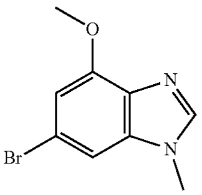

5-bromo-7-methoxy-1H-benzo[d]imidazole (100 mg, 0.440 mmol) and SODIUM HYDRIDE (22.90 mg, 0.573 mmol) were stirred in THF (4 mL) at ambient temperature for 0.25 h. IODOMETHANE (0.030 mL, 0.484 mmol) was added and stirring continued for 1 h. Added IODOMETHANE (0.006 mLl) and continued stirring for an additional 17 h. The mixture was concentrated, dissolved in DCM, and purified by column chromatography on silica gel (24 g column), eluting with hexanes/3:1 EtOAc:EtOH mix, 0-100% gradient. The desired fractions were concentrated and dried to afford the title compound. MS: 243.0, 244.0 [M+1].

Intermediate 16: 2-chloro-4-methoxyimidazo[2,1-f][1,2,4]triazine

Intermediate I6

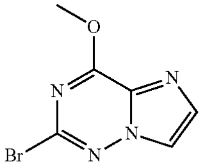

A solution of sodium methoxide (25 wt % in MeOH, 0.161 mL, 0.705 mmol) was added to a solution 2,4-dichloroimidazo[2,1-f][1,2,4]triazine (101 mg, 0.534 mmol) in THF (2 mL) and the mixture was stirred at ambient temperature for 1 h. The mixture was concentrated and purified by column chromatography on silica gel (24 g Isco Gold column), eluting with hexanes:EtOAc 100:0 to 0:100 to afford the title compound. MS: 185.0 [M+].

Intermediate I7: (R)-1-(4-bromo-5-methoxypyridin-2-yl)-N-ethylethan-1-amine

Intermediate I7

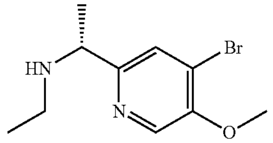

Step 1: (R,E)-N-((4-bromo-5-methoxypyridin-2-yl)methylene)-2-methylpropane-2-sulfinamide (I7-1)

I7-1

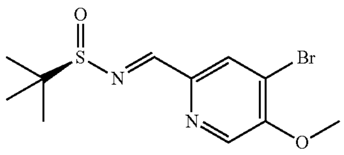

To a solution of 4-bromo-5-methoxypicolinaldehyde (5.00 g, 23.14 mmol) and (R)-2-methylpropane-2-sulfinamide (2.81 g, 23.14 mmol) in DCM (46.3 ml) at ambient temperature was added COPPER(II) SULFATE (8.13 g, 50.9 mmol) and the solution was stirred for 16 h. The mixture was filtered through celite, rinsing with DCM (10 mL×3) and concentrated. The crude was purified by column chromatography on silica gel (120 g column), eluting with 50-100% 3:1 EtOAc:EtOH/hexanes to afford the title compound. MS: 319.1, 321.1 [M+1].

Step 2: (R)—N—((R)-1-(4-bromo-5-methoxypyridin-2-yl)ethyl)-2-methylpropane-2-sulfinamide (Intermediate I8)

Intermediate I8

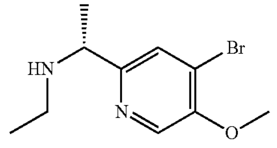

The title compound was prepared from (R,E)-N-((4-bromo-5-methoxypyridin-2-yl)methylene)-2-methylpropane-2-sulfinamide (17-1) using the procedures outlined in steps 2-4 in the synthesis of Intermediate H4. MS: 259.2, 261.2 [M+1].

Intermediate 19: 1-(5-bromo-2-methoxypyridin-3-yl)-N-ethyl-2,2,2-trifluoroethan-1-amine Intermediate I9

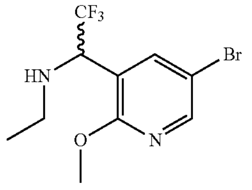

Step 1: 1-(5-bromo-2-methoxypyridin-3-yl)-2,2,2-trifluoroethan-1-one (I9-1)

I9-1

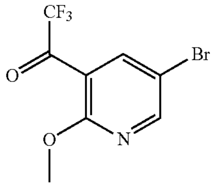

To a solution of methyl 5-bromo-2-methoxynicotinate (4 g, 16.26 mmol) in THF (50 mL) was added CsF (2.469 g, 16.26 mmol) and trimethyl(trifluoromethyl)silane (4.62 g, 32.5 mmol) at 0° C. slowly. The mixture was stirred at 0° C. for 1 h, and then allowed to warm to 15° C. for 15 h. TLC (petroleum ether:EtOAc=3:1) showed new spots were formed and LCMS showed the start material was consumed and product was formed. The reaction was poured into saturated $NH_4Cl$ (150 mL), extracted with EtOAc (50 mL×3). The combined organic phases were dried over $Na_2SO_4$, filtered and concentrated. The residue was purification by flash silica gel chromatography (ISCO®; 80 g SepaFlash® Silica Flash Column, eluent of 17% ethyl acetate) to afford the title compound. MS: 301.5 [M+18].

Step 2: 1-(5-bromo-2-methoxypyridin-3-yl)-N-ethyl-2,2,2-trifluoroethan-1-amine (Intermediate I9)

Intermediate I9

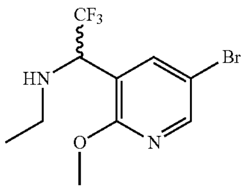

The title compound was prepared from 1-(5-bromo-2-methoxypyridin-3-yl)-2,2,2-trifluoroethan-1-one (19-1) using the procedure from step 3 in the synthesis of Intermediate B21. 1-H NMR (400 MHz, $CD_3OD$, ppm): δ 8.43 (d, J=2.3 Hz, 1H), 8.10 (d, J=2.4 Hz, 1H), 5.34 (q, J=7.5 Hz, 1H), 4.10-4.00 (m, 3H), 3.05-2.90 (m, 2H), 1.28 (t, J=7.3 Hz, 3H). MS: 314.4 [M+1].

Example 9-1 from Table 9: 1-ethyl-3-((S)-1,1,1,5,5,5-hexafluoropentan-2-yl)-1-((S)-2,2,2-trifluoro-1-(5-methoxy-4-(8-methoxyimidazo[1,2-a]pyridin-6-yl)pyridin-2-yl)ethyl)urea Example 9-1

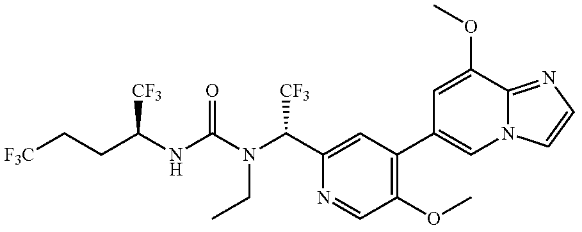

Step 1: 1-(1-(4-chloro-5-methoxypyridin-2-yl)-2,2,2-trifluoroethyl)-1-ethyl-3-((S)-1,1,1,5,5,5-hexafluoropentan-2-yl)urea (I10-1)

I10-1

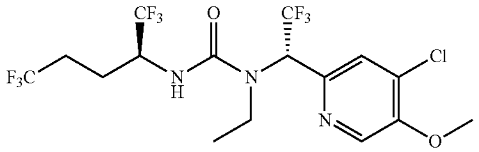

The title compound, as a mixture of diastereomers, was prepared from 1-(4-chloro-5-methoxypyridin-2-yl)-N-ethyl-2,2,2-trifluoroethan-1-amine (32-8) and Intermediate A13 using the procedure outlined in the synthesis of Example 2-1. The diastereomers were resolved via prep SFC using the following conditions: Whelk-01, (R, R) column (2×25 cM), 10% 4:1 heptane:IPA (DEA)/$CO_2$, 100 bar, flow rate=70 mL/min. The title compound was eluted as the first peak. MS: 491.2 [M+1].

Step 2: 1-ethyl-3-((S)-1,1,1,5,5,5-hexafluoropentan-2-yl)-1-((S)-2,2,2-trifluoro-1-(5-methoxy-4-(4,4,5,5-tetramethyl-1,3,2-dioxaborolan-2-yl)pyridin-2-yl)ethyl)urea (I10-2)

I10-2

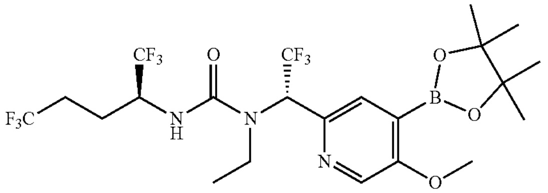

A vial was charged with the 1-(1-(4-chloro-5-methoxypyridin-2-yl)-2,2,2-trifluoroethyl)-1-ethyl-3-((S)-1,1,1,5,5,5-hexafluoropentan-2-yl)urea (110-1) (508 mg, 1.037 mmol), bis(pinacolato)diboron (527 mg, 2.074 mmol), 6-bromo-8-methoxyimidazo[1,2-a]pyridine (Intermediate A2), and chloro(2-dicyclohexylphosphino-2',4',6'-tri-i-propyl-1,1'-biphenyl)(2'-amino-1,1'-biphenyl-2-yl) palladium (II) (82 mg, 0.104 mmol) and $K_2CO_3$ (305 mg, 3.11 mmol) which were dissolved in degassed toluene (10 mL) and heated at 100° C. for 1 h. This was filtered through a pad of celite and concentrated to afford the title compound which was used without further purification. MS: 500.3 [M+1].

Step 3: 1-ethyl-3-((S)-1,1,1,5,5,5-hexafluoropentan-2-yl)-1-((S)-2,2,2-trifluoro-1-(5-methoxy-4-(8-methoxyimidazo[1,2-a]pyridin-6-yl)pyridin-2-yl)ethyl)urea (Example 9-1 from Table 9)

Example 9-1

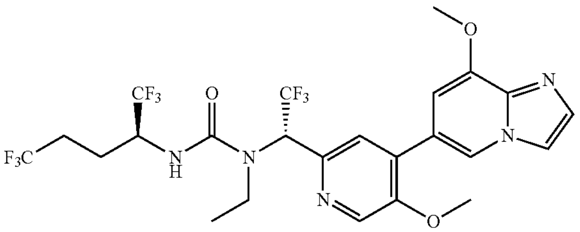

The title compound was prepared from 1-ethyl-3-((S)-1,1,1,5,5,5-hexafluoropentan-2-yl)-1-((S)-2,2,2-trifluoro-1-(5-methoxy-4-(4,4,5,5-tetramethyl-1,3,2-dioxaborolan-2-yl)pyridin-2-yl)ethyl)urea (110-2) and 6-bromo-8-methoxyimidazo[1,2-a]pyridine (Intermediate A2) using the procedure outlined in step 4 in the synthesis of Intermediate B21. MS: 602.3 [M+1].

The following compounds were prepared according to the general procedures herein and in an analogous manner to that used to synthesize the Examples above using the appropriate halogenated heterocycles and amines. The starting materials were either prepared as described in the intermediates section, commercial available, or prepared from commercially available reagents using conventional reactions well known in the art.

TABLE 9

| Example | Structure | Name | Exact Mass [M + H]+ |
|---|---|---|---|
| 9-2 | 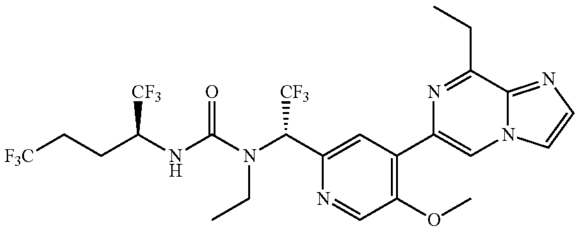 [SMILES: CCc1nc(-c2cc([C@H](N(CC)C(=O)N[C@@H](CCC(F)(F)F)C(F)(F)F)C(F)(F)F)ncc2OC)cn2ccnc12] | 1-ethyl-1-((S)-1-(4-(8-ethylimidazo[1,2-a]pyrazin-6-yl)-5-methoxypyridin-2-yl)-2,2,2-trifluoroethyl)-3-((S)-1,1,1,5,5,5-hexafluoropentan-2-yl)urea | 601.4 |
| 9-3 | 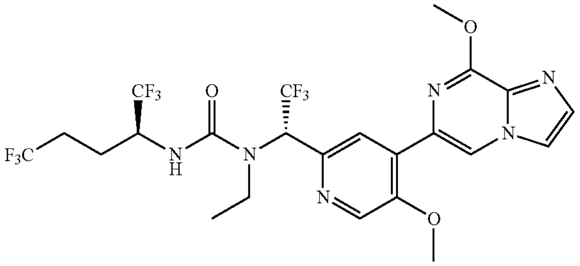 [SMILES: CCN(C(=O)N[C@@H](CCC(F)(F)F)C(F)(F)F)[C@@H](c1cc(-c2cn3ccnc3c(OC)n2)c(OC)cn1)C(F)(F)F] | 1-ethyl-3-((S)-1,1,1,5,5,5-hexafluoropentan-2-yl)-1-((S)-2,2,2-trifluoro-1-(5-methoxy-4-(8-methoxy-5-methylimidazo[1,2-a]pyrazin-6-yl)pyridin-2-yl)ethyl)urea | 617.4 |
| 9-4 | 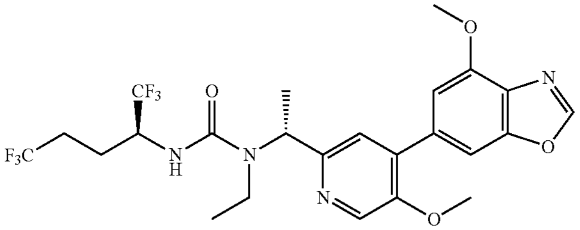 [SMILES: CCN(C(=O)N[C@@H](CCC(F)(F)F)C(F)(F)F)[C@H](C)c1cc(-c2cc(OC)c3ncoc3c2)c(OC)cn1] | 1-ethyl-3-((S)-1,1,1,5,5,5-hexafluoropentan-2-yl)-1-((R)-1-(5-methoxy-4-(4-methoxybenzo[d] oxazol-6-yl)pyridin-2-yl)ethyl)urea | 549.3 |
| 9-5 | 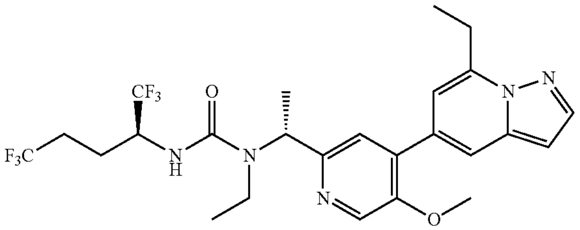 [SMILES: CCc1cc(-c2cc([C@@H](C)N(CC)C(=O)N[C@@H](CCC(F)(F)F)C(F)(F)F)ncc2OC)cc2ccnn12] | 1-ethyl-1-((R)-1-(4-(7-ethylpyrazolo[1,5-a]pyridin-5-yl)-5-methoxypyridin-2-yl)ethyl)-3-((S)-1,1,1,5,5,5-hexafluoropentan-2-yl)urea | 546.4 |
| 9-6 | 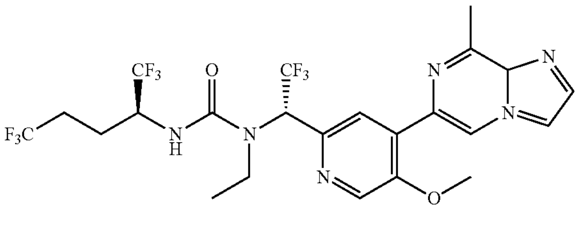 | 1-ethyl-3-((S)-1,1,1,5,5,5-hexafluoropentan-2-yl)-1-((S)-2,2,2-trifluoro-1-(5-methoxy-4-(8-methylimidazo[1,2-a]pyrazin-6-yl)pyridin-2-yl)ethyl)urea | 588.5 |
| 9-7 | 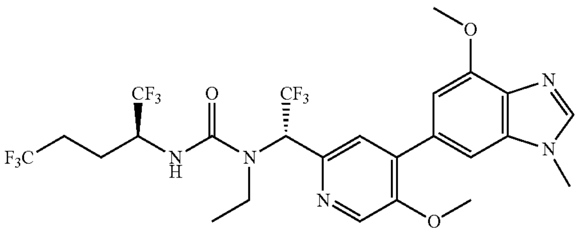 [SMILES: CCN(C(=O)N[C@@H](CCC(F)(F)F)C(F)(F)F)[C@@H](c1cc(-c2cc(OC)c3ncn(C)c3c2)c(OC)cn1)C(F)(F)F] | 1-ethyl-3-((S)-1,1,1,5,5,5-hexafluoropentan-2-yl)-1-((S)-2,2,2-trifluoro-1-(5-methoxy-4-(4-methoxy-1-methyl-1H-benzo[d]imidazol-6-yl)pyridin-2-yl)ethyl)urea | 617.2 |

TABLE 9-continued

| Example | Structure | Name | Exact Mass [M + H]+ |
|---|---|---|---|
| 9-8 | 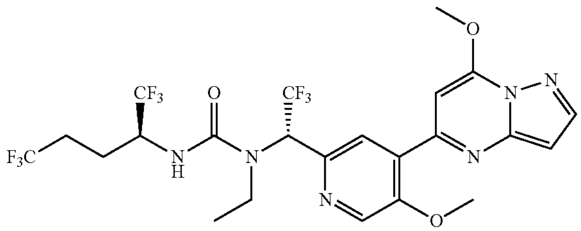 [SMILES: CCN(C(=O)N[C@@H](CCC(F)(F)F)C(F)(F)F)[C@@H](c1cc(-c2cc(OC)n3nccc3n2)c(OC)cn1)C(F)(F)F] | 1-ethyl-3-((S)-1,1,1,5,5,5-hexafluoropentan-2-yl)-1-((S)-2,2,2-trifluoro-1-(5-methoxy-4-(7-methoxypyrazolo[1,5-a]pyrimidin-5-yl)pyridin-2-yl)ethyl)urea | 604.5 |
| 9-10 | 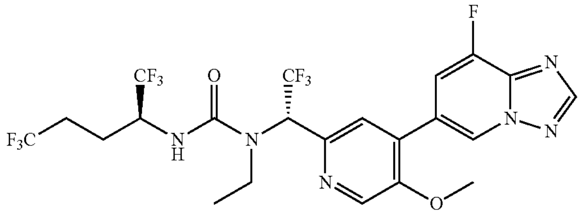 [SMILES: CCN(C(=O)N[C@@H](CCC(F)(F)F)C(F)(F)F)[C@@H](c1cc(-c2cc(F)c3ncnn3c2)c(OC)cn1)C(F)(F)F] | 1-ethyl-3-((S)-1,1,1,5,5,5-hexafluoropentan-2-yl)-1-((S)-2,2,2-trifluoro-1-(4-(8-fluoro-[1,2,4]triazolo[1,5-a]pyridin-6-yl)-5-methoxypyridin-2-yl)ethyl)urea | 537.2 |
| 9-11 | 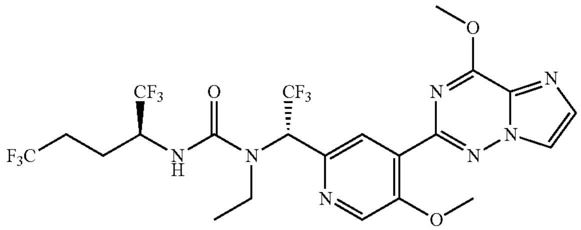 [SMILES: CCN(C(=O)N[C@@H](CCC(F)(F)F)C(F)(F)F)[C@@H](c1cc(-c2nc(OC)c3nccn3n2)c(OC)cn1)C(F)(F)F] | 1-ethyl-3-((S)-1,1,1,5,5,5-hexafluoropentan-2-yl)-1-((S)-2,2,2-trifluoro-1-(5-methoxy-4-(4-methoxyimidazo[2,1-f][1,2,4]triazin-2-yl)pyridin-2-yl)ethyl)urea | 605.3 |

Intermediate J1: (R)-1-(5-chloro-6-methoxypyridazin-3-yl)-N-ethylethan-1-amine

Intermediate J1

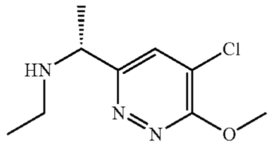

Step 1: (R)-1-(5-chloro-6-methoxypyridazin-3-yl)-N-ethylethan-1-amine (J1-1)

J1-1

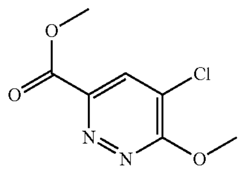

A solution of methyl 5,6-dichloropyridazine-3-carboxylate (30 g, 145 mmol) in MeOH (300 mL) was stirred at 20° C. for 3 h. The reaction mixture was concentrated and dissolved in water (500 mL). $NaHCO_3$ was added to adjusted pH=8. The mixture was extracted with EtOAc (200 mL×3). The organic layer was washed with brine (100 mL), dried over $Na_2SO_4$ and filtered. The filtrate was concentrated and purified by flash silica gel chromatography (ISCO®; 120 g SepaFlash® Silica Flash Column, eluent of 0-20% ethyl acetate/petroleum ether gradient) to give the title compound. 1-H NMR (400 MHz, $CDCl_3$, ppm): δ 8.16 (s, 1H), 4.30 (s, 3H), 4.04 (s, 3H).

Step 2: 1-(5-chloro-6-methoxypyridazin-3-yl)ethan-1-one (J1-2)

J1-2

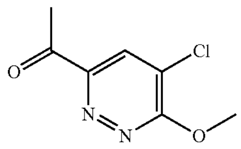

To a solution of (R)-1-(5-chloro-6-methoxypyridazin-3-yl)-N-ethylethan-1-amine (J1-1) (4 g, 19.74 mmol) in THF (40 mL) was added methylmagnesium bromide (13.16 mL, 39.5 mmol) at −78° C. and stirred at −78° C. for 4 h. LCMS showed the desired target was formed. The reaction mixture was poured into water (50 mL), extracted with EtOAc (30 mL×3). The organic layer was washed with brine (30 mL), dried over $Na_2SO_4$ and filtered. The filtrate was concentrated and purified by flash silica gel chromatography (ISCO®; 12 g SepaFlash® Silica Flash Column, eluent of 0-16% ethyl acetate/petroleum ether gradient) to give the title compound.

Step 3: (R-1-(5-chloro-6-methoxypyridazin-3-v-N-ethylethan-1-amine (Intermediate J1)

Intermediate J1

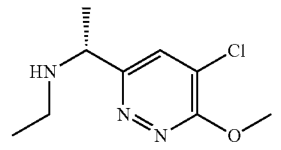

To a solution of 1-(5-chloro-6-methoxypyridazin-3-yl) ethan-1-one (J1-2) (1 g, 5.36 mmol) in MeOH (10 mL) were added ethylamine (0.483 g, 10.72 mmol), AcOH was added and adjusted pH=6 and $NaBH_3CN$ (0.674 g, 10.72 mmol) was added. The mixture was stirred at 60° C. for 15 h. LCMS showed that the most of starting material was remained and the desired target was formed. Then another batch of $NaBH_3CN$ (0.674 g, 10.72 mmol) was added to the reaction mixture and stirred at 60° C. for 3 h. LCMS showed the reaction was completed. The reaction mixture was poured into water (30 mL) and adjusted pH=8 with $NaHCO_3$, extracted with EtOAc (20 mL×3). The organic layer was washed with brine (30 mL), dried over $Na_2S04$ and filtered. The filtrate was concentrated and purified by reversed MPLC (Biotage; 12 g Agela, C18, 20-35 μm, eluent with a gradient of 1-15% $MeCN/H_2O$ with 0.5% TFA as a modifier) to give the crude compound. The diastereomers were resolved via prep SFC using the following conditions: Diacel CHIRALPAK AY-H column (250 mm×30 mm, 5 uM), 20% EtOH (0.1% $NH_3{\cdot}H_2O$), flow rate=60 mL/min. The title compound was eluted as the second eluting diastereomer. H-NMR (400 MHz, $CD_3OD$, ppm): δ 7.83 (s, 1H), 4.14 (s, 3H), 4.03 (q, J=6.8 Hz, 1H), 2.51 (qd, J=7.2, 11.5 Hz, 1H), 2.38 (qd, J=7.2, 11.4 Hz, 1H), 1.38 (d, J=6.8 Hz, 3H), 1.07 (t, J=7.1 Hz, 3H).

Intermediate J2: 1-(4-chloro-5-methoxypyrimidin-2-yl)-N-ethyl-2,2,2-trifluoroethan-1-amine Intermediate J2

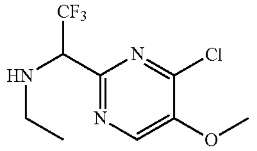

Step 1: 2-chloro-5-methoxy-4-(2-(trimethylsilyl) ethoxy)pyrimidine (J2-1)

J2-1

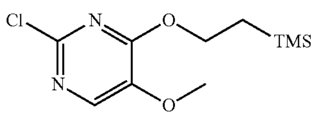

To a solution of 2-(trimethylsilyl)-ethanol (25 g, 211 mmol) in THF (500 mL) was added NaH (9.30 g, 233 mmol) at 0° C. for 30 min. Then 2,4-dichloro-5-methoxypyrimidine (37.8 g, 211 mmol) in THF (100 mL) was added to the mixture at 20° C. for 5 h. TLC (petroleum ether:EtOAc=5:1) showed the starting material was consumed and a new spot was detected. The reaction was poured into water (2000 mL) and extracted with EtOAc (2×1000 mL). The combined organic phases were washed with brine (600 mL), and dried over $Na_2SO_4$. Then the reaction was filtered, concentrated and purified by flash silica gel chromatography (ISCO®; 120 g Biotage® Silica Flash Column, eluent of 15% EtOAc/petroleum ether gradient) to give the title compound. 1-H NMR (400 MHz, $CDCl_3$, ppm): δ 7.83 (s, 1H), 4.58-4.46 (m, 2H), 3.94-3.84 (m, 3H), 1.27-1.13 (m, 2H), 0.06 (s, 9H).

Step 2: methyl 5-methoxy-4-(2-(trimethylsilyl) ethoxy)pyrimidine-2-carboxylate (J2-2)

J2-2

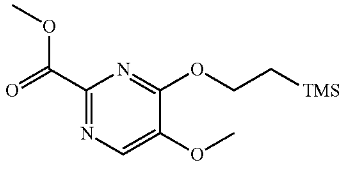

To a solution of 2-chloro-5-methoxy-4-(2-(trimethylsilyl) ethoxy)pyrimidine (J2-1) (19 g, 72.9 mmol) in anhydrous MeOH (500 mL) were added TEA (20.31 mL, 146 mmol) and $PdCl_2$ (dppf) (2.67 g, 3.64 mmol). And the resulting mixture was stirred at 80° C. under 50 psi CO (excess) for 18 h. TLC (petroleum ether:EtOAc=1:1) showed that new spots were found and LCMS showed desired product was found. The mixture was concentrated in vacuo to give the crude product. The crude product dissolved in EtOAc (100 mL) and washed with $NaHCO_3$ (100 mL), brine (100 mL), extracted with EtOAc (100 mL×3). The combined organic layers dried over $Na_2SO_4$, filtered and concentrated. The crude product was purified by flash silica gel chromatography (ISCO®; 120 g Biotage® Silica Flash Column, eluent of 58% EtOAc/petroleum ether gradient) to give the title compound. 1-H NMR (400 MHz, $CDCl_3$, ppm): δ 8.06-7.96 (m, 1H), 4.61-4.50 (m, 2H), 3.93-3.86 (m, 6H), 1.20-1.07 (m, 2H), 0.00 (s, 9H). MS: 285.1 [M+1].

Step 3: methyl 4-chloro-5-methoxypyrimidine-2-carboxylate (J2-3)

J2-4

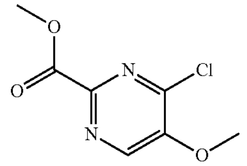

To a solution of methyl 5-methoxy-4-(2-(trimethylsilyl) ethoxy)pyrimidine-2-carboxylate (J2-2) (9 g, 31.6 mmol) in dioxane (150 mL) was added phosphoryl trichloride (14.79 mL, 158 mmol). The reaction mixture was stirred at 90° C., reflux, for 4 h. TLC (petroleum ether:EtOAc=0:1) showed that a new spot was found and LCMS showed desired product was formed. The reaction mixture was poured into water (400 mL) and extracted with EtOAc (300 mL×3). The combined organic layers were washed with saturated $NaHCO_3$ (200 mL), brine (200 mL), dried over $Na_2SO_4$, filtered and concentrated. The crude product was purified by recrystallization of EtOAc (50 mL) to give the title compound. 1-H NMR (400 MHz, $CDCl_3$) δ 8.41 (s, 1H), 4.10 (s, 3H), 4.03 (s, 3H). MS: 203.0 [M+1].

Step 4: 1-(4-chloro-5-methoxypyrimidin-2-yl)-2,2,2-trifluoroethan-1-one (J2-4)

J2-4

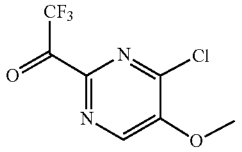

To a solution of methyl 4-chloro-5-methoxypyrimidine-2-carboxylate (J2-3) (3 g, 14.81 mmol) were added CsF (2.249 g, 14.81 mmol, then trimethyl-(trifluoromethyl)silane (4.21 g, 29.6 mmol) was added to the above solution at 0° C. slowly. The mixture was stirred at 0° C. to 20° C. for 15 h. TLC (petroleum ether:EtOAc=1:1) showed that new spots were found and LCMS showed desired product was formed. The residue was filtered and concentrated in vacuo to give the crude product. The crude product was stirred with 6 M HCl (50 mL) in THF (50 mL) for 24 h. Then the mixture was extracted with EtOAc (50 mL×3). The combined organic layers were dried over $Na_2SO_4$, filtered and concentrated. The crude product was purified by flash silica gel chromatography (ISCO®; 80 g Biotage® Silica Flash Column, eluent of 55% EtOAc/petroleum ether gradient) to give title compound. H-NMR (400 MHz, $CDCl_3$, ppm): δ 8.45-8.24 (m, 1H), 4.13-4.06 (m, 3H). MS: 241.1 [M+1].

Step 5: 1-(4-chloro-5-methoxypyrimidin-2-yl)-N-ethyl-2,2,2-trifluoroethan-1-amine (Intermediate J2)

Intermediate J2

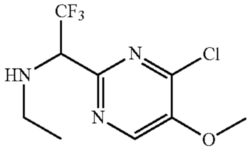

To a solution of 1-(4-chloro-5-methoxypyrimidin-2-yl)-2,2,2-trifluoroethan-1-one (J2-4) (1.4 g, 5.82 mmol) in DCM (100 mL) were added ethylamine (0.787 g, 17.46 mmol) and titanium (IV) chloride (4.42 g, 23.28 mmol). The mixture was stirred at 15° C. for 15 h. Then sodium cyanotrihydroborate (1.463 g, 23.28 mmol) was added to the above solution and stirred for 15 h. TLC (petroleum ether:EtOAc=3:1) showed that new spots were found and LCMS showed the desired product was formed. The reaction mixture was poured into water (150 mL) and neutralized with saturated $NaHCO_3$ to pH=8, then extracted with DCM (100 mL×3). The organic layer was washed with brine (150 mL), dried over $Na_2SO_4$, filtered and concentrated.

The crude product was purified by flash silica gel chromatography (ISCO®; 40 g Biotage® Silica Flash Column, eluent of 15% EtOAc/petroleum ether gradient) to give the crude title compound. The enantiomers were resolved via prep SFC using the following conditions: Cellulose 2 column (4.6×100 mm, 3 uM), 40% IPA (with 0.05% DEA)/$C_{02}$, column temperature=35° C., flow rate=2.8 mL/min. The title compound was obtained as the second eluting diastereomer. 1-H NMR (400 MHz, $CD_3OD$, ppm): δ 8.57 (s, 1H), 4.45 (q, J=7.3 Hz, 1H), 4.11-4.01 (m, 3H), 2.70-2.57 (m, 2H), 1.33-1.05 (m, 3H). MS: 270.2 [M+1].

Intermediate 3: 1-(6-bromo-5-methoxypyrazin-2-yl)-N-ethyl-2,2,2-trifluoroethan-1-amine Intermediate J3

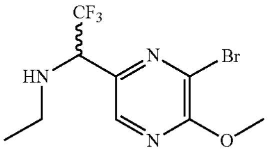

The title compound was prepared from 6-bromo-5-methoxypyrazine-2-carbaldehyde using the procedures outlined in steps 1-3 in the synthesis of Intermediate B21. MS: 314.1, 316.1 [M+1].

Intermediate J4: 1-(4-chloro-5-methoxy-6-methylpyridin-2-yl)-N-ethyl-2,2,2-trifluoroethan-1-amine Intermediate J4

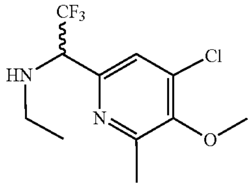

Step 1: 4-chloro-6-iodo-2-methylpyridin-3-ol (J4-1)

J4-1

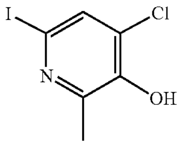

To a solution of 4-chloro-2-methylpyridin-3-ol (3.9 g, 27.2 mmol) in DMF (40 mL) was added N-iodosuccinimide (6.72 g, 29.9 mmol). The reaction mixture was stirred at 20° C. for 2 h. LCMS showed the reaction was complete. The reaction mixture was poured into water (200 mL), extracted with EtOAc (50 mL×3). The combined organic phases were dried over $Na_2SO_4$, filtered and concentrated to give the title compound, which was used directly to next step. MS: 269.8 [M+1].

Step 2: 4-chloro-6-iodo-3-methoxy-2-methylpyridine (J4-2)

J4-2

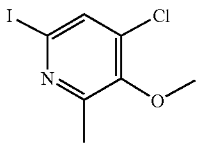

To a solution of 4-chloro-6-iodo-2-methylpyridin-3-ol (J4-1) (7.32 g, 27.2 mmol) in DMF (70 mL) were added Mel (1.359 mL, 21.73 mmol), $K_2CO_3$ (7.51 g, 54.3 mmol) at 22° C. for 1 h. TLC (petroleum ether:EtOAc=10:1) showed a new spot was found and LCMS showed the desired product was formed. The mixture was poured into water (200 mL) and extracted with EtOAc (100 mL×3). The organic layer was washed with brine (200 mL), dried over $Na_2SO_4$, filtered and concentrated. The crude product was purified by flash silica gel chromatography (ISCO®; 80 g SepaFlash® Silica Flash Column, eluent of 0-21% ethyl acetate/petroleum ether gradient) to give the title compound. H-NMR (400 MHz, $CDCl_3$, ppm): δ 7.59 (s, 1H), 3.91-3.68 (m, 3H), 2.59-2.42 (m, 3H). MS: 283.8 [M+1].

Step 3: 1-(4-chloro-5-methoxy-6-methylpyridin-2-yl)-2,2,2-trifluoroethan-1-one (U4-3)

J4-3

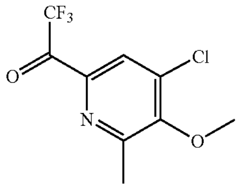

To a mixture solution of 4-chloro-6-iodo-3-methoxy-2-methylpyridine (J4-2) (2.5 g, 8.82 mmol) and ethyl 2,2,2-trifluoroacetate (1.629 g, 11.46 mmol) in THF (20 mL) was added isopropylmagnesium chloride (6.61 mL, 13.23 mmol) at 0° C. Then the reaction mixture was stirred at 0° C. for 30 min. TLC (petroleum ether:EtOAc=3:1) showed new spots were found and LCMS showed the desired product was formed. The reaction mixture was poured into $NH_4Cl$ (100 mL), extracted with EtOAc (50 mL×3). The combined organic phases were washed with brine (100 mL), dried over $Na_2SO_4$, filtered and concentrated. The crude was purified by flash silica gel chromatography (ISCO®; 12 g Sepa-Flash® Silica Flash Column, eluent of 0-23% ethyl acetate/petroleum ether gradient) to give the title compound. MS: 271.9 [M+18].

Step 4: 1-(4-chloro-5-methoxy-6-methylpyridin-2-yl)-N-ethyl-2,2,2-trifluoroethan-1-amine (Intermediate J4)

Intermediate J4

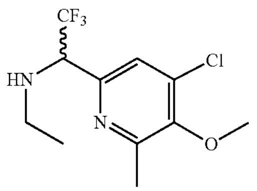

The title compound was prepared from 1-(4-chloro-5-methoxy-6-methylpyridin-2-yl)-2,2,2-trifluoroethan-1-one (J4-3) using the procedure from step 3 in the synthesis of Intermediate B21. MS: 282.9 [M+1].

Intermediate J5: N-(5-bromo-2,4-dimethoxybenzyl)ethylamine

Intermediate J5

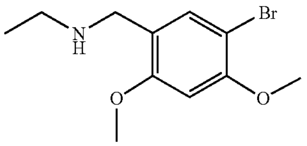

The title compound was prepared from 5-bromo-2,4-dimethoxybenzaldehyde using the procedure outlined in step 2 in the synthesis of Intermediate A10. MS: 274.1 [M+1].

Intermediate J6: 6-bromo-4-methoxythiazolo[4,5-c]pyridine

Intermediate J6

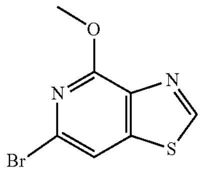

Step 1: N-(4,6-dibromo-2-methoxypyridin-3-yl) formamide (J6-1)

J6-1

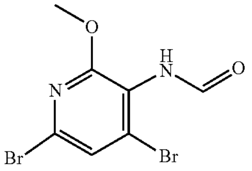

Formic acid (0.680 mL, 17.73 mmol) was added to the solution of acetic anhydride (0.669 mL, 7.09 mmol) in DCM (10 mL) at 0° C., and the resulting mixture was stirred at 30° C. for 1 h. Then 4,6-dibromo-2-methoxypyridin-3-amine (1 g, 3.55 mmol) was added and the resulting mixture was stirred at 30° C. for 6 h. LCMS showed desired mass. New spot was found on TLC. The reaction mixture was quenched with water (10 mL), then extracted with EtOAc (10 mL×3), washed with brine (10 mL×3). The organic layer was dried over $Na_2SO_4$, filtered and the residue was purified by column chromatography on silica gel (ISCO®; 40 g Sepa-Flash® Silica Flash Column, eluent of 5% EtOAc gradient) to give the title compound. MS: 308.7 [M+1].

Step 2: 6-bromo-4-methoxythiazolo[4,5-c]pyridine (Intermediate J6)

Intermediate J6

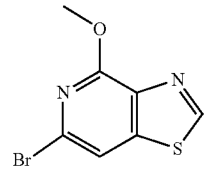

To a mixture of N-(4,6-dibromo-2-methoxypyridin-3-yl) formamide (J6-1) (600 mg, 1.936 mmol) in HMPA (5 mL) was added Lawesson's Reagent (783 mg, 1.936 mmol), and the resulting mixture was stirred at 100° C. for 6 h. LCMS showed desired mass. New spot was found on TLC. The reaction mixture was quenched with water (10 mL×5), then extracted with EtOAc (10 mL×3), washed with brine (10 mL×3). The organic layer was dried over $Na_2SO_4$, filtered and the filtrate was concentrated. The residue was purified by column chromatography on silica gel (ISCO®; 20 g SepaFlash® Silica Flash Column, eluent of 15% EtOAc gradient) to give the title compound. H-NMR (400 MHz, $CDCl_3$, ppm): δ 8.91 (s, 1H), 7.67 (s, 1H), 4.21 (s, 3H). MS: 244.8 [M+1].

Intermediate J6: 1-(5-bromo-2-methoxypyridin-3-yl)-N-ethyl-2,2,2-trifluoroethan-1-amine Intermediate J6

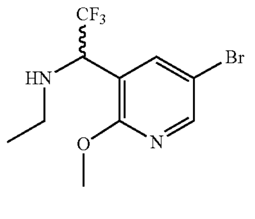

Step 1: 1-(5-bromo-2-methoxypyridin-3-yl)-2,2,2-trifluoroethan-1-one (J6-1)

J6-1

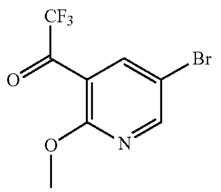

To a solution of methyl 5-bromo-2-methoxynicotinate (4 g, 16.26 mmol) in THF (50 mL) was added CsF (2.469 g, 16.26 mmol) and trimethyl(trifluoromethyl)silane (4.62 g, 32.5 mmol) at 0° C. slowly. The mixture was stirred at 0° C. for 1 h, and then allowed to warm to 15° C. for 15 h. TLC (petroleum ether:EtOAc=3:1) showed new spots were formed and LCMS showed the start material was consumed and product was formed. The reaction was poured into saturated $NH_4Cl$ (150 mL), extracted with EtOAc (50 mL×3). The combined organic phases were dried over $Na_2SO_4$, filtered and concentrated. The residue was purification by flash silica gel chromatography (ISCO®; 80 g SepaFlash® Silica Flash Column, eluent of 17% ethyl acetate) to afford the title compound. MS: 301.5 [M+18].

Step 2: 1-(5-bromo-2-methoxypyridin-3-yl)-N-ethyl-2,2,2-trifluoroethan-1-amine (Intermediate J6)

Intermediate J6

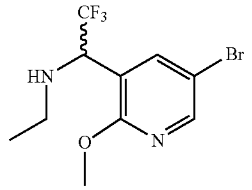

The title compound was prepared from 1-(5-bromo-2-methoxypyridin-3-yl)-2,2,2-trifluoroethan-1-one (J6-1) using the procedure from step 3 in the synthesis of Intermediate B21. 1-H NMR (400 MHz, $CD_3OD$, ppm): δ 8.43 (d, J=2.3 Hz, 1H), 8.10 (d, J=2.4 Hz, 1H), 5.34 (q, J=7.5 Hz, 1H), 4.10-4.00 (m, 3H), 3.05-2.90 (m, 2H), 1.28 (t, J=7.3 Hz, 3H). MS: 314.4 [M+1].

Intermediate J7: (R)-1-(5-bromo-6-methylpyridin-3-yl)-N-ethylethan-1-amine

Intermediate J7

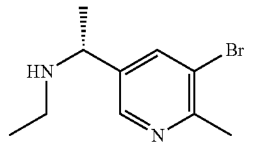

Step 1: 1-(5-bromo-6-methylpyridin-3-yl)ethan-1-one (J7-1)

J7-1

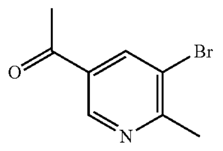

To a solution of 3,5-dibromo-2-methylpyridine (15 g, 59.8 mmol) in Dioxane (150 mL) were added tributyl (1-ethoxyvinyl)stannane (19.43 g, 53.8 mmol) and bis (triphenylphosphine)palladium (ii) dichloride (2.098 g, 2.99 mmol), then the solution was stirred at 100° C. for 10 h. LCMS showed the reaction was completed. The reaction mixture was cooled to 20° C. and 4 M HCl (100 mL) was added to the above mixture and stirred for 1 h. LCMS showed the desired product was found. TLC (petroleum ether:EtOAc=3:1) showed the starting material was consumed and new spots were found. The reaction mixture was poured into 10% KF aqueous solution (300 mL), extracted with EtOAc (200 mL×3). The organic layer was washed with brine (200 mL), dried over $Na_2SO_4$, filtered and concentrated. The crude product was purified by flash silica gel chromatography (ISCO®; 120 g SepaFlash® Silica Flash Column, eluent of 54% ethyl acetate/petroleum ether gradient@30 mL/min) to give the title compound. 1-H NMR (400 MHz, $CDCl_3$, ppm): δ 8.94 (d, J=2.0 Hz, 1H), 8.33 (d, J=2.0 Hz, 1H), 2.73 (s, 3H), 2.62-2.57 (m, 3H). MS: 213.9 [M+1].

Step 2: (R,E)-N-(1-(5-bromo-6-methylpyridin-3-yl) ethylidene)-2-methylpropane-2-sulfinamide (J7-2)

J7-2

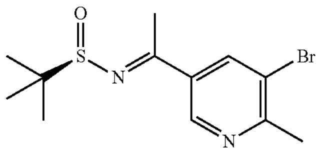

To a solution of 1-(5-bromo-6-methylpyridin-3-yl)ethan-1-one (J7-1) (5.1 g, 23.83 mmol) in THF (100 mL) were added (R)-(+)-2-methyl-2-propanesulfinamide (3.47 g, 28.6 mmol) and titanium (iv) ethoxide (27.2 g, 119 mmol). The mixture was stirred at 80° C. for 12 h under $N_2$. LCMS showed the desired product was formed and TLC (petroleum ether:EtOAc=0:1) showed the starting material was consumed and a new spot was generated. The mixture was poured into brine (300 mL) and was extracted with EtOAc (200 mL×3). The combined organic layers were dried over $Na_2SO_4$, filtered and concentrated. The residue was purified by flash silica gel chromatography (ISCO®; 80 g Biotage® Silica Flash Column, eluent of 90% EtOAc/petroleum ether gradient) to give the title compound. 1-H NMR (400 MHz, $CDCl_3$, ppm): δ 8.85 (d, J=1.7 Hz, 1H), 8.24 (d, J=1.7 Hz, 1H), 2.74 (s, 3H), 2.69 (s, 3H), 1.33-1.21 (m, 9H). MS: 318.9 [M+1].

Step 3: (R)—N—((R)-1-(5-bromo-6-methylpyridin-3-yl)ethyl)-2-methylpropane-2-sulfinamide (J7-3)

J7-3

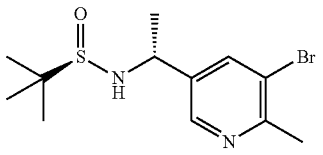

To a solution of (R,E)-N-(1-(5-bromo-6-methylpyridin-3-yl)ethylidene)-2-methylpropane-2-sulfinamide (J7-2) (6 g, 18.91 mmol) in THF (100 mL) was added DIBAL-H (47.3 mL, 47.3 mmol) (1 M in toluene) slowly at −78° C., the resulting mixture was stirred at −78° C. for 4 h. LCMS showed the desired product was formed. TLC (EtOAc: MeOH=20:1) showed starting material was consumed and new spots were formed. The reaction mixture was poured into saturated $NH_4Cl$ (300 mL), extracted with EtOAc (100 mL×3). The combined organic phases were washed with brine (100 mL), and dried over $Na_2SO_4$. After filtration and concentration, the residue was purified by flash silica gel chromatography (ISCO®; 80 g SepaFlash® Silica Flash Column, eluent of 100% ethyl acetate/petroleum ether gradient@30 mL/min) to give the title compound. 1-HNMR (400 MHz, $CDCl_3$, ppm): δ 8.41 (d, J=1.7 Hz, 1H), 7.81 (d, J=1.7 Hz, 1H), 4.61-4.49 (m, 1H), 3.43-3.36 (m, 1H), 2.66 (s, 2H), 1.54 (d, J=6.6 Hz, 3H), 1.33-1.17 (m, 9H). MS: 321.0 [M+1].

Step 4: (R)—N—((R)-1-(5-bromo-6-methylpyridin-3-yl)ethyl)-N-ethyl-2-methylpropane-2-sulfinamide (J7-4)

J7-4

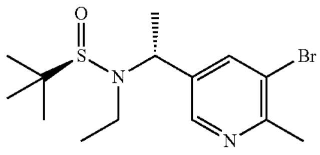

The title compound was prepared from (R)—N—((R)-1-(5-bromo-6-methylpyridin-3-yl)ethyl)-2-methylpropane-2-sulfinamide (J7-3) using the procedure outlined in step 3 in the synthesis of Intermediate H4.

Step 5: (R)-1-(5-bromo-6-methylpyridin-3-yl)-N-ethylethan-1-amine (Intermediate J7)

Intermediate J7

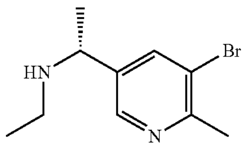

To a solution of (R)—N—((R)-1-(5-bromo-6-methylpyridin-3-yl)ethyl)-N-ethyl-2-methylpropane-2-sulfinamide (J7-4) (1.65 g, 4.75 mmol) in MeOH (12 mL) was added acetyl chloride (1.013 mL, 14.25 mmol) and stirred at 25° C. for 1 h. LCMS showed the desired product was found. The reaction mixture was concentrated to give the title compound, which was used in next step without purification. MS: 243.1 [M+1].

Intermediate JM: 1-(4-bromo-5-methylpyridin-2-yl)-N-ethyl-2,2,2-trifluoroethan-1-amine Intermediate J8

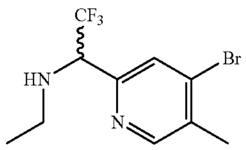

Step 1: (Z)-1-(4-bromo-5-methylpyridin-2-yl)-N-ethylmethanimine (J8-1)

J8-1

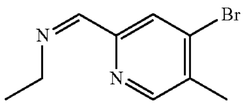

A solution of 4-bromo-5-methylpicolinaldehyde (1 g, 5.00 mmol) in ethylamine (5 mL, 5.00 mmol) was stirred at 20° C. for 15 h. The reaction mixture was concentrated to give the title compound as crude product which was used in next step without purification. H-NMR (400 MHz, $CDCl_3$, ppm): δ 8.40 (s, 1H), 8.29 (d, J=1.2 Hz, 1H), 8.16 (s, 1H), 3.68 (dq, J=1.3, 7.3 Hz, 2H), 2.39 (s, 3H), 1.30 (t, J=7.2 Hz, 3H).

Step 2: 1-(4-bromo-5-methylpyridin-2-yl)-N-ethyl-2,2,2-trifluoroethan-1-amine (Intermediate Intermediate J8

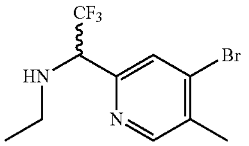

TFA (0.254 mL, 3.30 mmol) was added to a mixture of (Z)-1-(4-bromo-5-methylpyridin-2-yl)-N-ethylmethanimine (J8-1) (500 mg, 2.202 mmol), potassium hydrogen fluoride (129 mg, 1.651 mmol) and DMF (0.511 mL, 6.60 mmol) in $CH_3CN$ (4 mL) at 0° C. And stirred for 5 min, trimethyl (trifluoromethyl)silane (1878 mg, 13.21 mmol) was added to the above solution at 0° C. slowly. The mixture was stirred at 0° C. to 25° C. for 15 h. LCMS showed the desired product was formed. The reaction mixture was poured into sat. $NaHCO_3$ (50 mL), extracted with EtOAc (30 mL×3). The organic layer was washed with brine (50 mL), dried over $Na_2SO_4$ and filtered. The filtrate was concentrated and purified via reverse phase chromatography C18 (38-68% acetonitrile/water with 0.04% $NH_3$—$H_2O$ and 10 mM $NH_4HCO_3$ as a modifier). H-NMR (400 MHz, $CD_3OD$, ppm): δ 8.46 (s, 1H), 7.81 (s, 1H), 4.39 (q, J=7.8 Hz, 1H), 2.62-2.47 (m, 2H), 2.42 (s, 3H), 1.08 (t, J=7.2 Hz, 3H).

Intermediate J9: 1-(6-bromo-5-methoxypyridin-2-yl)-N-ethyl-2,2,2-trifluoroethan-1-amine Intermediate J9

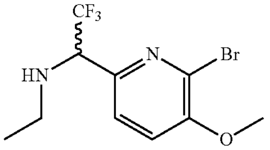

The title compound was prepared from 6-bromo-5-methoxypicolinaldehyde using the procedures outlined in steps 1-3 in the synthesis of Intermediate B21. MS: 313.3, 315.3 [M+1].

Intermediate J10: 1-(5-bromopyridin-3-yl)-N-ethyl-2,2,2-trifluoroethan-1-amine

Intermediate J10

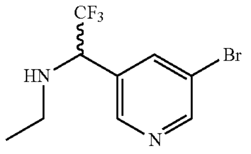

The title compound was prepared from 5-bromonicotinaldehyde using the procedures outlined in steps 1-3 in the synthesis of Intermediate B21. MS: 283.1, 285.1 [M+1].

Intermediate J11: (S)-1,1·5,5-pentafluorohexan-2-amine

Intermediate J11

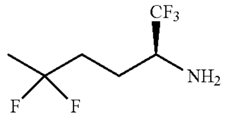

The title compound was prepared with 4,4-difluoropentanal using the procedures outlined in steps 1-4 in the synthesis of Intermediate A13. MS: 192.2 [M+1].

Intermediate J12: (8-methoxyimidazo[1,2-b]pyridazin-6-yl)boronic acid

Intermediate J12

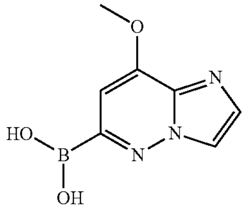

Step 1: 6-chloro-4-methoxypyridazin-3-amine (J12-1)

J12-1

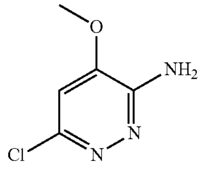

To a solution of 4-bromo-6-chloropyridazin-3-amine (5 g, 23.99 mmol) in anhydrous MeOH (50 mL) was added sodium methanolate (5.18 g, 96 mmol) at 0° C., and the resulting mixture was stirred at 10° C. under $N_2$ protection for 15 h. LCMS showed desired MS was found, and TLC (petroleum ether:EtOAc=0:1) showed new spot was found. The reaction mixture was poured into water (250 mL) and extracted with EtOAc (100 mL×3). The organic layer was washed with brine (200 mL), dried over $Na_2SO_4$. After filtration and concentration, the residue was purified by flash silica gel chromatography (ISCO®; 80 g SepaFlash® Silica Flash Column, eluent of 30% EtOAc gradient) to give the title compound. MS: 159.9 [M+1].

Step 2: 6-chloro-8-methoxyimidazo[1,2-b]pyridazine (J12-2)

J12-2

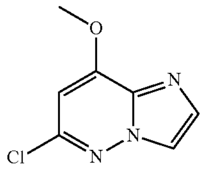

To a solution of 6-chloro-4-methoxypyridazin-3-amine (J12-1) (3 g, 18.80 mmol) in water (50 mL) was added 2-chloroacetaldehyde (6 g, 30.6 mmol) and stirred at 110° C. for 15 h. TLC (EtOAc) showed the reaction was completed. The reaction was concentrated and dissolved in water (150 mL), and then $NaHCO_3$ was added to adjusted pH=8. The mixture was extracted with EtOAc (100 mL×3). The organic layer was washed with brine (100 mL), dried over $Na_2SO_4$, filtered. The filtrate was concentrated and purified by flash silica gel chromatography (ISCO®; 40 g SepaFlash® Silica Flash Column, eluent of 43% EtOAc gradient) to give the title compound. 1-H NMR (400 MHz, $CDCl_3$, ppm): δ=7.84 (d, J=0.8 Hz, 1H), 7.64 (s, 1H), 6.40 (s, 1H), 4.16-4.05 (m, 3H). MS: 183.8 [M+1].

Step 3: (8-methoxyimidazo[1,2-b]pyridazin-6-yl)boronic acid (Intermediate J12)

Intermediate J12

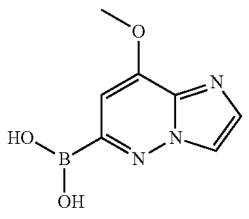

A vial was charged with 6-chloro-8-methoxyimidazo[1,2-b]pyridazine (J12-2) (300 mg, 1.634 mmol), BIS(PINACOLATO)DIBORON (523 mg, 2.059 mmol), POTASSIUM ACETATE (481 mg, 4.90 mmol), and $PdCl_2(dppf)-CH_2Cl_2$ (66.7 mg, 0.082 mmol) and these were combined in degassed dioxane (15 mL) and heated at 90° C. for 18 h. LC/MS shows the mass for the boronic acid. The reaction was filtered through a pad of celite and concentrated. The crude product was suspended in water (3 mL) and sat. $NaHCO_3$ (1 mL) and filtered again. This portion of the aqueous was purified via reverse phase chromatography on a C18 column (5-95% ACN/$H_2O$ with 0.1% TFA as a modifier) to afford the title compound. MS: 194.4 [M+1].

Intermediate J13: (2-cyano-8-methoxyimidazo[1,2-a]pyridin-6-yl)boronic acid

Intermediate J13

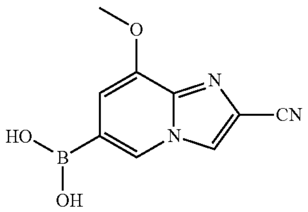

The title compound was prepared from 6-bromo-8-methoxyimidazo[1,2-a]pyridine-2-carbonitrile using the procedure described in the synthesis of Intermediate J12. MS: 218.1 [M+1].

Intermediate J14: (3-cyano-8-methoxyimidazo[1,2-a]pyrazin-6-yl)boronic acid

Intermediate J14

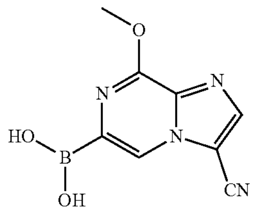

The title compound was prepared from 6-bromo-8-methoxyimidazo[1,2-a]pyrazine-3-carbonitrile using the procedure described in the synthesis of Intermediate J12. MS: 219.1 [M+1].

Intermediate J15: (8-methoxyquinoxalin-6-yl)boronic acid

Intermediate J15

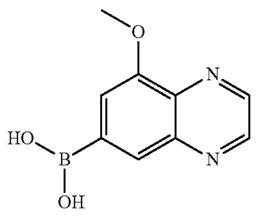

The title compound was prepared from 7-bromo-5-methoxyquinoxaline using the procedure described in the synthesis of Intermediate J12. MS: 205.1 [M+1].

Intermediate J16: (8-methoxyquinolin-6-yl)boronic acid

Intermediate J16

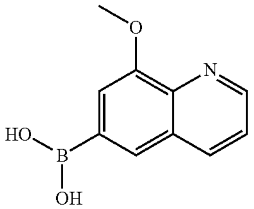

The title compound was prepared from 6-bromo-8-methoxyquinoline using the procedure described in the synthesis of Intermediate J12. MS: 204.1 [M+1].

Example 10-1 from Table 10: 1-ethyl-3-((S)-1,1,1,5,5,5-hexafluoropentan-2-yl)-1-((S)-2,2,2-trifluoro-1-(5-methoxy-4-(8-methoxyimidazo[1,2-a]pyrazin-6-yl)pyridin-2-yl)ethyl)urea Example 10-1

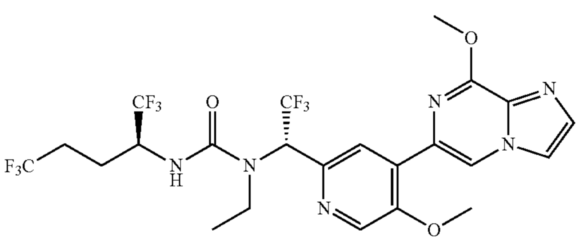

Step 1: 1-((S)-1-(4-bromo-5-methoxypyridin-2-yl)-2,2,2-trifluoroethyl)-1-ethyl-3-((S)-1,1,1,5,5,5-hexafluoropentan-2-yl)urea (J17-1)

J17-1

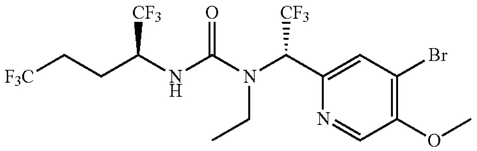

The title compound was prepared with 1-(4-bromo-5-methoxypyridin-2-yl)-N-ethyl-2,2,2-trifluoroethan-1-amine (B21-4) and (S)-1,1,1,5,5,5-hexafluoropentan-2-amine (Intermediate A13) using the procedure outlined in Example 2-1. The diastereomers were resolved via SFC using the following conditions: Whelk-01, (R, R) column (2×25 cM), 12% 8:2 heptane:IPA/$CO_2$, 100 bar, flow rate=70 mL/min. The title compound was eluted as the first peak. MS: 534.2, 536.2 [M+1].

Step 2: 1-ethyl-3-((S)-1,1,1,5,5,5-hexafluoropentan-2-yl)-1-((S)-2,2,2-trifluoro-1-(5-methoxy-4-(8-methoxyimidazo[1,2-a]pyrazin-6-yl)pyridin-2-yl)ethyl)urea (Example 10-1 for Table 10)

Example 10-1

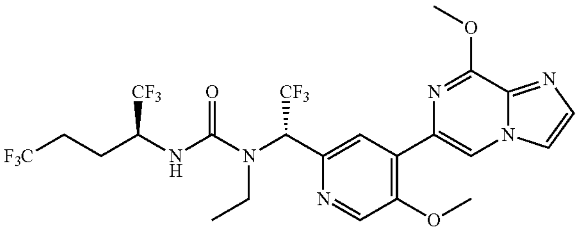

The title compound was prepared from 1-((S)-1-(4-bromo-5-methoxypyridin-2-yl)-2,2,2-trifluoroethyl)-1-ethyl-3-((S)-1,1,1,5,5,5-hexafluoropentan-2-yl)urea (J17-1) and 8-methoxy-6-(4,4,5,5-tetramethyl-1,3,2-dioxaborolan-2-yl)imidazo[1,2-a]pyrazine (Intermediate B1) according to the procedure outlined in step 2 of the synthesis of Intermediate A5. MS: 604.1 [M+1].

The following compounds were prepared according to the general procedures herein and in an analogous manner to that used to synthesize the Examples above using the appropriate borylated heterocycle and amine intermediates. The starting materials were either prepared as described in the intermediates section, commercial available, or prepared from commercially available reagents using conventional reactions well known in the art.

TABLE 10

| Example | Structure | Name | Exact Mass [M + H]+ |
|---|---|---|---|
| 10-2 | 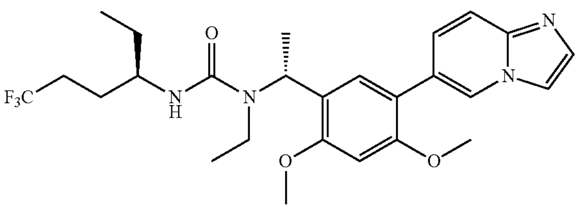 [SMILES: CC[C@H](CCC(F)(F)F)NC(=O)N(CC)[C@H](C)c1cc(-c2ccc3nccn3c2)c(OC)cc1OC] | (R)-1-ethyl-1-(5-(imidazo[1,2-a]pyridin-6-yl)-2,4-dimethoxybenzyl)-3-(6,6,6-trifluorohexan-3-yl)urea | 493.4 |

TABLE 10-continued

| Example | Structure | Name | Exact Mass [M + H]+ |
|---|---|---|---|
| 10-3 | 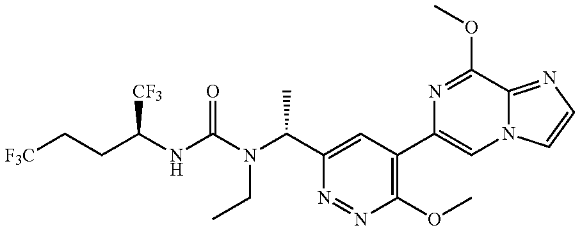 [SMILES: CCN(C(=O)N[C@@H](CCC(F)(F)F)C(F)(F)F)[C@H](C)c1cc(-c2cn3ccnc3c(OC)n2)c(OC)nn1] | 1-ethyl-3-((S)-1,1,1,5,5,5-hexafluoropentan-2-yl)-1-((R)-1-(6-methoxy-5-(8-methoxyimidazo[1,2-a]pyrazin-6-yl)pyridazin-3-yl)ethyl)urea | 550.4 |
| 10-4 | 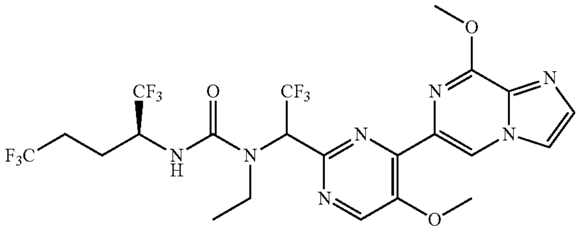 [SMILES: CCN(C(=O)N[C@@H](CCC(F)(F)F)C(F)(F)F)C(c1ncc(OC)c(-c2cn3ccnc3c(OC)n2)n1)C(F)(F)F] | 1-ethyl-3-((S)-1,1,1,5,5,5-hexafluoropentan-2-yl)-1-(2,2,2-trifluoro-1-(5-methoxy-4-(8-methoxyimidazo[1,2-a]pyrazin-6-yl)pyrimidin-2-yl)ethyl)urea | 605.2 |
| 10-5 | 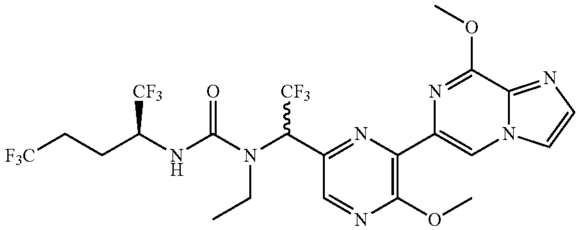 [SMILES: CCN(C(=O)N[C@@H](CCC(F)(F)F)C(F)(F)F)C(c1cnc(OC)c(-c2cn3ccnc3c(OC)n2)n1)C(F)(F)F] | 1-ethyl-3-((S)-1,1,1,5,5,5-hexafluoropentan-2-yl)-1-(2,2,2-trifluoro-1-(5-methoxy-6-(8-methoxyimidazo[1,2-a]pyrazin-6-yl)pyrazin-2-yl)ethyl)urea | 605.2 |
| 10-6 | 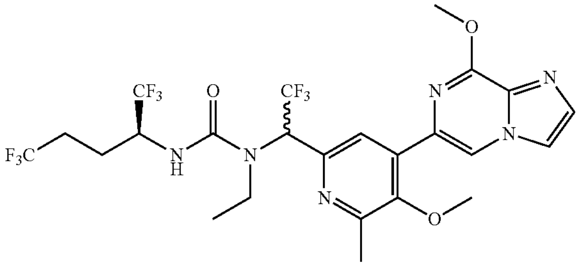 [SMILES: CCN(C(=O)N[C@@H](CCC(F)(F)F)C(F)(F)F)C(c1cc(-c2cn3ccnc3c(OC)n2)c(OC)c(C)n1)C(F)(F)F] | 1-ethyl-3-((S)-1,1,1,5,5,5-hexafluoropentan-2-yl)-1-(2,2,2-trifluoro-1-(5-methoxy-4-(8-methoxyimidazo[1,2-a]pyrazin-6-yl)-6-methylpyridin-2-yl)ethyl)urea | 618.4 |
| 10-7 | 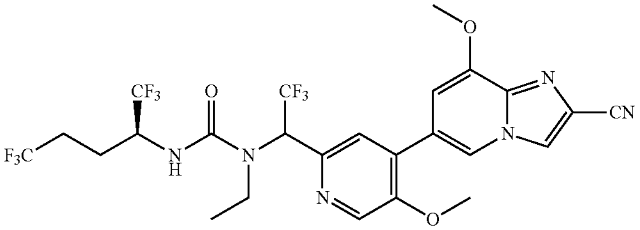 [SMILES: CCN(C(=O)N[C@@H](CCC(F)(F)F)C(F)(F)F)C(c1cc(-c2cc(OC)c3nc(C#N)cn3c2)c(OC)cn1)C(F)(F)F] | 1-(1-(4-(2-cyano-8-methoxyimidazo[1,2-a]pyridin-6-yl)-5-methoxypyridin-2-yl)-2,2,2-trifluoroethyl)-1-ethyl-3-((S)-1,1,1,5,5,5-hexafluoropentan-2-yl)urea | 628.2 |
| 10-8 | 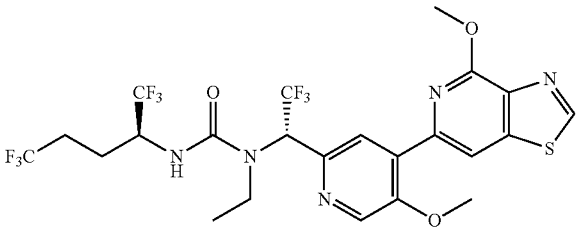 [SMILES: CCN(C(=O)N[C@@H](CCC(F)(F)F)C(F)(F)F)[C@@H](c1cc(-c2cc3scnc3c(OC)n2)c(OC)cn1)C(F)(F)F] | 1-ethyl-3-((S)-1,1,1,5,5,5-hexafluoropentan-2-yl)-1-((S)-2,2,2-trifluoro-1-(5-methoxy-4-(4-methoxythiazolo[4,5-c]pyridin-6-yl)pyridin-2-yl)ethyl)urea | 621.3 |

TABLE 10-continued

| Example | Structure | Name | Exact Mass [M + H]+ |
|---|---|---|---|
| 10-9 | 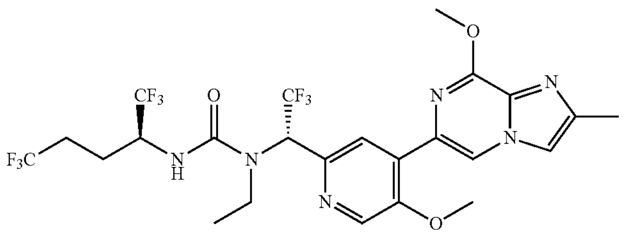 [SMILES: CCN(C(=O)N[C@@H](CCC(F)(F)F)C(F)(F)F)[C@@H](c1cc(-c2cn3cc(C)nc3c(OC)n2)c(OC)cn1)C(F)(F)F] | 1-ethyl-3-((S)-1,1,1,5,5,5-hexafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea | 618.2 |
| 10-10 | 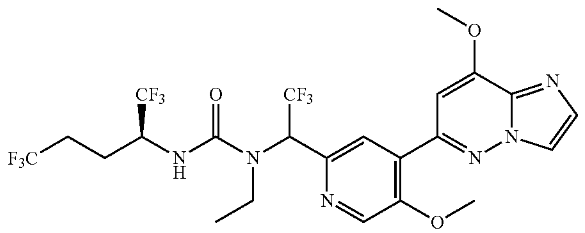 [SMILES: CCN(C(=O)N[C@@H](CCC(F)(F)F)C(F)(F)F)C(c1cc(-c2cc(OC)c3nccn3n2)c(OC)cn1)C(F)(F)F] | 1-ethyl-3-((S)-1,1,1,5,5,5-hexafluoropentan-2-yl)-1-(2,2,2-trifluoro-1-(5-methoxy-4-(8-methoxyimidazo[1,2-b]pyridazin-6-yl)pyridin-2-yl)ethyl)urea | 604.2 |
| 10-11 | 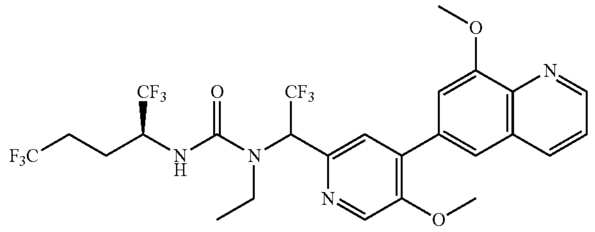 [SMILES: CCN(C(=O)N[C@@H](CCC(F)(F)F)C(F)(F)F)C(c1cc(-c2cc(OC)c3ncccc3c2)c(OC)cn1)C(F)(F)F] | 1-ethyl-3-((S)-1,1,1,5,5,5-hexafluoropentan-2-yl)-1-(2,2,2-trifluoro-1-(5-methoxy-4-(8-methoxyquinolin-6-yl)pyridin-2-yl)ethyl)urea | 614.2 |
| 10-12 | 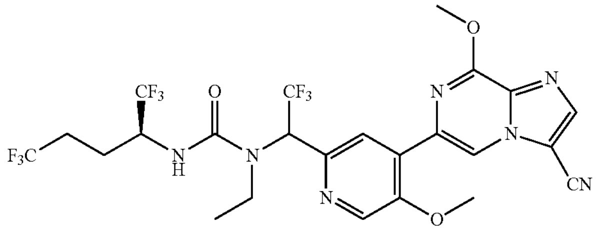 [SMILES: CCN(C(=O)N[C@@H](CCC(F)(F)F)C(F)(F)F)C(c1cc(-c2cn3c(C#N)cnc3c(OC)n2)c(OC)cn1)C(F)(F)F] | 1-(1-(4-(3-cyano-8-methoxyimidazo[1,2-a]pyrazin-6-yl)-5-methoxypyridin-2-yl)-2,2,2-trifluoroethyl)-1-ethyl-3-((S)-1,1,1,5,5,5-hexafluoropentan-2-yl)urea | 629.1 |
| 10-13 | 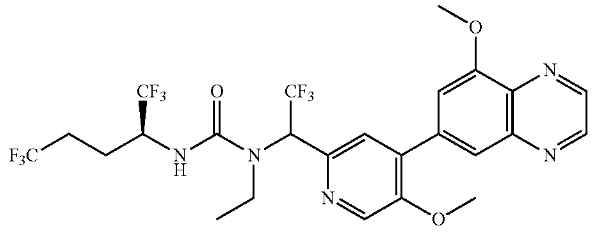 [SMILES: CCN(C(=O)N[C@@H](CCC(F)(F)F)C(F)(F)F)C(c1cc(-c2cc(OC)c3nccnc3c2)c(OC)cn1)C(F)(F)F] | 1-ethyl-3-((S)-1,1,1,5,5,5-hexafluoropentan-2-yl)-1-(2,2,2-trifluoro-1-(5-methoxy-4-(8-methoxyquinoxalin-6-yl)pyridin-2-yl)ethyl)urea | 615.6 |
| 10-15 | 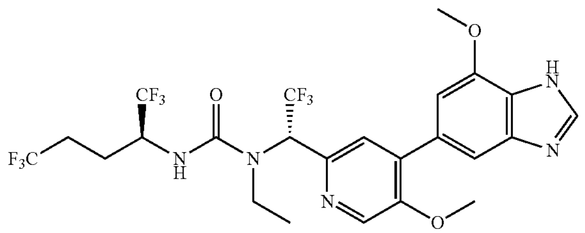 [SMILES: CCN(C(=O)N[C@@H](CCC(F)(F)F)C(F)(F)F)[C@@H](c1cc(-c2cc(OC)c3[nH]cnc3c2)c(OC)cn1)C(F)(F)F] | 1-ethyl-3-((S)-1,1,1,5,5,5-hexafluoropentan-2-yl)-1-((S)-2,2,2-trifluoro-1-(5-methoxy-4-(7-methoxy-1H-benzo[d]imidazol-5-yl)pyridin-2-yl)ethyl)urea | 603.5 |

TABLE 10-continued

| Example | Structure | Name | Exact Mass [M + H]+ |
|---|---|---|---|
| 10-16 | 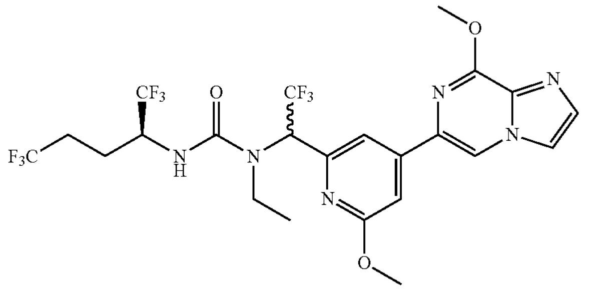 [SMILES: CCN(C(=O)N[C@@H](CCC(F)(F)F)C(F)(F)F)C(c1cc(-c2cn3ccnc3c(OC)n2)cc(OC)n1)C(F)(F)F] | 1-ethyl-3-((S)-1,1,1,5,5,5-hexafluoropentan-2-yl)-1-(2,2,2-trifluoro-1-(6-methoxy-4-(8-methoxyimidazo[1,2-a]pyrazin-6-yl)pyridin-2-yl)ethyl)urea | 604.5 |
| 10-17 | 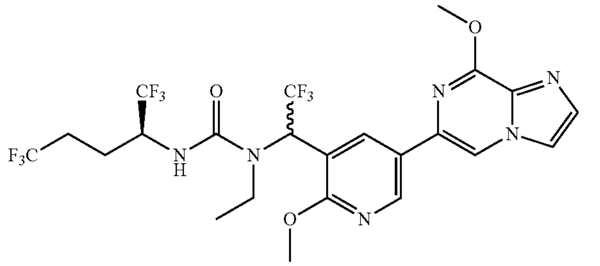 [SMILES: CCN(C(=O)N[C@@H](CCC(F)(F)F)C(F)(F)F)C(c1cc(-c2cn3ccnc3c(OC)n2)cnc1OC)C(F)(F)F] | 1-ethyl-3-((S)-1,1,1,5,5,5-hexafluoropentan-2-yl)-1-(2,2,2-trifluoro-1-(2-methoxy-5-(8-methoxyimidazo[1,2-a]pyrazin-6-yl)pyridin-3-yl)ethyl)urea | 604.3 |
| 10-18 | 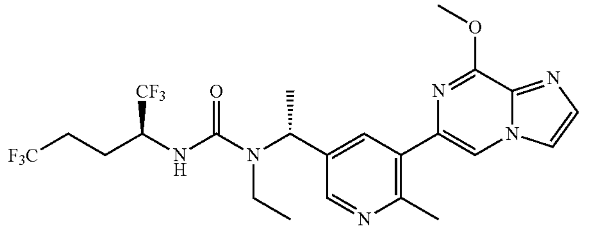 [SMILES: CCN(C(=O)N[C@@H](CCC(F)(F)F)C(F)(F)F)[C@H](C)c1cnc(C)c(-c2cn3ccnc3c(OC)n2)c1] | 1-ethyl-3-((S)-1,1,1,5,5,5-hexafluoropentan-2-yl)-1-((R)-1-(5-(8-methoxyimidazo[1,2-a]pyrazin-6-yl)-6-methylpyridin-3-yl)ethyl)urea | 533.3 |
| 10-19 | 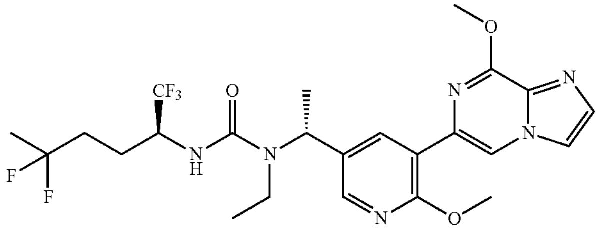 [SMILES: CCN(C(=O)N[C@@H](CCC(C)(F)F)C(F)(F)F)[C@H](C)c1cnc(OC)c(-c2cn3ccnc3c(OC)n2)c1] | 1-ethyl-1-((R)-1-(6-methoxy-5-(8-methoxyimidazo[1,2-a]pyrazin-6-yl)pyridin-3-yl)ethyl)-3-((S)-1,1,1,5,5-pentafluorohexan-2-yl)urea | 545.4 |
| 10-20 | 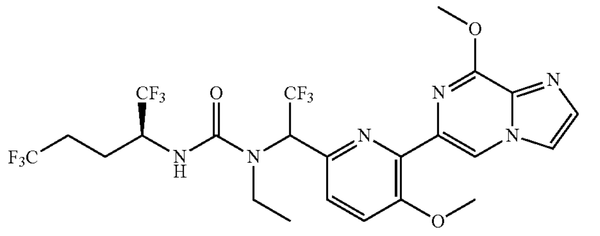 [SMILES: CCN(C(=O)N[C@@H](CCC(F)(F)F)C(F)(F)F)C(c1ccc(OC)c(-c2cn3ccnc3c(OC)n2)n1)C(F)(F)F] | 1-ethyl-3-((S)-1,1,1,5,5,5-hexafluoropentan-2-yl)-1-(2,2,2-trifluoro-1-(5-methoxy-6-(8-methoxyimidazo[1,2-a]pyrazin-6-yl)pyridin-2-yl)ethyl)urea | 604.2 |
| 10-21 | 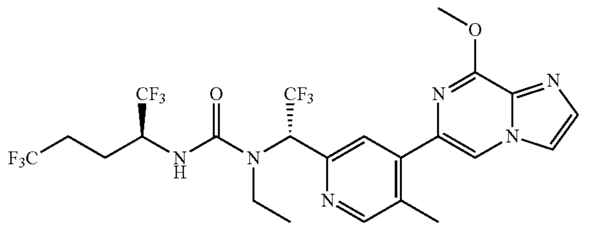 [SMILES: CCN(C(=O)N[C@@H](CCC(F)(F)F)C(F)(F)F)[C@@H](c1cc(-c2cn3ccnc3c(OC)n2)c(C)cn1)C(F)(F)F] | 1-ethyl-3-((S)-1,1,1,5,5,5-hexafluoropentan-2-yl)-1-((S)-2,2,2-trifluoro-1-(4-(8-methoxyimidazo[1,2-a]pyrazin-6-yl)-5-methylpyridin-2-yl)ethyl)urea | 588.5 |

TABLE 10-continued

| Example | Structure | Name | Exact Mass [M + H]+ |
|---|---|---|---|
| 10-22 | 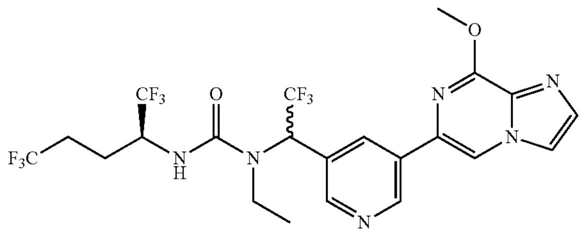 [SMILES: CCN(C(=O)N[C@@H](CCC(F)(F)F)C(F)(F)F)C(c1cncc(-c2cn3ccnc3c(OC)n2)c1)C(F)(F)F] | 1-ethyl-3-((S)-1,1,1,5,5,5-hexafluoropentan-2-yl)-1-(2,2,2-trifluoro-1-(5-(8-methoxyimidazo[1,2-a]pyrazin-6-yl)pyridin-3-yl)ethyl)urea | 574.4 |

Example 11-1 for Table 1: 1-ethyl-1-((R)-1-(7-(imidazo[1,2-a]pyridin-6-yl)-2,3-dihydrobenzofuran-5-yl)ethyl)-3-((R)-6,6,6-trifluorohexan-3-yl)urea Example 11-1

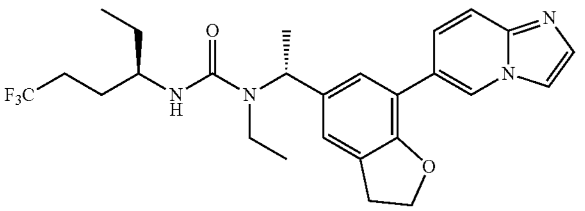

Step 1: (R)-1-(7-bromo-2,3-dihydrobenzofuran-5-yl)-N-ethylethan-1-amine (K1-1)

K1-1

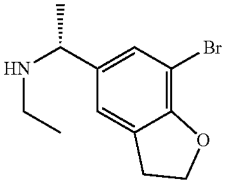

The title compound was prepared from 7-bromo-2,3-dihydrobenzofuran-5-carbaldehyde using the procedure outlined in steps 1-4 in the synthesis of Intermediate H4. MS: 270.1, 273.2 [M+1].

Step 2: 1-((R)-1-(7-bromo-2,3-dihydrobenzofuran-5-yl)ethyl)-1-ethyl-3-((R)-6,6,6-trifluorohexan-3-yl) urea (K1-2)

K1-2

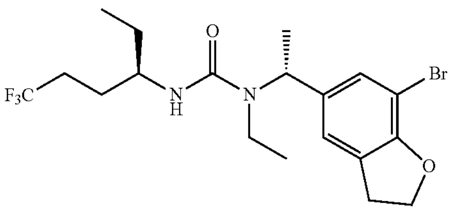

The title compound was prepared from (R)-1-(7-bromo-2,3-dihydrobenzofuran-5-yl)-N-ethylethan-1-amine (K1-1) and (R)-6,6,6-trifluorohexan-3-amine (Intermediate A14) using the procedure outlined in the synthesis of Example 1-1. MS: 453.3, 454.3 [M+1].

Step 3: 1-ethyl-1-((R)-1-(7-(imidazo[1,2-a]pyridin-6-yl)-2,3-dihydrobenzofuran-5-yl)ethyl)-3-((R)-6,6,6-trifluorohexan-3-yl)urea (Example 11-1 for Table 11)

Example 11-1

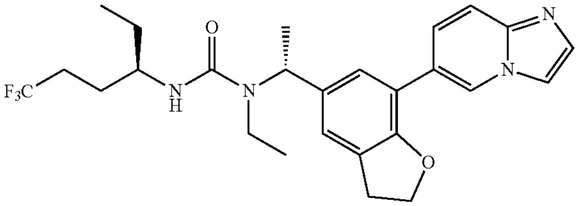

The title compound was prepared from 1-((R)-1-(7-bromo-2,3-dihydrobenzofuran-5-yl)ethyl)-1-ethyl-3-((R)-6,6,6-trifluorohexan-3-yl)urea (K1-2) and imidazo[1,2-a]pyridin-6-ylboronic acid (Intermediate A8) using the procedure in step 2 in the synthesis of Intermediate A2. MS: 489.5 [M+1].

The following compounds were prepared according to the general procedures herein and in an analogous manner to that used to synthesize the Examples above using the appropriate borylated heterocycles and amines as starting materials. The starting materials were either prepared as described in the intermediates section, commercial available, or prepared from commercially available reagents using conventional reactions well known in the art.

TABLE 11

| Example | Structure | Name | Exact Mass [M + H]+ |
|---|---|---|---|
| 11-2 | 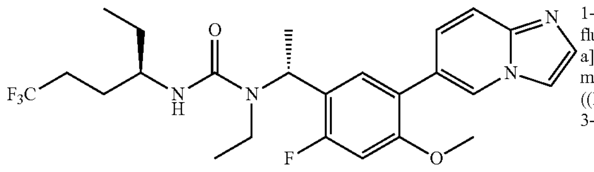 | 1-ethyl-1-((R)-1-(2-fluoro-5-(imidazo[1,2-a]pyridin-6-yl)-4-methoxyphenyl)ethyl)-3-((R)-6,6,6-trifluorohexan-3-yl)urea | 495.4 |
| 11-3 | 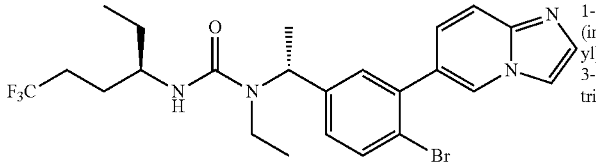 | 1-((R)-1-(4-bromo-3-(imidazo[1,2-a]pyridin-6-yl)phenyl)ethyl)-1-ethyl-3-((R)-6,6,6-trifluorohexan-3-yl)urea | 526.4 |
| 11-4 | 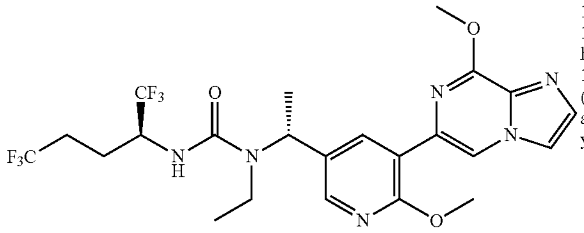 | 1-ethyl-3-((S)-1,1,1,5,5,5-hexafluoropentan-2-yl)-1-((R)-1-(6-methoxy-5-(8-methoxyimidazo[1,2-a]pyrazin-6-yl)pyridin-3-yl)ethyl)urea | 550.6 |
| 11-5 | 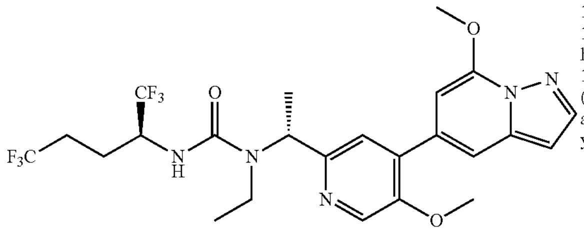 | 1-ethyl-3-((S)-1,1,1,5,5,5-hexafluoropentan-2-yl)-1-((R)-1-(5-methoxy-4-(7-methoxypyrazolo[1,5-a]pyridin-5-yl)pyridin-2-yl)ethyl)urea | 548.5 |
| 11-6 | 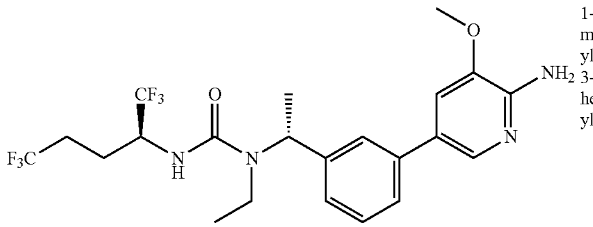 | 1-((R)-1-(3-(6-amino-5-methoxypyridin-3-yl)phenyl)ethyl)-1-ethyl-3-((S)-1,1,1,5,5,5-hexafluoropentan-2-yl)urea | 493.4 |

Intermediate L1: (S)-1-cyclopropyl-4,4,4-trifluorobutan-1-amine

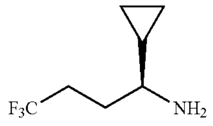

Intermediate L1

Step, 1: (S,E)-2-methyl-N-(4,4,4-trifluorobutylidene)propane-2-sulfinamide (L1-1)

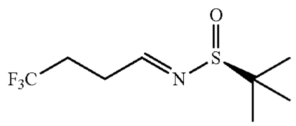

L1-1

The title compound was prepared from 4,4,4-trifluorobutanal (A13-2) and (R)-2-methylpropane-2-sulfinamide using the procedure described in step 2 in the synthesis of Intermediate A13. H-NMR (400 MHz, $CDCl_3$, ppm): δ 8.12 (s, 1H), 2.78-2.81 (m, 2H), 2.49-2.54 (m, 2H), 1.19 (s, 9H).

Step 2: (S)—N—((S)-1-cyclopropyl-4,4,4-trifluorobutyl-2-methylpropane-2-sulfinamide (L1-2)

L1-2

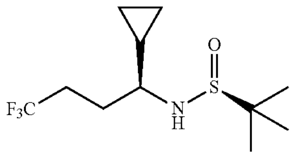

To a solution of (S,E)-2-methyl-N-(4,4,4-trifluorobutylidene)propane-2-sulfinamide (L1-1) (2 g, 8.72 mmol) in DCM (40 mL) was added cyclopropylmagnesium bromide (34.9 mL, 17.45 mmol) at 0° C., the mixture was stirred at 0° C. for 3 h. TLC showed the reaction was completed. LCMS showed the desired product was formed. The reaction mixture was poured into water (50 mL) and extracted with DCM (50 mL×3), the combined organic layer was dried over $Na_2SO_4$, filtered and concentrated. The crude product was purified by flash silica gel chromatography (ISCO®; 12 g SepaFlash® Silica Flash Column, eluent of 27% ethyl acetate/petroleum ether gradient@35 mL/min) to give the title compound. H-NMR (400 MHz, $CDCl_3$, ppm): δ 3.11 (br d, J=4.2 Hz, 1H), 2.46-2.37 (m, 1H), 2.22-2.07 (m, 2H), 1.91-1.73 (m, 2H), 1.16 (s, 9H), 0.84-0.75 (m, 1H), 0.65-0.51 (m, 2H), 0.40-0.32 (m, 1H), 0.30-0.22 (m, 1H).

Step 3: (S)-1-cyclopropyl-4,4,4-trifluorobutan-1-amine (Intermediate L)

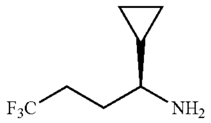

Intermediate L1

To a solution of (S)—N—((S)-1-cyclopropyl-4,4,4-trifluorobutyl)-2-methylpropane-2-sulfinamide (L-2) (630 mg, 2.322 mmol) in MeOH (10 mL) was added AcCl (0.330 mL, 4.64 mmol), and the mixture was stirred at 10° C. for 4 h. LCMS showed the reaction was completed. The reaction mixture was direct concentrated to give the crude product. The crude product was stirred in $Et_2O$ (5 mL) for 10 min, then the mixture was filtered, concentrated to give the title compound. H-NMR (400 MHz, $CD_3OD$, ppm): δ 2.16-2.08 (m, 1H), 2.07-1.88 (m, 2H), 1.68-1.52 (m, 2H), 0.60-0.47 (m, 1H), 0.42-0.22 (m, 2H), 0.12 1 0.01 (m, 2H).

Intermediate L2: (R)-1-(5-bromo-6-methoxypyridin-3-yl)-N-ethylethan-1-amine

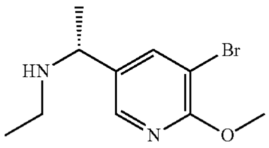

Intermediate L2

The title compound was prepared from 5-bromo-6-methoxynicotinaldehyde using the procedure described in the synthesis of Intermediate 18. MS: 259.0, 261.0 [M+1].

Intermediate L3: (8-methoxy-3-methylimidazo[1,2-a]pyrazin-6-yl)boronic acid

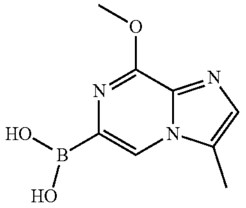

The title compound was prepared from 6-bromo-8-methoxy-3-methylimidazo[1,2-a]pyrazine using the procedure described in the synthesis of Intermediate B20. MS: 208.1 [M+1].

Example 12-1 for Table 12: 1-ethyl-3-((S)-1,1,1,5,5,5-hexafluoropentan-2-yl)-1-((R)-1-(5-methoxy-4-(8-methoxyimidazo[1,2-a]pyrazin-6-yl)pyridin-2-yl)ethyl)urea

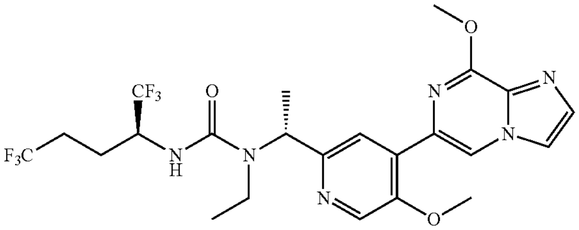

Example 12-1 for Table 12

Step 1: 1-((R)-1-(4-bromo-5-methoxypyridin-2-yl)ethyl)-1-ethyl-3-((S)-1,1,1,5,5,5-hexafluoropentan-2-yl)urea (L4-1)

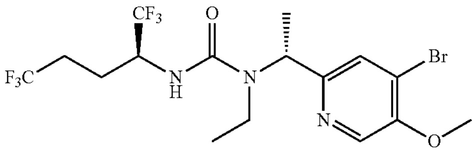

L4-1

The title compound was prepared from (R)—N—((R)-1-(4-bromo-5-methoxypyridin-2-yl)ethyl)-2-methylpropane-2-sulfinamide (Intermediate I8) and (S)-1,1,1,5,5,5-hexafluoropentan-2-amine (Intermediate A13) using the procedure described in the synthesis of Example 2-1. MS: 480.2, 482.2 [M+1].

Step 2: 1-ethyl-3-((S)-1,1,1,5,5,5-hexafluoropentan-2-yl)-1-((R)-1-(5-methoxy-4-(8-methoxyimidazo[1,2-a]pyrazin-6-yl)pyridin-2-yl)ethyl)urea (Example 12-1 for Table 12)

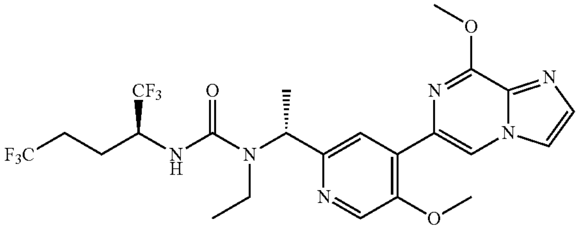

Example 12-1 for Table 12

The title compound was prepared with 1-((R)-1-(4-bromo-5-methoxypyridin-2-yl)ethyl)-1-ethyl-3-((S)-1,1,1,5,5,5-hexafluoropentan-2-yl)urea (L4-1) and 8-methoxy-6-(4,4,5,5-tetramethyl-1,3,2-dioxaborolan-2-yl)imidazo[1,2-a]pyrazine (Intermediate B1) using the procedure described in step 2 in the synthesis of Intermediate A5. MS: 549.5 [M+1].

The following compounds were prepared according to the general procedures herein and in an analogous manner to that used to synthesize the Examples above using the appropriate borylated heterocycles and amines as starting materials. The starting materials were either prepared as described in the intermediates section, commercial available, or prepared from commercially available reagents using conventional reactions well known in the art.

Example 13-1 for Table 13: 1-ethyl-3-((S)-1,1,1,5,5,5-hexafluoropentan-2-yl)-1-(1-(2-(8-methoxyimidazo[1,2-a]pyrazin-6-yl)pyridin-4-yl)ethyl)urea

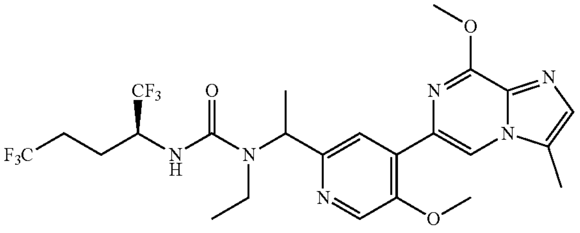

Example 13-1 for Table 13

Step 1: 1-(2-chloropyridin-4-yl)-N-ethylethan-1-amine (M1-1)

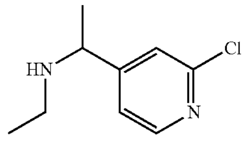

M1-1

A sealable vial was charged with 1-(2-chloropyridin-4-yl)ethan-1-one (297.5 mg, 1.912 mmol), which was dissolved in EtOH (10 mL) and treated with MAGNESIUM SULFATE (460 mg, 3.82 mmol) and ETHYLAMINE (2.0 M in THF) (4.78 mL, 9.56 mmol). ACETIC ACID (0.438 mL, 7.65 mmol) was added, and then SODIUM CYANOBOROHYDRIDE (240 mg, 3.82 mmol) was added. This was heated to 55° C. and stirred for 3 h. The mixture was cooled and poured onto sat. $NaHCO_3$ (50 mL) and extracted

TABLE 12

| Example | Structure | Name | Exact Mass [M + H]+ |
|---|---|---|---|
| 12-2 | 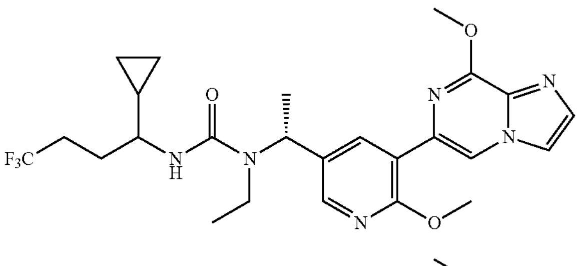 | 3-((S)-1-cyclopropyl-4,4,4-trifluorobutyl)-1-ethyl-1-((R)-1-(6-methoxy-5-(8-methoxyimidazo[1,2-a]pyrazin-6-yl)pyridin-3-yl)ethyl)urea | 521.4 |
| 12-2 | 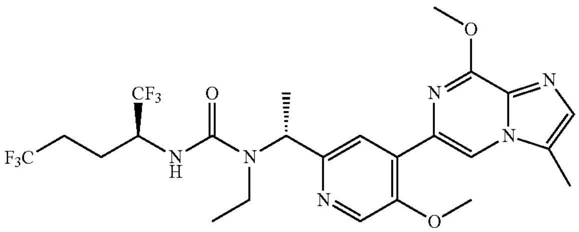 [SMILES: CCN(C(=O)N[C@@H](CCC(F)(F)F)C(F)(F)F)[C@H](C)c1cc(-c2cn3c(C)cnc3c(OC)n2)c(OC)cn1] | 1-ethyl-3-((S)-1,1,1,5,5,5-hexafluoropentan-2-yl)-1-((R)-1-(5-methoxy-3-methoxy-4-(8-methylimidazo[1,2-a]pyrazin-6-yl)pyridin-2-yl)ethyl)urea | 563.3 |

with DCM (3×20 mL). The combined organics were dried over $Na_2SO_4$, filtered and concentrated to give the title compound. MS: 228.9, 230.9 [M+1].

Step 2: 1-(1-(2-chloropyridin-4-yl)ethyl)-1-ethyl-3-((S)-1,1,1,5,5,5-hexafluoropentan-2-yl)urea (M1-2)

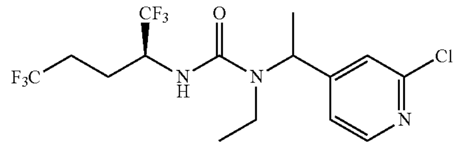

M1-2

This was prepared using 1-(2-chloropyridin-4-yl)-N-ethylethan-1-amine (M1-1) and (S)-1,1,1,5,5,5-hexafluoropentan-2-amine (Intermediate A13) using the procedure described in the synthesis of Example 2-1. MS: 406.3 [M+1].

Step 3: 1-ethyl-3-((S)-1,1,1,5,5,5-hexafluoropentan-2-yl)-1-(1-(2-(8-methoxyimidazo[1,2-a]pyrazin-6-yl)pyridin-4-yl)ethyl)urea (Example 13-1 for Table 13)

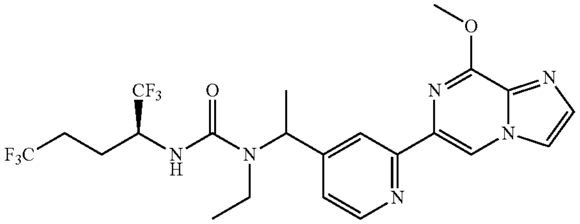 [SMILES: CCN(C(=O)N[C@@H](CCC(F)(F)F)C(F)(F)F)C(C)c1cc(-c2cn3ccnc3c(OC)n2)ncn1]

Example 13-1 for Table 13

The title compound was prepared with 1-(1-(2-chloropyridin-4-yl)ethyl)-1-ethyl-3-((S)-1,1,1,5,5,5-hexafluoropentan-2-yl)urea (M1-2) and 8-methoxy-6-(4,4,5,5-tetramethyl-1,3,2-dioxaborolan-2-yl)imidazo[1,2-a]pyrazine (Intermediate B1) using the procedure described in step 2 in the synthesis of Intermediate A5. MS: 519.4 [M+1].

The following compounds were prepared according to the general procedures herein and in an analogous manner to that used to synthesize the Examples above using the appropriate 1-(6-chloropyrimidin-4-yl)ethan-1-one and amines as starting materials. The starting materials were either prepared as described in the intermediates section, commercial available, or prepared from commercially available reagents using conventional reactions well known in the art.

Example 14-1 for Table 14: 1-ethyl-3-((S)-1,1,1,5,5,5-hexafluoropentan-2-yl)-1-((R)-1-(4-(8-methoxyimidazo[1,2-a]pyrazin-6-yl)pyridin-2-yl)ethyl)urea

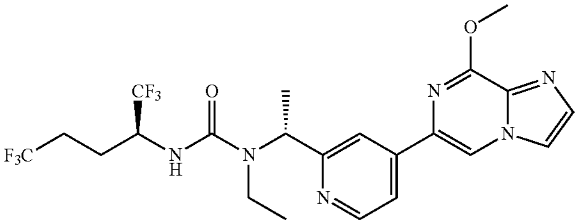

Example 14-1 for Table 14

Step 1: (R,E)-N-((4-chloropyridin-2-yl)methylene)-2-methylpropane-2-sulfinamide (N14-1)

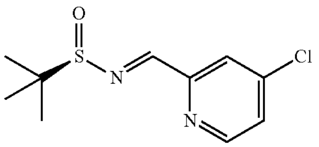

N14-1

To a solution of 4-chloropicolinaldehyde (9 g, 63.6 mmol) and (R)-2-methylpropane-2-sulfinamide (9.25 g, 76 mmol) in DCE (180 mL) were added $MgSO_4$ (38.3 g, 318 mmol) and PPTS (1.598 g, 6.36 mmol), and then the resulting mixture was stirred at 80° C. under $N_2$ protection for 4 hrs. TLC (petroleum ether:EtOAc=3:1) showed starting material was consumed and new spots were found, and LCMS showed the reaction was completed. The reaction mixture was filtered. The filtrate was concentrated and purified by flash silica gel chromatography (ISCO®; 120 g SepaFlash® Silica Flash Column, eluent of 0-16% ethyl acetate/petroleum ether gradient) to give the title compound. H-NMR (400 MHz, $CDCl_3$, ppm): δ 8.67-8.60 (m, 2H), 8.00 (d, J=1.7 Hz, 1H), 7.39 (dd, J=2.0, 5.4 Hz, 1H), 1.31-1.20 (m, 9H).

TABLE 13

| Example | Structure | Name | Exact Mass [M + H]+ |
|---|---|---|---|
| 13-2 | 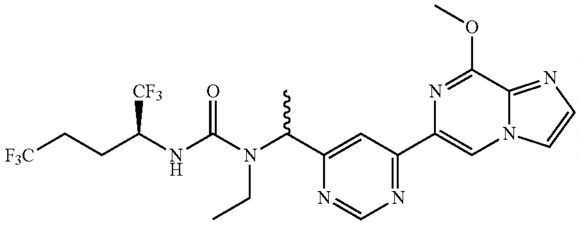 | 1-ethyl-3-((S)-1,1,1,5,5,5-hexafluoropentan-2-yl)-1-(1-(6-(8-methoxyimidazo[1,2-a]pyrazin-6-yl)pyrimidin-4-yl)ethyl)urea | 520.4 |

Step 2: (R)—N—((R)-1-(4-chloropyridin-2-yl) ethyl)-2-methylpropane-2-sulfinamide (N14-2)

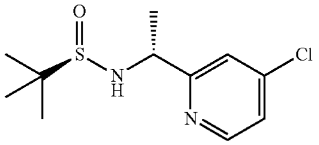

N14-2

To a solution of (R,E)-N-((4-chloropyridin-2-yl)methylene)-2-methylpropane-2-sulfinamide (N14-1) (11 g, 44.9 mmol) in THF (200 mL) were added methylmagnesium bromide (120 mL, 360 mmol) (3 M in $Et_2O$), the mixture was stirred at 0° C. under $N_2$ protection for 1 hrs. TLC (petroleum ether:EtOAc=1:1) showed starting material was consumed and new spots were found. The reaction was completed. The reaction mixture was poured into $NH_4Cl$ (300 mL), extracted with EtOAc (150 mL×3), dried over $Na_2S04$ and filtered. The filtrate was concentrated and purified by flash silica gel chromatography (ISCO®; 120 g SepaFlash® Silica Flash Column, eluent of 0-80% ethyl acetate/pet. ether gradient) to give the title compound. H-NMR (400 MHz, $CDCl_3$, ppm): δ 8.43 (d, J=5.4 Hz, 1H), 7.29 (d, J=2.0 Hz, 1H), 7.18 (dd, J=1.8, 5.3 Hz, 1H), 4.69 (br d, J=5.4 Hz, 1H), 4.57-4.50 (m, 1H), 1.49 (d, J=6.8 Hz, 3H), 1.26-1.22 (m, 1H), 1.26-1.22 (m, 8H).

Step 3: (R)—N—((R)-1-(4-chloropyridin-2-yl) ethyl)-N-ethyl-2-methylpropane-2-sulfinamide (N14-3)

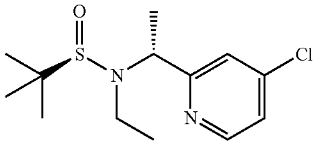

N14-3

The title compound was prepared from (R)—N—((R)-1-(4-chloropyridin-2-yl)ethyl)-2-methylpropane-2-sulfinamide (N14-2) using the procedure described in step 3 of the synthesis of Intermediate H4. 1H-NMR (400 MHz, $CDCl_3$, ppm): δ 8.44 (d, J=5.1 Hz, 1H), 7.37 (d, J=1.7 Hz, 1H), 7.16 (dd, J=2.0, 5.4 Hz, 1H), 4.70-4.60 (m, 1H), 3.29-3.20 (m, 1H), 3.01-2.93 (m, 1H), 1.64 (d, J=7.1 Hz, 3H), 1.19-1.12 (m, 3H), 1.09 (s, 9H).

Step 4: (R)—N-ethyl-2-methyl-N—((R)-1-(4-(4,4,5,5-tetramethyl-1,3,2-dioxaborolan-2-yl)pyridin-2-yl) ethyl)propane-2-sulfinamide (N14-4)

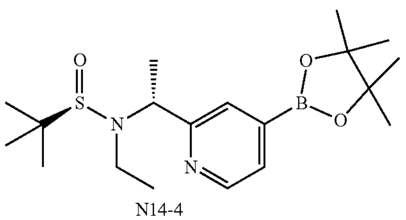 [SMILES: CCN([C@H](C)c1cc(B2OC(C)(C)C(C)(C)O2)ccn1)[S@](=O)C(C)(C)C ; "N14-4"]

N14-4

To a solution of (R)—N—((R)-1-(4-chloropyridin-2-yl) ethyl)-N-ethyl-2-methylpropane-2-sulfinamide ($N_{14}$-3) (3 g, 10.39 mmol) in dioxane (60 mL) was added 4,4,4',4',5,5,5',5'-octamethyl-2,2'-bi(1,3,2-dioxaborolane) (3.43 g, 13.50 mmol), potassium acetate (2.039 g, 20.77 mmol) and X—PHOS (0.495 g, 1.039 mmol), $Pd_2(dba)_3$ (0.476 g, 0.519 mmol) at 20° C. The mixture was stirred at 80° C. for 16 h. LCMS showed product was formed. The mixture of the title compound was used in next step without purification.

Step 5: (R)—N-ethyl-N—((R)-1-(4-(8-methoxyimidazo[1,2-a]pyrazin-6-yl)pyridin-2-yl)ethyl)-2-methylpropane-2-sulfinamide (N14-5)

N14-5

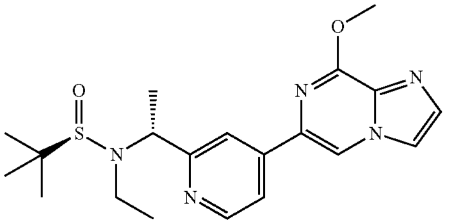

The title compound was prepared from (R)—N-ethyl-2-methyl-N—((R)-1-(4-(4,4,5,5-tetramethyl-1,3,2-dioxaborolan-2-yl)pyridin-2-yl)ethyl)propane-2-sulfinamide ($N_{14}$-4) and 6-bromo-8-methoxyimidazo[1,2-a]pyrazine (Intermediate A1) using the procedure described in step 2 of the synthesis of Intermediate A5. H-NMR (400 MHz, $CDCl_3$, ppm): δ 8.65 (d, J=5.1 Hz, 1H), 8.31 (s, 1H), 8.03 (s, 1H), 7.73-7.67 (m, 3H), 4.81 (q, J=6.9 Hz, 1H), 4.24 (s, 3H), 3.34 (dd, J=7.3, 14.7 Hz, 1H), 2.97 (td, J=6.9, 14.2 Hz, 1H), 1.75 (d, J=6.8 Hz, 3H), 1.19 (d, J=7.3 Hz, 3H), 1.16 (s, 9H).

Step 6: (R)—N-ethyl-1-(4-(8-methoxyimidazo[1,2-a]pyrazin-6-yl)pyridin-2-yl)ethan-1-amine (N14-6)

N14-6

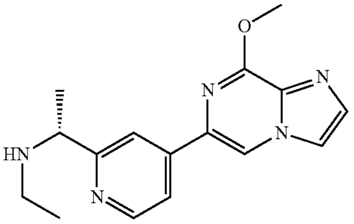

To a solution of (R)—N-ethyl-N—((R)-1-(4-(8-methoxyimidazo[1,2-a]pyrazin-6-yl)pyridin-2-yl)ethyl)-2-methylpropane-2-sulfinamide (N14-5) (500 mg, 1.245 mmol) in MeOH (1 mL) was added AcCl (0.354 mL, 4.98 mmol) and stirred at 25° C. for 1 h. LCMS showed desired product was formed. The reaction mixture was concentrated to give the title compound, which was used in next step without purification.

Step 7: 1-ethyl-3-((S)-1,1,1,5,5,5-hexafluoropentan-2-yl)-1-((R)-1-(4-(8-methoxyimidazo[1,2-a]pyrazin-6-yl)pyridin-2-yl)ethyl)urea (Example 14-1 for Table 14)

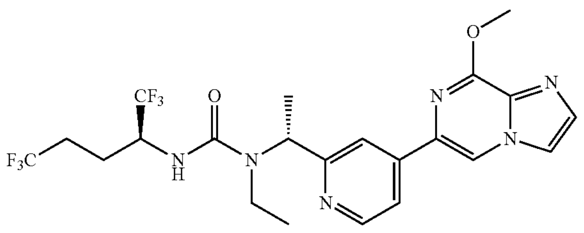

Example 14-1 for Table 14

The title compound was prepared from (R)—N-ethyl-1-(4-(8-methoxyimidazo[1,2-a]pyrazin-6-yl)pyridin-2-yl) ethan-1-amine (N14-6) and (S)-1,1,1,5,5,5-hexafluoropentan-2-amine (Intermediate A13) using the procedure described in the synthesis of Example 2-1. MS: 519.1 [M+1].

The following compounds were prepared according to the general procedures herein and in an analogous manner to that used to synthesize the Examples above using 3-bromo-4-chlorobenzaldehyde and other appropriate intermediates. The starting materials were either prepared as described in the intermediates section, commercial available, or prepared from commercially available reagents using conventional reactions well known in the art.

Intermediate O2: 1-(4-(8-fluoroimidazo[1,2-a]pyridin-6-yl)-5-methoxypyridin-2-yl)ethan-1-one Intermediate O2

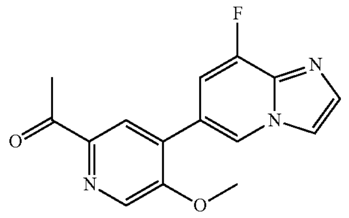

Step 1: 6-(2-chloro-5-methoxypyridin-4-yl)-8-fluoroimidazo[1,2-a]pyridine (O2-1)

O2-1

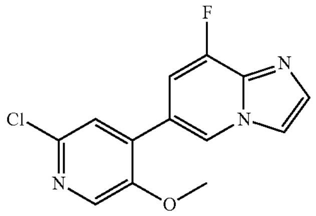

TABLE 14

| Example | Structure | Name | Exact Mass [M + H]+ |
|---|---|---|---|
| 14-2 | 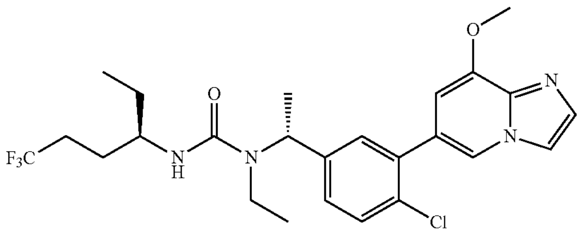 [SMILES: CC[C@H](CCC(F)(F)F)NC(=O)N(CC)[C@H](C)c1ccc(Cl)c(-c2cc(OC)c3nccn3c2)c1] | 1-((R)-1-(4-chloro-3-(8-methoxyimidazo[1,2-a]pyridin-6-yl)phenyl)ethyl)-1-ethyl-3-((R)-6,6,6-trifluorohexan-3-yl)urea | 511.3 |

Intermediate O1: (8-fluoroimidazo[1,2-a]pyridin-6-yl)boronic acid

Intermediate O1

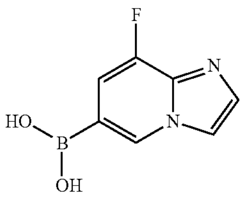

The title compound was prepared from 6-bromo-8-fluoroimidazo[1,2-a]pyridine using the procedure described in the synthesis of Intermediate B20. MS: 181.1 [M+1].

To a solution of 2-chloro-4-iodo-5-methoxypyridine (225 mg, 0.834 mmol) in 1,4-dioxane (5 mL) and water (1 mL) were added (8-fluoroimidazo[1,2-a]pyridin-6-yl)boronic acid (Intermediate O1) (100 mg, 0.556 mmol) and sodium carbonate (118 mg, 1.111 mmol) and $PdCl_2$(dppf) (40.7 mg, 0.056 mmol). The solution was stirred at 90° C. for 2 h under $N_2$ protection. LCMS showed the desired product was formed. TLC showed new spot was found. The reaction mixture was poured into water (10 mL), extracted with EtOAc (20 mL×3), washed with brine (10 mL), dried over $Na_2SO_4$ and filtered. The filtrate was concentrated in vacuo. The residue was purified by flash silica gel chromatography (ISCO®; 4 g SepaFlash® Silica Flash Column, eluent of 30% ethyl acetate/petroleum ether gradient@30 mL/min) to give the title compound. MS: 277.9 [M+1].

Step 2: 1-(4-(8-fluoroimidazo[1,2-a]pyridin-6-yl)-5-methoxypyridin-2-yl)ethan-1-one (Intermediate O2)

Intermediate O2

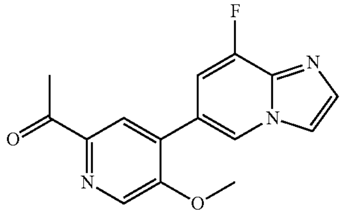

To a solution of compound 6-(2-chloro-5-methoxypyridin-4-yl)-8-fluoroimidazo[1,2-a]pyridine (02-1) (100 mg, 0.360 mmol) in dioxane (5 mL) were added tributyl(1-ethoxyvinyl)stannane (260 mg, 0.720 mmol) and $Pd(Ph_3P)_4$ (41.6 mg, 0.036 mmol). The solution was stirred at 105° C. for 8 h. LCMS showed the reaction was completed. TLC showed a new spot was found. The reaction mixture was cooled to 20° C. and 4 M HCl (1 mL) was added to the above mixture and stirred for 1 hr. LCMS showed the reaction had desired product. The reaction mixture was poured into water (10 mL), extracted with EtOAc (10 mL×3). The organic layer was washed with brine (10 mL), dried over $Na_2SO_4$ and filtered. After filtration it was concentrated to give crude product. The crude product was purified by flash silica gel chromatography (ISCO®; 4 g SepaFlash® Silica Flash Column, eluent of 10-35% ethyl acetate/petroleum ether gradient@30 mL/min) to give the title compound. MS: 286.1 [M+1].

Example 15-1 for Table 15: 1-(1-(5-chloro-4-(8-fluoroimidazo[1,2-a]pyridin-6-yl)pyridin-2-yl)ethyl)-1-ethyl-3-((S)-1,1,1,5,5,5-hexafluoropentan-2-yl)urea

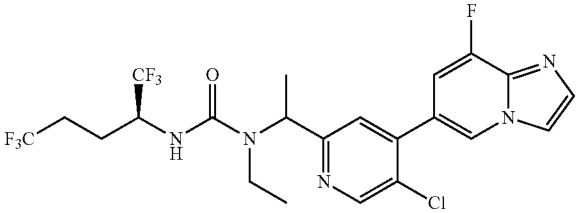

Example 15-1 for Table 15

Step 1: 1-(4,5-dichloropyridin-2-yl)ethan-1-one (03-1)

O3-1

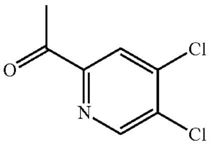

The title compound was prepared from 2,4,5-trichloropyridine using the procedure described in step 2 of the synthesis of Intermediate O2. MS: 190.0 [M+1].

Step 2: 1-(5-chloro-4-(8-fluoroimidazo[1,2-a]pyridin-6-yl)pyridin-2-yl)ethan-1-one (O3-2)

O3-2

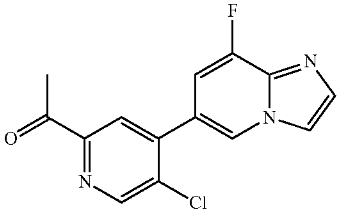

To a solution of 1-(4,5-dichloropyridin-2-yl)ethan-1-one (03-1) (1.5 g, 7.89 mmol) in dioxane (20 mL) and water (2 mL) were added (8-fluoroimidazo[1,2-a]pyridin-6-yl)boronic acid (Intermediate O1) (1.420 g, 7.89 mmol), $K_2CO_3$ (2.182 g, 15.79 mmol) and $PdCl_2(dppf)$ (0.578 g, 0.789 mmol). The mixture was stirred at 80° C. for 4 h. LCMS showed the desired product was formed. The reaction mixture was poured into water (50 mL), extracted with EtOAc (30 mL×3). The organic layer was washed with brine (50 mL), dried over $Na_2SO_4$ and filtered. After filtrate was concentrated to give crude product, the crude product was purified by flash silica gel chromatography (ISCO®; 20 g SepaFlash® Silica Flash Column, eluent of 0-45% ethyl acetate/petroleum ether gradient) to give the title compound. MS: 290.1 [M+1].

Step 3: 1-(5-chloro-4-(8-fluoroimidazo[1,2-a]pyridin-6-yl)pyridin-2-yl)-N-ethylethan-1-amine (O3-3)

O3-3

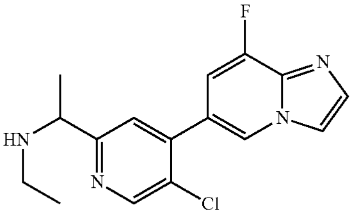

To a mixture solution of 1-(5-chloro-4-(8-fluoroimidazo[1,2-a]pyridin-6-yl)pyridin-2-yl)ethan-1-one (03-2) in EtOH (2 mL) was added ethylamine (23.34 mg, 0.518 mmol), AcOH (1.976 μl, 0.035 mmol), $MgSO_4$ (104 mg, 0.863 mmol) and $NaBH_3CN$ (43.4 mg, 0.690 mmol) at 28° C., then stirred for 2 h at 90° C. LCMS showed the desired product was formed. The reaction mixture was filtered and concentrated to give the title compound. MS: 319.0 [M+1].

Step 4: 1-(1-(5-chloro-4-(8-fluoroimidazo[1,2-a]pyridin-6-yl)pyridin-2-yl)ethyl)-1-ethyl-3-((S)-1,1,1,5,5,5-hexafluoropentan-2-yl)urea (Example 15-1 for Table 15)

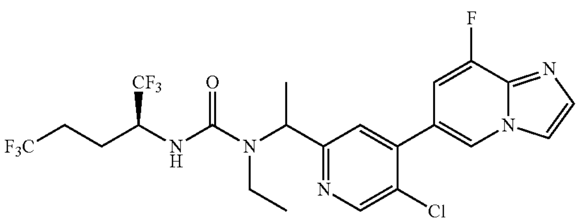

Example 15-1 for Table 15

The title compound was prepared from 1-(5-chloro-4-(8-fluoroimidazo[1,2-a]pyridin-6-yl)pyridin-2-yl)-N-ethylethan-1-amine (03-3) and (S)-1,1,1,5,5,5-hexafluoropentan-2-amine (Intermediate A13). The mixture of diastereomers was via reverse phase chromatography with a C18 column (32-52% ACN/$H_2O$ with 0.1% TFA as the modifier) to afford the title compound as the first eluting product. H-NMR (400 MHz, $CD_3OD$, ppm): δ 8.79-8.59 (m, 2H), 8.18 (s, 1H), 7.90 (s, 1H), 7.58 (d, J=10.5 Hz, 1H), 7.50 (s, 1H), 6.81 (d, J=8.3 Hz, 1H), 5.47 (d, J=7.0 Hz, 1H), 4.60 (s, 1H), 3.52-3.34 (m, 2H), 2.43-2.17 (m, 2H), 2.00 (br d, J=10.1 Hz, 2H), 1.67 (d, J=7.5 Hz, 3H), 1.04 (t, J=7.0 Hz, 3H). MS: 540.3 [M+1].

The following compounds were prepared according to the general procedures herein and in an analogous manner to that used to synthesize the Examples above using the appropriate intermediates. The starting materials were either prepared as described in the intermediates section, commercial available, or prepared from commercially available reagents using conventional reactions well known in the art.

Step 1: methyl 2-cyano-2-(3-oxocyclohexyl)acetate (16-1)

16-1

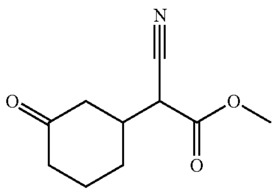

To a solution of cyclohex-2-en-1-one (10 g, 104 mmol) in MeCN (200 mL) were added methyl cyanoacetate (11.34 g, 114 mmol) and $K_2CO_3$ (2.88 g, 20.81 mmol). The mixture was stirred at 25° C. for 15 h. TLC (petroleum ether: EtOAc=3:1) showed the reaction was completed. The reaction mixture was poured into $H_2O$ (200 mL), extracted with EtOAc (200 mL×3). The organic layer was washed with brine (150 mL), dried over $Na_2SO_4$ and filtered. The filtrate was concentrated to give crude product and purified by flash silica gel chromatography (ISCO®; 80 g SepaFlash® Silica Flash Column, eluent of 15% ethyl acetate/petroleum ether gradient) to the title compound. H-NMR (400 MHz, $CDCl_3$, ppm): δ 3.83 (d, J=5.1 Hz, 3H), 3.67-3.46 (m, 1H), 2.59-2.24 (m, 5H), 2.22-2.09 (m, 1H), 2.00-1.90 (m, 1H), 1.81-1.59 (m, 2H).

TABLE 15

| Example | Structure | Name | Exact Mass [M + H]+ |
|---|---|---|---|
| 15-2 | 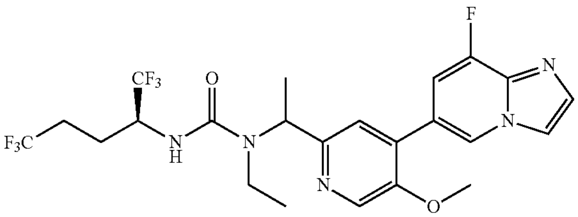 [SMILES: CCN(C(=O)N[C@@H](CCC(F)(F)F)C(F)(F)F)C(C)c1cc(-c2cc(F)c3nccn3c2)c(OC)cn1] | 1-ethyl-1-(1-(4-(8-fluoroimidazo[1,2-a]pyridin-6-yl)-5-methoxypyridin-2-yl)ethyl)-3-((S)-1,1,1,5,5,5-hexafluoropentan-2-yl)urea | 536.2 |

Example 16: 3-(cyano(3,3-difluorocyclohexyl)methyl)-1-ethyl-1-((R)-1-(3-(8-methoxyimidazo[1,2-a]pyrazin-6-yl)phenyl)ethyl)urea Example 16

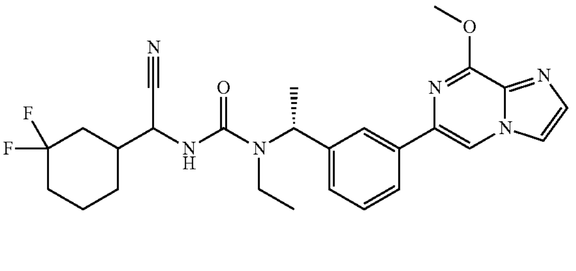

Step 2: methyl 2-cyano-2-(3,3-difluorocyclohexyl)acetate (16-2)

16-2

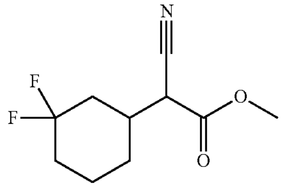

To a solution of methyl 2-cyano-2-(3-oxocyclohexyl)acetate (16-1) (5 g, 25.6 mmol) in DCM (100 mL) was added DAST (6.77 mL, 51.2 mmol) slowly at 0° C. and stirred for 3 h. TLC (petroleum ether:EtOAc=3:1) showed the reaction was completed. The reaction mixture was poured into water (100 mL), extracted with DCM (50 mL×3). The organic layer was washed with brine (50 mL), dried over $Na_2S04$ and filtered. The filtrate was concentrated and purified by flash silica gel chromatography (ISCO®; 40 g SepaFlash® Silica Flash Column, eluent of 0-27% ethyl acetate/petroleum ether gradient) to give the title compound. H-NMR (400 MHz, $CDCl_3$, ppm): δ 3.90-3.77 (m, 3H), 3.59-3.43 (m, 1H), 2.52-2.34 (m, 1H), 2.32-2.05 (m, 3H), 2.00-1.50 (m, 5H).

Step 3: 2-cyano-2-(3,3-difluorocyclohexyl)acetic acid (16-3)

16-3

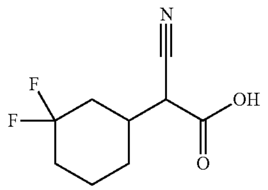

To a solution of methyl 2-cyano-2-(3,3-difluorocyclohexyl)acetate (16-2) (3 g, 13.81 mmol) in MeOH (40 mL) was added lithium hydroxide hydrate (2.90 g, 69.1 mmol) and stirred at 25° C. for 3 h. TLC (petroleum ether:EtOAc=3:1) showed the reaction was completed. The reaction mixture was poured into water (100 mL) and neutralized with 1 M HCl to pH=5, extracted with EtOAc (50 mL×3). The organic layer was washed with brine (50 mL), dried over $Na_2SO_4$ and filtered. The filtrate was concentrated to give the title compound which was used without further purification.

Step 4: 3-(cyano(3,3-difluorocyclohexyl)methyl)-1-ethyl-1-((R)-1-(3-(8-methoxyimidazo[1,2-a]pyrazin-6-yl)phenyl)ethyl)urea (Example 16)

Example 16

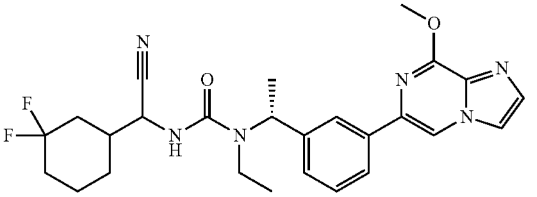

A solution of 2-cyano-2-(3,3-difluorocyclohexyl)acetic acid (16-3) (100 mg, 0.492 mmol) in $SOCl_2$ (2.5 mL) was stirred at 80° C. for 2 h. The mixture was concentrated and the oil was dissolved in acetone (1 mL). A solution of sodium azide (64.0 mg, 0.984 mmol) in water (0.25 mL) was added to the mixture and stirred at 20° C. for 1 h. The reaction mixture was poured into water (30 mL), extracted with EtOAc (20 mL×3). The organic layer was washed with brine (50 mL), dried over $Na_2S04$ and filtered and concentrated. The residue was dissolved in toluene (10 mL) and stirred at 100° C. for 1 h. The mixture was cooled and (R)—N-ethyl-1-(3-(8-methoxyimidazo[1,2-a]pyrazin-6-yl)phenyl)ethan-1-amine (Intermediate A5) (29.2 mg, 0.098 mmol) and $Et_3N$ (0.137 mL, 0.984 mmol) was added. The mixture was stirred at 20° C. for 15 h. LCMS showed the desired product was formed. This was purified via reverse phase chromatography C18 (24-44% acetonitrile/water with 0.1% TFA as a modifier). This material was subjected to prep SFC using the following conditions: Diacel CHIRALPAK AD-H column (250 mm×30 mm, 5 uM), 15% EtOH (0.1% $NH_3 \cdot H_2O$), flow rate=50 mL/min. The title compound eluted as the second peak. MS: 497.2 [M+1].

Example 17: N-{3-[(dimethylsulfamoyl)amino]-1,1,1-trifluoropropan-2-yl}-N-ethyl-N-{(1R)-1-[3-(8-methoxyimidazo[1,2-a]pyrazin-6-yl)phenyl]ethyl}urea Example 17

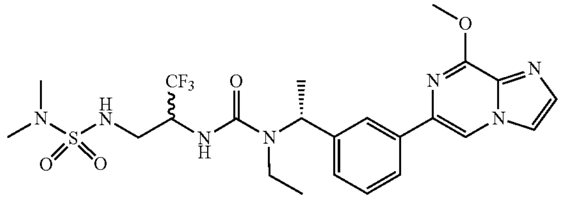

Step 1: tert-butyl (2-(3-ethyl-3-((R)-1-(3-(8-methoxyimidazo[1,2-a]pyrazin-6-yl)phenyl)ethyl)ureido)-3,3,3-trifluoropropyl)carbamate (17-1)

17-1

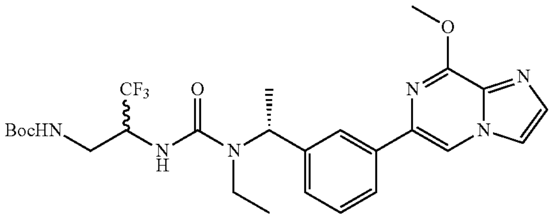

The title compound was prepared using tert-butyl (2-amino-3,3,3-trifluoropropyl)carbamate and (R)—N-ethyl-1-(3-(8-methoxyimidazo[1,2-a]pyrazin-6-yl)phenyl)ethan-1-amine (Intermediate A5) using the procedure outlined in Example 1-1. MS: 551.3 [M+1].

Step 2: 3-(3-amino-1,1,1-trifluoropropan-2-yl)-1-ethyl-1-((R)-1-(3-(8-methoxyimidazo[1,2-a]pyrazin-6-yl)phenyl)ethyl)urea (17-2)

17-2

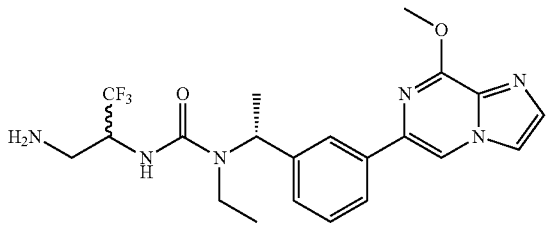

The tert-butyl (2-(3-ethyl-3-((R)-1-(3-(8-methoxyimidazo[1,2-a]pyrazin-6-yl)phenyl)ethyl)ureido)-3,3,3-trifluoropropyl)carbamate (17-1) (28 mg, 0.051 mmol) was dissolved in ethyl acetate (254 μl). HCl (4M in dioxane) (127 μl, 0.509 mmol) was added and the reaction was stirred at ambient temperature for 18 h. The reaction mixture was concentrated in vacuo to afford the title compound. MS: 451.3 [M+1].

Step 3: N-{3-[(dimethylsulfamoyl)amino]-1,1,1-trifluoropropan-2-yl}-N-ethyl-N-{(1R)-1-[3-(8-methoxyimidazo[1,2-a]pyrazin-6-yl)phenyl]ethyl}urea (Example 17)

Example 17

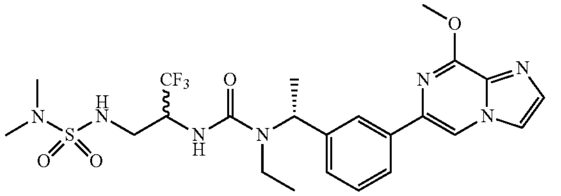

3-(3-amino-1,1,1-trifluoropropan-2-yl)-1-ethyl-1-((R)-1-(3-(8-methoxyimidazo[1,2-a]pyrazin-6-yl)phenyl)ethyl)urea (17-2) (28 mg, 0.062 mmol) was dissolved in DCM (311 μl). TRIETHYLAMINE (17.33 μl, 0.124 mmol) was added followed by DIMETHYLSULFAMOYL CHLORIDE (8.92 mg, 0.062 mmol). The reaction mixture was stirred at ambient temperature for 1 h and then concentrated in vacuo. The crude residue was purified by column chromatography (0-100%, 3:1 EtOAc:EtOH)/Hexanes) which afforded the title compound. MS: 558.3 [M+1].

Example 18: (R)-1-ethyl-1-(2-(3-(imidazo[1,2-a]pyridin-6-yl)phenyl)propan-2-yl)-3-(6,6,6-trifluorohexan-3-yl)urea Example 18

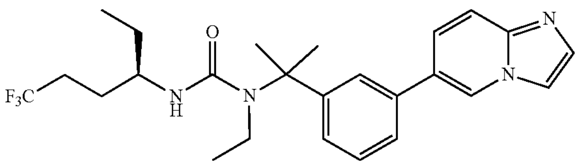

Step 1: 1-(3-(imidazo[1,2-a]pyridin-6-yl)phenyl)ethan-1-one (18-1)

18-1

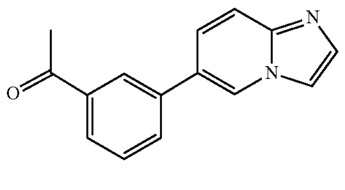

The title compound was prepared from 1-(3-bromophenyl)ethanone and imidazo[1,2-a]pyridin-6-ylboronic acid (Intermediate A8) using the procedure outlined in step 2 in the synthesis of Intermediate A5. MS: 237.1 [M+1].

Step 2: (S,E)-N-(1-(3-(imidazo[1,2-a]pyridin-6-yl)phenyl)ethylidene)-2-methylpropane-2-sulfinamide (18-2)

18-2

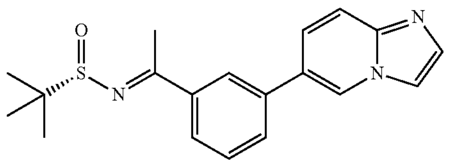

The title compound was prepared from (S)-2-methylpropane-2-sulfinamide and 1-(3-(imidazo[1,2-a]pyridin-6-yl)phenyl)ethan-1-one (18-1) using the procedure outlined in step 3 in the synthesis of Intermediate A14.

Step 3: (S)—N-ethyl-N-(2-(3-(imidazo[1,2-a]pyridin-6-yl)phenyl)propan-2-yl)-2-methylpropane-2-sulfinamide (18-3)

18-3

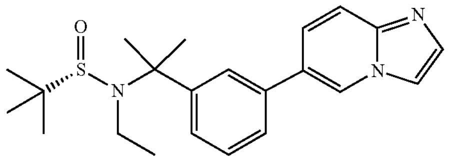

A sealed tube was charged with (S,E)-N-(1-(3-(imidazo[1,2-a]pyridin-6-yl)phenyl)ethylidene)-2-methylpropane-2-sulfinamide (18-2) (63 mg, 0.186 mmol) and dissolved in DCM (928 μl) and treated with METHYLMAGNESIUM BROMIDE (1.0 M in diethyl ether) (371 μl, 0.371 mmol). The vial was capped and the reaction contents were heated to 70° C. and 18 h. This was diluted with EtOAc, washed with sat. brine, dried by filtering though a hydrophobic frit and concentrated to give the crude product. This was purified via chromatography (silica gel, 0-10% MeOH/DCM) to afford the title compound. MS: 356.3 [M+1].

Step 4: N-ethyl-2-(3-(imidazo[1,2-a]pyridin-6-yl)phenyl)propan-2-amine (18-4)

18-4

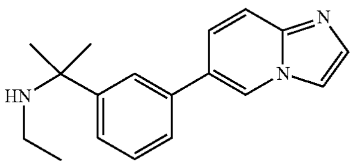

The title compound was prepared from (S)—N-ethyl-N-(2-(3-(imidazo[1,2-a]pyridin-6-yl)phenyl)propan-2-yl)-2- methylpropane-2-sulfinamide (18-3) following the procedure outlined in step 5 of Intermediate A14. MS: 280.3 [M+1].

Step 5: (R)-1-ethyl-1-(2-(3-(imidazo[1,2-a]pyridin-6-yl)phenyl)propan-2-yl)-3-(6,6,6-trifluorohexan-3-yl)urea (Example 18)

Example 18

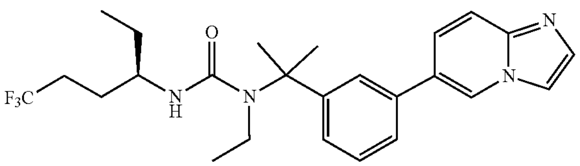

The title compound was prepared from N-ethyl-2-(3-(imidazo[1,2-a]pyridin-6-yl)phenyl)propan-2-amine (18-4) and (R)-6,6,6-trifluorohexan-3-amine (Intermediate A14) using the procedure outlined in the synthesis of Example 2-1. MS: 461.4 [M+1].

Example 19: 1-ethyl-1-((R)-1-(3-(imidazo[1,2-a]pyridin-6-yl)-4-vinylphenyl)ethyl)-3-((R)-6,6,6-trifluorohexan-3-yl)urea Example 19

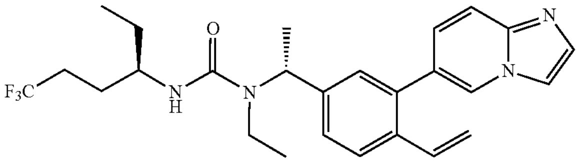

A sealable vial was charged with N-((1R)-1-[4-bromo-3-(imidazo[1,2-a]pyridin-6-yl)phenyl]ethyl)-N-ethyl-N-[(3R)-6,6,6-trifluorohexan-3-yl]urea (Example 11-2) (20 mg, 0.038 mmol) and VINYLBORONIC ACID PINACOL ESTER (11.73 mg, 0.076 mmol) which were dissolved in dioxane (305 μl) and treated with POTASSIUM CARBONATE (15.78 mg, 0.114 mmol) which had been sparged with nitrogen for 10 min. To this was added water (76 μl) which had also been sparged with nitrogen for 10 min. The [1,1'-BIS(DIPHENYLPHOSPHINO-)FERROCENE]DICHLOROPALLADIUM(II) (2.79 mg, 3.81 μmol) was added and the vial was capped and heated to 80° C. and stirred 18 h. The reaction contents were concentrated under vacuum to give a residue. This was diluted with DMSO and syringe-filtered and purified via reverse phase chromatography (SunFire Prep C18 OBD column, 5 micron, 30×150 mm, 5-60% $CH_3CN$/water with 0.1% TFA as a modifier, 25 min, 50 mL/min) to afford the title compound. MS: 473.5 [M+1].

Example 20: 1-ethyl-1-((R)-1-(3-(8-methoxyimidazo[1,2-a]pyrazin-6-yl)phenyl)ethyl)-3-((S)-1,1,1-trifluoro-4-methylpent-3-en-2-yl)urea Example 20

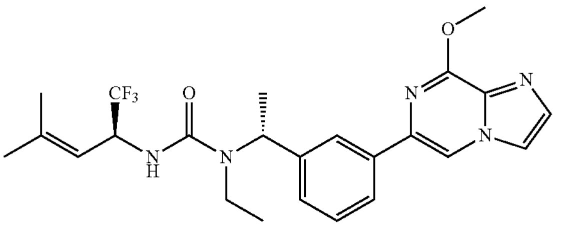

Step 1: 1-ethyl-1-((R)-1-(3-(8-methoxyimidazo[1,2-a]pyrazin-6-yl)phenyl)ethyl)-3-((S)-1,1,1-trifluorobut-3-en-2-yl)urea (20-1)

20-1

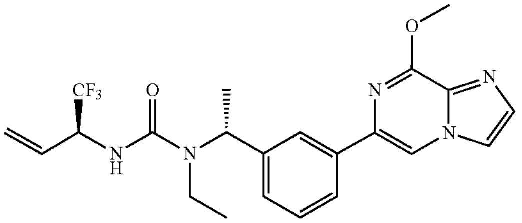

The title compound was prepared from (S)-1,1,1-trifluorobut-3-en-2-amine and (R)—N-ethyl-1-(3-(8-methoxyimidazo[1,2-a]pyrazin-6-yl)phenyl)ethan-1-amine (Intermediate A5) using the procedure outlined in the synthesis of Example 2-1. MS: 448.5 [M+1].

Step 2: 1-ethyl-1-((R)-1-(3-(8-methoxyimidazo[1,2-a]pyrazin-6-yl)phenyl)ethyl)-3-((S)-1,1,1-trifluoro-4-methylpent-3-en-2-yl)urea (Example 20)

Example 20

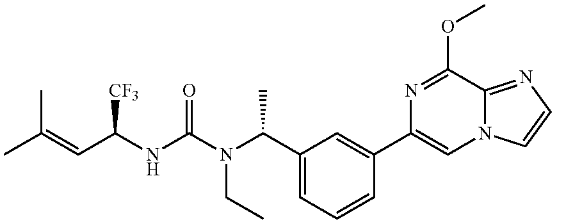

The 3-METHYL-1-BUTENE (14.11 mg, 0.201 mmol) was condensed from the gas and used as a liquid. A sealable vial was charged with 1-ethyl-1-((R)-1-(3-(8-methoxyimidazo[1,2-a]pyrazin-6-yl)phenyl)ethyl)-3-((S)-1,1,1-trifluorobut-3-en-2-yl)urea (20-1) (30 mg, 0.067 mmol) and dissolved in DCE (670 μl) which had been sparged with nitrogen for 10 min. To this, 3-METHYL-1-BUTENE (14.11 mg, 0.201 mmol) and Grubbs II (5.69 mg, 6.70 μmol)

was added and the reaction contents were heated to 65° C. and stirred 18 h. This was diluted with EtOAc and water and filtered through celite and concentrated to give an oil. This was purified via reverse phase chromatography (SunFire Prep C18 OBD column, 5 micron, 30×150 mm, 30-55% $CH_3CN$/water with 0.1% TFA as a modifier, 25 min, 50 mL/min) to give the title compound. MS: 490.3 [M+1].

Example 21: 2-(3-ethyl-3-((R)-1-(3-(8-methoxyimidazo[1,2-a]pyrazin-6-yl)phenyl)ethyl)ureido)-3,3,3-trifluoropropyl acetate Example 21

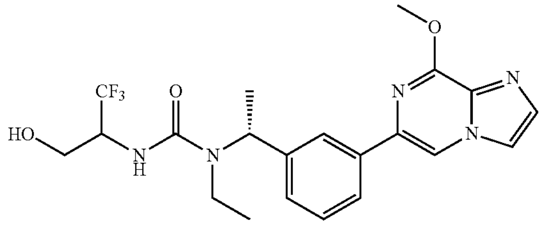

Step 1: 3-(3-((tert-butyldimethylsilyl)oxy)-1,1,1-trifluoropropan-2-yl)-1-ethyl-1-((R)-1-(3-(8-methoxyimidazo[1,2-a]pyrazin-6-yl)phenyl)ethyl) urea (21-1)

21-1

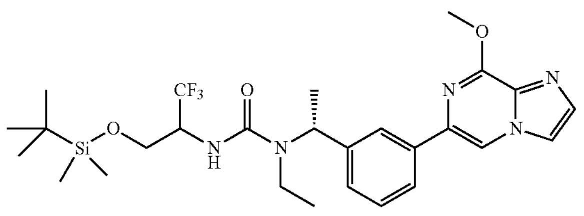

The title compound was prepared using 3-((tert-butyldimethylsilyl)oxy)-1,1,1-trifluoropropan-2-amine and (R)—N-ethyl-1-(3-(8-methoxyimidazo[1,2-a]pyrazin-6-yl)phenyl)ethan-1-amine (Intermediate A5) using the procedure outlined in Example 1-1. MS: 566.4 [M+1].

Step 2: 1-ethyl-1-((R)-1-(3-(8-methoxyimidazo[1,2-a]pyrazin-6-yl)phenyl)ethyl)-3-(1,1,1-trifluoro-3-hydroxypropan-2-yl)urea (Example 21)

Example 21

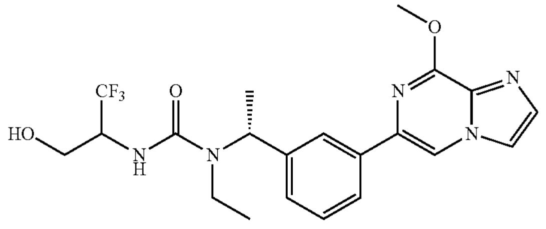

A flask was charged with 3-(3-((tert-butyldimethylsilyl)oxy)-1,1,1-trifluoropropan-2-yl)-1-ethyl-1-((R)-1-(3-(8-methoxyimidazo[1,2-a]pyrazin-6-yl)phenyl)ethyl)urea (21-1) (1.07 g, 1.891 mmol) which was dissolved in THF (9.46 ml) and treated with TBAF (1.0 M in THF) (3.78 ml, 3.78 mmol) and stirred at ambient temperature for 18 h. This was diluted with 3:1 $HCCl_3$:IPA and washed with sat. $NH_4Cl$ (×4), dried ($Na_2SO_4$), filtered and concentrated to give an oil. This was purified via chromatography ($SiO_2$, 120 g RediSep column, 0-80% 3:1 EtOAc:EtOH/hexanes, 85 mL/min, 35 min) to give the second eluting product as the title compound. MS: 452.3 [M+1].

Step 3: 2-(3-ethyl-3-((R)-1-(3-(8-methoxyimidazo[1,2-a]pyrazin-6-yl)phenylethyl)ureido)-3,3,3-trifluoropropyl acetate (Example 22)

Example 22

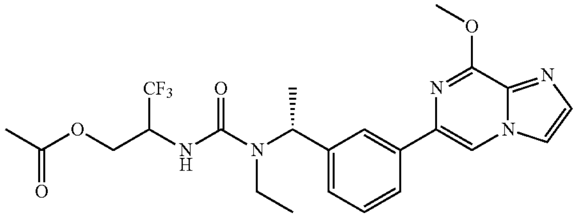

The racemic 1-ethyl-1-((R)-1-(3-(8-methoxyimidazo[1,2-a]pyrazin-6-yl)phenyl)ethyl)-3-(1,1,1-trifluoro-3-hydroxypropan-2-yl)urea (Example 22) (30 mg, 0.066 mmol) was dissolved in pyridine (332 µl) and treated with acetyl chloride (14.18 µl, 0.199 mmol) and DMAP (0.812 mg, 6.65 µmol) and stirred at ambient temperature for 18 h. This was diluted with $CH_2Cl_2$, washed with sat. $NaHCO_3$, dried by filtering though a hydrophobic frit and concentrated to give the crude product. This was purified via reverse phase chromatography (SunFire Prep C18 OBD column, 5 micron, 30×150 mm, 15-40% $CH_3CN$/water with 0.1% TFA as a modifier, 25 min, 50 mL/min) to give the first eluting product as the title compound. MS: 494.3 [M+1].

Example 23: 2-(3-ethyl-3-((R)-1-(3-(8-methoxyimidazo[1,2-a]pyrazin-6-yl)phenyl)ethyl)ureido)-3,3,3-trifluoropropyl dimethylcarbamate Example 23

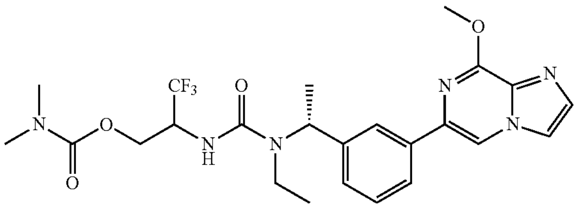

The racemic 1-ethyl-1-((R)-1-(3-(8-methoxyimidazo[1,2-a]pyrazin-6-yl)phenyl)ethyl)-3-(1,1,1-trifluoro-3-hydroxypropan-2-yl)urea (Example 23) (30 mg, 0.066 mmol) was dissolved in pyridine (332 µl) and treated with CDI (12.93 mg, 0.080 mmol) and stirred at 60° C. for 1 h, then treated with dimethylamine (40% in water) (33.7 µl, 0.266 mmol)

and heated to 100° C. and stirred for 18 h. The contents of the reaction were concentrated in vacuo and this was purified via reverse phase chromatography (SunFire Prep C18 OBD column, 5 micron, 30×150 mm, 13-38% $CH_3CN$/water with 0.1% TFA as a modifier, 25 min, 50 mL/min) to afford the first eluting product as the title compound. MS: 523.3 [M+1].

Example 24: 3-(3-ethyl-3-((R)-1-(3-(8-methoxyimidazo[1,2-a]pyrazin-6-yl)phenyl)ethyl)ureido)-4,4,4-trifluoro-N,N-dimethylbutanamide Example 24

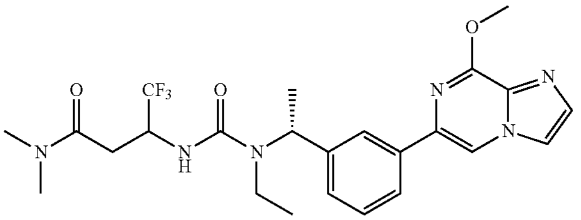

Step 1: 3-(3-ethyl-3-((R)-1-(3-(8-methoxyimidazo[1,2-a]pyrazin-6-yl)phenyl)ethyl)ureido)-4,4,4-trifluorobutanoic acid (24-1)

24-1

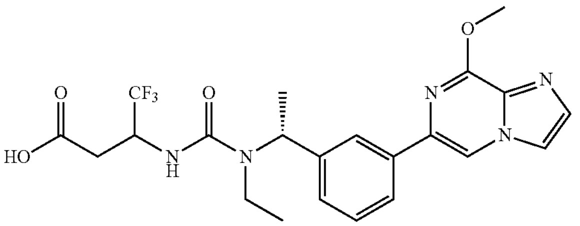

3-Amino-4,4,4-trifluorobutyric acid (0.583 g, 3.71 mmol) was dissolved in DCM (16.87 ml) and treated with CDI (0.602 g, 3.71 mmol) and TEA (0.705 ml, 5.06 mmol) and stirred, at ambient temperature for 30 min, then treated with (R)—N-ethyl-1-(3-(8-methoxyimidazo[1,2-a]pyrazin-6-yl)phenyl)ethan-1-amine (Intermediate A5) (1.0 g, 3.37 mmol) and stirred at ambient temperature for 18 h. This was diluted with 3:1 $HCCl_3$:IPA, washed with 2 M NaOH. The aqueous layer was acidified with concentrated HCl such that the pH was between 5 and 6 and this was back-extracted with 3:1 $HCCl_3$:IPA. The organic portions were combined and dried ($Na_2SO_4$), filtered and concentrated to give the title compound which was used without further purification. MS: 480.4 [M+1].

Step 2: 3-(3-ethyl-3-((R)-1-(3-(8-methoxyimidazo[1,2-a]pyrazin-6-yl)phenyl)ethyl)ureido)-4,4,4-trifluorobutanovl chloride (24-2)

24-2

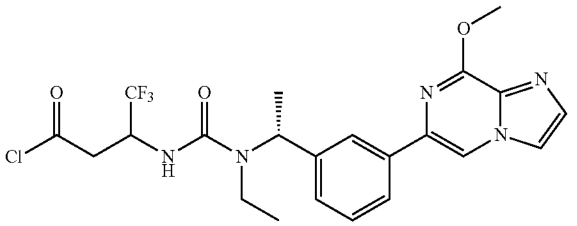

A flask was charged with the 3-(3-ethyl-3-((R)-1-(3-(8-methoxyimidazo[1,2-a]pyrazin-6-yl)phenyl)ethyl)ureido)-4,4,4-trifluorobutanoic acid (24-1) (60 mg, 0.125 mmol) which was dissolved in DCM (1251 μl) and treated with OXALYL CHLORIDE (2 M in DCM) (94 μl, 0.188 mmol) followed by DMF (1.938 μl, 0.025 mmol). This was stirred, at ambient temperature for 30 min. The contents of the reaction was concentrated under vacuum to afford the title compound which was used immediately in the next reaction.

Step 3: 3-(3-ethyl-3-((R)-1-(3-(8-methoxyimidazo[1,2-a]pyrazin-6-yl)phenyl)ethyl)ureido)-4,4,4-trifluoro-N,N-dimethylbutanamide (Example 24)

Example 24

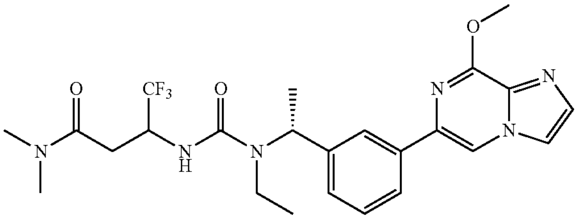

A flask was charged with the 3-(3-ethyl-3-((R)-1-(3-(8-methoxyimidazo[1,2-a]pyrazin-6-yl)phenyl)ethyl)ureido)-4,4,4-trifluorobutanoyl chloride (24-2) (20 mg, 0.040 mmol) which was dissolved in DCM (402 μl) and treated with DIMETHYLAMINE (40% in water, 45.3 mg, 0.402 mmol) and stirred at ambient temperature for 18 h. This was diluted with DCM, washed with sat. $NaHCO_3$, dried by filtering through a hydrophobic frit and evaporating to give a residue. This was purified via reverse phase chromatography (SunFire Prep C18 OBD column, 5 micron, 30×150 mm, 10-35% $CH_3CN$/water with 0.1% TFA as a modifier, 25 min, 50 mL/min) to afford the first eluting product as the title compound. MS: 507.4 [M+1].

Example 25: 1-ethyl-1-((R)-1-(3-(7-methoxyindolin-5-yl)phenyl)ethyl)-3-((R)-6,6,6-trifluorohexan-3-yl) urea Example 25

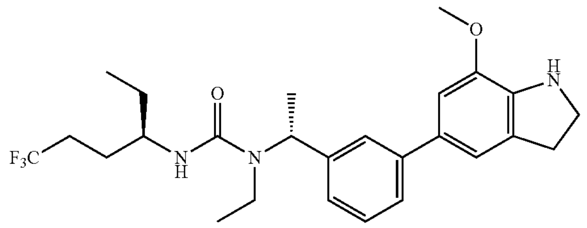

Step 1: tert-butyl 5-(3-((R)-1-(1-ethyl-3-((R)-6,6,6-trifluorohexan-3-yl)ureido)ethyl)phenyl)-methoxyinoline-1-carboxylate (25-1)

25-1

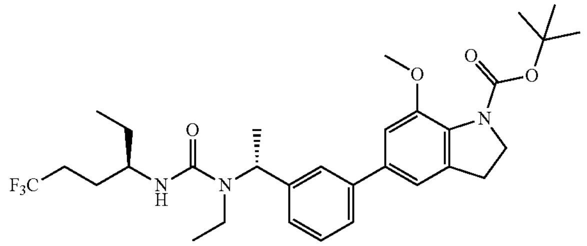

A solution of 1-ethyl-1-((R)-1-(3-(4,4,5,5-tetramethyl-1,3,2-dioxaborolan-2-yl)phenyl)ethyl)-3-((R)-6,6,6-trifluorohexan-3-yl)urea (H5-2) (72 mg, 0.158 mmol) and tert-butyl 5-bromo-7-methoxyinoline-1-carboxylate (155 mg, 0.473 mmol) in dioxane (3 mL) was degassed. Degassed 1 M aqueous tripotassium phosphate (0.316 mL, 0.316 mmol) and CHLORO(2-DICYCLOHEXYLPHOSPHINO-2',4',6'-TRI-I-PROPYL-1,1'-BIPHENYL)(2'-AMINO-1,1'-BIPHENYL-2-YL) PALLADIUM(II) (12.41 mg, 0.016 mmol) were added and the mixture was heated at 55° C. for 18 h. The solvent was removed and the crude mixture was purified directly by column chromatography on silica gel (40 g ISCO gold column), eluting with Hexanes:EtOAc/EtOH mix (3:1) 100:0 to 60:40 to afford the title compound. MS: 578.4 [M+1].

Step 2: 1-ethyl-1-((R)-1-(3-(7-methoxyindolin-5-yl) phenyl)ethyl)-3-((R)-6,6,6-trifluorohexan-3-yl)urea (Example 25)

Example 25

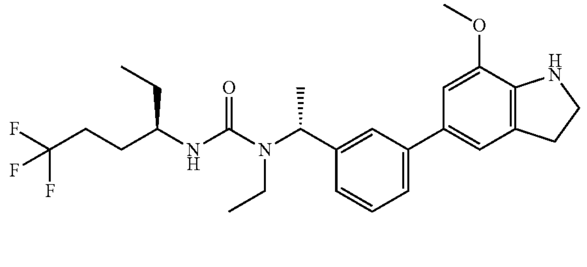

A solution of 4 M HCl (467 µl, 1.870 mmol) in dioxane was added to tert-butyl 5-(3-((R)-1-(1-ethyl-3-((R)-6,6,6-trifluorohexan-3-yl)ureido)ethyl)phenyl)-methoxyinoline-1-carboxylate (25-1) (72.0 mg, 0.125 mmol) and the mixture was aged at RT for 2 h. The solvent was removed, the crude dissolved in DCM (0.5 mL) and DIEA (0.1 mL) and purified by column chromatography on silica gel (24 g ISCO gold column), eluting with DCM:MeOH/$NH_4OH$ mix (100:1) 100:0 to 95:5 to afford the title compound. MS: 478.4 [M+1].

Example 26: 1-ethyl-3-((S)-1,1,1,5,5,5-hexafluoropentan-2-yl)-1-((R)-1-(3-(2-hydroxy-8-methoxyimidazo[1,2-a]pyridin-6-yl)phenyl)ethyl)urea Example 26

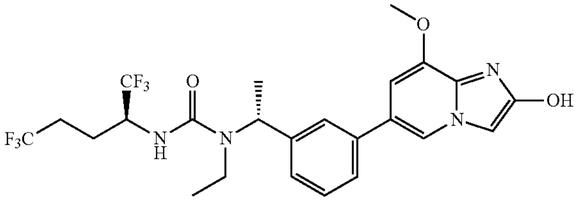

A solution of 1-((R)-1-(3-(6-amino-5-methoxypyridin-3-yl)phenyl)ethyl)-1-ethyl-3-((S)-1,1,1,5,5,5-hexafluoropentan-2-yl)urea (11-6) (22 mg, 0.045 mmol), ethyl bromoacetate (5.47 µl, 0.049 mmol), and TEA (0.019 mL, 0.134 mmol) in acetonitrile (0.5 mL) was heated at 90° C. for 18 h. The reaction mixture was diluted with DMF (0.5 mL) and purified on the Gilson HPLC (5-95% ACN/$H_2O$ with 0.1% TFA as a modifier, Luna C18 column) to afford the title compound. MS: 533.3 [M+1].

Example 27: 1-ethyl-3-((S)-1,1,1,5,5,5-hexafluoropentan-2-yl)-1-((R)-1-(3-(8-methoxy-2-(trifluoromethyl)imidazo[1,2-a]pyridin-6-yl)phenyl)ethyl)urea Example 27

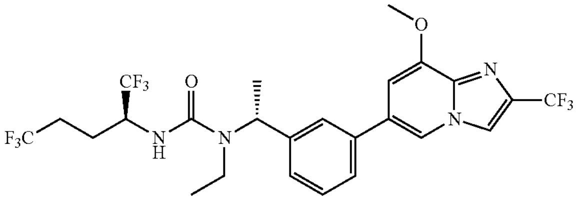

A solution of 1-((R)-1-(3-(6-amino-5-methoxypyridin-3-yl)phenyl)ethyl)-1-ethyl-3-((S)-1,1,1,5,5,5-hexafluoropentan-2-yl)urea (11-6) (20 mg, 0.041 mmol) and 3-bromo-1,1,1-trifluoroacetone (5.48 µl, 0.053 mmol) in EtOH (0.5 mL) was heated at 70° C. for 18 h. The reaction mixture was diluted with DMF (0.5 mL) and purified on the Gilson HPLC (5-95% ACN/$H_2O$ with 0.1% TFA as the modifier, YMC PRO C18 column) to afford the title compound. MS: 585.4 [M+1].

Example 28: (S)-1-(2,2-difluoro-1-(5-methoxy-4-(8-methoxyimidazo[1,2-a]pyrazin-6-yl)pyridin-2-yl)vinyl)-1-ethyl-3-(1,1,1,5,5,5-hexafluoropentan-2-yl)urea Example 28

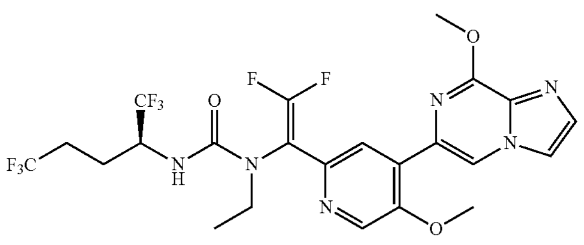

Step 1: 1-(1-(4-bromo-5-methoxypyridin-2-yl)-2,2,2-trifluoroethyl)-1-ethyl-3-((S)-1,1,1,5,5,5-hexafluoropentan-2-yl)urea (28-1)

28-1

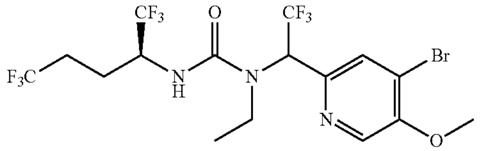

The title compound was prepared from 1-(4-bromo-5-methoxypyridin-2-yl)-N-ethyl-2,2,2-trifluoroethan-1-amine (21-4) and (S)-1,1,1,5,5,5-hexafluoropentan-2-amine (Intermediate A13) using the procedure described in the synthesis of Example 2-1. MS: 534.2, 536.2 [M+1].

Step 2: (S)-1-(2,2-difluoro-1-(5-methoxy-4-(8-methoxyimidazo[1,2-a]pyrazin-6-yl)pyridin-2-yl)vinyl)-1-ethyl-3-(1,1,1,5,5,5-hexafluoropentan-2-yl)urea (Example 28)

Example 28

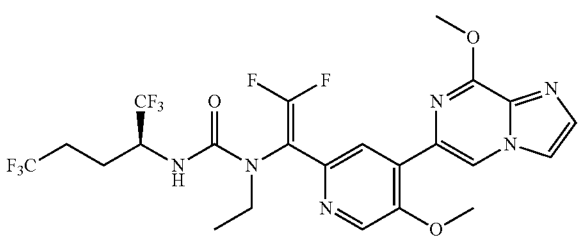

A solution of (S)-1-(2,2-difluoro-1-(5-methoxy-4-(8-methoxyimidazo[1,2-a]pyrazin-6-yl)pyridin-2-yl)vinyl)-1-ethyl-3-(1,1,1,5,5,5-hexafluoropentan-2-yl)urea (Example 28) (92.7 mg, 0.174 mmol), 8-methoxy-6-(4,4,5,5-tetramethyl-1,3,2-dioxaborolan-2-yl)imidazo[1,2-a]pyrazine (Intermediate B1) (67.0 mg, 0.347 mmol), and 1 M aqueous tripotassium phosphate (0.347 mL, 0.347 mmol) in dioxane (2 mL) was degassed. Chloro(2-dicyclohexylphosphino-2',4',6'-tri-i-propyl-1,1'-biphenyl)(2'-amino-1,1'-biphenyl-2-yl) palladium(ii) (13.6 mg, 0.017 mmol) was added and the mixture was heated at 65° C. for 4.5 h. The mixture was concentrated and purified by column chromatography on silica gel (80 g ISCO gold column), eluting with Hexanes: EtOAc/EtOH mix (3:1) 100:0 to 40:60. Mixed fractions were further purified on the Gilson HPLC (5-95% ACN/$H_2O$ w/0.1% $NH_4OH$, Gemini-NX C18 column) to afford the title compound. MS: 583.3 [M+1].

Example 29: 1-ethyl-3-((S)-1,1,1,5,5,5-hexafluoropentan-2-yl)-1-((R)-1-(5-(8-methoxyimidazo[1,2-a]pyrazin-6-yl)-1-methyl-6-oxo-1,6-dihydropyridin-3-yl)ethyl)urea Example 29

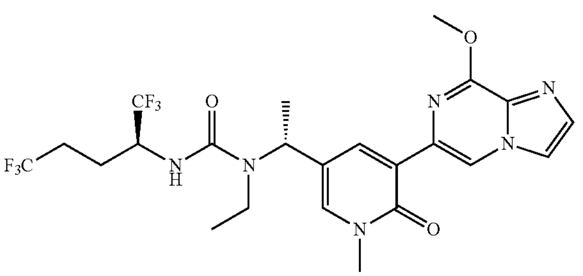

Step 1: (S)—N—((R)-1-(5-bromo-6-methoxypyridin-3-yl)ethyl)-N-ethyl-2-methylpropane-2-sulfinamide (29-1)

29-1

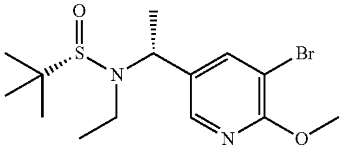

The title compound was prepared from 5-bromo-6-methoxynicotinaldehyde using the procedure described in steps 1-3 in the synthesis of Intermediate H4. MS: 365.2, 366.2 [M+1].

Step 2: (R)-3-bromo-5-(1-(ethylamino)ethyl)pyridin-2-ol (29-2)

29-2

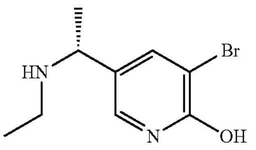

To a solution of (S)—N—((R)-1-(5-bromo-6-methoxypyridin-3-yl)ethyl)-N-ethyl-2-methylpropane-2-sulfinamide (29-1) (1.572 g, 4.33 mmol) in MeOH (10.82 mL) at ambient temperature was added 4 M HCl (4.00 mL, 16.00 mmol) in dioxane and the solution was stirred for 9 h. The reaction mixture was concentrated and dried to afford the title compound. MS: 245.0, 247.0 [M+1].

Step 3: 1-((R)-1-(5-bromo-6-hydroxypyridin-3-yl) ethyl)-1-ethyl-3-((S)-1,1,1,5,5,5-hexafluoropentan-2-yl)urea (29-3)

29-3

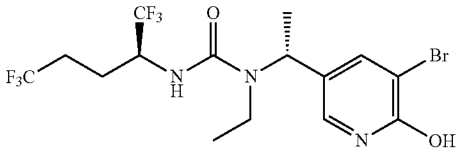

A solution of (S)-1,1,1,5,5,5-hexafluoropentan-2-amine (Intermediate A13) (509 mg, 2.199 mmol), CDI (357 mg, 2.199 mmol), and TEA (0.943 mL, 6.77 mmol) in DCM (15 mL) was stirred at ambient temperature for 3 d. 1-((R)-1-(5-Bromo-6-hydroxypyridin-3-yl)ethyl)-1-ethyl-3-((S)-1,1,1,5,5,5-hexafluoropentan-2-yl)urea (29-2) (500 mg, 1.691 mmol) was then added and the solution was stirred for 18 h at 45° C. The mixture was purified by column chromatography on silica gel (80 g ISCO gold column), eluting with Hexanes:EtOAc/EtOH mix (3:1) 100:0 to 0:100 to afford the title compound. MS: 466.3, 468.3 [M+1].

Step 4: 1-((R)-1-(5-bromo-1-methyl-6-oxo-1,6-dihydropyridin-3-yl)ethyl)-1-ethyl-3-((S)-1,1,1,5,5,5-hexafluoropentan-2-yl)urea (29-4)

29-4

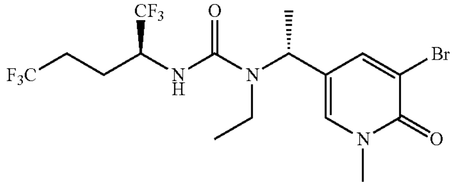

A suspension of 1-((R)-1-(5-bromo-6-hydroxypyridin-3-yl)ethyl)-1-ethyl-3-((S)-1,1,1,5,5,5-hexafluoropentan-2-yl) urea (29-3) (369 mg, 0.791 mmol), silver carbonate (436 mg, 1.583 mmol), and iodomethane (0.064 mL, 1.029 mmol) in toluene (5 mL) was heated at 85° C. for 16 h. After 4 h, additional iodomethane (0.064 mL, 1.029 mmol) was added. The mixture was filtered through a pad of Celite, concentrated, and the crude purified by column chromatography on silica gel (24 g ISCO gold column), eluting with Hexanes:EtOAc/EtOH mix (3:1) 100:0 to 50:50 to afford the title compound. MS: 480.2, 482.2 [M+1].

Step 5: 1-ethyl-3-((S)-1,1,1,5,5,5-hexafluoropentan-2-yl)-1-((R)-1-(5-(8-methoxyimidazo[1,2-a]pyrazin-6-yl)-1-methyl-6-oxo-1,6-dihydropyridin-3-yl)ethyl) urea (Example 29)

Example 29

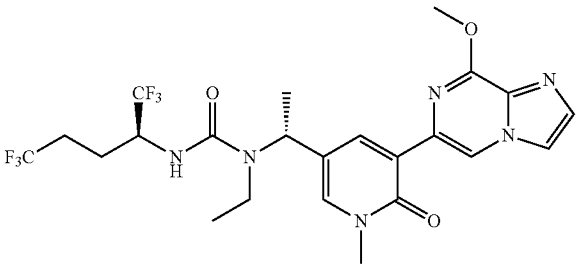

A solution of 1-((R)-1-(5-bromo-1-methyl-6-oxo-1,6-dihydropyridin-3-yl)ethyl)-1-ethyl-3-((S)-1,1,1,5,5,5-hexafluoropentan-2-yl)urea (29-4) (17.2 mg, 0.036 mmol), 8-methoxy-6-(4,4,5,5-tetramethyl-1,3,2-dioxaborolan-2-yl) imidazo[1,2-a]pyrazine (Intermediate B1) (34.6 mg, 0.179 mmol), and 1 M aqueous tripotassium phosphate (0.072 mL, 0.072 mmol) in dioxane (0.5 mL) was degassed. Chloro(2-dicyclohexylphosphino-2',4',6'-tri-i-propyl-1,1'-biphenyl) (2'-amino-1,1'-biphenyl-2-yl) palladium(II) (2.82 mg, 3.58 μmol) was added and the mixture was heated at 55° C. for 3 h. The mixture was diluted with DMF (1 mL), filtered, and purified on the Gilson HPLC (5-95% ACN/$H_2O$ w/0.1% $NH_4OH$, Gemini-NX C18 column). The mixed fractions were further purified by column chromatography on silica gel (12 g ICSO gold column), eluting with Hexanes:EtOAc/EtOH mix (3:1) 100:0 to 0:100 to afford the title compound. MS: 549.5 [M+1].

Example 30: 1-ethyl-3-((S)-1,1,1,5,5,5-hexafluoropentan-2-yl)-1-((R)-1-(6-hydroxy-5-(7-methoxypyrazolo[1,5-a]pyridin-5-yl)pyridin-3-yl)ethyl)urea Example 30

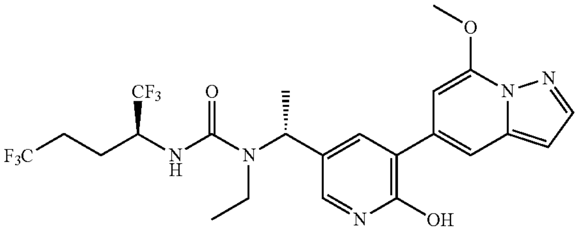

The title compound was prepared from 1-((R)-1-(5-bromo-6-hydroxypyridin-3-yl)ethyl)-1-ethyl-3-((S)-1,1,1,5,5,5-hexafluoropentan-2-yl)urea (29-3) and (S)-1,1,1,5,5,5-hexafluoropentan-2-amine (Intermediate A13) using the procedure described in step 2 in the synthesis of Intermediate A5. MS: 534.4 [M+1].

The following table shows representative data for the compounds of the Examples as orexin receptor agonists as determined by the assays described herein.

| Example | OX2R Potency, EC50 (nM) | % Inhibition |
|---|---|---|
| 1-1 | 7.1 | 98.4 |
| 1-2 | 5.2 | 98.3 |
| 1-3 | 6.5 | 99.9 |
| 1-4 | 6.9 | 96.1 |
| 1-5 | 73.4 | 94.9 |
| 1-6 | 192.9 | 99.0 |
| 1-7 | 17.5 | 97.3 |
| 1-8 | 0.8 | 96.5 |
| 1-9 | 0.6 | 99.8 |
| 1-10 | 8.3 | 101.0 |
| 1-11 | 20.1 | 98.0 |
| 1-12 | 19.8 | 99.1 |
| 1-13 | 146.1 | 80.7 |
| 1-14 | 18.5 | 101.3 |
| 1-15 | 271.3 | 99.7 |
| 1-16 | 2.8 | 100.1 |
| 1-17 | 10.5 | 98.7 |
| 2-1 | 6.8 | 100.1 |
| 2-2 | 3.7 | 99.1 |
| 2-3 | 4.6 | 100.6 |
| 2-4 | 4.3 | 100.6 |

-continued

| Example | OX2R Potency, EC50 (nM) | % Inhibition |
|---|---|---|
| 2-5 | 10.7 | 100.7 |
| 2-6 | 12.1 | 101.5 |
| 2-7 | 12.5 | 100.1 |
| 2-8 | 13.3 | 100.0 |
| 2-9 | 20.3 | 100.0 |
| 2-10 | 22.5 | 98.5 |
| 2-11 | 30.3 | 97.6 |
| 2-12 | 45.8 | 99.8 |
| 2-13 | 2.1 | 99.9 |
| 2-14 | 8.7 | 100.1 |
| 2-15 | 24.0 | 98.4 |
| 2-16 | 54.5 | 101.1 |
| 2-17 | 3.2 | 101.7 |
| 2-18 | 29.9 | 99.6 |
| 2-19 | 5.7 | 102.0 |
| 2-20 | 341.0 | 99.7 |
| 2-21 | 0.8 | 99.6 |
| 2-22 | 2.8 | 101.5 |
| 2-23 | 2.7 | 100.8 |
| 2-24 | 0.7 | 100.2 |
| 2-25 | 359.9 | 98.0 |
| 2-26 | 8.6 | 100.5 |
| 2-27 | 9.4 | 101.1 |
| 2-28 | 16.1 | 99.1 |
| 2-29 | 23.8 | 96.0 |
| 2-30 | 34.6 | 99.0 |
| 2-31 | 35.1 | 99.0 |
| 2-32 | 40.8 | 101.0 |
| 2-33 | 0.8 | 101.6 |
| 2-34 | 2.7 | 101.1 |
| 2-35 | 0.9 | 102.3 |
| 2-36 | 0.7 | 100.5 |
| 2-37 | 20.0 | 100.8 |
| 2-38 | 4.2 | 99.7 |
| 2-39 | 5.8 | 99.3 |
| 2-40 | 15.8 | 99.3 |
| 2-41 | 16.3 | 101.2 |
| 2-42 | 27.8 | 101.7 |
| 2-43 | 1.1 | 99.8 |
| 2-44 | 4.8 | 100.6 |
| 2-45 | 1.9 | 99.8 |
| 2-46 | 11.7 | 100.9 |
| 2-47 | 16.7 | 100.7 |
| 2-48 | 17.6 | 101.0 |
| 2-49 | 99.4 | 100.1 |
| 2-50 | 1.4 | 100.5 |
| 2-51 | 1.0 | 98.7 |
| 2-52 | 35.8 | 100.6 |
| 2-53 | 1.5 | 101.6 |
| 2-54 | 1.6 | 99.4 |
| 2-55 | 129.1 | 99.4 |
| 2-56 | 0.8 | 100.1 |
| 2-57 | 15.3 | 96.2 |
| 2-58 | 17.8 | 100.0 |
| 2-59 | 20.9 | 100.2 |
| 2-60 | 64.4 | 97.4 |
| 2-61 | 5.8 | 99.5 |
| 2-62 | 13.1 | 95.6 |
| 2-63 | 1058 | 96.2 |
| 2-64 | 2874 | 81.2 |
| 2-65 | 4.0 | 100.1 |
| 2-66 | 5.2 | 97.2 |
| 2-67 | 7.7 | 98.7 |
| 2-68 | 178.6 | 83.3 |
| 3-1 | 0.9 | 100.8 |
| 3-2 | 3.3 | 102.4 |
| 3-3 | 3.6 | 101.6 |
| 3-4 | 27.8 | 100.5 |
| 3-5 | 40.5 | 99.3 |
| 3-6 | 2.6 | 99.7 |
| 3-7 | 4.4 | 100.5 |
| 4-1 | 4.8 | 101.6 |
| 4-2 | 5.9 | 99.9 |
| 4-3 | 17.2 | 101.4 |
| 5-1 | 4.8 | 100.4 |
| 5-2 | 9.6 | 99.1 |

-continued

| Example | OX2R Potency, EC50 (nM) | % Inhibition |
|---|---|---|
| 5-3 | 37.4 | 100.5 |
| 6-1 | 22.6 | 101.0 |
| 6-2 | 8.1 | 100.1 |
| 6-3 | 13.6 | 100.2 |
| 6-4 | 16.0 | 100.3 |
| 6-5 | 18.9 | 100.0 |
| 6-6 | 71.4 | 101.5 |
| 6-7 | 8.5 | 100.9 |
| 7-1 | 29.3 | 96.8 |
| 7-2 | 395.8 | 100.4 |
| 7-3 | 491.2 | 86.1 |
| 7-4 | 594.6 | 97.8 |
| 7-5 | 851.2 | 93.7 |
| 7-6 | 1415 | 100.8 |
| 8-1 | 210.6 | 96.1 |
| 8-2 | 6.5 | 97.7 |
| 8-3 | 10.4 | 96.6 |
| 8-4 | 25.9 | 98.7 |
| 8-5 | 47.8 | 96.1 |
| 8-7 | 179.5 | 99.3 |
| 8-8 | 248.3 | 102.1 |
| 8-9 | 0.7 | 99.7 |
| 8-10 | 1.5 | 99.6 |
| 8-11 | 2.0 | 95.4 |
| 8-12 | 17.4 | 96.7 |
| 8-14 | 109.1 | 100.1 |
| 8-15 | 188.3 | 94.1 |
| 9-1 | 0.9 | 99.7 |
| 9-2 | 5.5 | 100.5 |
| 9-3 | 6.2 | 100.7 |
| 9-4 | 7.5 | 99.6 |
| 9-5 | 16.3 | 99.6 |
| 9-6 | 18.8 | 102.5 |
| 9-7 | 29.8 | 100.4 |
| 9-8 | 44.0 | 99.5 |
| 9-10 | 608.4 | 97.1 |
| 9-11 | 2.6 | 99.5 |
| 10-1 | 1.1 | 100.4 |
| 10-2 | 340.6 | 98.6 |
| 10-3 | 0.8 | 101.7 |
| 10-4 | 1.3 | 100.7 |
| 10-5 | 2.5 | 101.6 |
| 10-6 | 9.2 | 98.9 |
| 10-7 | 1.5 | 102.7 |
| 10-8 | 2.3 | 100.7 |
| 10-9 | 2.7 | 102.5 |
| 10-10 | 4.7 | 100.8 |
| 10-11 | 7.3 | 101.3 |
| 10-12 | 70.1 | 100.5 |
| 10-13 | 132.2 | 101.7 |
| 10-15 | 6.4 | 99.8 |
| 10-16 | 35.2 | 97.9 |
| 10-17 | 88.8 | 100.5 |
| 10-18 | 11.9 | 99.8 |
| 10-19 | 0.8 | 100.6 |
| 10-20 | 0.7 | 101.0 |
| 10-21 | 1.6 | 100.9 |
| 10-22 | 76.9 | 99.4 |
| 11-1 | 5.6 | 97.4 |
| 11-2 | 80.5 | 98.5 |
| 11-3 | 128.8 | 91.8 |
| 11-4 | 0.7 | 101.6 |
| 11-5 | 0.6 | 100.1 |
| 12-1 | 0.6 | 100.1 |
| 12-2 | 1.2 | 100.6 |
| 12-3 | 4.7 | 102.1 |
| 13-1 | 11.7 | 101.4 |
| 13-2 | 16.8 | 101.4 |
| 14-1 | 1.5 | 100.3 |
| 14-2 | 2.6 | 96.0 |
| 15-1 | 5.8 | 100.5 |
| 15-2 | 1.0 | 99.1 |
| 16 | 3.2 | 100.8 |
| 17 | 0.7 | 101.8 |
| 18 | 126.4 | 99.6 |
| 19 | 23.2 | 94.9 |

-continued

| Example | OX2R Potency, EC50 (nM) | % Inhibition |
|---|---|---|
| 20 | 2.9 | 100.1 |
| 21 | 50.9 | 96.3 |
| 22 | 25.3 | 97.0 |
| 23 | 124.8 | 95.3 |
| 24 | 143.6 | 89.1 |
| 25 | 619.2 | 98.5 |
| 26 | 143.6 | 89.1 |
| 27 | 619.2 | 98.5 |
| 28 | 2128 | 97.2 |
| 29 | 10.5 | 102.6 |
| 30 | 4734 | 97.0 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the following formula:

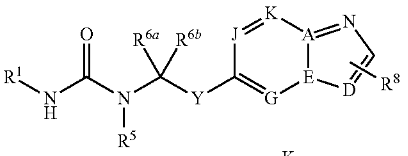

or

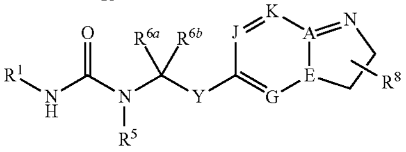

or a pharmaceutically acceptable salt or stereoisomer thereof, wherein:

$R^1$ is $C_{1-6}$ alkyl, $C_{2-4}$ alkenyl, or $C_{3-6}$ cycloalkyl;

wherein the $C_{1-6}$ alkyl or $C_{2-4}$ alkenyl is optionally substituted with one or more substituents independently selected from the group consisting of halogen, CN, $C(O)N(C_{1-6}$ alkyl$)_2$, C(O)OH, $C(O)OC_{1-6}$ alkyl, $NH_2$, $NHC_{1-6}$ alkyl, $N(C_{1-6}$ alkyl$)_2$, OH, $OC_{1-6}$ alkyl, $OC(O)C_{1-6}$ alkyl, $OC(O)N(C_{1-6}$ alkyl$)_2$, $OC_{3-6}$ cycloalkyl, =O, $S(O)_2C_{1-6}$ alkyl, $S(O)_2N(C_{1-6}$ alkyl$)_2$, $S(O)_2C_{3-5}$ cycloalkyl, $C_{3-6}$ cycloalkyl, azetidinyl, oxetanyl, tetrahydrofyranyl, oxo-oxazolidinyl, piperidinyl, tetrahydropyranyl, morpholinyl, oxomorpholinyl, phenyl, imidazolyl, triazolyl, and oxadiazolyl;

wherein the $C_{3-6}$ cycloalkyl is optionally substituted with one or more substituents independently selected from the group consisting of halogen, CN, $C_{1-6}$ alkyl, $C_{2-4}$ alkenyl, $C_{2-4}$ alkynyl, $C(O)N(C_{1-6}$ alkyl$)_2$, C(O)OH, $C(O)OC_{1-6}$ alkyl, $NH_2$, $NHC_{1-6}$ alkyl, $N(C_{1-6}$ alkyl$)_2$, OH, $OC_{1-6}$ alkyl, $OC(O)C_{1-6}$ alkyl, $OC(O)N(C_{1-6}$ alkyl$)_2$, $OC_{3-6}$ cycloalkyl, =O, $S(O)_2C_{1-6}$ alkyl, $S(O)_2N(C_{1-6}$ alkyl$)_2$, $S(O)_2C_{3-5}$ cycloalkyl, $C_{3-6}$ cycloalkyl, azetidinyl, oxetanyl, tetrahydrofyranyl, oxo-oxazolidinyl, piperidinyl, tetrahydropyranyl, morpholinyl, oxomorpholinyl, phenyl, imidazolyl, triazolyl, and oxadiazolyl;

wherein each $C_{1-6}$ alkyl substituent is optionally and independently substituted with 1, 2, 3, 4, 5, or 6 F substituents;

wherein each $C_{3-6}$ cycloalkyl substituent is optionally and independently substituted with 1, 2, 3, 4, 5, or 6 F, 1 $C_{1-6}$ alkyl substituent, or 1 $CF_3$ substituent;

wherein each azetidinyl substituent is optionally and independently substituted with 1 $C_{1-6}$ alkyl substituent; and wherein each tetrahydrofuranyl, piperidinyl, tetrahydropyranyl, and phenyl substituent is optionally and independently substituted with 1 F, 1 $C_{1-6}$ alkyl substituent, or 1 $CF_3$ substituent;

$R^5$ is $CH_3$, $CH_2CH_3$, $CH_2CF_3$, or cyclopropyl;

$R^{6a}$ is H, $C_{1-6}$ alkyl or $C_{3-6}$ cycloalkyl;

wherein the $C_{1-6}$ alkyl is optionally substituted with 1, 2, 3, 4, 5, or 6 independently selected halogen substituents; and wherein the $C_{3-6}$ cycloalkyl is optionally substituted with 1 halogen substituent or 1 $C_{1-6}$ alkyl substituent;

$R^{6b}$ is H, $C_{1-6}$ alkyl or $C_{3-6}$ cycloalkyl;

wherein the $C_{1-6}$ alkyl is optionally substituted with 1, 2, 3, 4, 5, or 6 independently selected halogen substituents; and wherein the $C_{3-6}$ cycloalkyl is optionally substituted with 1 halogen substituent or 1 $C_{1-6}$ alkyl substituent; or $R^{6a}$ and $R^{6b}$, taken together with the carbon atom to which they are attached, form a $C_{3-6}$ cycloalkylidene;

Y is phenylene, pyridinylene, pyridazinylene, pyrimidinylene, pyrazinylene, pyridofuranylene, or imidazopyridinylene, wherein the phenylene, pyridinylene, pyridazinylene, pyrimidinylene, pyrazinylene, pyridofuranylene, or imidazopyridinylene is optionally substituted with one or more independently selected $R^4$ substituents;

each $R^4$ is independently halogen, $C_{1-6}$ alkyl, $C_{2-6}$ alkenyl, OH, $OC_{1-6}$ alkyl, or $SC_{1-4}$ alkyl, wherein each $C_{1-6}$ alkyl, $C_{2-6}$ alkenyl, or $OC_{1-6}$ alkyl is optionally and independently substituted with 1, 2, 3, 4, 5, or 6 F substituents;

A is C;

D is CH, CH=CH, N, or N=CH;

E is CH or N;

G is CH, CCl, $CCH_3$, or N;

J is CH, CCl, $CCH_3$, $CCH_2OCH_3$, $COCH_3$, or N;

K is $CR^7$ or N;

$R^7$ is H, halogen, $C_{1-6}$ alkyl, $NH_2$, $NHC_{1-6}$ alkyl, $N(C_{1-6}$ alkyl$)_2$, $OC_{1-6}$ alkyl, or $SC_{1-4}$ alkyl;

wherein the $C_{1-6}$ alkyl is optionally substituted with 1, 2, 3, 4, 5, or 6 independently selected halogen substituents or 1 $OC_{1-6}$ alkyl substituent; and wherein the $OC_{1-6}$ alkyl is optionally substituted with 1, 2, 3, 4, 5, or 6 independently selected halogen substituents; and $R^8$ is H, halogen, CN, $C_{1-6}$ alkyl, $NH_2$, or OH, wherein the $C_{1-6}$ alkyl is optionally substituted with 1, 2, 3, 4, 5, or 6 independently selected halogen substituents.

2. The compound of claim 1, or a pharmaceutically acceptable salt or stereoisomer thereof, wherein $R^1$ is $C_{1-6}$ alkyl, wherein the $C_{1-6}$ alkyl is optionally substituted with one or more substituents independently selected from the group consisting of F and cyclopropyl.

3. The compound of claim 1, or a pharmaceutically acceptable salt or stereoisomer thereof, wherein:

$R^{6a}$ is $CH_3$ or $CF_3$; and $R^{6b}$ is H.

4. The compound of claim 1, or a pharmaceutically acceptable salt or stereoisomer thereof, wherein each $R^4$ is independently $C_{1-6}$ alkyl, OH, or $OC_{1-6}$ alkyl.

5. The compound of claim 1, or a pharmaceutically acceptable salt or stereoisomer thereof, wherein

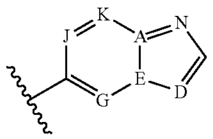

is:

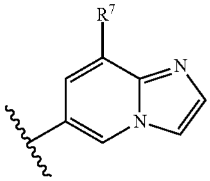, 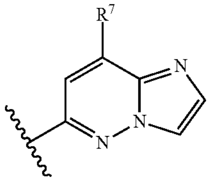, 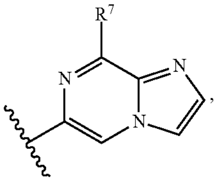, 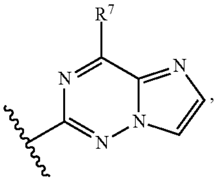, or 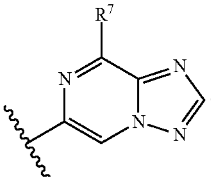.

6. The compound of claim 1, or a pharmaceutically acceptable salt or stereoisomer thereof, wherein

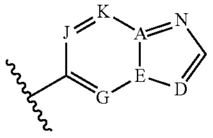

is

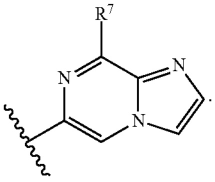.

7. The compound of claim 1, or a pharmaceutically acceptable salt or stereoisomer thereof, wherein $R^7$ is H, $CH_3$, or $OCH_3$.

8. The compound of claim 1, or a pharmaceutically acceptable salt or stereoisomer thereof, wherein $R^8$ is H or $CH_3$.

9. A pharmaceutical composition comprising an inert carrier and a compound of claim 1, or a pharmaceutically acceptable salt or stereoisomer thereof.

10. A method for treating hypersomnia in a subject, wherein the method comprises administering to the subject in need thereof a therapeutically effective amount of a compound of claim 1, or a pharmaceutically acceptable salt or stereoisomer thereof.

11. The method of claim 10 wherein the subject is a mammal.

12. A method for treating narcolepsy in a subject, wherein the method comprises administering to the subject in need thereof a therapeutically effective amount of a compound of claim 1, or a pharmaceutically acceptable salt or stereoisomer thereof.

13. The method of claim 12 wherein the subject is a mammal.

14. A compound selected from the group consisting of:

1-ethyl-3-((S)-1,1,1,5,5,5-hexafluoropentan-2-yl)-1-((R)-1-(3-(imidazo[1,2-a]pyridin-6-yl)phenyl)ethyl)urea;

1-ethyl-3-((R)-1-(3-fluorophenyl)ethyl)-1-((R)-1-(3-(8-methoxyimidazo[1,2-a]pyrazin-6-yl)phenyl)ethyl) urea;

1-ethyl-1-((R)-1-(3-(8-methoxyimidazo[1,2-a]pyrazin-6-yl)phenyl)ethyl)-3-((1R,3S)-3-(trifluoromethyl)cyclopentyl)urea;

3-((R)-1-(4,4-difluorocyclohexyl)ethyl)-1-ethyl-1-((R)-1-(3-(8-methoxyimidazo[1,2-a]pyrazin-6-yl)phenyl) ethyl)urea;

(R)-1-ethyl-1-(1-(3-(8-methoxyimidazo[1,2-a]pyrazin-6-yl)phenyl)ethyl)-3-(2,2,2-trifluoroethyl)urea;

1-ethyl-1-((R)-1-(3-(8-methoxyimidazo[1,2-a]pyrazin-6-yl)phenyl)ethyl)-3-(((S)-5-oxomorpholin-3-yl)methyl) urea;

3-(2-(dimethylamino)-3,3,3-trifluoropropyl)-1-ethyl-1-((R)-1-(3-(8-methoxyimidazo[1,2-a]pyridin-6-yl)phenyl)ethyl)urea;

(R)-1-ethyl-1-(4-methoxy-3-(8-methoxyimidazo[1,2-a] pyridin-6-yl)benzyl)-3-(6,6,6-trifluorohexan-3-yl)urea;

3-(1-(3,3-difluorocyclohexyl)ethyl)-1-ethyl-1-((R)-1-(3-(8-methoxyimidazo[1,2-a]pyrazin-6-yl)phenyl)ethyl) urea;

3-(cyano(cyclopentyl)methyl)-1-ethyl-1-((R)-1-(3-(8-methoxyimidazo[1,2-a]pyrazin-6-yl)phenyl)ethyl) urea;

ethyl 3-(3-ethyl-3-((R)-1-(3-(8-methoxyimidazo[1,2-a] pyrazin-6-yl)phenyl)ethyl)ureido)-4,4,4-trifluorobutanoate 3-(cyano(3-(trifluoromethyl)phenyl)methyl)-1-ethyl-1-((R)-1-(3-(8-methoxyimidazo[1,2-a]pyrazin-6-yl)phenyl)ethyl)urea;

3-(3-(dimethylamino)-1,1,1-trifluoropropan-2-yl)-1-ethyl-1-((R)-1-(3-(7-methoxypyrazolo[1,5-a]pyridin-5-yl)phenyl)ethyl)urea;

3-(3-cyano-1,1,1-trifluoropropan-2-yl)-1-ethyl-1-((R)-1-(3-(8-methoxyimidazo[1,2-a]pyrazin-6-yl)phenyl) ethyl)urea;

1-ethyl-1-((R)-1-(3-(8-methoxyimidazo[1,2-a]pyrazin-6-yl)phenyl)ethyl)-3-(2,2,2-trifluoro-1-(1-methylazetidin-3-yl)ethyl)urea;

1-ethyl-1-((R)-1-(3-(8-methoxyimidazo[1,2-a]pyrazin-6-yl)phenyl)ethyl)-3-(1,1,1-trifluoro-3-(2H-1,2,3-triazol-2-yl)propan-2-yl)urea;

1-ethyl-1-((R)-1-(3-(8-methoxyimidazo[1,2-a]pyrazin-6-yl)phenyl)ethyl)-3-(1,1,1-trifluoro-3-(1H-1,2,3-triazol-1-yl)propan-2-yl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-((S)-1,1,1-trifluoropropan-2-yl)urea;

1-ethyl-3-(1,1,1,5,5,5-hexafluoro-4-methylpentan-2-yl)-1-((R)-1-(3-(8-methoxyimidazo[1,2-a]pyrazin-6-yl)phenyl)ethyl)urea;

1-ethyl-1-((R)-1-(3-(8-methoxyimidazo[1,2-a]pyrazin-6-yl)phenyl)ethyl)-3-(6,6,6-trifluoro-5-methylhexan-3-yl)urea;

3-(1-(4,4-difluoro-6,6-dimethyltetrahydro-2H-pyran-2-yl)-2,2,2-trifluoroethyl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;

3-(1-cyclobutyl-2,2,2-trifluoroethyl)-1-ethyl-1-((S)-2,2,2-trifluoro-1-(5-methoxy-4-(8-methoxyimidazo[1,2-a]pyrazin-6-yl)pyridin-2-yl)ethyl)urea;

3-(1-cyclopropyl-2,2,2-trifluoroethyl)-1-ethyl-1-(2,2,2-trifluoro-1-(5-methoxy-4-(8-methoxyimidazo[1,2-a]pyrazin-6-yl)pyridin-2-yl)ethyl)urea;

3-(1-cyclopropyl-2,2-difluoroethyl)-1-ethyl-1-((S)-2,2,2-trifluoro-1-(5-methoxy-4-(8-methoxyimidazo[1,2-a]pyrazin-6-yl)pyridin-2-yl)ethyl)urea;

1-ethyl-1-(2,2,2-trifluoro-1-(5-methoxy-4-(8-methoxyimidazo[1,2-a]pyrazin-6-yl)pyridin-2-yl)ethyl)-3-((S)-1,1,1-trifluorobutan-2-yl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-(2-(trifluoromethyl)cyclobutyl)urea;

3-(1,1-difluorobutan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-(3,3,3-trifluoro-2-methylpropyl)urea;

(S)-1-ethyl-1-(2,2,2-trifluoro-1-(5-methoxy-4-(8-methoxyimidazo[1,2-a]pyrazin-6-yl)pyridin-2-yl)ethyl)-3-(1-(trifluoromethyl)cyclobutyl)urea;

1-ethyl-3-((S)-1,1,1,5,5,5-hexafluoropentan-2-yl)-1-(2,2,2-trifluoro-1-(7-(8-methoxyimidazo[1,2-a]pyrazin-6-yl)furo[3,2-b]pyridin-5-yl)ethyl)urea;

1-ethyl-3-((S)-1,1,1,5,5,5-hexafluoropentan-2-yl)-1-(2,2,2-trifluoro-1-(8-(8-methoxyimidazo[1,2-a]pyrazin-6-yl)imidazo[1,2-a]pyridin-6-yl)ethyl)urea;

1-ethyl-3-((S)-1,1,1,5,5,5-hexafluoropentan-2-yl)-1-(2,2,2-trifluoro-1-(5-(7-methoxypyrazolo[1,5-a]pyridin-5-yl)-6-(methylthio)pyridin-3-yl)ethyl)urea;

1-(cyclopropyl(5-methoxy-4-(8-methoxy-2-methylimidazo[1,2-a]pyrazin-6-yl)pyridin-2-yl)methyl)-1-ethyl-3-((S)-1,1,1,5,5,5-hexafluoropentan-2-yl)urea;

1-(2,2-difluoro-1-(5-methoxy-4-(8-methoxy-2-methylimidazo[1,2-a]pyrazin-6-yl)pyridin-2-yl)ethyl)-1-ethyl-3-((S)-1,1,1,5,5,5-hexafluoropentan-2-yl)urea;

3-((S)-3-cyclopropoxy-1,1,1-trifluoropropan-2-yl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;

1-cyclopropyl-3-((S)-1,1,1,5,5,5-hexafluoropentan-2-yl)-1-(2,2,2-trifluoro-1-(5-methoxy-4-(8-methoxy-2-methylimidazo[1,2-a]pyrazin-6-yl)pyridin-2-yl)ethyl)urea;

1-(2,2-difluoroethyl)-1-(2,2,2-trifluoro-1-(5-methoxy-4-(8-methoxy-[1,2,4]triazolo[1,5-a]pyrazin-6-yl)pyridin-2-yl)ethyl)-3-((R)-6,6,6-trifluorohexan-3-yl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-((R)-6,6,6-trifluorohexan-3-yl)urea;

N-ethyl-N'—[(2S)-1,1,1,5,5,5-hexafluoropentan-2-yl]-N-{2,2,2-trifluoro-1-[3-(8-methoxyimidazo[1,2-a]pyrazin-6-yl)phenyl]ethyl}urea;

1-ethyl-3-((S)-1,1,1,5,5,5-hexafluoropentan-2-yl)-1-((S)-2,2,2-trifluoro-1-(3-(imidazo[1,2-a]pyridin-6-yl)-4-methoxyphenyl)ethyl)urea;

3-((R)-1-(cyanomethyl)piperidin-3-yl)-1-ethyl-1-((R)-1-(3-(8-methoxyimidazo[1,2-a]pyrazin-6-yl)phenyl)ethyl)urea;

(R)-3-(2-cyanopropan-2-yl)-1-ethyl-1-(1-(3-(8-methoxyimidazo[1,2-a]pyrazin-6-yl)phenyl)ethyl)urea;

1-ethyl-3-(1-(3-methyl-1,2,4-oxadiazol-5-yl)ethyl)-1-((S)-2,2,2-trifluoro-1-(5-methoxy-4-(8-methoxyimidazo[1,2-a]pyrazin-6-yl)pyridin-2-yl)ethyl)urea;

1-ethyl-3-((1R,2R)-2-methyl-2-(trifluoromethyl)cyclopropyl)-1-((S)-2,2,2-trifluoro-1-(5-methoxy-4-(8-methoxyimidazo[1,2-a]pyrazin-6-yl)pyridin-2-yl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-((S)-1,1,1-trifluoro-3,3-dimethylbutan-2-yl)urea;

(S)-1-ethyl-3-isopropyl-1-(2,2,2-trifluoro-1-(5-methoxy-4-(8-methoxyimidazo[1,2-a]pyrazin-6-yl)pyridin-2-yl)ethyl)urea;

(S)-1-ethyl-1-(2,2,2-trifluoro-1-(5-methoxy-4-(8-methoxyimidazo[1,2-a]pyrazin-6-yl)pyridin-2-yl)ethyl)-3-(3-(2,2,2-trifluoroethyl)cyclobutyl)urea;

1-ethyl-3-((1R,2R)-1-methyl-2-(trifluoromethyl)cyclopropyl)-1-((S)-2,2,2-trifluoro-1-(5-methoxy-4-(8-methoxyimidazo[1,2-a]pyrazin-6-yl)pyridin-2-yl)ethyl)urea;

(S)-3-cyclopropyl-1-ethyl-1-(2,2,2-trifluoro-1-(5-methoxy-4-(8-methoxyimidazo[1,2-a]pyrazin-6-yl)pyridin-2-yl)ethyl)urea;

3-(1-(4,4-difluorotetrahydro-2H-pyran-2-yl)-2,2,2-trifluoroethyl)-1-ethyl-1-((R)-1-(3-(8-methoxyimidazo[1,2-a]pyrazin-6-yl)phenyl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-(1,1,1-trifluoro-4-oxopentan-2-yl)urea;

3-((S)-4-cyano-1,1,1-trifluorobutan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-((S)-1,1,1-trifluoro-4-(methylsulfonyl)butan-2-yl)urea;

3-(1-cyanobutyl)-1-ethyl-1-((R)-1-(3-(8-methoxyimidazo[1,2-a]pyrazin-6-yl)phenyl)ethyl)urea;

(S)-1-ethyl-1-(2,2,2-trifluoro-1-(5-methoxy-4-(8-methoxyimidazo[1,2-a]pyrazin-6-yl)pyridin-2-yl)ethyl)-3-(3-(trifluoromethyl)cyclobutyl)urea;

1-ethyl-3-((1S,2R)-2-methyl-2-(trifluoromethyl)cyclopropyl)-1-((S)-2,2,2-trifluoro-1-(5-methoxy-4-(8-methoxyimidazo[1,2-a]pyrazin-6-yl)pyridin-2-yl)ethyl)urea;

3-(3,3-difluorobutan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea;

3-(1,1-difluoropropan-2-yl)-1-ethyl-1-((S)-2,2,2-trifluoro-1-(5-methoxy-4-(8-methoxyimidazo[1,2-a]pyrazin-6-yl)pyridin-2-yl)ethyl)urea;

3-(2,2-difluorocyclopropyl)-1-ethyl-1-((S)-2,2,2-trifluoro-1-(5-methoxy-4-(8-methoxyimidazo[1,2-a]pyrazin-6-yl)pyridin-2-yl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-(1,1,1-trifluoro-3-(2-oxooxazolidin-3-yl)propan-2-yl)urea;

1-ethyl-3-((2S)-1,1,1,5,5,5-hexafluoro-4-methoxypentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-(4,4,4-trifluoro-1-(oxetan-2-yl)butyl)urea;

1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(1,1,1-trifluoro-3-(tetrahydrofuran-2-yl)propan-2-yl)urea;

1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(2,2,2-trifluoro-1-(tetrahydro-2H-pyran-3-yl)ethyl)urea;

1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(2,2,2-trifluoro-1-(tetrahydro-2H-pyran-4-yl)ethyl)urea;

1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(5,5,5-trifluoro-1-methoxypentan-2-yl)urea;

1-ethyl-3-((S)-1,1,1,5,5,5-hexafluoropentan-2-yl)-1-(2,2,2-trifluoro-1-(6-methoxy-5-(8-methoxyimidazo[1,2-a]pyrazin-6-yl)pyridin-3-yl)ethyl)urea;

1-ethyl-3-((S)-1,1,1,5,5,5-hexafluoropentan-2-yl)-1-((R)-1-(5-methoxy-4-(7-methoxypyrazolo[1,5-c]pyrimidin-5-yl)pyridin-2-yl)ethyl)urea;

1-ethyl-1-((R)-1-(3-(8-methoxyimidazo[1,2-a]pyrazin-6-yl)phenyl)ethyl)-3-(1,1,1,4,4-pentafluorobutan-2-yl)urea;

3-(1-(4,4-difluoro-1-methylpiperidin-2-yl)-2,2,2-trifluoroethyl)-1-ethyl-1-((R)-1-(3-(7-methoxypyrazolo[1,5-a]pyridin-5-yl)phenyl)ethyl)urea;

1-ethyl-1-((R)-1-(3-(8-methoxyimidazo[1,2-a]pyrazin-6-yl)phenyl)ethyl)-3-(1,1,1-trifluoro-5-oxohexan-2-yl)urea;

1-ethyl-1-((R)-1-(3-(8-methoxyimidazo[1,2-a]pyrazin-6-yl)phenyl)ethyl)-3-(2,2,6,6,6-pentafluorohexan-3-yl)urea;

3-((1R)-1-(4,4-difluorotetrahydro-2H-pyran-2-yl)propyl)-1-ethyl-1-((R)-1-(3-(8-methoxyimidazo[1,2-a]pyrazin-6-yl)phenyl)ethyl)urea;

3-(3-(1-ethoxycyclopropyl)-1,1,1-trifluoropropan-2-yl)-1-ethyl-1-((R)-1-(3-(8-methoxyimidazo[1,2-a]pyrazin-6-yl)phenyl)ethyl)urea;

1-((R)-1-(3-(8-methoxyimidazo[1,2-a]pyrazin-6-yl)phenyl)ethyl)-1-methyl-3-((R)-6,6,6-trifluorohexan-3-yl)urea;

1-((R)-1-(3-(8-methoxyimidazo[1,2-a]pyrazin-6-yl)phenyl)ethyl)-1-propyl-3-((R)-6,6,6-trifluorohexan-3-yl)urea;

1-isopropyl-1-((R)-1-(3-(8-methoxyimidazo[1,2-a]pyrazin-6-yl)phenyl)ethyl)-3-((R)-6,6,6-trifluorohexan-3-yl)urea;

1-(2,2-difluoroethyl)-3-((S)-1,1,1,5,5,5-hexafluoropentan-2-yl)-1-(1-(3-(8-methoxyimidazo[1,2-a]pyrazin-6-yl)phenyl)ethyl)urea;

1-ethyl-1-(2,2,2-trifluoro-1-(6-methoxy-5-(8-methoxyimidazo[1,2-a]pyrazin-6-yl)pyridin-3-yl)ethyl)-3-((S)-1,1,1-trifluoropropan-2-yl)urea;

1-ethyl-3-((S)-1,1,1,5,5,5-hexafluoropentan-2-yl)-1-(1-(2-(8-methoxyimidazo[1,2-a]pyrazin-6-yl)pyrimidin-4-yl)ethyl)urea;

1-ethyl-3-((S)-1,1,1,5,5,5-hexafluoropentan-2-yl)-1-(1-(6-(8-methoxyimidazo[1,2-a]pyrazin-6-yl)pyridazin-4-yl)ethyl)urea;

1-ethyl-1-((R)-1-(3-(8-methoxyimidazo[1,2-a]pyrazin-6-yl)phenyl)ethyl)-3-(6,6,6-trifluorohex-1-yn-3-yl)urea;

1-ethyl-1-((S)-2,2,2-trifluoro-1-(3-(8-methoxyimidazo[1,2-a]pyrazin-6-yl)phenyl)ethyl)-3-(2,2,2-trifluoro-1-(3-fluorophenyl)ethyl)urea;

1-ethyl-3-(1-methyl-6-(trifluoromethyl)piperidin-3-yl)-1-((S)-2,2,2-trifluoro-1-(3-(8-methoxyimidazo[1,2-a]pyrazin-6-yl)phenyl)ethyl)urea;

(R)-1,3-diethyl-1-(1-(3-(8-methoxyimidazo[1,2-a]pyridin-6-yl)phenyl)ethyl)urea;

3-((1S)-1-(3,3-difluorocyclohexyl)-2,2,2-trifluoroethyl)-1-ethyl-1-((R)-1-(3-(8-methoxyimidazo[1,2-a]pyrazin-6-yl)phenyl)ethyl)urea;

1-ethyl-3-((S)-1,1,1,5-tetrafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;

1-ethyl-3-((S)-1,1,1,5,5-pentafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;

1-ethyl-3-((S)-1,1,1,5,6,6-hexafluorohex-5-en-2-yl)-1-((S)-2,2,2-trifluoro-1-(5-methoxy-4-(8-methoxy-2-methylimidazo[1,2-a]pyrazin-6-yl)pyridin-2-yl)ethyl)urea;

3-((S)-3-cyclopropyl-1,1,1-trifluoropropan-2-yl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;

3-(4-cyclopropyl-1,1,1-trifluorobutan-2-yl)-1-ethyl-1-((R)-1-(3-(8-methoxyimidazo[1,2-a]pyrazin-6-yl)phenyl)ethyl)urea;

1-ethyl-1-((R)-1-(3-(8-methoxyimidazo[1,2-a]pyrazin-6-yl)phenyl)ethyl)-3-(1,1,1-trifluorohept-6-yn-2-yl)urea;

1-ethyl-3-((S)-1,1,5,5,5-pentafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;

1-ethyl-3-((S)-1,1,5,5-tetrafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;

1-ethyl-1-((S)-2,2,2-trifluoro-1-(5-methoxy-4-(8-methoxy-[1,2,4]triazolo[1,5-a]pyrazin-6-yl)pyridin-2-yl)ethyl)-3-((S)-1,1,5-trifluoropentan-2-yl)urea;

1-ethyl-1-(2,2,2-trifluoro-1-(5-methoxy-4-(8-methoxyimidazo[1,2-a]pyrazin-6-yl)pyridin-2-yl)ethyl)-3-((S)-1,1,1-trifluoropent-4-en-2-yl)urea;

1-ethyl-1-((R)-1-(3-(8-methoxyimidazo[1,2-a]pyrazin-6-yl)phenyl)ethyl)-3-((S)-1,1,1-trifluoro-4-methylpent-3-en-2-yl)urea;

1-ethyl-1-((S)-2,2,2-trifluoro-1-(5-methoxy-4-(8-methoxyimidazo[1,2-a]pyrazin-6-yl)pyridin-2-yl)ethyl)-3-(1,1,1-trifluorobut-3-yn-2-yl)urea;

3-((R)-6,6-difluorohexan-3-yl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;

1-ethyl-1-(2,2,2-trifluoro-1-(5-methoxy-4-(8-methoxyimidazo[1,2-a]pyrazin-6-yl)pyridin-2-yl)ethyl)-3-((R)-1,1,1-trifluoropentan-3-yl)urea;

3-(1-cyclopropyl-3,3,3-trifluoropropyl)-1-ethyl-1-(2,2,2-trifluoro-1-(5-methoxy-4-(8-methoxyimidazo[1,2-a]pyrazin-6-yl)pyridin-2-yl)ethyl)urea;

3-(1-cyclopropyl-4-fluorobutyl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;

1-ethyl-1-((S)-2,2,2-trifluoro-1-(5-methoxy-4-(8-methoxy-2-methylimidazo[1,2-a]pyrazin-6-yl)pyridin-2-yl)ethyl)-3-((E)-6,6,6-trifluorohex-4-en-3-yl)urea;

1-ethyl-1-((S)-2,2,2-trifluoro-1-(5-methoxy-4-(8-methoxy-2-methylimidazo[1,2-a]pyrazin-6-yl)pyridin-2-yl)ethyl)-3-(1-(2-(trifluoromethyl)cyclopropyl)propyl)urea;

3-((S)-1-cyclopropyl-4,4-difluorobutyl)-1-ethyl-1-((S)-2,2,2-trifluoro-1-(5-methoxy-4-(8-methoxy-2-methylimidazo[1,2-a]pyrazin-6-yl)pyridin-2-yl)ethyl)urea;

1-((R)-1-(3-(8-(difluoromethoxy)imidazo[1,2-a]pyridin-6-yl)phenyl)ethyl)-1-ethyl-3-((R)-6,6,6-trifluorohexan-3-yl)urea;

1-ethyl-1-((R)-1-(3-(7-methoxyimidazo[1,2-a]pyridin-6-yl)phenyl)ethyl)-3-(6,6,6-trifluorohexan-3-yl)urea;

1-((R)-1-(3-(8-(difluoromethyl)imidazo[1,2-a]pyridin-6-yl)phenyl)ethyl)-1-ethyl-3-((R)-6,6,6-trifluorohexan-3-yl)urea;

1-ethyl-1-((R)-1-(3-(8-(methoxymethyl)imidazo[1,2-a]pyridin-6-yl)phenyl)ethyl)-3-((R)-6,6,6-trifluorohexan-3-yl)urea;

1-((R)-1-(3-(7-chloropyrazolo[1,5-a]pyridin-5-yl)phenyl)ethyl)-1-ethyl-3-((R)-6,6,6-trifluorohexan-3-yl)urea;

1-ethyl-1-((R)-1-(3-(7-(methoxymethyl)imidazo[1,2-a]pyridin-6-yl)phenyl)ethyl)-3-(6,6,6-trifluorohexan-3-yl)urea;

1-ethyl-1-((R)-1-(3-(8-(methylthio)imidazo[1,2-a]pyrazin-6-yl)phenyl)ethyl)-3-((R)-6,6,6-trifluorohexan-3-yl)urea;

1-((R)-1-(3-(8-ethoxyimidazo[1,2-a]pyridin-6-yl)phenyl)ethyl)-1-ethyl-3-((R)-6,6,6-trifluorohexan-3-yl)urea;

1-ethyl-1-((R)-1-(4-methoxy-3-(8-methylimidazo[1,2-a]pyridin-6-yl)phenyl)ethyl)-3-((R)-6,6,6-trifluorohexan-3-yl)urea;

1-((R)-1-(3-(8-aminoimidazo[1,2-a]pyridin-6-yl)-4-methoxyphenyl)ethyl)-1-ethyl-3-((R)-6,6,6-trifluorohexan-3-yl)urea;

1-ethyl-1-((R)-1-(4-methoxy-3-(1H-pyrrolo[2,3-b]pyridin-5-yl)phenyl)ethyl)-3-((R)-6,6,6-trifluorohexan-3-yl)urea;

1-ethyl-1-((R)-1-(3-(imidazo[1,2-a]pyrimidin-6-yl)phenyl)ethyl)-3-(6,6,6-trifluorohexan-3-yl)urea;

1-ethyl-1-((R)-1-(3-(7-methylimidazo[1,2-a]pyridin-6-yl)phenyl)ethyl)-3-(6,6,6-trifluorohexan-3-yl)urea;

1-((R)-1-(3-(3-chloro-8-methoxyimidazo[1,2-a]pyridin-6-yl)phenyl)ethyl)-1-ethyl-3-((S)-1,1,1,5,5,5-hexafluoropentan-2-yl)urea;

1-((R)-1-(3-(2-chloro-8-methoxyimidazo[1,2-a]pyridin-6-yl)phenyl)ethyl)-1-ethyl-3-((S)-1,1,1,5,5,5-hexafluoropentan-2-yl)urea;

1-ethyl-3-((S)-1,1,1,5,5,5-hexafluoropentan-2-yl)-1-((R)-1-(3-(8-methoxy-[1,2,4]triazolo[1,5-a]pyridin-6-yl)phenyl)ethyl)urea;

1-((R)-1-(3-(3-aminoimidazo[1,2-a]pyridin-6-yl)phenyl)ethyl)-1-ethyl-3-((S)-1,1,1,5,5,5-hexafluoropentan-2-yl)urea;

1-((R)-1-(3-(3,5-dichloro-8-methoxyimidazo[1,2-a]pyridin-6-yl)phenyl)ethyl)-1-ethyl-3-((S)-1,1,1,5,5,5-hexafluoropentan-2-yl)urea;

1-((R)-1-(3-(7-chloroimidazo[1,2-a]pyridin-6-yl)phenyl)ethyl)-1-ethyl-3-((R)-6,6,6-trifluorohexan-3-yl)urea;

1-ethyl-3-((S)-1,1,1,5,5,5-hexafluoropentan-2-yl)-1-((S)-2,2,2-trifluoro-1-(5-methoxy-4-(8-methoxyimidazo[1,2-a]pyridin-6-yl)pyridin-2-yl)ethyl)urea;

1-ethyl-1-((S)-1-(4-(8-ethylimidazo[1,2-a]pyrazin-6-yl)-5-methoxypyridin-2-yl)-2,2,2-trifluoroethyl)-3-((S)-1,1,1,5,5,5-hexafluoropentan-2-yl)urea;

1-ethyl-3-((S)-1,1,1,5,5,5-hexafluoropentan-2-yl)-1-((S)-2,2,2-trifluoro-1-(5-methoxy-4-(8-methoxy-5-methylimidazo[1,2-a]pyrazin-6-yl)pyridin-2-yl)ethyl)urea;

1-ethyl-3-((S)-1,1,1,5,5,5-hexafluoropentan-2-yl)-1-((R)-1-(5-methoxy-4-(4-methoxybenzo[d]oxazol-6-yl)pyridin-2-yl)ethyl)urea;

1-ethyl-1-((R)-1-(4-(7-ethylpyrazolo[1,5-a]pyridin-5-yl)-5-methoxypyridin-2-yl)ethyl)-3-((S)-1,1,1,5,5,5-hexafluoropentan-2-yl)urea;

1-ethyl-3-((S)-1,1,1,5,5,5-hexafluoropentan-2-yl)-1-((S)-2,2,2-trifluoro-1-(5-methoxy-4-(8-methylimidazo[1,2-a]pyrazin-6-yl)pyridin-2-yl)ethyl)urea;

1-ethyl-3-((S)-1,1,1,5,5,5-hexafluoropentan-2-yl)-1-((S)-2,2,2-trifluoro-1-(5-methoxy-4-(4-methoxy-1-methyl-1H-benzo[d]imidazol-6-yl)pyridin-2-yl)ethyl)urea;

1-ethyl-3-((S)-1,1,1,5,5,5-hexafluoropentan-2-yl)-1-((S)-2,2,2-trifluoro-1-(5-methoxy-4-(7-methoxypyrazolo[1,5-a]pyrimidin-5-yl)pyridin-2-yl)ethyl)urea;

1-ethyl-3-((S)-1,1,1,5,5,5-hexafluoropentan-2-yl)-1-((S)-2,2,2-trifluoro-1-(4-(8-fluoro-[1,2,4]triazolo[1,5-a]pyridin-6-yl)-5-methoxypyridin-2-yl)ethyl)urea;

1-ethyl-3-((S)-1,1,1,5,5,5-hexafluoropentan-2-yl)-1-((S)-2,2,2-trifluoro-1-(5-methoxy-4-(4-methoxyimidazo[2,1-f][1,2,4]triazin-2-yl)pyridin-2-yl)ethyl)urea;

1-ethyl-3-((S)-1,1,1,5,5,5-hexafluoropentan-2-yl)-1-((S)-2,2,2-trifluoro-1-(5-methoxy-4-(8-methoxyimidazo[1,2-a]pyrazin-6-yl)pyridin-2-yl)ethyl)urea;

(R)-1-ethyl-1-(5-(imidazo[1,2-a]pyridin-6-yl)-2,4-dimethoxybenzyl)-3-(6,6,6-trifluorohexan-3-yl)urea;

1-ethyl-3-((S)-1,1,1,5,5,5-hexafluoropentan-2-yl)-1-((R)-1-(6-methoxy-5-(8-methoxyimidazo[1,2-a]pyrazin-6-yl)pyridazin-3-yl)ethyl)urea;

1-ethyl-3-((S)-1,1,1,5,5,5-hexafluoropentan-2-yl)-1-(2,2,2-trifluoro-1-(5-methoxy-4-(8-methoxyimidazo[1,2-a]pyrazin-6-yl)pyrimidin-2-yl)ethyl)urea;

1-ethyl-3-((S)-1,1,1,5,5,5-hexafluoropentan-2-yl)-1-(2,2,2-trifluoro-1-(5-methoxy-6-(8-methoxyimidazo[1,2-a]pyrazin-6-yl)pyrazin-2-yl)ethyl)urea;

1-ethyl-3-((S)-1,1,1,5,5,5-hexafluoropentan-2-yl)-1-(2,2,2-trifluoro-1-(5-methoxy-4-(8-methoxyimidazo[1,2-a]pyrazin-6-yl)-6-methylpyridin-2-yl)ethyl)urea;

1-(1-(4-(2-cyano-8-methoxyimidazo[1,2-a]pyridin-6-yl)-5-methoxypyridin-2-yl)-2,2,2-trifluoroethyl)-1-ethyl-3-((S)-1,1,1,5,5,5-hexafluoropentan-2-yl)urea;

1-ethyl-3-((S)-1,1,1,5,5,5-hexafluoropentan-2-yl)-1-((S)-2,2,2-trifluoro-1-(5-methoxy-4-(4-methoxythiazolo[4,5-c]pyridin-6-yl)pyridin-2-yl)ethyl)urea;

1-ethyl-3-((S)-1,1,1,5,5,5-hexafluoropentan-2-yl)-1-((S)-2,2,2-trifluoro-1-(5-methoxy-4-(8-methoxy-2-methylimidazo[1,2-a]pyrazin-6-yl)pyridin-2-yl)ethyl)urea;

1-ethyl-3-((S)-1,1,1,5,5,5-hexafluoropentan-2-yl)-1-(2,2,2-trifluoro-1-(5-methoxy-4-(8-methoxyimidazo[1,2-b]pyridazin-6-yl)pyridin-2-yl)ethyl)urea;

1-ethyl-3-((S)-1,1,1,5,5,5-hexafluoropentan-2-yl)-1-(2,2,2-trifluoro-1-(5-methoxy-4-(8-methoxyquinolin-6-yl)pyridin-2-yl)ethyl)urea;

1-(1-(4-(3-cyano-8-methoxyimidazo[1,2-a]pyrazin-6-yl)-5-methoxypyridin-2-yl)-2,2,2-trifluoroethyl)-1-ethyl-3-((S)-1,1,1,5,5,5-hexafluoropentan-2-yl)urea;

1-ethyl-3-((S)-1,1,1,5,5,5-hexafluoropentan-2-yl)-1-(2,2,2-trifluoro-1-(5-methoxy-4-(8-methoxyquinoxalin-6-yl)pyridin-2-yl)ethyl)urea;

1-ethyl-3-((S)-1,1,1,5,5,5-hexafluoropentan-2-yl)-1-((S)-2,2,2-trifluoro-1-(5-methoxy-4-(7-methoxy-1H-benzo[d]imidazol-5-yl)pyridin-2-yl)ethyl)urea;

1-ethyl-3-((S)-1,1,1,5,5,5-hexafluoropentan-2-yl)-1-(2,2,2-trifluoro-1-(6-methoxy-4-(8-methoxyimidazo[1,2-a]pyrazin-6-yl)pyridin-2-yl)ethyl)urea;

1-ethyl-3-((S)-1,1,1,5,5,5-hexafluoropentan-2-yl)-1-(2,2,2-trifluoro-1-(2-methoxy-5-(8-methoxyimidazo[1,2-a]pyrazin-6-yl)pyridin-3-yl)ethyl)urea;

1-ethyl-3-((S)-1,1,1,5,5,5-hexafluoropentan-2-yl)-1-((R)-1-(5-(8-methoxyimidazo[1,2-a]pyrazin-6-yl)-6-methylpyridin-3-yl)ethyl)urea;

1-ethyl-1-((R)-1-(6-methoxy-5-(8-methoxyimidazo[1,2-a]pyrazin-6-yl)pyridin-3-yl)ethyl)-3-((S)-1,1,1,5,5-pentafluorohexan-2-yl)urea;

1-ethyl-3-((S)-1,1,1,5,5,5-hexafluoropentan-2-yl)-1-(2,2,2-trifluoro-1-(5-methoxy-6-(8-methoxyimidazo[1,2-a]pyrazin-6-yl)pyridin-2-yl)ethyl)urea;

1-ethyl-3-((S)-1,1,1,5,5,5-hexafluoropentan-2-yl)-1-((S)-2,2,2-trifluoro-1-(4-(8-methoxyimidazo[1,2-a]pyrazin-6-yl)-5-methylpyridin-2-yl)ethyl)urea;

1-ethyl-3-((S)-1,1,1,5,5,5-hexafluoropentan-2-yl)-1-(2,2,2-trifluoro-1-(5-(8-methoxyimidazo[1,2-a]pyrazin-6-yl)pyridin-3-yl)ethyl)urea;

1-ethyl-1-((R)-1-(7-(imidazo[1,2-a]pyridin-6-yl)-2,3-dihydrobenzofuran-5-yl)ethyl)-3-((R)-6,6,6-trifluorohexan-3-yl)urea;

1-ethyl-1-((R)-1-(2-fluoro-5-(imidazo[1,2-a]pyridin-6-yl)-4-methoxyphenyl)ethyl)-3-((R)-6,6,6-trifluorohexan-3-yl)urea;

1-((R)-1-(4-bromo-3-(imidazo[1,2-a]pyridin-6-yl)phenyl)ethyl)-1-ethyl-3-((R)-6,6,6-trifluorohexan-3-yl)urea;

1-ethyl-3-((S)-1,1,1,5,5,5-hexafluoropentan-2-yl)-1-((R)-1-(6-methoxy-5-(8-methoxyimidazo[1,2-a]pyrazin-6-yl)pyridin-3-yl)ethyl)urea;

1-ethyl-3-((S)-1,1,1,5,5,5-hexafluoropentan-2-yl)-1-((R)-1-(5-methoxy-4-(7-methoxypyrazolo[1,5-a]pyridin-5-yl)pyridin-2-yl)ethyl)urea;

1-((R)-1-(3-(6-amino-5-methoxypyridin-3-yl)phenyl)ethyl)-1-ethyl-3-((S)-1,1,1,5,5,5-hexafluoropentan-2-yl)urea;

1-ethyl-3-((S)-1,1,1,5,5,5-hexafluoropentan-2-yl)-1-((R)-1-(5-methoxy-4-(8-methoxyimidazo[1,2-a]pyrazin-6-yl)pyridin-2-yl)ethyl)urea;

3-((S)-1-cyclopropyl-4,4,4-trifluorobutyl)-1-ethyl-1-((R)-1-(6-methoxy-5-(8-methoxyimidazo[1,2-a]pyrazin-6-yl)pyridin-3-yl)ethyl)urea;

1-ethyl-3-((S)-1,1,1,5,5,5-hexafluoropentan-2-yl)-1-((R)-1-(5-methoxy-4-(8-methoxy-3-methylimidazo[1,2-a]pyrazin-6-yl)pyridin-2-yl)ethyl)urea;

1-ethyl-3-((S)-1,1,1,5,5,5-hexafluoropentan-2-yl)-1-(1-(2-(8-methoxyimidazo[1,2-a]pyrazin-6-yl)pyridin-4-yl)ethyl)urea;

1-ethyl-3-((S)-1,1,1,5,5,5-hexafluoropentan-2-yl)-1-(1-(6-(8-methoxyimidazo[1,2-a]pyrazin-6-yl)pyrimidin-4-yl)ethyl)urea;

1-ethyl-3-((S)-1,1,1,5,5,5-hexafluoropentan-2-yl)-1-((R)-1-(4-(8-methoxyimidazo[1,2-a]pyrazin-6-yl)pyridin-2-yl)ethyl)urea;

1-((R)-1-(4-chloro-3-(8-methoxyimidazo[1,2-a]pyridin-6-yl)phenyl)ethyl)-1-ethyl-3-((R)-6,6,6-trifluorohexan-3-yl)urea;

1-(1-(5-chloro-4-(8-fluoroimidazo[1,2-a]pyridin-6-yl)pyridin-2-yl)ethyl)-1-ethyl-3-((S)-1,1,1,5,5,5-hexafluoropentan-2-yl)urea;

1-ethyl-1-(1-(4-(8-fluoroimidazo[1,2-a]pyridin-6-yl)-5-methoxypyridin-2-yl)ethyl)-3-((S)-1,1,1,5,5,5-hexafluoropentan-2-yl)urea;

3-(cyano(3,3-difluorocyclohexyl)methyl)-1-ethyl-1-((R)-1-(3-(8-methoxyimidazo[1,2-a]pyrazin-6-yl)phenyl)ethyl)urea;

N'-{3-[(dimethylsulfamoyl)amino]-1,1,1-trifluoropropan-2-yl}-N-ethyl-N-{(1R)-1-[3-(8-methoxyimidazo[1,2-a]pyrazin-6-yl)phenyl]ethyl}urea;

(R)-1-ethyl-1-(2-(3-(imidazo[1,2-a]pyridin-6-yl)phenyl)propan-2-yl)-3-(6,6,6-trifluorohexan-3-yl)urea;

1-ethyl-1-((R)-1-(3-(imidazo[1,2-a]pyridin-6-yl)-4-vinylphenyl)ethyl)-3-((R)-6,6,6-trifluorohexan-3-yl)urea;

1-ethyl-1-((R)-1-(3-(8-methoxyimidazo[1,2-a]pyrazin-6-yl)phenyl)ethyl)-3-((S)-1,1,1-trifluoro-4-methylpent-3-en-2-yl)urea;

2-(3-ethyl-3-((R)-1-(3-(8-methoxyimidazo[1,2-a]pyrazin-6-yl)phenyl)ethyl)ureido)-3,3,3-trifluoropropyl acetate;

2-(3-ethyl-3-((R)-1-(3-(8-methoxyimidazo[1,2-a]pyrazin-6-yl)phenyl)ethyl)ureido)-3,3,3-trifluoropropyl acetate;

2-(3-ethyl-3-((R)-1-(3-(8-methoxyimidazo[1,2-a]pyrazin-6-yl)phenyl)ethyl)ureido)-3,3,3-trifluoropropyl dimethylcarbamate;

3-(3-ethyl-3-((R)-1-(3-(8-methoxyimidazo[1,2-a]pyrazin-6-yl)phenyl)ethyl)ureido)-4,4,4-trifluoro-N,N-dimethylbutanamide;

1-ethyl-1-((R)-1-(3-(7-methoxyindolin-5-yl)phenyl)ethyl)-3-((R)-6,6,6-trifluorohexan-3-yl)urea;

1-ethyl-3-((S)-1,1,1,5,5,5-hexafluoropentan-2-yl)-1-((R)-1-(3-(2-hydroxy-8-methoxyimidazo[1,2-a]pyridin-6-yl)phenyl)ethyl)urea;

1-ethyl-3-((S)-1,1,1,5,5,5-hexafluoropentan-2-yl)-1-((R)-1-(3-(8-methoxy-2-(trifluoromethyl)imidazo[1,2-a]pyridin-6-yl)phenyl)ethyl)urea;

(S)-1-(2,2-difluoro-1-(5-methoxy-4-(8-methoxyimidazo[1,2-a]pyrazin-6-yl)pyridin-2-yl)vinyl)-1-ethyl-3-(1,1,1,5,5,5-hexafluoropentan-2-yl)urea;

1-ethyl-3-((S)-1,1,1,5,5,5-hexafluoropentan-2-yl)-1-((R)-1-(5-(8-methoxy-imidazo[1,2-a]pyrazin-6-yl)-1-methyl-6-oxo-1,6-dihydropyridin-3-yl)ethyl)urea; and 1-ethyl-3-((S)-1,1,1,5,5,5-hexafluoropentan-2-yl)-1-((R)-1-(6-hydroxy-5-(7-methoxypyrazolo[1,5-a]pyridin-5-yl)pyridin-3-yl)ethyl)urea; or a pharmaceutically accept or stereoisomer thereof.

* * * * *